United States Patent
Sage et al.

[11] Patent Number: 5,961,483
[45] Date of Patent: Oct. 5, 1999

[54] IONTOPHORETIC DELIVERY OF CELL ADHESION INHIBITORS

[76] Inventors: Burton H. Sage, 7001 Jeffrey Dr., Raleigh, N.C. 27603; Carl Randolph Bock, 1334 Welcome Cir., Durham, N.C. 17705; Philip G. Green, 17G Carlyle Towers South 100 Winston Dr., Cliffside Park, N.J. 07010; Munir A. Hussain, 619 Andover Rd., Wilmington, Del. 19803; Arnold J. Repta, 920 Fairborne Ave., Greenville, Del. 19807

[21] Appl. No.: 08/878,493

[22] Filed: Jun. 18, 1997

Related U.S. Application Data

[63] Continuation-in-part of application No. 08/724,105, Sep. 30, 1996, abandoned, and application No. 08/724,106, Sep. 30, 1996, abandoned
[60] Provisional application No. 60/020,277, Jun. 19, 1996.
[51] Int. Cl.⁶ ..................................................... A61N 1/30
[52] U.S. Cl. ............................................. 604/20; 424/449
[58] Field of Search ................................ 604/20; 424/449

[56] References Cited

U.S. PATENT DOCUMENTS

| | | |
|---|---|---|
| 3,991,755 | 11/1976 | Vernon et al. |
| 4,141,359 | 2/1979 | Jacobsen et al. |
| 4,250,878 | 2/1981 | Jacobsen et al. |
| 4,383,529 | 5/1983 | Webster |
| 4,395,545 | 7/1983 | Adam et al. |
| 4,474,570 | 10/1984 | Ariura et al. |
| 4,522,803 | 6/1985 | Lenk et al. |
| 4,557,723 | 12/1985 | Sibalis |
| 4,610,868 | 9/1986 | Fountain et al. |
| 4,708,716 | 11/1987 | Sibalis |
| 4,713,050 | 12/1987 | Sibalis |
| 4,731,049 | 3/1988 | Parsi |
| 4,744,787 | 5/1988 | Phipps et al. |
| 4,747,819 | 5/1988 | Phipps et al. |
| 4,752,285 | 6/1988 | Petelenz et al. |
| 4,764,164 | 8/1988 | Sasaki |
| 4,820,263 | 4/1989 | Spevak et al. |
| 4,865,582 | 9/1989 | Sibalis |
| 4,927,408 | 5/1990 | Haak et al. |
| 4,950,229 | 8/1990 | Sage, Jr. |
| 5,051,435 | 9/1991 | Paradies |
| 5,068,226 | 11/1991 | Weinshenker et al. |
| 5,080,646 | 1/1992 | Theeuwes et al. |
| 5,084,006 | 1/1992 | Lew et al. |
| 5,084,008 | 1/1992 | Phipps |
| 5,087,242 | 2/1992 | Petelenz et al. |
| 5,125,894 | 6/1992 | Phipps et al. |
| 5,135,477 | 8/1992 | Untereker et al. |
| 5,135,480 | 8/1992 | Bannon et al. |
| 5,147,296 | 9/1992 | Theeuwes et al. |
| 5,147,297 | 9/1992 | Myers et al. |
| 5,158,537 | 10/1992 | Haak et al. |

(List continued on next page.)

FOREIGN PATENT DOCUMENTS 0 625 061 B1   3/1997   European Pat. Off.

OTHER PUBLICATIONS

Lefkovits, J. et al., "Platelet Glycoprotein IIb/IIIa Receptors in Cardiovascular Medicine," New England J. Med 332: 1553–1559 (1995).

*Primary Examiner*—D. Gabrielle Brouillette
*Attorney, Agent, or Firm*—Hoffmann & Baron, LLP

[57] ABSTRACT

This invention relates to novel methods and devices for iontophoretically administering therapeutic doses of cell adhesion receptor antagonists in a controlled manner through the skin. Such antagonist compounds include but are not limited to antagonists of the IIb/IIIa and $\alpha_v\beta_3$ integrins and related cell surface adhesive protein receptors. The present invention includes iontophoretic delivery devices comprising cell adhesion receptor antagonists. Such methods and devices are useful, alone or in combination with other therapeutic agents, for the treatment of thromboembolic disorders, angiogenic disorders, inflammation, bone degradation, cancer metastasis, diabetic retinopathy, restenosis, macular degeneration, and other conditions mediated by cell adhesion and/or cell migration and/or angiogenesis.

26 Claims, 8 Drawing Sheets

U.S. PATENT DOCUMENTS

| | | |
|---|---|---|
| 5,162,042 | 11/1992 | Gyory et al. . |
| 5,162,043 | 11/1992 | Lew et al. . |
| 5,167,616 | 12/1992 | Haak et al. . |
| 5,169,382 | 12/1992 | Theeuwes et al. . |
| 5,169,383 | 12/1992 | Gyory et al. . |
| 5,203,768 | 4/1993 | Haak et al. . |
| 5,207,752 | 5/1993 | Sorenson et al. . |
| 5,221,254 | 6/1993 | Phipps . |
| 5,232,438 | 8/1993 | Theeuwes et al. . |
| 5,234,992 | 8/1993 | Gyory et al. . |
| 5,236,412 | 8/1993 | Lloyd et al. . |
| 5,239,113 | 8/1993 | Bovy et al. . |
| 5,240,995 | 8/1993 | Gyory et al. . |
| 5,246,417 | 9/1993 | Haak et al. . |
| 5,246,418 | 9/1993 | Haynes et al. . |
| 5,256,137 | 10/1993 | Sage, Jr. . |
| 5,276,049 | 1/1994 | Himmelsbach et al. . |
| 5,281,287 | 1/1994 | Lloyd et al. . |
| 5,281,585 | 1/1994 | Duggan et al. . |
| 5,284,471 | 2/1994 | Sage, Jr. . |
| 5,288,389 | 2/1994 | Yamada et al. . |
| 5,298,017 | 3/1994 | Theeuwes et al. . |
| 5,302,172 | 4/1994 | Sage, Jr. et al. . |
| 5,306,235 | 4/1994 | Haynes . |
| 5,310,403 | 5/1994 | Haynes . |
| 5,310,404 | 5/1994 | Gyory et al. . |
| 5,312,326 | 5/1994 | Myers et al. . |
| 5,314,502 | 5/1994 | McNichols et al. . |
| 5,320,597 | 6/1994 | Sage, Jr. et al. . |
| 5,320,598 | 6/1994 | Haak et al. . |
| 5,322,502 | 6/1994 | Theeuwes et al. . |
| 5,326,341 | 7/1994 | Lew et al. . |
| 5,334,596 | 8/1994 | Hartman et al. . |
| 5,344,394 | 9/1994 | Gyory et al. . |
| 5,374,242 | 12/1994 | Haak et al. . |
| 5,380,271 | 1/1995 | Gyory . |
| 5,385,543 | 1/1995 | Haak et al. . |
| 5,387,189 | 2/1995 | Gory et al. . |
| 5,395,310 | 3/1995 | Untereker et al. . |
| 5,403,275 | 4/1995 | Phipps . |
| 5,405,317 | 4/1995 | Myers et al. . |
| 5,415,628 | 5/1995 | Untereker et al. . |
| 5,423,739 | 6/1995 | Phipps et al. . |
| 5,443,442 | 8/1995 | Phipps et al. . |
| 5,445,606 | 8/1995 | Haak et al. . |
| 5,445,609 | 8/1995 | Lattin et al. . |
| 5,446,056 | 8/1995 | Wityak et al. . |
| 5,458,569 | 10/1995 | Kirk, III et al. . |
| 5,464,387 | 11/1995 | Haak et al. . |
| 5,466,217 | 11/1995 | Myers et al. . |
| 5,494,679 | 2/1996 | Sage, Jr. et al. . |
| 5,498,235 | 3/1996 | Flower . |
| 5,510,328 | 4/1996 | Polarek et al. . |
| 5,558,633 | 9/1996 | Phipps et al. . |
| 5,607,691 | 3/1997 | Hale et al. . |
| 5,622,530 | 4/1997 | Phipps . |

IONTOPHORETIC DELIVERY OF CELL ADHESION INHIBITORS

This application is a continuation-in-part of copending U.S. applications Ser. Nos.:
08/724,105, filed on Sep. 30, 1996, now abandoned, 08/724,106, filed on Sep. 30, 1996, now abandoned and 06/020,277, filed on Jun. 19, 1996, the entire disclosures of which, including the specifications and claims, are incorporated herein by reference.

FIELD OF THE INVENTION

This invention relates to methods and devices for iontophoretically administering therapeutic doses of cell adhesion receptor antagonists in a controlled manner through the skin. Such cell adhesion receptor antagonists include but are not limited to antagonists of the IIb/IIIa and $\alpha_v\beta_3$ integrins and related cell surface adhesive protein receptors. Such methods and devices are useful, alone or in combination with other therapeutic agents, for the treatment of conditions mediated by cell adhesion and/or cell migration and/or angiogenesis such as thromboembolic disorders, angiogenic disorders, inflammation, bone degradation, cancer metastasis, diabetic retinopathy, restenosis, macular degeneration, and the like.

BACKGROUND OF THE INVENTION

A number of cell surface receptor proteins, referred to as "cell adhesion receptors" (CARs) have been identified that bind to extracellular matrix ligands or other cell adhesion protein ligands thereby mediating cell-cell and cell-matrix adhesion processes. The CARs are encoded by genes belonging to a gene superfamily and are composed of heterodimeric transmembrane glycoproteins containing $\alpha$- and $\beta$-subunits. CAR subfamilies contain a common $\beta$-subunit combined with different $\alpha$-subunits to form adhesion protein receptors with different specificities. The genes for at least eight distinct $\beta$-subunits have been cloned and sequenced to date.

One of the larger classes of CARs includes the integrins, which comprise inter alia perhaps the most significant CAR, that is glycoprotein IIb/IIIa ("GPIIb/IIIa" or "IIb/IIIa"), GP IIb/IIIa is also referred to as the fibrinogen receptor, and is the principal membrane protein mediating platelet aggregation. GP IIb/IIIa in activated platelets is known to a group of soluble proteins defined by their common amino acid motif Arg-Gly-Asp (RGD). These proteins include fibrinogen, von Willebrand factor, fibronectin, and vitronectin. The RGD recognition sequence is important to the binding of these proteins to the IIb/IIIa receptor, as well as other integrins.

As noted, a number of cell surface cell adhesion receptors have been identified and their functions are being elucidated. For example, certain members of the $\beta_1$ subfamily, i.e., $\alpha_4\beta_1$ and $\alpha_5\beta_1$, have been implicated in various inflammatory processes, including rheumatoid arthritis. In addition, studies with monoclonal anti-$\alpha_4$ antibodies provide evidence that $\alpha_4\beta_1$ may additionally have a role in allergy, asthma, and autoimmune disorders. Anti-$\alpha_4$ antibodies block the migration of leukocytes to the site of inflammation.

The $\alpha_v\beta_3$ integrin, also referred to as the vitronectin receptor, is a heterodimer and is a member of the $\beta_3$ integrin subfamily. The $\alpha_v\beta_3$ integrin is found on platelets, endothelial cells, melanoma cells, smooth muscle cells, and osteoclasts. Like the CAR IIb/IIIa, the $\alpha_v\beta_3$ integrin binds a variety of RGD-containing adhesive proteins such as vitronectin, fibronectin, von Willebrand factor, fibrinogen, osteopontin, bone sialo protein II and thrombospondin, again mediated by the RGD sequence. Thus, $\alpha_v\beta_3$ acts as the endothelial cell, fibroblast, and smooth muscle cell receptor for adhesive proteins including von Willebrand factor, fibrinogen (fibrin), vitronectin, thrombospondin, and osteopontin.

The $\alpha_v\beta_3$ integrin allows endothelial cells to interact with a wide variety of extracellular matrix components. These adhesive interactions are considered to be important for angiogenesis since vascular cells must ultimately be capable of invading virtually all tissues. $\alpha_v\beta_3$ is also involved in bone resorption since a key event in bone resorption is the adhesion of osteoclasts to the matrix of bone. As a consequence of injury to the endothelium, the basement membrane zones of blood vessels express several adhesive proteins, including von Willebrand factor, fibronectin, and fibrin. Additionally, several members of the integrin family of adhesion protein receptors are expressed on the surface of endothelial, smooth muscle and on other circulating cells. Among these CARs is the $\alpha_v\beta_3$ integrin. These CARs initiate a calcium-dependent signaling pathway that can lead to endothelial cell, smooth muscle cell migration and, therefore, may play a fundamental role in vascular cell biology.

Several cell adhesion inhibitory molecules, that act as CAR antagonists, are currently being investigated as drug candidates. Inhibitors of $\alpha_v\beta_3$ have been shown to inhibit angiogenesis and are recognized as being useful as therapeutic agents for the treatment of human diseases such as cancer, restenosis, thromboembolic disorders, rheumatoid arthritis and ocular vasculopathies. The binding of fibrinogen and von Willebrand factor to the RGD-binding domain of GP IIb/IIIa causes platelets to aggregate. RGD-peptidomimetic IIb/IIIa antagonist compounds are known to block fibrinogen binding and prevent platelet aggregation and the formation of platelet thrombi. Therefore, IIb/IIIa antagonists represent an important new approach for antiplatelet therapy for the treatment of thromboembolic disorders. See, for example, the discussion of $\alpha_v\beta_3$ antagonists in Lefkovitz J et al., "Platelet glycoprotein IIb/IIIa receptors in cardiovascular medicine," *New Engl J Med* 332:1553–1559 (1995), indicating the potential utility of such compounds in the treatment of various disease states, e.g., restenosis, unstable angina, stroke, prevention of secondary myocardial infarction, etc.

The usefulness of pharmacological intervention at the level of the cell adhesion receptor has already been demonstrated with the commercially available murine monoclonal antibody Abciximab sold under the trade name ReoPro™. This agent is directed against the human GPIIb/IIIa receptor, and is currently marketed as an intravenous infusion for prevention of restenosis following angioplasty.

Smaller molecules that bind to platelets at the GPIIb/IIIa receptor are currently being developed as intravenous infusion, oral, and passive transdermal preparations. To be effective and safe, such agents would have to be administered, to target plasma levels, continuously with little variation in blood level concentrations. This is required since the therapeutic window for the drug is likely to be narrow. Consequently, intravenous infusions of these drugs would be ideal from a pharmacokinetic viewpoint. Unfortunately, prolonged intravenous infusion is both costly and impractical, particularly if these agents have to be given chronically in the home setting.

Oral dosing of such agents has the advantage of being well-tolerated. However, to be useful an oral agent would have to be found with a relatively long elimination plasma half-life, as a short elimination plasma half-life would necessitate frequent daily dosing. In addition, oral bioavailability would need to be relatively high and not be affected by food, alcohol, etc., to avoid variations in dosing.

Ester prodrugs are often developed to improve the oral bioavailability of poorly absorbed drugs. Such prodrugs are rapidly broken down by hydrolysis or through esterase metabolism to the parent carboxylic acid. For certain drugs, such as the narcotic analgesic remifentanil, the ester function allows the drug to be rapidly metabolized to less active metabolites and, therefore, its pharmacological action can be rapid when given by intravenous infusion. For prodrugs, ester degradation is desirable to allow for transformation to the active agent. However, certain drugs that have narrow therapeutic windows and/or that require continuous delivery are unsuitable for oral delivery. A viable alternative to intravenous infusion or oral delivery of medicaments is transdermal delivery, which has recently become acceptable and increasingly important means of administering drugs.

Presently there are two types of transdermal drug delivery systems, i.e., "passive" and "active." In passive transdermal systems chemical potential gradients provide the dominant driving force to deliver the drug through the skin. For these drugs, a patch containing the drug is applied to the surface of the body and the drug moves into the body predominantly driven by diffusion controlled transport. Passive transdermal delivery has been shown to be an effective and convenient form for delivering a number of molecules. Some examples of passive transdermal systems include: delivery of nicotine, nitroglycerine, scopolamine, clonidine, fentanyl, testosterone, estradiol, etc. However, this method of delivery may not be amenable for certain ester drugs since it has been shown that the skin contains esterases that are sufficient to metabolize topically applied esters. See, Zhou XH and Li Wan Po A, "Comparison of enzymatic activities of tissues lining portals of drug absorption, using the rat as the model," *Int J Pharmacol* 62:259–267 (1990). Additionally, passive transdermal delivery is only really effective for delivery of potent small molecules that are relatively lipophilic.

Passive transdermal administration is also unlikely to provide enough drug input, for these agents are typically charged and hydrophilic in nature and therefore would not expect to permeate readily across the lipophilic outermost layer of the skin. Chemical enhancers have also been employed to improve passive transdermal delivery of GPIIb/IIIa receptor inhibitors, see WO 95/13825 to Feigen L P and Griffen M J, entitled: "Transdermal compositions of N-[N-[5-[4[(aminoethyl)phenyl]-1-oxopentyl]-L-phenylalanine or its ester and their pharmaceutically acceptable salts," and incorporated herein by reference. However, the variability associated with this delivery technique is likely to be too high for drugs with high or narrow therapeutic windows, such as cell adhesion molecules.

The second type of transdermal drug delivery is active transdermal delivery. In active transdermal systems, additional, extrinsically applied driving forces, either electrical (iontophoresis) or ultrasonic (phonophoresis), are used to control delivery of the drugs through the skin.

Iontophoresis, according to *Stedman's Medical Dictionary*, is defined as "the introduction into the tissues, by means of an electric current, of the ions of a chosen medicament." Iontophoretic devices have been known since the 1900's to be an effective means of delivery of hydrophilic and charged drugs across the skin and into the systemic circulation. In iontophoretic transdermal systems applied electric potential provide the dominant driving force to deliver the ionized drug through the skin. For these drugs, an iontophoretic patch containing the drug is applied to the surface of the body, controlled current is driven through the patch via electrodes in contact with the patch and the drug moves into the body predominantly driven by migration controlled transport. Some examples of iontophoretic transdermal systems include: delivery of pilocarpine in diagnosing cystic fibrosis, delivery of topical anesthetic to name a few.

The iontophoretic patch primarily consists, at a minimum, of two compartments, an anode and a cathode, each of which is individually in contact with the body. The electrode compartments house the electrodes in contact with the ionic media and are disposed to be in intimate ionic contact with some portion of the body through the skin, to complete the internal electrical circuit. The electrodes are connected externally to a power supply to complete the external electrical circuit. During operation the entire system, power source, electrode, electrolyte, the skin and the body, forms one integrated electrochemical cell.

The electrode connected to the positive pole of the power supply is called the anode and the electrode connected to the negative pole of the power supply is called the cathode. When the current is turned on at the power supply, current flows from the anode to the cathode in the system controlled externally (to the patch) by electron transport and internally (inside the patch between the electrodes) by ion transport. This is possible because the electrodes act as transducers converting electron transport to ion transport via an electron transfer reaction (electrochemical reaction) at the electrode.

In general positive ions (cations) will tend to carry portion of the current and move towards the cathode and the negative (anions) ions will tend to carry portion of the current and move towards the anode. Hence by loading cationic drugs in the anode compartment and/or anionic drugs in the cathode compartment, iontophoresis can be used to deliver the ionized drug across the skin separator into the body.

In general, the flux of a drug across the skin from an iontophoretic device is directly proportional to the applied current. Thus, a way to obtain varied flux or drug delivery profiles would be to vary the current. By way of example, if one wanted to administer a bolus-like (or peaked) flux, one would need to increase the current at first and then decrease the current after the bolus has been achieved.

The iontophoresis process has been found to be useful in the transdermal administration of therapeutic drugs including lidocaine hydrochloride, hydrocortisone, fluoride, penicillin, dexamethasone sodium phosphate, insulin and other drugs. A common use of iontophoresis is in the diagnosis of cystic fibrosis by delivering pilocarpine salts iontophoretically, where the pilocarpine stimulates sweat production and the sweat is collected and analyzed for its chloride content to detect the presence of the disease.

As mentioned above, for a drug to be iontophoresed across the skin effectively it must be ionizable. In addition, it has been found that the drug must be able to maintain its charge during its passage across the epidermis. See, for example, U.S. Pat. No. 5,494,679 to Sage et al., entitled "Molecules for iontophoretic delivery," the entire disclosure of which is incorporated herein by reference. For positively charged ester compounds, metabolism of the positively charged ester compound in the skin will result in the exposure of one or more charged carboxylic acid groups on the compound and, therefore, a neutralization or reversal of the positive charge on the compound as it is iontophoresed across the skin. One of ordinary skill in the art would expect that such metabolism would result in poor mobility and irregular delivery of the compound via an iontophoretic route.

SUMMARY OF THE INVENTION

The present invention provides novel methods and devices for iontophoretically administering therapeutic doses of CAR antagonists in a controlled manner through the skin. Such CAR antagonists include but are not limited to antagonists of the IIb/IIIa integrin and related cell surface adhesive protein receptors. The present invention includes iontophoretic delivery devices comprising cell adhesion receptor antagonists, such as integrin inhibitors.

In one embodiment, the invention is an iontophoresis device for non-invasively administering a therapeutic dose of an $\alpha_v\beta_3$ integrin antagonist to a mammal at a delivery rate of 0.5 μg/h or greater, comprising:

(a) a current distributing member;

(b) an agent reservoir containing an ionized or ionizable substance, in electrical communication with the current distributing member and adapted to be placed in ionic communication with an epithelial surface, wherein the ionized or ionizable substance is an $\alpha_v\beta_3$ integrin antagonist; and (c) an electrolyte reservoir containing an electrolyte, in electrical communication with an indifferent electrode and adapted to be placed in ionic communication with an epithelial surface;

(d) an electrical power source in current delivering connection with the current distribution member and the electrolyte reservoir.

Preferably, the agent reservoir further comprises competing ions having a like charge to the ionized form of the $\alpha_v\beta_3$ integrin antagonist.

In another embodiment, the invention is an iontophoresis device, comprising an $\alpha_v\beta_3$ integrin inhibitor compound. Preferably, the device further comprises:

a cathode and an anode each disposed so as to be in electrical connection with a source of electrical energy and in intimate contact with skin of a subject, and a drug reservoir electrically connected to the cathode or the anode for containing the $\alpha_v\beta_3$ integrin inhibitor compound for delivery into the body of the subject.

Also in this embodiment, the drug reservoir preferably further comprises competing ions having a like charge to the $\alpha_v\beta_3$ integrin inhibitor compound.

In another embodiment, the invention is a method of administering an $\alpha_v\beta_3$ integrin inhibitor compound to a mammal, comprising iontophoretically administering to the mammal a therapeutically effective amount of the $\alpha_v\beta_3$ integrin antagonist using an iontophoresis device according to the invention. Again, the agent reservoir of the iontophoresis device useful according to this method preferably further comprises competing ions having a like charge to the $\alpha_v\beta_3$ integrin antagonist.

In another embodiment, the invention is a method of non-invasively administering a therapeutic dose of a $\alpha_v\beta_3$ integrin antagonist to a mammal, comprising the step of iontophoretically driving the $\alpha_v\beta_3$ integrin antagonist through a predetermined area of skin of the mammal at a delivery rate of 0.5 μg/h or greater. Preferably, the iontophoretically driving step of the method comprises driving the $\alpha_v\beta_3$ integrin antagonist with competing ions thereto.

In the method according to this embodiment, the $\alpha_v\beta_3$ integrin antagonist is administered continuously at a current of from about 10 μA to about 3 mA over a period of time up to about 24 hours, or the $\alpha_v\beta_3$ integrin antagonist is administered discontinuously at a current of from about 10 μA to about 3 mA over a period of time up to about 24 hours.

In another embodiment, the invention is an iontophoretic device for non-invasively administering a therapeutic dose of an $\alpha_v\beta_3$ integrin antagonist to a mammal at a delivery rate of 0.5 μg/h or greater, comprising:

(a) a current distributing member;

(b) an agent reservoir containing an ionized or ionizable substance, in electrical communication with the current distributing member and adapted to be placed in ionic communication with an epithelial surface, wherein the ionized or ionizable substance comprises an $\alpha_v\beta_3$ integrin antagonist and competing ions thereto having a like charge to the ionized form of the $\alpha_v\beta_3$ integrin antagonist; and (c) an electrolyte reservoir containing an electrolyte, in electrical communication with an indifferent electrode and adapted to be placed in ionic communication with an epithelial surface;

(d) an electrical power source in current delivering connection with the current distribution member and the electrolyte reservoir.

In still another embodiment, the invention is an iontophoretic device, comprising a cell adhesion inhibitor compound and competing ion thereto, wherein the cell adhesion inhibitor compound has Formula I:

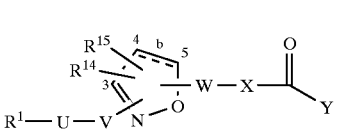

(I)

or a pharmaceutically acceptable salt form thereof, wherein:

b is a carbon-carbon single or double bond;

$R^1$ is selected from:
$R^{2a}(R^3)N—$, $R^2(R^3)N(R^2N=)C—$, $R^{2a}(R^3)N(CH_2)_{p'}$ $Z—$, $R^2(R^3)N(R^2N=)C(CH_2)_{p''}Z—$, $R^2(R^3)N(R^2N=)CN(R^2)—$, $R^2(R^3)NC(O)—$, $R^2(R^5O)N(R^2N=)C—$, $R^2(R^3)N(R^5ON=)C—$,

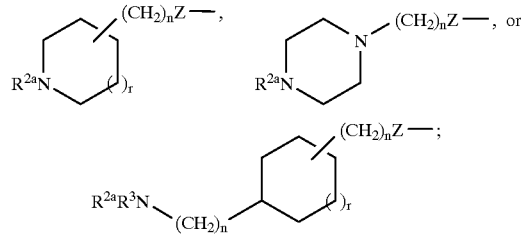

Z is selected from:
a bond, O, S, S(=O), S(=O)$_2$;

$R^2$ and $R^3$ are selected independently from:
H; $C_1$–$C_{10}$ alkyl; $C_3$–$C_6$ alkenyl; $C_3$–$C_{11}$ cycloalkyl; $C_4$–$C_{11}$ cycloalkylalkyl; $C_6$–$C_{10}$ aryl optionally substituted with 0–3 groups selected from hydroxy, halogen, $C_1$–$C_6$ alkoxy, $C_1$–$C_6$ alkyl, $CF_3$, $S(O)_m$ $CH_3$, $—N(CH_3)_2$, $C_1$–$C_4$ haloalkyl, methylenedioxydiyl, ethylenedioxydiyl;

$C_7$–$C_{11}$ arylalkyl optionally substituted with 0–3 groups selected from hydroxy, halogen, $C_1$–$C_6$ alkoxy, $C_1$–$C_6$ alkyl, $CF_3$, $S(O)_m CH_3$, —$N(CH_3)_2$, $C_1$–$C_4$ haloalkyl, methylenedioxydiyl, ethylenedioxydiyl;

$C_2$–$C_7$ alkylcarbonyl;

$C_7$–$C_{11}$ arylcarbonyl optionally substituted with 0–3 groups selected from hydroxy, halogen, $C_1$–$C_6$ alkoxy, $C_1$–$C_6$ alkyl, $CF_3$, $S(O)_m CH_3$, —$N(CH_3)_2$, $C_1$–$C_4$ haloalkyl, methylenedioxydiyl, ethylenedioxydiyl;

($C_1$–$C_{10}$ alkoxy)carbonyl;

$C_4$–$C_{11}$ cycloalkoxycarbonyl;

$C_7$–$C_{11}$ bicycloalkoxycarbonyl;

$C_7$–$C_{11}$ aryloxycarbonyl optionally substituted with 0–3 groups selected from hydroxy, halogen, $C_1$–$C_6$ alkoxy, $C_1$–$C_6$ alkyl, $CF_3$, $S(O)_m CH_3$, —$N(CH_3)_2$, $C_1$–$C_4$ haloalkyl, methylenedioxydiyl, ethylenedioxydiyl;

aryl($C_1$–$C_{10}$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_m CH_3$, —$N(CH_3)_2$, $C_1$–$C_4$ haloalkyl, methylenedioxydiyl, ethylenedioxydiyl;

($C_1$–$C_6$ alkyl)carbonyloxy($C_1$–$C_4$ alkoxy)carbonyl;

($C_6$–$C_{10}$ aryl)carbonyloxy($C_1$–$C_4$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_m CH_3$, —$N(CH_3)_2$, $C_1$–$C_4$ haloalkyl, methylenedioxydiyl, ethylenedioxydiyl;

($C_4$–$C_{11}$ cycloalkylcarbonyl)oxy($C_1$–$C_4$ alkoxy) carbonyl;

heteroaryl optionally substituted with 0–2 groups selected from hydroxy, halogen, $C_1$–$C_6$ alkoxy, $C_1$–$C_6$ alkyl, $CF_3$, $S(O)_m CH_3$, —$N(CH_3)_2$, $C_1$–$C_4$ haloalkyl, methylenedioxydiyl, ethylenedioxydiyl; or heteroaryl($C_1$–$C_5$)alkyl where the heteroaryl group is optionally substituted with 0–2 groups selected from hydroxy, halogen, $C_1$–$C_6$ alkoxy, $C_1$–$C_6$ alkyl, $CF_3$, $S(O)_m CH_3$, —$N(CH_3)_2$, $C_1$–$C_4$ haloalkyl, methylenedioxydiyl, ethylenedioxydiyl;

provided that only one of $R^2$ and $R^3$ can be hydroxy;

$R^{2a}$ is:
$R^2$ or $R^2(R^3)N(R^2N=)C—$;

U is selected from:
a single bond, -($C_1$–$C_7$ alkyl)-, -($C_2$–$C_7$ alkenyl)-, -($C_2$–$C_7$ alkynyl)-;

V is selected from:
a single bond; -($C_2$–$C_7$ alkyl)-, substituted with 0–3 groups selected independently from $R^6$ or $R^7$; -($C_2$–$C_7$ alkenyl)-, substituted with 0–3 groups selected independently from $R^6$ or $R^7$; -($C_2$–$C_7$ alkynyl)-, substituted with 0–3 groups selected independently from $R^6$ or $R^7$; -(phenyl)-Q-, the phenyl substituted with 0–2 groups selected independently from $R^6$ or $R^7$; -(pyridyl)-Q-, the pyridyl substituted with 0–2 groups selected independently from $R^6$ or $R^7$; or -(pyridazinyl)-Q-, the pyridazinyl substituted with 0–2 groups selected independently from $R^6$ or $R^7$;

Q is selected from:
a single bond, —O—, —$S(O)_m$—, —$N(R^{12})$—, —$(CH_2)_m$—, —$C(=O)$—, —$N(R^{5a})C(=O)$—, —$C(=O)N(R^{5a})$—, —$CH_2O$—, —$OCH_2$—, —$CH_2N(R^{12})$—, —$N(R^{12})CH_2$—, —$CH_2C(=O)$—, —$C(=O)CH_2$—, —$CH_2S(O)_m$—, or —$S(O)_m CH_2$—, provided that:
when b is a single bond, and $R^1$—U—V— is a substituent on $C^5$ of the central 5-membered ring of Formula I, then Q is not —O—, —$S(O)_m$—, —$N(R^{12})$—, —$C(=O)N(R^{5a})$—, —$CH_2O$—, —$CH_2N(R^{12})$—, or —$CH_2S(O)_m$—;

W is selected from:
—$(C(R^4)_2)_{n'}C(=O)N(R^{5a})$—, or —$C(=O)$—N$(R^{5a})$—$(C(R^4)_2)_{n'}$—;

X is:
—$(C(R^4)_2)_{n'}$—$C(R^4)(R^8)$—$C(R^4)(R^{4a})$—;

Y is selected from:
hydroxy, $C_1$–$C_{10}$ alkyloxy, $C_3$–$C_{11}$ cycloalkyloxy, $C_6$–$C_{10}$ aryloxy, $C_7$–$C_{11}$ aralkyloxy, $C_3$–$C_{10}$ alkylcarbonyloxyalkyloxy, $C_3$–$C_{10}$ alkoxycarbonyloxyalkyloxy, $C_2$–$C_{10}$ alkoxycarbonylalkyloxy, $C_5$–$C_{10}$ cycloalkylcarbonyloxyalkyloxy, $C_5$–$C_{10}$ cycloalkoxycarbonyloxyalkyloxy, $C_5$–$C_{10}$ cycloalkoxycarbonylalkyloxy, $C_7$–$C_{11}$ aryloxycarbonylalkyloxy, $C_8$–$C_{12}$ aryloxycarbonyloxyalkyloxy, $C_8$–$C_{12}$ arylcarbonyloxyalkyloxy, $C_5$–$C_{10}$ alkoxyalkylcarbonyloxyalkyloxy, $C_5$–$C_{10}$ (5-alkyl-1,3-dioxa-cyclopenten-2-one-yl)-methyloxy, $C_{10}$–$C_{14}$ (5-aryl-1,3-dioxa-cyclopenten-2-one-yl)-methyloxy, $(R^2)(R^3)N$—($C_1$–$C_{10}$ alkoxy)-;

$R^4$ is selected from:
H, $C_1$–$C_{10}$ alkyl, $C_1$–$C_{10}$ alkylcarbonyl, aryl, arylalkyl, cycloalkyl, or cycloalkylalkyl;

alternately, two $R^4$ groups on adjacent carbon atoms can join to form a carbon-carbon double or triple bond between such adjacent carbon atoms;

$R^{4a}$ is selected from:
hydroxy, $C_1$–$C_{10}$ alkoxy, nitro, —$N(R^5)R^{5a}$, —$N(R^{12})R^{13}$, —$N(R^{16})R^{17}$, aryl substituted with 0–3 $R^6$, or ($C_1$–$C_{10}$ alkyl)carbonyl;

$R^{4b}$ is selected from:
H, $C_1$–$C_6$ alkyl, $C_2$–$C_6$ alkenyl, $C_2$–$C_6$ alkynyl, $C_3$–$C_7$ cycloalkyl, $C_7$–$C_4$ bicycloalkyl, hydroxy, $C_1$–$C_6$ alkoxy, $C_1$–$C_6$ alkylthio, $C_1$–$C_6$ alkylsulfinyl, $C_1$–$C_6$ alkylsulfonyl, nitro, ($C_1$–$C_6$ alkyl)carbonyl, $C_6$–$C_{10}$ aryl, —$N(R^{12})R^{13}$, halo, $CF_3$, CN, ($C_1$–$C_6$ alkoxy) carbonyl, carboxy, piperidinyl, morpholinyl, or pyridinyl;

$R^5$ is selected from:
H, $C_1$–$C_8$ alkyl, $C_3$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–6 $R^{4b}$;

$R^{5a}$ is selected from:
hydrogen, hydroxy, $C_1$–$C_8$ alkyl, $C_3$–$C_6$ alkenyl, $C_3$–$C_{11}$ cycloalkyl, $C_4$–$C_{11}$ cycloalkylmethyl, $C_1$–$C_6$ alkoxy, benzyloxy, $C_6$–$C_{10}$ aryl, heteroaryl, heteroarylalkyl, $C_7$–$C_{11}$ arylalkyl, adamantylmethyl, or $C_1$–$C_{10}$ alkyl substituted with 0–2 $R^{4b}$;

alternately, $R^5$ and $R^{5a}$ when both are substituents on the same nitrogen atom (as in —$NR^5 R^{5a}$) can be taken together with the nitrogen atom to which they are attached to form 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, or 1-piperazinyl, each being optionally substituted with $C_1$–$C_6$ alkyl, $C_6$–$C_{10}$ aryl, heteroaryl, $C_7$–$C_{11}$ arylalkyl, ($C_1$–$C_6$ alkyl)carbonyl, ($C_3$–$C_7$ cycloalkyl)carbonyl, ($C_1$–$C_6$ alkoxy)carbonyl, ($C_7$–$C_{11}$ arylalkoxy) carbonyl, $C_1$–$C_6$ alkylsulfonyl or $C_6$–$C_{10}$ arylsulfonyl;

$R^{5b}$ is selected from:
$C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^{4b}$;

$R^6$ is selected from:
H, $C_1$–$C_{10}$ alkyl, hydroxy, $C_1$–$C_{10}$ alkoxy, nitro, ($C_1$–$C_{10}$ alkyl)carbonyl, —N($R^{12}$)$R^{13}$, cyano, halo, $CF_3$, CHO, $CO_2R^5$, C(=O)$R^{5a}$, $CONR^5R^{5a}$, OC(=O)$R^{5a}$, OC(=O)$OR^{5b}$, $OR^{5a}$, OC(=O) $NR^5R^{5a}$, $OCH_2CO_2R^5$, $CO_2CH_2CO_2R^5$, $NO_2$, $NR^{5a}C(=O)R^{5a}$, $NR^{5a}C(=O)OR^{5b}$, $NR^{5a}C(=O) NR^5R^{5a}$, $NR^{5a}SO_2NR^5R^{5a}$, $NR^{5a}SO_2R^5$, $SR^{5a}$, $SOR^{5a}$, $SO_2R^{5a}$, $SO_2NR^5R^{5a}$, $Si(CH_3)_3$, $C_2$–$C_6$ alkenyl, $C_3$–$C_{11}$ cycloalkyl, $C_4$–$C_{11}$ cycloalkylmethyl;

$C_6$–$C_{10}$ aryl optionally substituted with 1–3 groups selected from halogen, $C_1$–$C_6$ alkoxy, $C_1$–$C_6$ alkyl, $CF_3$, $S(O)_mCH_3$, or —$N(CH_3)_2$;

$C_7$–$C_{11}$ arylalkyl, the aryl being optionally substituted with 1–3 groups selected from halogen, $C_1$–$C_6$ alkoxy, $C_1$–$C_6$ alkyl, $CF_3$, $S(O)_mCH_3$, or —$N(CH_3)_2$;

methylenedioxy when $R^6$ is a substituent on aryl; or a 5–10 membered heterocyclic ring containing 1–3 N, O, or S heteroatoms, wherein the heterocyclic ring can be saturated, partially saturated, or fully unsaturated, the heterocyclic ring being substituted with 0–2 $R^7$;

$R^7$ is selected from:
H, $C_1$–$C_{10}$ alkyl, hydroxy, $C_1$–$C_{10}$ alkoxy, nitro, ($C_1$–$C_{10}$ alkyl)carbonyl, —N($R^{12}$)$R^{13}$, cyano, halo, $CF_3$, CHO, $CO_2R^5$, C(=O)$R^{5a}$, $CONR^5R^{5a}$, OC(=O)$R^{5a}$, OC(=O)$OR^{5b}$, $OR^{5a}$, OC(=O) $NR^5R^{5a}$, $OCH_2CO_2R^5$, $CO_2CH_2CO_2R^5$, $NO_2$, $NR^{5a}C(=O)R^{5a}$, $NR^{5a}C(=O)OR^{5b}$, $NR^{5a}C(=O) NR^5R^{5a}$, $NR^{5a}SO_2NR^5R^{5a}$, $NR^{5a}SO_2R^5$,$S(O)_mR^{5a}$, $SO_2NR^5R^{5a}$, $C_2$–$C_6$ alkenyl, $C_3$–$C_{11}$ cycloalkyl, $C_4$–$C_{11}$ cycloalkylmethyl, $C_6$–$C_{10}$ aryl, or $C_7$–$C_{11}$ arylalkyl;

$R^8$ is selected from:
$R^6$; $C_1$–$C_{10}$ alkyl, substituted with 0–3 $R^6$; $C_2$–$C_{10}$ alkenyl, substituted with 0–3 $R^6$;
$C_2$–$C_{10}$ alkynyl, substituted with 0–3 $R^6$; $C_3$–$C_8$ cycloalkyl, substituted with 0–3 $R^6$;
$C_5$–$C_6$ cycloalkenyl, substituted with 0–3 $R^6$; aryl, substituted with 0–3 $R^6$; 5–10 membered heterocyclic ring containing 1–3 N, O, or S heteroatoms, wherein the heterocyclic ring can be saturated, partially saturated, or fully unsaturated, the heterocyclic ring being substituted with 0–2 $R^6$;

$R^{12}$ and $R^{13}$ are selected independently from:
H, $C_1$–$C_{10}$ alkyl, ($C_1$–$C_{10}$ alkoxy)carbonyl, ($C_1$–$C_{10}$ alkyl)carbonyl, $C_1$–$C_{10}$ alkylsulfonyl, aryl($C_1$–$C_{10}$ alkyl)sulfonyl, arylsulfonyl, aryl($C_2$–$C_{10}$ alkenyl) sulfonyl, heteroarylsulfonyl, aryl, $C_2$–$C_6$ alkenyl, $C_3$–$C_{11}$ cycloalkyl, $C_4$–$C_{11}$ cycloalkylalkyl, $C_7$–$C_{11}$ arylalkyl, $C_7$–$C_{11}$ arylcarbonyl, $C_4$–$C_{11}$ cycloalkoxycarbonyl, $C_7$–$C_{11}$ bicycloalkoxycarbonyl, $C_7$–$C_{11}$ aryloxycarbonyl, heteroarylcarbonyl, heteroarylsulfonyl, heteroarylalkylcarbonyl, or aryl($C_1$–$C_{10}$ alkoxy) carbonyl, wherein the aryl groups are optionally substituted with 0–3 substituents selected from the group consisting of: $C_1$–$C_4$ alkyl, $C_1$–$C_4$ alkoxy, halo, $CF_3$, and $NO_2$;

$R^{14}$ is selected from:
H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or ($C_1$–$C_{10}$ alkoxy) carbonyl, $CO_2R^5$, or —C(=O)N($R^5$)$R^{5a}$;

$R^{15}$ is selected from:
H; $R^6$; —$CO_2R^5$; —C(=O)N($R^5$)$R^{5a}$; $C_1$–$C_{10}$ alkoxycarbonyl substituted with 0–2 $R^6$;
$C_1$–$C_{10}$ alkyl, substituted with 0–3 $R^6$; $C_2$–$C_{10}$ alkenyl, substituted with 0–3 $R^6$;
$C_1$–$C_{10}$ alkoxy, substituted with 0–3 $R^6$; aryl, substituted with 0–3 $R^6$; or 5–10 membered heterocyclic ring containing 1–3 N, O, or S heteroatoms, wherein the heterocyclic ring can be saturated, partially saturated, or fully unsaturated, the heterocyclic ring being substituted with 0–2 $R^6$;

provided that when b is a double bond, only one of $R^{14}$ or $R^{15}$ is present;

$R^{16}$ is selected from:
—C(=O)—O—$R^{18a}$, —C(=O)—$R^{18b}$, —C(=O)N ($R^{18b}$)$_2$, —C(=O)$NHSO_2R^{18a}$, —C(=O)NHC (=O)$R^{18b}$, —C(=O)NHC(=O)$OR^{18a}$, —C(=O) $NHSO_2NHR^{18b}$, —C(=S)—NH—$R^{18b}$, —NH—C (=O)—O—$R^{18a}$, —NH—C(=O)—$R^{18b}$, —NH—C(=O)—NH—$R^{18b}$, —$SO_2$—O—$R^{18a}$, —$SO_2$—$R^{18a}$, —$SO_2$—N($R^{18b}$)$_2$, —$SO_2$—NHC(=O)$OR^{18b}$, —P(=S)($OR^{18a}$)$_2$, —P(=O)($OR^{18a}$)$_2$, —P(=S) ($R^{18a}$)$_2$, —P(=O)($R^{18a}$)$_2$, or

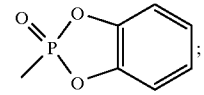

$R^{17}$ is selected from:
H, $C_1$–$C_{10}$ alkyl, $C_2$–$C_6$ alkenyl, $C_3$–$C_{11}$ cycloalkyl, $C_4$–$C_{15}$ cycloalkylalkyl, aryl, aryl($C_1$–$C_{10}$ alkyl)-;

$R^{18a}$ is selected from:
$C_1$–$C_8$ alkyl substituted with 0–2 $R^{19}$, $C_2$–$C_8$ alkenyl substituted with 0–2 $R^{19}$, $C_2$–$C_8$ alkynyl substituted with 0–2 $R^{19}$, $C_3$–$C_8$ cycloalkyl substituted with 0–2 $R^{19}$, aryl substituted with 0–4 $R^{19}$, aryl($C_1$–$C_6$ alkyl)- substituted with 0–4 $R^{19}$;
a 5–10 membered heterocyclic ring system having 1–3 heteroatoms selected independently from O, S, and N, the heterocyclic ring being substituted with 0–4 $R^{19}$; $C_1$–$C_6$ alkyl substituted with a 5–10 membered heterocyclic ring system having 1–3 heteroatoms selected independently from O, S, and N, the heterocyclic ring being substituted with 0–4 $R^{19}$;

$R^{18b}$ is selected from: $R^{18a}$ or H;

$R^{19}$ is selected from:
H, halogen, $CF_3$, CN, $NO_2$, —$NR^{12}R^{13}$, $C_1$–$C_8$ alkyl, $C_2$–$C_6$ alkenyl, $C_2$–$C_6$ alkynyl, $C_3$–$C_{11}$ cycloalkyl, $C_4$–$C_{11}$ cycloalkylalkyl, aryl, aryl($C_1$–$C_6$ alkyl)-, $C_1$–$C_6$ alkoxy, heteroaryl, ($C_1$–$C_4$ alkyl)sulfonyl, aryl-sulfonyl, or $C_1$–$C_4$ alkoxycarbonyl;

m is 0–2;
n is 0–4;
n' is 0–4;
p' is 1–7;
p" is 1–7;
r is 0–3;
provided that:
n' is chosen such that the number of in-chain atoms connecting $R^1$ and Y is in the range of 8–18.

In this embodiment, the device can include a compound of Formula Ic:

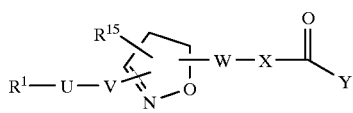

(Ic)

wherein:

$R^1$ is selected from:
$R^{2a}(R^3)N—$, $R^2(R^3)N(R^2N=)C—$, $R^{2a}(R^3)N(CH^2)_pZ—$, $R^2(R^3)N(R^2N=)C(CH_2)_{p''}Z—$, $R^2(R^3)N(R^2N=)CN(R^2)—$, $R^2(R^3)NC(O)—$, $R^2(R^5O)N(R^2N=)C—$, $R^2(R^3)N(R^5ON=)C—$;

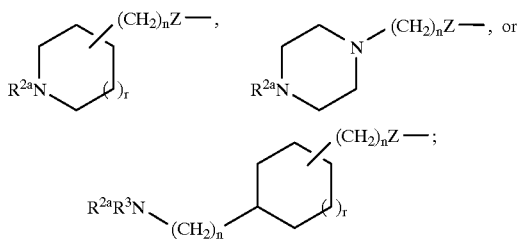

Z is selected from a bond, O, or S;

$R^2$ and $R^3$ are selected independently from:
H; $C_1$–$C_6$ alkyl; $C_7$–$C_{11}$ arylalkyl optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; ($C_1$–$C_{10}$ alkoxy)carbonyl;

aryl($C_1$–$C_{10}$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; or heteroaryl($C_1$–$C_5$)alkyl where the heteroaryl group is optionally substituted with 0–2 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl;

$R^{2a}$ is $R^2$ or $R^2(R^3)N(R^2N=)C$;

U is a single bond;

V is selected from:
a single bond; -($C_1$–$C_7$ alkyl)-, substituted with 0–3 groups selected independently from $R^6$ or $R^7$; -($C_2$–$C_7$ alkenyl)-, substituted with 0–3 groups selected independently from $R^6$ or $R^7$; -($C_2$–$C_7$ alkynyl)-, substituted with 0–3 groups selected independently from $R^6$ or $R^7$; -(phenyl)-Q-, the phenyl substituted with 0–2 groups selected independently from $R^6$ or $R^7$; -(pyridyl)-Q-, the pyridyl substituted with 0–2 groups selected independently from $R^6$ or $R^7$; or -(pyridazinyl)-Q-, the pyridazinyl substituted with 0–2 groups selected independently from $R^6$ or $R^7$;

Q is selected from:
a single bond, —O—, —$S(O)_m$—, —$N(R^{12})$—, —$(CH_2)_m$—, —$C(=O)$—, —$N(R^{5a})C(=O)$—, —$C(=O)N(R^{5a})$—, —$CH_2O$—, —$OCH_2$—, —$CH_2N(R^{12})$—, —$N(R^{12})CH_2$—, —$CH_2C(=O)$—, —$C(=O)CH_2$—, —$CH_2S(O)_m$—, —$S(O)_mCH_2$—;

provided that when $R^1$—U—V— is a substituent on $C^5$ of the central 5-membered ring of Formula Ic, then Q is not —O—, $S(O)_m$, —$N(R^{12})$—, —$C(=O)N(R^{5a})$—, —$CH_2O$—, —$CH_2N(R^{12})$— or —$CH_2S(O)_m$—;

W is selected from:
—$(C(R^4)_2)$—$C(=O)$—$N(R^{5a})$—, or —$C(=O)$—$N(R^{5a})$—$(C(R^4)_2)$—;

X is:
—$C(R^4)(R^8)$—$CHR^{4a}$—;

$R^4$ is selected from:
H, $C_1$–$C_{10}$ alkyl, $C_1$–$C_{10}$ alkylcarbonyl, aryl, arylalkyl, cycloalkyl, or cycloalkylalkyl;

$R^{4a}$ is selected from:
hydroxy, $C_1$–$C_{10}$ alkoxy, nitro, —$N(R^5)R^{5a}$, —$N(R^{12})R^{13}$, or —$N(R^{16})R^{17}$, aryl substituted with 0–3 $R^6$, or ($C_1$–$C_{10}$ alkyl)carbonyl;

$R^{4b}$ is selected from:
H, $C_1$–$C_6$ alkyl, $C_2$–$C_6$ alkenyl, $C_2$–$C_6$ alkynyl, hydroxy, $C_1$–$C_6$ alkoxy, $C_1$–$C_6$ alkylthio, $C_1$–$C_6$ alkylsulfinyl, $C_1$–$C_6$ alkylsulfonyl, nitro, ($C_1$–$C_6$ alkyl)carbonyl, $C_6$–$C_{10}$ aryl, —$N(R^{12})R^{13}$, halo, $CF_3$, CN, ($C_1$–$C_6$ alkoxy)carbonyl, carboxy, piperidinyl, morpholinyl or pyridyl;

$R^5$ is selected from:
H or $C_1$–$C_{10}$ alkyl substituted with 0–6 $R^{4b}$;

$R^{5a}$ is selected from:
hydrogen, hydroxy, $C_1$–$C_8$ alkyl, $C_2$–$C_6$ alkenyl, $C_3$–$C_{11}$ cycloalkyl, $C_4$–$C_{11}$ cycloalkylmethyl, $C_1$–$C_6$ alkoxy, benzyloxy, $C_6$–$C_{10}$ aryl, heteroaryl, heteroarylalkyl, $C_7$–$C_{11}$ arylalkyl, or adamantylmethyl, $C_1$–$C_{10}$ alkyl substituted with 0–2 $R^{4b}$;

alternately, $R^5$ and $R^{5a}$ can be taken together to be:
3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl, each being optionally substituted with $C_1$–$C_6$ alkyl, $C_6$–$C_{10}$ aryl, heteroaryl, $C_7$–$C_{11}$ arylalkyl, ($C_1$–$C_6$ alkyl)carbonyl, ($C_3$–$C_7$ cycloalkyl)carbonyl, ($C_1$–$C_6$ alkoxy) carbonyl, or ($C_7$–$C_{11}$ arylalkoxy)carbonyl;

$R^{5b}$ is selected from:
$C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^{4b}$;

Y is selected from:
hydroxy, $C_1$–$C_{10}$ alkyloxy, $C_3$–$C_{11}$ cycloalkyloxy, $C_6$–$C_{10}$ aryloxy, $C_7$–$C_{11}$ aralkyloxy, $C_3$–$C_{10}$ alkylcarbonyloxyalkyloxy, $C_3$–$C_{10}$ alkoxycarbonyloxyalkyloxy, $C_2$–$C_{10}$ alkoxycarbonylalkyloxy, $C_5$–$C_{10}$ cycloalkylcarbonyloxyalkyloxy, $C_5$–$C_{10}$ cycloalkoxycarbonyloxyalkyloxy, $C_5$–$C_{10}$ cycloalkoxycarbonylalkyloxy, $C_7$–$C_{11}$ aryloxycarbonylalkyloxy, $C_8$–$C_{12}$ aryloxycarbonyloxyalkyloxy, $C_8$–$C_{12}$ arylcarbonyloxyalkyloxy, $C_5$–$C_{10}$ alkoxyalkylcarbonyloxyalkyloxy, $C_5$–$C_{10}$ (5-alkyl-1,3-dioxa-cyclopenten-2-one-yl)-methyloxy, or $C_{10}$–$C_{14}$ (5-aryl-1,3-dioxa-cyclopenten-2-one-yl)-methyloxy;

$R^6$ and $R^7$ are each selected independently from:
H, $C_1$–$C_{10}$ alkyl, hydroxy, $C_1$–$C_{10}$ alkoxy, nitro, ($C_1$–$C_{10}$ alkyl)carbonyl, —$N(R^{13})R^{13}$, cyano, or halo;

$R^{12}$ and $R^{13}$ are each selected independently from:
  H, $C_1$–$C_{10}$ alkyl, ($C_1$–$C_{10}$ alkoxy)carbonyl, ($C_1$–$C_{10}$ alkyl)carbonyl, $C_1$–$C_{10}$ alkylsulfonyl, aryl($C_1$–$C_{10}$ alkyl)sulfonyl, arylsulfonyl, heteroarylsulfonyl, heteroarylcarbonyl, heteroarylalkylcarbonyl or aryl, wherein the aryl groups being optionally substituted with 0–3 substituents selected from the group consisting of: $C_1$–$C_4$ alkyl, $C_1$–$C_4$ alkoxy, halo, $CF_3$, and $NO_2$;

$R^{15}$ is selected from:
  H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or ($C_1$–$C_{10}$ alkoxy)carbonyl, $CO_2R^5$ or —C(=O)N($R^5$)$R^{5a}$;

$R^{16}$ is selected from:
  —C(=O)—O—$R^{18a}$, —C(=O)—$R^{18b}$, —C(=O)N($R^{18b}$)$_2$, —$SO_2$—$R^{18a}$, or —$SO_2$—N($R^{18b}$)$_2$;

$R^{17}$ is selected from:
H or $C_1$–$C_5$ alkyl;

$R^{18a}$ is selected from:
  $C_1$–$C_8$ alkyl substituted with 0–2 $R^{19}$, $C_2$–$C_8$ alkenyl substituted with 0–2 $R^{19}$, $C_2$–$C_8$ alkynyl substituted with 0–2 $R^{19}$, $C_3$–$C_8$ cycloalkyl substituted with 0–2 $R^{19}$, aryl substituted with 0–4 $R^{19}$, aryl($C_1$–$C_6$ alkyl)- substituted with 0–4 $R^{19}$, a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, pyrrolidinyl, piperidinyl, indolinyl, or morpholinyl, the heterocyclic ring being substituted with 0–4 $R^{19}$;
  $C_1$–$C_6$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, pyrrolidinyl, piperidinyl, indolinyl, or morpholinyl, the heterocyclic ring being substituted with 0–4 $R^{19}$;

$R^{18b}$ is selected from:
  $R^{18a}$ or H;

$R^{19}$ is selected from:
  H, halogen, $CF_3$, CN, $NO_2$, $NR^{12}R^{13}$, $C_1$–$C_8$ alkyl, $C_2$–$C_6$ alkenyl, $C_2$–$C_6$ alkynyl, $C_1$–$C_6$ alkoxy, $C_3$–$C_{11}$ cycloalkyl, $C_4$–$C_{11}$ cycloalkylalkyl, aryl, heteroaryl, aryl($C_1$–$C_6$ alkyl)-, ($C_1$–$C_4$ alkyl) sulfonyl, aryl-sulfonyl, or $C_1$–$C_4$ alkoxycarbonyl;

n is 0–4;
p' is 1–7;
p" is 1–7;
r is 0–3.

The iontophoresis device according to this embodiment can comprise a compound of Formula Ib:

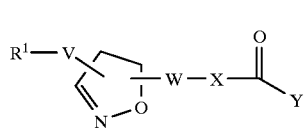

(Ib)

wherein:
  $R^1$ is selected from:
    $R^{2a}$—($R^3$)N—, $R^2$NH($R^2$N=)C—, $R^2$NH($R^2$N=)CNH—, $R^{2a}R^3$N($CH_2$)$_{p'}$Z—, $R^2$NH($R^2$N=)C($CH_2$)$_{p''}$Z—, $R^2$($R^3$)NC(O)—, $R^2$($R^5$O)N($R^2$N=)C—, $R^2$($R^3$)N($R^5$ON=)C—;

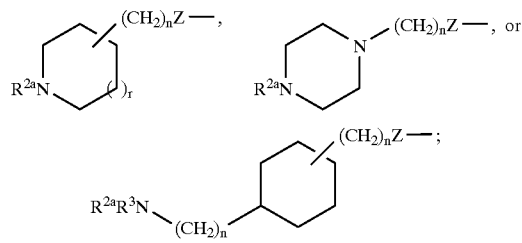

n is 0–1;
p' is 4–6;
p" is 2–4;
Z is selected from:
  a bond or O;
V is selected from:
  a single bond, -(phenyl)-, or -(pyridyl)-;
W is selected from:
  —(C($R^4$)$_2$)—C(=O)—N($R^{5a}$)—, or —C(=O)—N($R^{5a}$)—$CH_2$—;
X is selected from:
  —$CH_2$—CH(N($R^{16}$)$R^{17}$)—, or —$CH_2$—CH(N$R^5R^{5a}$)—;
Y is selected from:
  hydroxy; $C_1$–$C_{10}$ alkoxy; methylcarbonyloxymethoxy; ethylcarbonyloxymethoxy;
  t-butylcarbonyloxymethoxy; cyclohexylcarbonyloxymethoxy;
  1-(methylcarbonyloxy)-ethoxy; 1-(ethylcarbonyloxy)-ethoxy;
  1-(t-butylcarbonyloxy)-ethoxy; 1-(cyclohexylcarbonyloxy)-ethoxy;
  i-propyloxycarbonyloxymethoxy; t-butyloxycarbonyloxymethoxy;
  1-(i-propyloxycarbonyloxy)-ethoxy; 1-(cyclohexyloxycarbonyloxy)-ethoxy;
  1-(t-butyloxycarbonyloxy)-ethoxy; dimethylaminoethoxy; diethylaminoethoxy;
  (5-methyl-1,3-dioxacyclopenten-2-on-4-yl)-methoxy;
  (5-(t-butyl)-1,3-dioxacyclopenten-2-on-4 yl)-methoxy;
  (1,3-dioxa-5-phenyl-cyclopenten-2-on-4-yl)-methoxy;
  1-(2-(2-methoxypropyl)carbonyloxy)-ethoxy;

$R^{16}$ is selected from:
  —C(=O)—O—$R^{18a}$, —C(=O)—$R^{18b}$, —S(=O)$_2$—$R^{18a}$, or $SO_2$—N($R^{18b}$)$_2$;

$R^{17}$ is selected from: H or $C_1$–$C_5$ alkyl;

$R^{18a}$ is selected from:
  $C_1$–$C_8$ alkyl substituted with 0–2 $R^{19}$, $C_2$–$C_8$ alkenyl substituted with 0–2 $R^{19}$, $C_2$–$C_8$ alkynyl substituted with 0–2 $R^{19}$, $C_3$–$C_8$ cycloalkyl substituted with 0–2 $R^{19}$, aryl substituted with 0–4 $R^{19}$, aryl($C_1$–$C_6$ alkyl)- substituted with 0–4 $R^{19}$, a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, pyrrolidinyl, or morpholinyl, the heterocyclic ring being substituted with 0–4 $R^{19}$;

$C_1$–$C_6$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolinyl, quinolinyl, isoquinolinyl, benzimidazolyl, piperidinyl, tetrahydrofuranyl, pyranyl, 3H-indolyl, pyrrolidinyl, or morpholinyl, the heterocyclic ring being substituted with 0–4 $R^{19}$.

Also in this embodiment, the iontophoresis device can comprise a compound wherein:

either:
$R^1$ is $R^2NH(R^2N=)C-$ or $R^2HN(R^2N=)CNH-$ and V is phenylene or pyridylene, or:
$R^1$ is

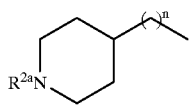

and V is a single bond, and n is 1 or 2;

$R^{18a}$ is selected from:
$C_1$–$C_4$ alkyl substituted with 0–2 $R^{19}$, $C_2$–$C_4$ alkenyl substituted with 0–2 $R^{19}$, $C_2$–$C_4$ alkynyl substituted with 0–2 $R^{19}$, $C_3$–$C_7$ cycloalkyl substituted with 0–2 $R^{19}$, aryl substituted with 0–4 $R^{19}$, aryl($C_1$–$C_4$ alkyl)- substituted with 0–4 $R^{19}$, a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, pyrrolidinyl, or morpholinyl, the heterocyclic ring being substituted with 0–4 $R^{19}$;

$C_1$–$C_4$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolinyl, quinolinyl, isoquinolinyl, benzimidazolyl, piperidinyl, tetrahydrofuranyl, pyranyl, 3H-indolyl, pyrrolidinyl, piperidinyl, or morpholinyl, the heterocyclic ring being substituted with 0–4 $R^{19}$.

Preferably, in this embodiment, the iontophoresis device comprises a compound, or a pharmaceutically acceptable salt form thereof, selected from:

$N^3$-[2-{3-(4-formamidinophenyl)-isoxazolin-5(R,S)-yl}-acetyl]-$N^2$-(phenylsulfonyl)-2,3(S)-diaminopropanoic acid;

$N^3$-[2-{3-(4-formamidinophenyl)-isoxazolin-5-(R,S)-yl}-acetyl]-$N^2$-(4-methyl-phenyl-sulfonyl)-2,3(S)-diaminopropanoic acid;

$N^3$-[2-{3-(4-formamidinophenyl)-isoxazolin-5(R,S)-yl}-acetyl]-$N^2$-(butanesulfonyl)-2,3(S)-diaminopropanoic acid;

$N^3$-[2-{3-(4-formamidinophenyl)-isoxazolin-5(R,S)-yl}-acetyl]-$N^2$-(propanesulfonyl)-2,3(S)-diaminopropanoic acid;

$N^3$-[2-{3-(4-formamidinophenyl)-isoxazolin-5(R,S)-yl}-acetyl]-$N^2$-(ethanesulfonyl)-2,3(S)-diaminopropanoic acid;

$N^3$-[2-{3-(4-formamidinophenyl)-isoxazolin-5(R,S)-yl}-acetyl]-$N^2$-(methyloxycarbonyl)-2,3(S)-diaminopropanoic acid;

$N^3$-[2-{3-(4-formamidinophenyl)-isoxazolin-5(R,S)-yl}-acetyl]-$N^2$-(ethyloxycarbonyl)-2,3(S) diaminopropanoic acid;

$N^3$-[2-{3-(4-formamidinophenyl)-isoxazolin-5(R,S)-yl}-acetyl]-$N^2$-(1-propyloxycarbonyl)-2,3(S)-diaminopropanoic acid;

$N^3$-[2-{3-(4-formamidinophenyl)-isoxazolin-5(R,S)-yl}-acetyl]-$N^2$-(2-propyloxycarbonyl)-2,3(S)-diaminopropanoic acid;

$N^3$-[2-{3-(4-formamidinophenyl)-isoxazolin-5(R,S)-yl}-acetyl]-$N^2$-(n-butyloxycarbonyl)-2,3(S)-diaminopropanoic acid;

$N^3$-[2-{3-(4-formamidinophenyl)-isoxazolin-5(R)-yl}-acetyl]-$N^2$-(n-butyloxycarbonyl)-2,3(S)-diaminopropanoic acid;

$N^3$-[2-{3-(4-formamidinophenyl)-isoxazolin-5(S)-yl}-acetyl]-$N^2$-(n-butyloxycarbonyl)-2,3(S)-diaminopropanoic acid;

$N^3$-[2-{3-(4-formamidinophenyl)-isoxazolin-5(R)-yl}-acetyl]-$N^2$-(n-butyloxycarbonyl)-2,3(R)-diaminopropanoic acid;

$N^3$-[2-{3-(4-formamidinophenyl)-isoxazolin-5(S)-yl}-acetyl]-$N^2$-(n-butyloxycarbonyl)-2,3(R)-diaminopropanoic acid;

$N^3$-[2-{3-(4-formamidinophenyl)-isoxazolin-5(R,S)-yl}-acetyl]-$N^2$-(2-butytoxycarbonyl)-2,3(S)-diaminopropanoic acid;

$N^3$-[2-{3-(4-formamidinophenyl)-isoxazolin-5(R,S)-yl}-acetyl]-$N^2$-(1-(2-methyl)-propyloxycarbonyl)-2,3(S)-diaminopropanoic acid;

$N^3$-[2-{3-(4-formamidinophenyl)-isoxazolin-5(R,S)-yl}-acetyl]-$N^2$-(2-(2-methyl)-propyloxycarbonyl)-2,3(S)-diaminopropanoic acid;

$N^3$-[2-{3-(4-formamidinophenyl)-isoxazolin-5(R,S)-yl}-acetyl]-$N^2$-(benzyloxycarbonyl)-2,3(S)-diaminopropanoic acid;

$N^3$-[2-{3-(4-formamidinophenyl)-isoxazolin-5(R)-yl}-acetyl]-$N^2$-(benzyloxycarbonyl)-2,3(S)-diaminopropanoic acid;

$N^3$-[2-{3-(4-formamidinophenyl)-isoxazolin-5(S)-yl}-acetyl]-$N^2$-(benzyloxycarbonyl)-2,3(S)-diaminopropanoic acid;

$N^3$-[2-{3-(4-formamidinophenyl)-isoxazolin-5(R,S)-yl}-acetyl]-$N^2$-(4-methylbenzyloxycarbonyl)-2,3(S)-diaminopropanoic acid;

$N^3$-[2-{3-(4-formamidinophenyl)-isoxazolin-5(R,S)-yl}-acetyl]-$N^2$-(4-methoxybenzyloxycarbonyl)-2,3(S)-diaminopropanoic acid;

$N^3$-[2-{3-(4-formamidinophenyl)-isoxazolin-5(R,S)-yl}-acetyl]-$N^2$-(4-chlorobenzyloxycarbonyl)-2,3(S)-diaminopropanoic acid;

$N^3$-[2-{3-(4-formamidinophenyl)-isoxazolin-5(R,S)-yl}-acetyl]-$N^2$-(4-bromobenzyloxycarbonyl)-2,3(S)-diaminopropanoic acid;

$N^3$-[2-{3-(4-formamidinophenyl)-isoxazolin-5(R,S)-yl}-acetyl]-$N^2$-(4-fluorobenzyloxycarbonyl)-2,3(S)-diaminopropanoic acid;

$N^3$-[2-{3-(4-formamidinophenyl)-isoxazolin-5(R,S)-yl}-acetyl]-$N^2$-(4-phenoxybenzyloxycarbonyl)-2,3(S)-diaminopropanoic acid;

$N^3$-[2-{3-(4-formamidinophenyl)-isoxazolin-5(R,S)-yl}-acetyl]-$N^2$-(2-(methyloxyethyl)-oxycarbonyl)-2,3(S)-diaminopropanoic acid;

$N^3$-[2-{3-(4-formamidinophenyl)-isoxazolin-5(R,S)-yl}-acetyl]-$N^2$-(2-pyridinylcarbonyl)-2,3(S)-diaminopropanoic acid;

$N^3$-[2-{3-(4-formamidinophenyl)-isoxazolin-5(R,S)-yl}-acetyl]-$N^2$-(3-pyridinylcarbonyl)-2,3(S)-diaminopropanoic acid;

$N^3$-[2-{3-(4-formamidinophenyl)-isoxazolin-5(R,S)-yl}-acetyl]-$N^2$-(4-pyridinyl-carbonyl)-2,3(S)-diaminopropanoic acid;

$N^3$-[2-{3-(4-formamidinophenyl)-isoxazolin-5(R,S)-yl}-acetyl]-$N^2$-(2-(2-pyridinyl)-acetyl)-2,3(S)-diaminopropanoic acid;

$N^3$-[2-{3-(4-formamidinophenyl)-isoxazolin-5(R,S)-yl}-acetyl]-$N^2$-(2-(3-pyridinyl)-acetyl)-2,3(S)-diaminopropanoic acid;

$N^3$-[2-{3-(4-formamidinophenyl)-isoxazolin-5(R,S)-yl}-acetyl]-$N^2$-(2-(4-pyridinyl)-acetyl)-2,3(S)-diaminopropanoic acid;

$N^3$-[2-{3-(4-formamidinophenyl)-isoxazolin-5(R,S)-yl}-acetyl]-$N^2$-(2-pyridyl-methyloxycarbonyl)-2,3(S)-diaminopropanoic acid;

$N^3$-[2-{3-(4-formamidinophenyl)-isoxazolin-5(R,S)-yl}-acetyl]-$N^2$-(3-pyridyl-methyloxycarbonyl)-2,3 (S)-diaminopropanoic acid;

$N^3$-[2-{3-(4-formamidinophenyl)-isoxazolin-5(R,S)-yl}-acetyl]-$N^2$-(4-pyridyl-methyloxycarbonyl)-2,3(S)-diaminopropanoic acid;

$N^3$-[2-{3-(4-formamidinophenyl)-isoxazolin-5(R,S)-yl}-acetyl]-$N^2$-(4-butyloxyphenylsulfonyl)-2,3(S)-diaminopropanoic acid;

$N^3$-[2-{3-(4-formamidinophenyl)-isoxazolin-5(R,S)-yl}-acetyl]-$N^2$-(2-thienylsulfonyl)-2,3(S)-diaminopropanoic acid;

$N^3$-[2-{3-(4-formamidinophenyl)-isoxazolin-5(R,S)-yl}-acetyl]-$N^2$-(3-methylphenylsulfonyl)-2,3(R,S)-diaminopropanoic acid;

$N^3$-[2-{3-(4-formamidinophenyl)-isoxazolin-5(R,S)-yl}-acetyl]-$N^2$-(3-methylphenylsulfonyl)-2,3(S)-diaminopropanoic acid;

$N^3$-[2-{3-(4-formamidinophenyl)-isoxazolin-5(R,S)-yl}-acetyl]-$N^2$-(3-methylphenylsulfonyl)-2,3(R)-diaminopropanoic acid;

$N^3$-[2-{3-(4-formamidinophenyl)-isoxazolin-5(R)-yl}-acetyl]-$N^2$-(3-methylphenylsulfonyl)-2,3(S)-diaminopropanoic acid;

$N^3$-[2-{3-(4-formamidinophenyl)-isoxazolin-5(S)-yl}-acetyl]-$N^2$-(3-methylphenylsulfonyl)-2,3(S)-diaminopropanoic acid;

$N^3$-[2-{3-(4-formamidinophenyl)-isoxazolin-5(S)-yl}-acetyl]-$N^2$-(3-methylphenylsulfonyl)-2,3(R)-diaminopropanoic acid;

$N^3$-[2-{3-(4-formamidinophenyl)-isoxazolin-5(R)-yl}-acetyl]-$N^2$-(3-methylphenylsulfonyl)-2,3(R)-diaminopropanoic acid;

$N^3$-[2-{3-(4-formamidinophenyl)-isoxazolin-5(R,S)-yl}-acetyl]-$N^2$-(4-iodophenylsulfonyl)-2,3(S)-diaminopropanoic acid;

$N^3$-[2-{3-(4-formamidinophenyl)-isoxazolin-5(R,S)-yl}-acetyl]-$N^2$-(3-trifluoromethylphenylsulfonyl)-2,3(S)-diaminopropanoic acid;

$N^3$-[2-{3-(4-formamidinophenyl)-isoxazolin-5(R,S)-yl}-acetyl]-$N^2$-(3-chlorophenylsulfonyl)-2,3(S)-diaminopropanoic acid;

$N^3$-[2-{3-(4-formamidinophenyl)-isoxazolin-5(R,S)-yl}-acetyl]-$N^2$-(3-2-methoxycarbonylphenylsulfonyl)-2,3(S)-diaminopropanoic acid;

$N^3$-[2-{3-(4-formamidinophenyl)-isoxazolin-5(R,S)-yl}-acetyl]-$N^2$-(2,4,6-trimethylphenylsulfonyl)-2,3(S)-diaminopropanoic acid;

$N^3$-[2-{3-(4-formamidinophenyl)-isoxazolin-5(R,S)-yl}-acetyl]-$N^2$-(2-chlorophenylsulfonyl)-2,3(S)-diaminopropanoic acid;

$N^3$-[2-{3-(4-formamidinophenyl)-isoxazolin-5(R,S)-yl}-acetyl]-$N^2$-(4-trifluoromethylphenylsulfonyl)-2,3(S)-diaminopropanoic acid;

$N^3$-[2-{3-(4-formamidinophenyl)-isoxazolin-5(R,S)-yl}-acetyl]-$N^2$-(2-trifluoromethylphenylsulfonyl)-2,3(S)-diaminopropanoic acid;

$N^3$-[2-{3-(4-formamidinophenyl)-isoxazolin-5(R,S)-yl}-acetyl]-$N^2$-(2-fluorophenylsulfonyl)-2,3(S)-diaminopropanoic acid;

$N^3$-[2-{3-(4-formamidinophenyl)-isoxazolin-5(R,S)-yl}-acetyl]-$N^2$-(4-fluorophenylsulfonyl)-2,3(S)-diaminopropanoic acid;

$N^3$-[2-{3-(4-formamidinophenyl)-isoxazolin-5(R,S)-yl}-acetyl]-$N^2$-(4-methoxyphenylsulfonyl)-2,3(S)-diaminopropanoic acid;

$N^3$-[2-{3-(4-formamidinophenyl)-isoxazolin-5(R,S)-yl}-acetyl]-$N^2$-(2,3,5,6-tetramethylphenylsulfonyl)-2,3(S)-diaminopropanoic acid;

$N^3$-[2-{3-(4-formamidinophenyl)-isoxazolin-5(R,S)-yl}-acetyl]-$N^2$-(4-cyanophenylsulfonyl)-2,3(S)-diaminopropanoic acid;

$N^3$-[2-{3-(4-formamidinophenyl)-isoxazolin-5(R,S)-yl}-acetyl]-$N^2$-(4-chlorophenylsulfonyl)-2,3(S)-diaminopropanoic acid;

$N^3$-[2-{3-(4-formamidinophenyl)-isoxazolin-5(R,S)-yl}-acetyl]-$N^2$-(4-propylphenylsulfonyl)-2,3(S)-diaminopropanoic acid;

$N^3$-[2-{3-(4-formamidinophenyl)-isoxazolin-5(R,S)-yl}-acetyl]-$N^2$-(2-phenylethylsulfonyl)-2,3(S)-diaminopropanoic acid;

$N^3$-[2-{3-(4-formamidinophenyl)-isoxazolin-5(R,S)-yl}-acetyl]-$N^2$-(4-isopropylphenylsulfonyl)-2,3(S)-diaminopropanoic acid;

$N^3$-[2-{3-(4-formamidinophenyl)-isoxazolin-5(R,S)-yl}-acetyl]-$N^2$-(3-phenylpropylsulfonyl)-2,3(S)-diaminopropanoic acid;

$N^3$-[2-{3-(4-formamidinophenyl)-isoxazolin-5(R,S)-yl}-acetyl]-$N^2$-(3-pyridylsulfonyl)-2,3(S)-diaminopropanoic acid;

$N^3$-[2-{3-(4-formamidinophenyl)-isoxazolin-5(R,S)-yl}-acetyl]-$N^2$-(phenylaminosulfonyl)-2,3(S)-diaminopropanoic acid;

$N^3$-[2-{3-(4-formamidinophenyl)-isoxazolin-5(R,S)-yl}-acetyl]-$N^2$-(benzylaminosulfonyl)-2,3(S)-diaminopropanoic acid;

$N^3$-[2-{3-(4-formamidinophenyl)-isoxazolin-5(R,S)-yl}-acetyl]-$N^2$-(dimethylaminosulfonyl)-2,3(S)-diaminopropanoic acid;

$N^3$-[2-{3-(2-fluoro-4-formamidinophenyl)-isoxazolin-5(R,S)-yl}-acetyl]-$N^2$-(3-methylphenylsulfonyl)-2,3(S)-diaminopropanoic acid;

$N^3$-[2-{3-(2-formamidino-5-pyridinyl)-isoxazolin-5(R,S)-yl}-acetyl]-$N^2$-(n-butyloxycarbonyl)-2,3(S)-diaminopropanoic acid;

$N^3$-[2-{3-(2-formamidino-5-pyridinyl)-isoxazolin-5(R,S)-yl}-acetyl]-$N^2$-(3-methylphenylsulfonyl)-2,3(S)-diaminopropanoic acid;

$N^3$-[2-{3-(3-formamidino-6-pyridinyl)-isoxazolin-5(R,S)-yl}-acetyl]-$N^2$-(n-butyloxycarbonyl)-2,3(S)-diaminopropanoic acid;

$N^3$-[2-{3-(3-formamidino-6-pyridinyl)-isoxazolin-5(R,S)-yl}-acetyl]-$N^2$-(3-methylphenylsulfonyl)-2,3(S)-diaminopropanoic acid;

$N^3$-[2-{3-(4-formamidinophenyl)-isoxazolin-5(R,S)-yl}-acetyl]-$N^2$-(phenylaminocarbonyl)-2,3(S)-diaminopropanoic acid;

$N^3$-[2-{3-(4-formamidinophenyl)-isoxazolin-5(R,S)-yl}-acetyl]-$N^2$-(4-fluorophenylaminocarbonyl)-2,3(S)-diaminopropanoic acid;

$N^3$-[2-{3-(4-formamidinophenyl)-isoxazolin-5(R,S)-yl}-acetyl]-$N^2$-(1-naphthylaminocarbonyl)-2,3(S)-diaminopropanoic acid;

$N^3$-[2-{3-(4-formamidinophenyl)-isoxazolin-5(R,S)-yl}-acetyl]-$N^2$-(benzylaminocarbonyl)-2,3(S)-diaminopropanoic acid;

N³-[2-{3-(4-formamidinophenyl)-isoxazolin-5(R,S)-yl}-acetyl]-N²-(3-bromo-2-thienylsulfonyl)-2,3(S)-diaminopropanoic acid;

N³-[2-{3-(4-formamidinophenyl)-isoxazolin-5(R,S)-yl}-acetyl]-N²-(3-methyl-2-benzothienylsulfonyl)-2,3(S)-diaminopropanoic acid;

N³-[2-{3-(4-formamidinophenyl)-isoxazolin-5(R,S)-yl}-acetyl]-N²-(isobutyloxycarbonyl)-2,3(S)-diaminopropanoic acid;

N³-[2-{3-(4-formamidinophenyl)-isoxazolin-5(R)-yl}-acetyl]-N²-(isobutyloxycarbonyl)-2,3(S)-diaminopropanoic acid;

N³-[2-{3-(4-formamidinophenyl)-isoxazolin-5(S)-yl}-acetyl]-N²-(isobutyloxycarbonyl)-2,3(S)-diaminopropanoic acid;

N³-[2-{3-(4-formamidinophenyl)-isoxazolin-5(R,S)-yl}-acetyl]-N²-(2-cyclopropylethoxycarbonyl)-2,3(S)-diaminopropanoic acid;

N³-[2-{3-(4-formamidinophenyl)-isoxazolin-5(R)-yl}-acetyl]-N²-(2-cyclopropylethoxycarbonyl)-2,3(S)-diaminopropanoic acid;

N³-[2-{3-(4-formamidinophenyl)-isoxazolin-5(S)-yl}-acetyl]-N²-(2-cyclopropylethoxycarbonyl)-2,3(S)-diaminopropanoic acid;

N³-[2-{3-(4-guanidinophenyl)-isoxazolin-5(R,S)-yl}-acetyl]-N²-(n-butyloxycarbonyl)-2,3(S)-diaminopropanoic acid;

N³-[2-{3-(4-guanidinophenyl)-isoxazolin-5(R)-yl}-acetyl]-N²-(n-butyloxycarbonyl)-2,3(S)-diaminopropanoic acid;

N³-[2-{3-(4-guanidinophenyl)-isoxazolin-5(R)-yl}-acetyl]-N²-(3-methylphenylsulfonyl)-2,3(S)-diaminopropanoic acid;

N³-[2-{5-(4-formamidinophenyl)-isoxazolin-3(R,S)-yl}-acetyl]-N²-(n-butyloxycarbonyl)-2,3(S)-diaminopropanoic acid;

or a propanoate ester prodrug form of the compound, wherein the hydrogen of the hydroxy group of the diaminopropanoic acid moiety is substituted with a group selected from:

methyl; ethyl; isopropyl; methylcarbonyloxymethyl; ethylcarbonyloxymethyl;

t-butylcarbonyloxymethyl; cyclohexylcarbonyloxymethyl;

1-(methylcarbonyloxy)-ethyl; 1-(ethylcarbonyloxy)-ethyl;

1-(t-butylcarbonyloxy)-ethyl; 1-(cyclohexylcarbonyloxy)-ethyl;

i-propyloxycarbonyloxymethyl; cyclohexylcarbonyloxymethyl;

t-butyloxycarbonyloxymethyl; 1-(i-propyloxycarbonyloxy)-ethyl;

1-(cyclohexyloxycarbonyloxy)-ethyl; 1-(t-butyloxycarbonyloxy)-ethyl;

dimethylaminoethyl; diethylaminoethyl;

(5-methyl-1,3-dioxacyclopenten-2-on-4-yl)-methyl;

(5-(t-butyl)-1,3-dioxacyclopenten-2-on 4-yl)-methyl;

(1,3-dioxa-5-phenyl-cyclopenten-2-on-4-yl)-methyl;

1-(2-(2-methoxypropyl)carbonyloxy)-ethyl.

Alternatively preferable, the iontophoresis device according to this embodiment can comprise a compound, or enantiomeric or diastereomeric forms thereof, or mixtures of enantiomeric or diastereomeric forms thereof, or a pharmaceutically acceptable salt form thereof, selected from:

N³-[2-{3-(4-formamidinophenyl)-isoxazolin-5-yl}-acetyl]-N²-(phenylsulfonyl)-2,3-diaminopropanoic acid;

N³-[2-{3-(4-formamidinophenyl)-isoxazolin-5-yl}-acetyl]-N²-(4-methyl-phenyl-sulfonyl)-2,3-diaminopropanoic acid;

N³-[2-{3-(4-formamidinophenyl)-isoxazolin-5-yl}-acetyl]-N²-(butanesulfonyl)-2,3-diaminopropanoic acid;

N³-[2-{3-(4-formamidinophenyl)-isoxazolin-5-yl}-acetyl]-N²-(propanesulfonyl)-2,3-diaminopropanoic acid;

N³-[2-{3-(4-formamidinophenyl)-isoxazolin-5-yl}-acetyl]-N²-(ethanesulfonyl)-2,3-diaminopropanoic acid;

N³-[2-{3-(4-formamidinophenyl)-isoxazolin-5-yl}-acetyl]-N²-(methyloxycarbonyl)-2,3-diaminopropanoic acid;

N³-[2-{3-(4-formamidinophenyl)-isoxazolin-5-yl}-acetyl]-N²-(ethyloxycarbonyl)-2,3-diaminopropanoic acid;

N³-[2-{3-(4-formamidinophenyl)-isoxazolin-5-yl}-acetyl]-N²-(1-propyloxycarbonyl)-2,3-diaminopropanoic acid;

N³-[2-{3-(4-formamidinophenyl)-isoxazolin-5-yl}-acetyl]-N²-(2-propyloxycarbonyl)-2,3-diaminopropanoic acid;

N³-[2-{3-(4-formamidinophenyl)-isoxazolin-5-yl}-acetyl]-N²-(n-butyloxycarbonyl)-2,3-diaminopropanoic acid;

N³-[2-{3-(4-formamidinophenyl)-isoxazolin-5-yl}-acetyl]-N²-(1-(2-methyl)-propyloxycarbonyl)-2,3-diaminopropanoic acid;

N³-[2-{3-(4-formamidinophenyl)-isoxazolin-5-yl}-acetyl]-N²-(2-(2-methyl)-propyloxycarbonyl)-2,3-diaminopropanoic acid;

N³-[2-{3-(4-formamidinophenyl)-isoxazolin-5-yl}-acetyl]-N²-(benzyloxycarbonyl)-2,3-diaminopropanoic acid;

N³-[2-{3-(4-formamidinophenyl)-isoxazolin-5-yl}-acetyl]-N²-(4-methylbenzyloxycarbonyl)-2,3-diaminopropanoic acid;

N³-[2-{3-(4-formamidinophenyl)-isoxazolin-5-yl}-acetyl]-N²-(4-methoxybenzyloxycarbonyl)-2,3-diaminopropanoic acid;

N³-[2-{3-(4-formamidinophenyl)-isoxazolin-5-yl}-acetyl]-N²-(4-chlorobenzyloxycarbonyl)-2,3-diaminopropanoic acid;

N³-[2-{3-(4-formamidinophenyl)-isoxazolin-5-yl}-acetyl]-N²-(4-bromobenzyloxycarbonyl)-2,3-diaminopropanoic acid;

N³-[2-{3-(4-formamidinophenyl)-isoxazolin-5-yl}-acetyl]-N²-(4-fluorobenzyloxycarbonyl)-2,3-diaminopropanoic acid;

N³-[2-{3-(4-formamidinophenyl)-isoxazolin-5-yl}-acetyl]-N²-(4-phenoxybenzyloxycarbonyl)-2,3-diaminopropanoic acid;

N³-[2-{3-(4-formamidinophenyl)-isoxazolin-5-yl}-acetyl]-N²-(2-methyloxyethyl)-oxycarbonyl)-2,3-diaminopropanoic acid;

N³-[2-{3-(4-formamidinophenyl)-isoxazolin-5-yl}-acetyl]-N²-(2-pyridinylcarbonyl)-2,3-diaminopropanoic acid;

N³-[2-{3-(4-formamidinophenyl)-isoxazolin-5-yl}-acetyl]-N²-(3-pyridinylcarbonyl)-2,3-diaminopropanoic acid;

N³-[2-{3-(4-formamidinophenyl)-isoxazolin-5-yl)}-acetyl]-N²-(4-pyridinyl-carbonyl)-2,3-diaminopropanoic acid;

N³-[2-{3-(4-formamidinophenyl)-isoxazolin-5-yl}-acetyl]-N²-(2-(2-pyridinyl)-acetyl)-2,3-diaminopropanoic acid;

N³-[2-{3-(4-formamidinophenyl)-isoxazolin-5-yl}-acetyl]-N²-(2-(3-pyridinyl)-acetyl)-2,3-diaminopropanoic acid;

N³-[2-{3-(4-formamidinophenyl)-isoxazolin-5-yl}-acetyl]-N²-(2-(4-pyridinyl)-acetyl)-2,3-diaminopropanoic acid;

N³-[2-{3-(4-formamidinophenyl)-isoxazolin-5-yl}-acetyl]-N²-(2-pyridyl-methyloxycarbonyl)-2,3-diaminopropanoic acid;

N³-[2-{3-(4-formamidinophenyl)-isoxazolin-5-yl}-acetyl]-N²-(3-pyridyl-methyloxycarbonyl)-2,3-diaminopropanoic acid;

N³-[2-{3-(4-formamidinophenyl)-isoxazolin-5-yl}-acetyl]-N²-(4-pyridyl-methyloxycarbonyl)-2,3-diaminopropanoic acid;

N³-[2-{3-(4-formamidinophenyl)-isoxazolin-5-yl}-acetyl]-N²-(4-butyloxyphenylsulfonyl)-2,3-diaminopropanoic acid;

N³-[2-{3-(4-formamidinophenyl)-isoxazolin-5-yl}-acetyl]-N²-(2-thienylsulfonyl)-2,3-diaminopropanoic acid;

N³-[2-{3-(4-formamidinophenyl)-isoxazolin-5-yl}-acetyl]-N²-(3-methylphenylsulfonyl)-2,3-diaminopropanoic acid;

N³-[2-{3-(4-formamidinophenyl)-isoxazolin-5-yl}-acetyl]-N²-(4-iodophenylsulfonyl)-2,3-diaminopropanoic acid;

N³-[2-{3-(4-formamidinophenyl)-isoxazolin-5-yl}-acetyl]-N²-(3-trifluoromethylphenylsulfonyl)-2,3-diaminopropanoic acid;

N³-[2-{3-(4-formamidinophenyl)-isoxazolin-5-yl}-acetyl]-N²-(3-chlorophenylsulfonyl)-2,3-diaminopropanoic acid;

N³-[2-{3-(4-formamidinophenyl)-isoxazolin-5-yl}-acetyl]-N²-(2-methoxycarbonylphenylsulfonyl)-2,3-diaminopropanoic acid;

N³-[2-{3-(4-formamidinophenyl)-isoxazolin-5-yl}-acetyl]-N²-(2,4,6-trimethylphenylsulfonyl)-2,3-diaminopropanoic acid;

N³-[2-{3-(4-formamidinophenyl)-isoxazolin-5-yl}-acetyl]-N²-(2-chlorophenylsulfonyl)-2,3-diaminopropanoic acid;

N³-[2-{3-(4-formamidinophenyl)-isoxazolin-5-yl}-acetyl]-N²-(4-trifluoromethylphenylsulfonyl)-2,3-diaminopropanoic acid;

N³-[2-{3-(4-formamidinophenyl)-isoxazolin-5-yl}-acetyl]-N²-(2-trifluoromethylphenylsulfonyl)-2,3-diaminopropanoic acid;

N³-[2-{3-(4-formamidinophenyl)-isoxazolin-5-yl}-acetyl]-N²-(2-fluorophenylsulfonyl)-2,3-diaminopropanoic acid;

N³-[2-{3-(4-formamidinophenyl)-isoxazolin-5-yl}-acetyl]-N²-(4-fluorophenylsulfonyl)-2,3-diaminopropanoic acid;

N³-[2-{3-(4-formamidinophenyl)-isoxazolin-5-yl}-acetyl]-N²-(4-methoxyphenylsulfonyl)-2,3-diaminopropanoic acid;

N³-[2-{3-(4-formamidinophenyl)-isoxazolin-5-yl}-acetyl]-N²-(2,3,5,6-tetramethylphenylsulfonyl)-2,3-diaminopropanoic acid;

N³-[2-{3-(4-formamidinophenyl)-isoxazolin-5-yl}-acetyl]-N²-(4-cyanophenylsulfonyl)-2,3-diaminopropanoic acid;

N³-[2-{3-(4-formamidinophenyl)-isoxazolin-5-yl}-acetyl]-N²-(4-chlorophenylsulfonyl)-2,3-diamninopropanoic acid;

N³-[2-{3-(4-formamidinophenyl)-isoxazolin-5-yl}-acetyl]-N²-(4-propylphenylsulfonyl)-2,3-diaminopropanoic acid;

N³-[2-{3-(4-formamidinophenyl)-isoxazolin-5-yl}-acetyl]-N²-(2-phenylethylsulfonyl)-2,3-diaminopropanoic acid;

N³-[2-{3-(4-formamidinophenyl)-isoxazolin-5-yl}-acetyl]-N²-(4-isopropylphenylsulfonyl)-2,3-diaminopropanoic acid;

N³-[2-{3-(4-formamidinophenyl)-isoxazolin-5-yl}-acetyl]-N²-(3-phenylpropylsulfonyl)-2,3-diaminopropanoic acid;

N³-[2-{3-(4-formamidinophenyl)-isoxazolin-5-yl}-acetyl]-N²-(3-pyridylsulfonyl)-2,3-diaminopropanoic acid;

N³-[2-{3-(4-formamidinophenyl)-isoxazolin-5-yl}-acetyl]-N²-(phenylaminosulfonyl)-2,3-diaminopropanoic acid;

N³-[2-{3-(4-formamidinophenyl)-isoxazolin-5-yl}-acetyl]-N²-(benzylaminosulfonyl)-2,3-diaminopropanoic acid;

N³-[2-{3-(4-formamidinophenyl)-isoxazolin-5-yl}-acetyl]-N²-(dimethylaminosulfonyl)-2,3-diaminopropanoic acid;

N³-[2-{3-(2-fluoro-4-formamidinophenyl)-isoxazolin-5-yl}-acetyl]-N²-(3-methylphenylsulfonyl)-2,3-diaminopropanoic acid;

N³-[2-{3-(2-formamidino-5-pyridinyl)-isoxazolin-5-yl}-acetyl]-N²-(n-butyloxycarbonyl)-2,3-diaminopropanoic acid;

N³-[2-{3-(2-formamidino-5-pyridinyl)-isoxazolin-5-yl}-acetyl]-N²-(3-methylphenylsulfonyl)-2,3-diaminopropanoic acid;

N³-[2-{3-(3-formamidino-6-pyridinyl)-isoxazolin-5-yl}-acetyl]-N²-(n-butyloxycarbonyl)-2,3-diaminopropanoic acid, N³-[2-{3-(3-formamidino-6-pyridinyl)-isoxazolin-5-yl}-acetyl]-N²-(3-methylphenylsulfonyl)-2,3-diaminopropanoic acid, N³-[2-{3-(4-formamidinophenyl)-isoxazolin-5-yl}-acetyl]-N²-(phenylaminocarbonyl)-2,3-diaminopropanoic acid;

N³-[2-{3-(4-formamidinophenyl)-isoxazolin-5-yl}-acetyl]-N²-(4-fluorophenylaminocarbonyl)-2,3-diaminopropanoic acid;

N³-[2-{3-(4-formamidinophenyl)-isoxazolin-5-yl}-acetyl]-N²-(1-naphthylaminocarbonyl)-2,3-diaminopropanoic acid;

N³-[2-{3-(4-formamidinophenyl)-isoxazolin-5-yl}-acetyl]-N²-(benzylaminocarbonyl)-2,3-diaminopropanoic acid;

N³-[2-{3-(4-formamidinophenyl)-isoxazolin-5-yl}-acetyl]-N²-(3-bromo-2-thienylsulfonyl)-2,3-diaminopropanoic acid;

N³-[2-{3-(4-formamidinophenyl)-isoxazolin-5-yl}-acetyl]-N²-(3-methyl-2-benzothienylsulfonyl)-2,3-diaminopropanoic acid, N³-[2-{3-(4-formamidinophenyl)-isoxazolin-5-yl}-acetyl]-N²-(isobutyloxycarbonyl)-2,3-diaminopropanoic acid, N³-[2-{3-(4-formamidinophenyl)-isoxazolin-5-yl}-acetyl]-N²-(isobutyloxycarbonyl)-2,3-diaminopropanoic acid, N³-[2-{3-(4-formamidinophenyl)-isoxazolin-5-yl}-acetyl]-N²-(isobutyloxycarbonyl)-2,3-diaminopropanoic acid, N³-[2-{3-(4-formamidinophenyl)-isoxazolin-5-yl}-acetyl]-N²-(2-cyclopropylethoxycarbonyl)-2,3-diaminopropanoic acid, N³-[2-{3-(4-guanidinophenyl)-isoxazolin-5-yl}-acetyl]-N₂-(n-butyloxycarbonyl)-2,3-diaminopropanoic acid;

N³-[2-{3-(4-guanidinophenyl)-isoxazolin-5-yl}-acetyl]-N²-(3-methylphenylsulfonyl)-2,3-diaminopropanoic acid;

N³-[2-{5-(4-formamidinophenyl)-isoxazolin-3-yl}-acetyl]-N²-(n-butyloxycarbonyl)-2,3-diaminopropanoic acid;

N³-[2-{3-(4-formamidinophenyl)-isoxazolin-5-yl}-acetyl]-N²-(2-bromo-phenylsulfonyl)-2,3-diaminopropionic acid;

N³-[2-{3-(4-formamidinophenyl)-isoxazolin-5-yl}-acetyl]-N²-(2-methyl-phenylsulfonyl)-2,3-diaminopropionic acid;

N³-[2-{3-(3-formamidino-6-pyridinyl)-isoxazolin-5-yl}-acetyl]-N²-(3-methylphenylsulfonyl)-2,3-diaminopropionic acid;

N³-[2-{3-(2-formamidino-5-pyridinyl)-isoxazolin-5-yl}-acetyl]-N²-(3-methylphenylsulfonyl)-2,3-diaminopropionic acid;

N³-[2-{3-(2-fluoro-4-formamidinophenyl)-isoxazolin-5-yl}-acetyl]-N²-(3-methylphenylsulfonyl)-2,3-diaminopropionic acid;

N³-[2-{3-(4-formamidinophenyl)-isoxazolin-5-yl-acetyl]-N²-(3-bromo-phenylsulfonyl)-2,3-diaminopropionic acid; and N³-[2-{3-(4-formamidinophenyl)-isoxazolin-5-yl}-acetyl]-N²-(4-bromo-phenylsulfonyl)-2,3-diaminopropionic acid;

or a propanoate ester prodrug form of the compound, wherein the hydrogen of the hydroxy group of the propanoic acid moiety is substituted with a group selected from:
methyl; ethyl; isopropyl; methylcarbonyloxymethyl; ethylcarbonyloxymethyl;
t-butylcarbonyloxymethyl; cyclohexylcarbonyloxymethyl;

1-(methylcarbonyloxy)-ethyl; 1-(ethylcarbonyloxy)-ethyl;

1-(t-butylcarbonyloxy)-ethyl; 1-(cyclohexylcarbonyloxy)-ethyl;

1-propyloxycarbonyloxymethyl; cyclohexylcarbonyloxymethyl;

t-butyloxycarbonyloxymethyl; 1-(i-propyloxycarbonyloxy)-ethyl;

1-(cyclohexyloxycarbonyloxy)-ethyl; 1-(t-butyloxycarbonyloxy)-ethyl;

dimethylaminoethyl; diethylaminoethyl;

(5-methyl-1,3-dioxacyclopenten-2-on-4-yl)-methyl;

(5-(t-butyl)-1,3-dioxacyclopenten-2-on-4-yl)-methyl;

(1,3-dioxa-5-phenyl-cyclopenten-2-on-4-yl)-methyl; and 1-(2-(2-methoxypropyl)carbonyloxy)-ethyl;

the enantiomeric and diastereomeric forms being selected from:

(R,S), (R,S);

(R), (R,S);

(S), (R,S);

(R), (R);

(S), (R);

(R), (S); and (S), (S).

Among these compounds useful in the iontophoresis device according to Claim 18, it is further preferred that the hydrogen of the hydroxy group of the diaminopropanoic acid moiety is substituted with a group selected from:

methyl; ethyl; and isopropyl.

Preferred pharmaceutically acceptable salt forms of the compounds are selected from:

acetate, methanesulfonate, hydrochloride, benzenesulfonate, and para-toluenesulfonate.

One more preferred compound capable of being included in the device is:

$N^3$-[2-{3-(4-formamidinophenyl)-isoxazolin-5(R)-yl}-acetyl]-$N^2$-(n-butyloxycarbonyl)-2,3-(S)-diaminopropanoic acid, or a pharmaceutically acceptable salt form or propanoate ester prodrug from thereof.

More preferably, the device includes a compound:

methyl-$N^3$-[2-{3-(4-formamidinophenyl)-isoxazolin-5(R)-yl}-acetyl]-$N^2$-(n-butyloxycarbonyl)-2,3-(S)-diaminopropanoate methanesulfonate salt.

Preferably, the iontophoresis device according to this embodiment further comprises:

a cathode and an anode each disposed so as to be in electrical connection with a source of electrical energy and in intimate contact with skin of a subject, and a drug reservoir electrically connected to the cathode or the anode for containing the $\alpha_v\beta_3$ integrin inhibitor compound for delivery into the body of the subject.

Thus, the device according to this embodiment is useful in iontophoresis methods.

Accordingly, in another embodiment, the invention is a method for the treatment of thromboembolic disorders, the method comprising iontophoretically administering to a mammal a therapeutically effective amount of an integrin inhibitor using an iontophoresis device as described above.

Also, in another embodiment, the invention is a method of administering an integrin inhibitor compound, the method comprising iontophoretically administering to a mammal a therapeutically effective amount of the integrin inhibitor using the described iontophoresis device.

In still another embodiment, the invention is a method for the treatment of thrombosis, the method comprising administering to a mammal a therapeutically effective amount of an integrin inhibitor using the described iontophoresis device.

In another embodiment, the invention is a method of inhibiting the aggregation of blood platelets, the method comprising administering to a mammal a therapeutically effective amount of a IIb/IIIa inhibitor using the described iontophoresis device.

Furthermore, the invention, in another embodiment, is a method of treating a thromboembolic disorder selected from thrombus or embolus formation, harmful platelet aggregation, reocclusion following thrombolysis, reperfusion injury, restenosis, atherosclerosis, stroke, myocardial infarction, and unstable angina, the method comprising administering to a mammal a therapeutically effective amount of an integrin inhibitor using the described iontophoresis device.

Such methods and devices are useful, alone or in combination with other therapeutic agents, for the treatment of thromboembolic disorders, angiogenic disorders, inflammation, bone degradation, cancer metastasis, diabetic retinopathy, restenosis, macular degeneration, and other conditions mediated by cell adhesion and/or cell migration and/or angiogenesis.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawing, wherein.

DETAILED DESCRIPTION OF THE PREFERRED EMBODIMENTS

Figure 1:
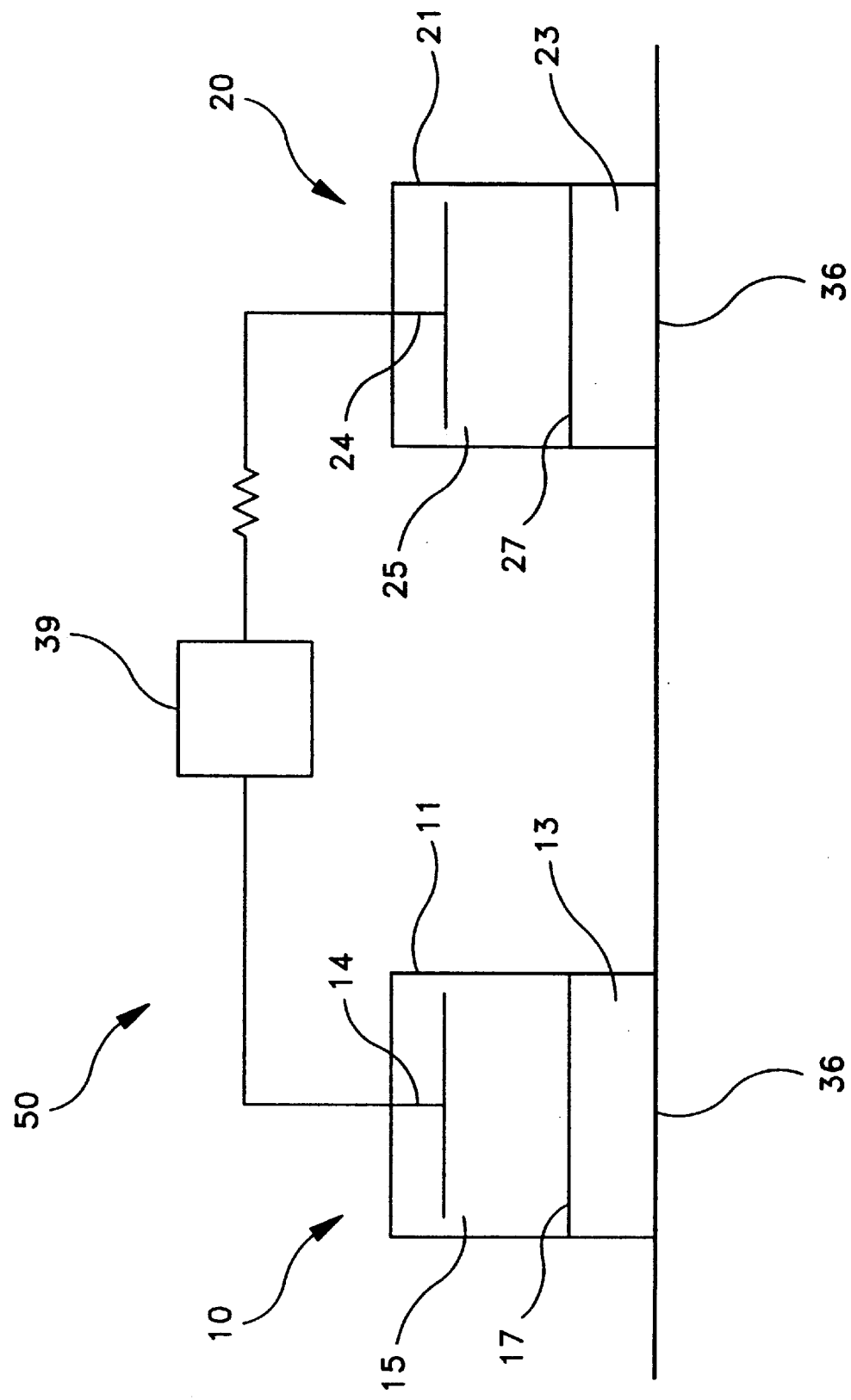
FIG. 1 is a cross-sectional view of an idealized iontophoresis device suitable for use according to the invention.

The present invention provides novel methods and devices for iontophoretically administering therapeutic doses of cell adhesion receptor antagonists in a controlled manner through the skin. Such cell adhesion receptor antagonists include but are not limited to antagonists of the IIb/IIIa and $\alpha_v\beta_3$ integrins and related cell surface adhesive protein receptors. The present invention includes iontophoretic delivery devices comprising cell adhesion receptor inhibitors/antagonists. Such methods and devices are useful, alone or in combination with other therapeutic agents, for the treatment of thromboembolic disorders, angiogenic disorders, inflammation, bone degradation, cancer metastasis, diabetic retinopathy, restenosis, macular degeneration, and other conditions mediated by cell adhesion and/or cell migration and/or angiogenesis.

The therapeutic compounds deliverable by the iontophoresis method of the invention are compounds that bind to CAR proteins, thereby mediating controllable alteration of cell-matrix and cell-cell adhesion processes. Such compounds are referred to herein as "cell adhesion receptor inhibitors" or "cell adhesion receptor antagonists," and act as inhibitors of the binding of the CAR protein(s) to endogenous protein ligands of such CAR. Preferred cell adhesion receptor antagonists (inhibitors) used in the present invention are RGD-peptidomimetic compounds. As used herein, the term "RGD-peptidomimetic compounds" refers to chemical compounds that bind to the RGD-binding region of the cell adhesion receptor and that block RGD-mediated binding of one or more adhesive proteins to the receptor.

The present invention provides methods of CAR antagonist drug delivery that permit controlled, continuous delivery of the drug at a relatively low rate. Such controlled, continuous delivery of the CAR antagonist ensures relatively constant plasma concentrations and control of pharmacologic and toxic drug effects. This is particularly desirable for drugs having steep dose versus response profiles, for which there are relatively small differences between ineffective, therapeutic, and toxic plasma concentrations or doses. Transdermal iontophoretic delivery provides a means of controlled, continuous drug delivery and avoids the uncertainties of oral administration and the inconvenience and discomfort of administration by injection. In addition, iontophoresis transdermal delivery methods are used in the present invention since generally the CAR antagonist compounds do not passively diffuse through skin at rates sufficient for delivering therapeutic doses and the skin is especially impermeable to polar and ionic drugs.

The present invention relates to iontophoretic delivery of a cell adhesion receptor antagonist to constant therapeutic levels at remarkably low variability, as demonstrated in the Examples contained herein. Applicants have conducted in vitro iontophoretic transport experiments involving an esterified CAR antagonist, and have discovered unexpectedly that a positively charged ester, although metabolized to some extent in the skin or in the receptor fluid to the net uncharged zwitterion, can be transported in a reproducible and constant manner, to flux levels capable of producing therapeutic plasma levels. Additional in vivo studies in pigs have also demonstrated that a positively charged ester will be transported across the skin by iontophoresis in such a manner. One of the significant advantages of this invention is that it overcomes the shortcomings of the current routes of administration for the identified therapeutics and may therefore be an enabling technology for such therapeutics to be administered chronically, as well as for the ability to deliver drugs rapidly to the systemic circulation and to control delivery profiles.

Cell adhesion receptor antagonists are exemplary compounds capable of delivery as positively charged esters for the treatment of various disease states, e.g., restenosis following coronary angioplasty, unstable angina, stroke, prevention of secondary myocardial infarction, etc. For example, GPIIb/IIIa antagonists bind to receptors on a platelet to block fibrinogen binding and inhibit platelet aggregation. Such compounds, therefore, have enormous potential for the treatment of arterial thrombosis. Other examples of positively charged esters and various diseases treatable by administration of the esters to the afflicted patient are by way of example and not limitation, remifentanil which is a narcotic analgesic used in the treatment of acute pain.

Iontophoretic Apparatus

As used herein, the term "iontophoresis device" or "iontophoresis patch" or "patch" refers generally to an electrically assisted device or apparatus suitable for the transdermal iontophoretic delivery of therapeutic levels of a compound to a mammal. Such iontophoresis devices are well known in the art and are also referred to as "iontophoretic delivery devices" or "electrotransport devices."

The iontophoretic drug delivery device used in the present invention comprises a power source for generation of an electrical current and two electrode compartments that, when adhering to the skin of a subject, will pass a generated electrical current through the subject's skin. In the presence of the electrical current, the passage of the CAR antagonist from the agent reservoir through the skin is enhanced. As is appreciated by one of skill in the art of iontophoresis drug delivery, the rate of transdermal delivery of the CAR antagonist in accordance with the present invention can be controlled by appropriate selection of the patch design, including the selection of the contents of the electrode compartments, the surface area of the patch, and by the strength of the generated electrical current.

The iontophoretic device of the present invention can include, by way of example and not limitation, the following components and materials.

In general, the iontophoretic device includes at least two electrodes. Both of the electrodes are disposed so as to be in intimate electrical contact with some portion of the skin of the body. The circuit of the device is completed by connection of the electrodes to a source of electrical energy, for example, a battery, in conjunction with the electrode contacts with the patient's skin.

In electrical terms, the electrodes include a positive electrode or "anode," and a negative electrode or a "cathode." In functional terms, however, the electrodes are characterized independently of their electrical nature. Thus, in relation to their function in iontophoresis, one electrode is the electrode from which the ionic CAR antagonist drug precursor or drug is delivered into the body by iontophoresis. This is called the "active" or "donor" electrode. The other electrode serves to close the electrical circuit through the body. The latter electrode is called the "counter" or "return" electrode, or the "indifferent" electrode.

The functional definition of the electrodes is dependent upon the charge sign of the agent to be delivered. To illustrate, if the CAR antagonist to be delivered is positively charged (i.e., a cation), then the anode (positive electrode) will be the active electrode and the cathode will serve to complete the circuit. If the CAR antagonist to be delivered is negatively charged (i.e., an anion), then the cathode (negative electrode) will be the active electrode and the anode (positive electrode) will be the counter electrode.

Alternatively, both the anode and cathode can be used to deliver drugs of opposite charge into the body simultaneously. In such a case, both electrodes are considered to be active or donor electrodes. In this situation, the anode is used to deliver a positively charged ionic substance into the body while the cathode is used to deliver a negatively charged ionic substance into the body.

A. The Current Distributing Member (Active Electrode)

The iontophoretic device of the invention includes a current distributing member that conveys electrical current into the iontophoretic reservoirs for the delivery of an agent (ionized substance). The current distributing member can be constructed of any of a large variety of electrically conductive materials, including inert and sacrificial materials.

Inert conductive materials are those electrically conductive materials that, when employed in the iontophoretic devices of the invention, do not themselves undergo or participate in electrochemical reactions. Thus, an inert material distributes current without being eroded or depleted due to the distribution of the current, and conducts current through generation of hydronium ions ($H_3O^+$) or hydroxyl ions ($OH^-$) by, respectively, reduction or oxidation of water. Inert conductive materials typically include, for example, stainless steel, platinum, gold, and carbon or graphite.

Alternatively, the current distributing member can be constructed from a sacrificial conductive material. A material can be considered sacrificial if, when employed as an electrode in an iontophoretic device of the invention, the material is eroded or depleted due to its oxidation or reduction. Such erosion or depletion occurs when the materials and formulations used in the iontophoresis device enable a specific electrochemical reaction, such as when a silver electrode is used with a formulation containing chloride ions. In this situation, the current distributing member would not cause electrolysis of water, but would itself be oxidized or reduced.

Typically, for anodes, a sacrificial material would include an oxidizable metal such as silver, zinc, copper, etc. In contrast to the hydroxyl and hydronium ions electrochemically generated via an inert material, the ions electrochemically generated via a sacrificial material would include metal cations resulting from oxidation of the metal. Metal/metal salt anodes can also be employed. In such cases, the metal would oxidize to metal ions, which would then be precipitated as an insoluble salt.

For cathodes, a sacrificial current distributing member can be constructed from any electrically conductive material provided an appropriate electrolyte formulation is provided. For example, a cathodic current distributing member can be constructed from a metal/metal salt material. A preferred cathodic material is a silver/silver halide material. In such embodiments, a metal halide salt is preferably employed as the electrolyte. In this case, the device would generate halide ions from the electrode as the metal is reduced electrochemically. Also, accompanying silver ions ($Ag^+$) in a formulation would be reduced to silver metal ($Ag_{(s)}$) and would deposit (plate) onto the electrode. In other embodiments, the cathode material can be an intercalation material, an amalgam, or other material that can take electrolyte cations such as sodium out of solution, below the reduction potential of water.

In addition, other materials can be used that permit the plating out of a metal from the appropriate electrolyte solution. Thus, metals such as silver, copper, zinc, and nickel, and other materials, such as carbon, can be employed when an appropriate metal salt such as silver nitrate or zinc sulfate is in solution in the electrolyte reservoir. While such materials may develop increased resistivity as a metal plates out during use, they are not eroded or depleted during use as cathodic current distributing members. They are therefore not strictly "sacrificial" in this context. Nonetheless, the term "sacrificial" encompasses such materials as it is intended to include materials that undergo physical and/or chemical changes during iontophoresis, such as to affect their function as measured by their lifetime or current carrying capacity, etc.

Additional types of materials useful as current distributing members according to the invention are disclosed in detail in a co-pending application Ser. No. 08/536,029 to Reddy et al., entitled "Low-Cost Electrodes for an Iontophoretic Device," filed on Sep. 29, 1995, the disclosure of which is incorporated by reference herein.

The current distributing member can take any form known in the art, such as the form of a plate, foil layer, screen, wire, dispersion of conductive particles embedded in a conductive matrix, and the like.

B. The Electrolyte Reservoir

In the iontophoretic device of the invention, an electrolyte reservoir is constructed to permit electrical communication with a current distributing member. Typically, electrical communication requires that electrons of the current distributing member are exchanged with ions in the electrolyte reservoir upon the application of electrical current. Such electrical communication is preferably not impeded to any excessive degree by any intervening material(s) used in the construction of the iontophoretic device. In other words, the resistivity of the interface between the current distributing member and the electrolyte reservoir is preferably low.

The electrolyte reservoir comprises at least one electrolyte, i.e., an ionic or ionizable component that can act to conduct current toward or away from the current distributing member. Typically, the electrolyte comprises one or more mobile ions, the selection of which is dependent upon the desired application. Examples of suitable electrolytes include aqueous solutions of salts. A preferred electrolyte is an aqueous solution of sodium chloride (NaCl), having a concentration of less than 1 mole/liter (<1 M), more preferably at about physiological concentration. Other suitable electrolytes include salts of physiological ions including, but not limited to, potassium ($K^+$), chloride ($Cl^-$), and phosphate ($PO_4^{3-}$). The salt and its concentration can be selected as desired for particular applications.

Other chemical species can be selected by the skilled artisan for inclusion in the electrolyte reservoir. Such other species include, without limitation, chelation agents (e.g., citrate ions, EDTA) surfactants (e.g., non-ionic, cationic, or anionic), buffers, ionic excipients, osmolarity adjusters (e.g., polyethylene glycols, sugars), ionic antibiotics, penetration enhancers (e.g., alkanols), stabilizers, enzyme inhibitors, preservatives, thickening agents (e.g., acrylic acids, cellulosic resins, clays, polyoxyethylenes), and the like. Inclusion of such species is made to selectively control or modulate the function of the electrolyte reservoir in particular circumstances.

Alternatively, the electrolyte can comprise a material that is itself relatively immobile in the absence of an electric field, but that acts to deliver mobile ions in the presence of an electric field. In the latter case, the electrolyte can more properly be termed an "ion source." Examples of ion sources according to the invention include polyelectrolytes, ion exchange membranes and resins, non-ionic buffers that become ionic upon pH change, and other known ion sources.

Alternatively, the electrolyte reservoir can contain counterions, i.e., ions that form a soluble salt with an electrochemically generated ion. For example, in an apparatus employing a silver anodic current distributing member, a suitable counterion might be acetate ($CH_3COO^-$) or nitrate ($NO_3^-$). Such counterions are useful when other means are provided for sequestering electrochemically generated ions.

Thus, the electrolyte reservoir can provide at least one ion of the same charge as the electrochemically generated ion, to permit current to be conducted, and at least one oppositely charged ion.

C. The Agent Reservoir

The reservoir structure of the iontophoretic apparatus of the invention further includes an agent reservoir in the active electrode, containing the agent to be delivered, i.e., the CAR antagonist. Preferably, the agent is present as an ionized or ionizable form of the agent or a precursor of the agent such as an ester prodrug. The agent reservoir must be capable of ionic communication with an epithelial surface, which means that the boundary between the agent reservoir and the epithelial surface must be permeable to some form of the agent (and may also be permeable to other ions), as the current is carried by ions traversing across the boundary. The agent reservoir is also in electrical communication with the anode or the cathode of the iontophoresis device.

The construction of the agent reservoir must be consistent with the requirements for ionic communication with the epithelial surface and electrical communication with the current distribution member. Accordingly, the structure of the agent reservoir would vary, depending upon the desired application. The agent reservoir can include a liquid, semi-liquid, semi-solid, or solid material. With a flowable material, the agent reservoir preferably further comprises means for at least substantially inhibiting the flow of the contents out of the reservoir. In such situations, the flow of the contents is desirably minimized when the device is in storage. For example, a membrane can be deployed to define a wall of the agent reservoir. In certain situations the flow of the contents of the reservoir can be minimized while in storage, but increased in use. For example, a membrane can be used that increases in porosity, permeability, or conductivity upon the application of an electric field across the membrane. Examples of such membranes are disclosed in U.S. Pat. Nos. 5,080,546; 5,169,382; and 5,232,438, the disclosures of which are incorporated by reference herein.

In preferred embodiments, the agent reservoir is constructed to retain its physical integrity and to inherently resist passive migration and loss of the ionized substance. Such embodiments include those in which the agent reservoir includes a solid or semi-solid material such as a gel or other polymeric material. In an especially preferred embodiment, the agent reservoir includes a polymeric film in which the substance to be iontophoretically delivered is dispersed. While such a film would resist passive loss or dispersion of the ionized substance in the absence of an applied electrical field, the mobility of the substance to be delivered is substantially increased upon the application of the electric field, permitting effective and controlled delivery across the target epithelial surface. Such a film need not contain any significant amount of hydrating material. In preferred embodiments, a cross-linked hydrogel, a material that inherently contains significant amounts of water, can be used in the electrolyte reservoir to serve as a water reservoir during iontophoresis.

It may be desirable to provide the solution of active ingredient with a buffer. The buffer ion having a charge of the same sign as the drug ion should have low ionic mobility. The limiting ionic mobility of this ion is preferably no greater that $1\times10^{-4}$ $cm^2$/volt-sec.

Additionally, as disclosed and claimed in U.S. patent application Ser. No. 60/026,862, filed on Sep. 30, 1996, and entitled "Selectable Drug Delivery Profiles Using Competing Ions" (Attorney Docket No. P-3730), it may be desirable to control the flux profile of the drug being delivered by iontophoresis by adding to or having present in the agent reservoir, ions that would compete with the drug ions for current (competing ions). To achieve various flux profiles for the drug being iontophoretically delivered, one can apply constant current but vary the concentration of the competing ions.

D. The Ionizable Substance (Agent) for Iontophoretic Delivery

As noted, ionic drugs can be delivered from either the anode, the cathode, or both simultaneously. For example, if the agent to be driven into the body has a net positive charge, i.e, a cation, then the positive electrode (anode) will be the active electrode, and the negative electrode (cathode) will serve to complete the electrochemical circuit. This method of delivery is termed "anodic delivery." Alternatively, if the agent to be delivered has a net negative charge, i.e., an anion, then the negative electrode (cathode) will be the active electrode and the positive electrode (anode) will be the indifferent electrode. This method of delivery is termed "cathodic delivery."

It is believed that this invention has utility in connection with the delivery of agents within the broad class of cell adhesion antagonist molecules as well as chemical modifications of cell adhesion antagonist molecules.

E. Protective Backing

The iontophoretic apparatus of the invention can also include a suitable backing film positioned on top of the electrolyte reservoir. The backing film provides protection against contamination and damage to the current distributing member, if present, and the electrolyte reservoir of the apparatus.

F. Release Liner

The iontophoretic apparatus of the invention optionally includes a release liner that can be affixed to the underside of the agent reservoir by an adhesive. The release liner protects the surface of the agent reservoir that contacts the epithelial surface from contamination and damage when the device is not in use. When the device is ready for use, the release liner can be peeled off to expose the epithelial contacting surface of the agent reservoir for application of the device to a patient.

G. Indifferent Electrode

Again, as noted above, iontophoretic devices require at least two electrodes to provide a potential to drive drug ions into the skin of a patient. Both electrodes are disposed to be in intimate electrical contact with the skin thereby completing the electrochemical circuit formed by the anode pad and cathode pad of the iontophoretic device. The electrode pads can be further defined as an active electrode from which an ionic drug is delivered into the body. An indifferent or ground electrode serves to complete the electrochemical circuit. Various types of electrodes can be employed, such as is described in U.S. application Ser. No. 08/536,029, mentioned hereinabove.

To further illustrate the iontophoretic device of the invention, the reader's attention is directed to FIG. 1. As shown in FIG. 1, an embodiment of the iontophoretic device of the invention 50 is configured as follows:

An anode patch 10 has an anode electrode compartment 11 in ionic communication with a skin contacting compartment 13. The skin contacting compartment 13 and the anode electrode compartment 11 are separated by a compartment separation means (membrane) 17. The anode electrode compartment 11 also contains an anode 14 and an electrolyte (anolyte) 15. The skin contacting compartment is attached to the patient's skin 36. A cathode patch 20, has a cathode electrode compartment 21 in ionic communication with a skin contacting compartment 23. The skin contacting compartment 23 and the cathode electrode compartment 21 are separated by a compartment separation means (membrane) 27. The cathode electrode compartment 21 also contains a cathode 24 and an electrolyte (catholyte) 25. The skin contacting compartment is attached to the patient's skin 36.

Another embodiment of the present invention relates to an iontophoretic device for non-invasively administering a therapeutic concentration of cell adhesion antagonist molecules to a mammal, such therapeutic concentration of cell adhesion antagonist molecules being capable of inhibiting platelet aggregation.

(a) a current distributing member;

(b) an agent reservoir containing an ionized or ionizable substance, in electrical communication with the current distributing member and adapted to be placed in ionic communication with the epithelial surface;

wherein the ionized or ionizable substances are cell adhesion antagonist molecules. This device is capable of delivering an amount of cell adhesion antagonist molecules effective for inhibiting platelet aggregation in the patient to whom its delivered for a selected period of time; and (c) an electrolyte reservoir containing an electrolyte, in electrical communication with an indifferent electrode and in ionic communication with the epithelial surface;

(d) an electrical power source in current delivering connection with the current distribution member and the electrolyte reservoir.

A variety of iontophoresis patch designs can be suitably used in the present invention. For example, iontophoretic delivery devices have been developed in which the donor and counter electrode assemblies have a "multi-laminate" construction. In these devices, the donor and counter electrode assemblies are each formed by multiple layers of usually polymeric matrices. For example, U.S. Pat. No. 4,731,049 discloses a donor electrode assembly having a hydrophilic polymer based electrolyte reservoir and drug reservoir layers, a skin-contacting hydrogel layer, and optionally one or more semipermeable membrane layers. U.S. Pat. No. 4,474,570 discloses an iontophoresis device wherein the electrode assemblies include a conductive resin film electrode layer, a hydrophilic gel reservoir layer, and aluminum foil conductor layer and an insulating backing layer.

The drug and electrolyte reservoir layers of the iontophoretic delivery device can be, for example, formed of hydrophilic polymers, as described, for example, in U.S. Pat. Nos. 4,474,570, 4,383,529, 4,764,164. Hydrophilic polymers may be desired since water is the preferred solvent for ionizing many drug salts, and hydrophilic polymer components of the drug reservoir in the donor electrode and the electrolyte reservoir in the counter electrode can be hydrated in situ while attached to the body by absorbing water from the skin through transepidermal water loss or sweat or from a mucosal membrane by absorbing saliva in the case of oral mucosal membranes. Once hydrated, the device begins to deliver ionized agent to the body. This enables the drug reservoir to be manufactured in a dry state, giving the device a longer shelf life. Hydrogels have been particularly favored for use as the drug reservoir matrix and electrolyte reservoir matrix in iontophoretic delivery devices, in part due to their high equilibrium water content and their ability to quickly absorb water. In addition, hydrogels tend to have good biocompatibility with the skin and with mucosal membranes.

Iontophoresis devices useful in the present invention are described, for example, in the following U.S. Patent documents, the disclosures of which are incorporated herein by reference: U.S. Pat. Nos. 3,991,755; 4,141,359; 4,250, 878; 4,395,545; 4,744,787; 4,747,819; 4,927,408; 5,080, 646; 5,084,006; 5,125,894; 5,135,477; 5,135,480; 5,147, 296; 5,147,297; 5,158,537; 5,162,042; 5,162,043; 5,167, 616; 5,169,382; 5,169,383; 5,415,628; 5,203,768; 5,207, 752; 5,221,254; 5,232,438; 5,234,992; 5,240,995; 5,246, 417; 5,288,389; 5,298,017; 5,310,404; 5,312,326; 5,314, 502; 5,320,598; 5,322,502; 5,326,341; 5,344,394; 5,374, 242; 5,380,271; 5,385,543; 5,387,189; 5,395,310; 5,403, 275; 5,405,317; 5,415,628; 5,423,739; 5,443,442; 5,445, 606; 5,445,609; 5,464,387; 5,466,217; 4,950,229; 5,246, 418; 5,256,137; 5,284,471; 5,302,172; 5,306,235; 5,310, 403; 5,320,597; 5,458,569; 5,498,235; 4,557,723; 4,713, 050; 4,865,582; 4,752,285; 5,087,242; 5,236,412; 5,281, 287.

Other useful iontophoretic methods and devices are described in U.S. applications Ser. Nos. 08/707,555, filed on Sep. 4, 1996; 08/722,813, filed on Sep. 27, 1996; 08/722, 816, filed on Sep. 27, 1996; 08/720,125, filed on Sep. 27, 1996; 08/722,814, filed on Sep. 27, 1996; and 08/722,760, filed on Sep. 27, 1996; the disclosures of which are incorporated herein by reference.

Nonetheless, while the present invention is generally described in connection with iontophoresis, it should be appreciated that other principles of active introduction, i.e., motive forces, can be employed to deliver CAR antagonists as contemplated herein. Accordingly, the invention is understood to be operative in connection with electrophoresis, which includes the movement of particles in an electric field toward one or the other electric pole (anode or cathode), and electroosmosis, which includes the transport of uncharged compounds due to the bulk migration of water induced by an electric field.

In particular, the delivery of an uncharged medicament into a patient cannot directly be achieved through iontophoresis, as by definition the compound has no net charge. However, the delivery of an uncharged medicament into a patient may be accomplished by modifying the process in any of several ways. For example, uncharged compounds (an charged compounds having no net charge, i.e., zwitterions) can be delivered through the process of electroosmosis. In electroosmosis, an electrical device is used to induce the flow of a polar liquid medium, carrying the medicament, into a patient by imposing an electric field across the skin. As a result of this bulk flow of the liquid medium, the uncharged medicament is indirectly transported along with the liquid medium into the patient. The delivery of a medicament through electroosmosis is highly dependent on skin pH. The drug delivery aspect of electroosmosis is a minor or secondary effect in comparison to iontophoretic repulsion. Accordingly, the amount of the medicament delivered by electroosmosis tends to be lower than that in iontophoresis.

Iontophoresis of agents having no net charge can also be accomplished by combining the agent with a charged carrier moiety. For example the promotion of iontophoresis by combining the agent with ionic or charge-bearing cyclodextrins is disclosed in U.S. Pat. No. 5,068,226 to Weinshenker et al. Alternatively, the agent can be incorporated into the device with an amphipathic material as the carrier moiety, i.e., a material having lipophilic and hydrophilic domains. The hydrophilic domains can present with either net positive or net negative charge, permitting the electric field applied through the iontophoretic device to impel the amphipathic carrier moiety across the skin of the subject. Preferred amphipathic materials include, for example, phospholipids. The amphipathic material can be delivered in a variety of structural (supramolecular) forms, such as liposomes, unilamellar or multi-lamellar vesicles, micelles, and the like. The production of the structural forms can be accomplished using known methods, such as the methods for making liposomes described in U.S. Pat. No. 4,522,803 to Lenk et al. and U.S. Pat. No. 4,610,868 to Fountain et al., or the method for making micelles incorporating medicaments as described in U.S. Pat. No. 5,051,435 to Paradies.

Methods of Use

Generally, the present invention is a method and system for the non-invasive administration of therapeutic concentration of cell adhesion antagonist molecules to a human or animal subject. The invention permits iontophoretic transdermal administration of numerous cell adhesion receptor antagonists or inhibitors, including:

Integrin inhibitors such as, for example, glycoprotein IIb/IIIa ($\alpha_{IIb}\beta_3$) antagonists, glycoprotein Ic/IIIa antagonists, $\alpha_v\beta_3$ antagonists, $\alpha_v\beta_5$ antagonists, $\alpha_5\beta_1$ (GP Ic/IIa) antagonists, $\alpha_2\beta_1$ (GP Ia/IIa) antagonists, and $\alpha_6\beta_1$ antagonists;

Non-Integrin Receptor inhibitors such as, for example, glycoprotein Ib (GP Ib) antagonists, and glycoprotein IV (GP IV) antagonists;

as well as other CAR antagonists.

The present invention enables non-invasive administration of a therapeutic concentration of cell adhesion antagonist molecules to a mammal. The cell adhesion antagonist molecules are iontophoretically passed through a predetermined area of skin of the mammal, and a therapeutic concentration of cell adhesion antagonist molecules is achieved.

The method and device of the present invention can be used to administer a cell adhesion antagonist molecule to a mammal. Mammals include, for example, humans, as well as pet animals such as dogs and cats, laboratory animals such as rats and mice, and farm animals such as horses, pigs, sheep, and cows.

Inhibitors of the IIb/IIIa CAR are useful as therapeutic antithrombotic agents. IIb/IIIa antagonists bind to IIb/IIIa expressed on the membranes of platelets. By binding to IIb/IIIa, these agents prevent platelets from aggregating. Platelet aggregation is associated with various cardiovascular and cerebrovascular disorders, including unstable angina, myocardial infarction, stroke, and atherosclerosis. IIb/IIIa antagonists are useful in preventing platelet aggregation and thrombosis, and for the treatment, including prevention, of various cardiovascular and cerebrovascular disorders.

IIb/IIIa antagonists have been found to have relatively steep dose versus response profiles. Thus, within a relatively narrow range of plasma concentrations, the effect of a IIb/IIIa antagonist could vary from no anticoagulant effect, to partial inhibition of platelet aggregation, to excessive prolongation of coagulation. In addition, IIb/IIIa antagonists can have relatively low to modest or variable oral bioavailability. Low and variable oral bioavailability can be associated with variability, if not unpredictability, in plasma concentrations and poor control of pharmacologic and toxic responses.

By contrast, the controlled iontophoretic transdermal delivery methods of the present invention, provide methods for administering a IIb/IIIa antagonist at a constant, relatively low rate, thereby to provide plasma concentrations and effects that do not vary excessively with time or from patient to patient. Accordingly, the methods and apparatus of the invention provide therapeutic advantages over methods of drug delivery that produce variable plasma concentrations and effects.

Another preferred aspect of this invention relates to iontophoretic methods of pharmaceutical delivery of compounds that are antagonists of the $\alpha_v\beta_3$ integrin. Such compounds inhibit the binding of vitronectin or other RGD-containing ligands to $\alpha_v\beta_3$ and inhibit cell adhesion. The present invention also includes iontophoresis devices containing such $\alpha_v\beta_3$ inhibitor compounds and methods of using such devices for the inhibition of angiogenesis, the treatment of disorders mediated by angiogenesis, thrombosis, restenosis, and other diseases or conditions mediated by or involving cell adhesion and/or cell migration and/or angiogenesis, including, but not limited to, other thromboembolic disorders, inflammation, inflammatory bowel disease and other autoimmune diseases, rheumatoid arthritis, asthma, allergies, adult respiratory distress syndrome, graft versus host disease, organ transplantation, septic shock, psoriasis, eczema, contact dermatitis, osteoporosis, osteoarthritis, atherosclerosis, cancer metastasis, wound healing, diabetic retinopathy, ocular vasculopathies, bone degradation, diabetic retinopathy, macular degeneration, and wound healing.

In preferred embodiments, the cell adhesion antagonist molecule is administered to the mammal in the treatment of diseases associated with any of the following conditions: abnormal platelet aggregation, thrombosis, rheumatoid arthritis, osteoporosis, coronary angioplasty, restenosis, cancer metastasis, asthma, organ transplant, septic shock, osteoarthritis, diabetes retinopathy, inflammatory bowel disease, atherosclerosis.

In a preferred scenario, the device is used to administer such molecules to a human or animal patient during coronary angioplasty, or for the treatment of diseases associated with abnormal platelet aggregation, thrombosis, rheumatoid arthritis, osteoporosis, restenosis, cancer metastasis, asthma, organ transplantation, septic shock, osteoarthritis, diabetes retinopathy, inflammatory bowel disease, or atherosclerosis.

As used herein, the term "treatment" of a disorder includes not only the clinical intervention in an existing disorder in the mammal, but also the prevention of the incidence or recurrence of such a disorder.

As used herein the term "angiogenic disorders" means conditions involving abnormal neovascularization, such as tumor metastasis and ocular neovascularization, including, for example, diabetic retinopathy, neovascular glaucoma, age-related macular degeneration, and retinal vein occlusion.

The term "thromboembolic disorders" as used herein includes conditions involving platelet activation and aggregation, such as arterial or venous cardiovascular or cerebrovascular thromboembolic disorders, including, for example, thrombosis, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolism, kidney embolisms, pulmonary embolisms, or such disorders associated with diabetes.

The term "therapeutically effective amount" as used herein means an amount of a CAR antagonist that when administered alone or in combination with an additional therapeutic agent to a cell or mammal is effective to treat, i.e., prevent or ameliorate, the specified disease condition or its progression.

In the method, the extrinsic current applied to drive the agent from the agent reservoir into the skin is selected by the artisan. Preferably, the current applied is from about 10 $\mu$A to about 3 mA. The current is preferably applied continuously to the system for periods of up to about 24 hours, to provide smooth, constant flux of the agent effective to provide therapeutic blood concentration. However, a current of from about 10 $\mu$A to about 3 mA can also be applied discontinuously to the system for periods of up to about 24 hours.

Applicants have recognized that some cell adhesion antagonist molecules are zwitterions, carrying both positive and negative charges. Typically, the charges offset one another, such that the individual zwitterionic molecules have no net charge—they are electrically neutral and, therefore, substantially insensitive to electromotive force such as that imposed during iontophoresis. To deliver a zwitterionic molecule iontophoretically across the skin in adequate quantity, the molecule must have a net charge. Therefore, it is recognized that the molecules may need to be modified in order to deliver them iontophoretically. Such modification can be accomplished through processes and methods known to those of ordinary skill in the art. By way of example and not limitation, such modification can be accomplished by esterification of the molecule, or by addition or deletion of amino acids, or by association with a charged carrier moiety as mentioned hereinabove.

Chemical Structures of CAR Antagonists

Representative CAR antagonist compounds, including IIb/IIIa inhibitors, that can be delivered iontophoretically in the method of the present invention are disclosed in the following patents and patent applications: PCT Patent Application 95/14683; copending, commonly assigned U.S. patent application Ser. No. 08/455,768 filed May 31, 1995; copending, commonly assigned U.S. patent application Ser. No. 08/449,597 filed May 24, 1995; copending, commonly assigned U.S. patent application Ser. No. 08/455,768 filed May 31, 1995; copending, commonly assigned U.S. patent application Ser. No. 60/009,088 filed Dec. 22, 1995; copending, commonly assigned U.S. patent application Ser. No. 60/013,539 filed Mar. 15, 1996; PCT Patent Application 95/32710; U.S. Pat. No. 5,334,596; U.S. Pat. No. 5,276,049; U.S. Pat. No. 5,281,585; European Patent Application 478, 328; European Patent Application 478,363; European Patent Application 512,831; PCT Patent Application 94/08577; PCT Patent Application 94/08962; PCT Patent Application 94/18981; PCT Patent Application 93/16697; Canada Patent Application 2,075,590; PCT Patent Application 93/18057; European Patent Application 445,796; Canada Patent Application 2,093,770; Canada Patent Application 2,094,773; Canada Patent Application 2,101,179; Canada Patent Application 2,074,685; Canada Patent Application 2,094,964; Canada Patent Application 2,105,934; Canada Patent Application 2,114,178; Canada Patent Application 2,116,068; European Patent Application 513,810; PCT Patent Application 95/06038; European Patent Application 381,033; PCT Patent Application 93/07867; and PCT Patent Application 94/02472. Other useful compounds are disclosed in PCT publication WO 96/41803. The entire disclosures of all of these documents are incorporated herein by reference.

One aspect of this invention provides novel compounds of Formula I:

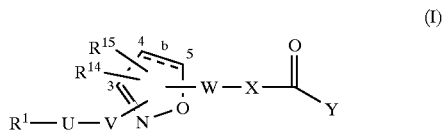

(I)

in which the substituent groups are as defined hereinbelow. These compounds are useful as antagonists of, for example, the $\alpha_v\beta_3$ or vitronectin receptor. The compounds of the present invention inhibit the binding of vitronectin and other RGD-containing ligands to $\alpha_v\beta_3$ and inhibit cell adhesion. The present invention also includes pharmaceutical compositions containing such compounds of Formula I with or without a pharmaceutically acceptable carrier, and methods of using such compounds for the inhibition of angiogenesis, and/or for the treatment of angiogenic disorders.

The compounds herein described can have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention that contain asymmetrically substituted carbon atoms can be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable (for example, but not limited to, $R^2$, $R^4$, $R^6$, $R^7$, $R^8$, $R^{12}$, and $R^{14}$, n, etc.) occurs more than one time in any constituent or in any formula, its definition on each occurrence is independent of its definition at every other occurrence. Thus, for example, if a group is shown to be substituted with 0-2 $R^4$, then the group can optionally be substituted with up to two $R^4$, and $R^4$ at each occurrence is selected independently from the defined list of possible $R^4$. Also, by way of example, for the group —N($R^{5a}$)$_2$, each of the two $R^{5a}$ substituents on N is selected independently from the defined list of possible $R^{5a}$. Similarly, by way of example, for the group —C($R^7$)$_2$—, each of the two $R^7$ substituents on C is selected independently from the defined list of possible $R^7$.

When a bond to a substituent is shown to cross the bond connecting two atoms in a ring, then such substituent can be bonded to any atom on the ring. When a bond joining a substituent to another group is not specifically shown or the atom in such other group to which the bond joins is not specifically shown, then such substituent can form a bond with any atom on such other group.

When a substituent is listed without indicating the atom via which such substituent is bonded to the rest of the compound, then such substituent can be bonded via any atom in such substituent. For example, when the substituent is piperazinyl, piperidinyl, or tetrazolyl, unless specified otherwise, the piperazinyl, piperidinyl, tetrazolyl group can be bonded to the rest of the compound via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted," as used herein, means that any one or more hydrogen on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

As used herein, "alkyl" is intended to include both branched and straight-chain saturated aliphatic hydrocarbon groups having the specified number of carbon atoms (for example, "$C_0$–$C_{10}$" denotes alkyl having 0 to 10 carbon atoms; thus, $C_0$ denotes a direct bond between the groups linked by the $C_0$ group); "haloalkyl" is intended to include both branched and straight-chain saturated aliphatic hydrocarbon groups having the specified number of carbon atoms, substituted with 1 or more halogen (for example –$C_vF_w$, where v=1 to 3 and w=1 to (2v+1)); "alkoxy" represents an alkyl group of indicated number of carbon atoms attached through an oxygen bridge; "cycloalkyl" is intended to include saturated ring groups, including mono-,bi- or polycyclic ring systems, such as cyclopropyl, cyclobutyl, cyclopentyl, cyclohexyl, cycloheptyl, cyclooctyl, and adamantyl; and "biycloalkyl" is intended to include saturated bicyclic ring groups such as [3.3.0]bicyclooctane, [4.3.0] bicyclononane, [4.4.0]bicyclodecane (decalin), [2.2.2] bicyclooctane, and so forth. "Alkenyl" is intended to include hydrocarbon chains of either a straight or branched configuration and one or more unsaturated carbon-carbon bonds that can occur in any stable point along the chain, such as ethenyl, propenyl and the like; and "alkynyl" is intended to include hydrocarbon chains of either a straight or branched configuration and one or more triple carbon-carbon bonds that can occur in any stable point along the chain, such as ethynyl, propynyl and the like.

The terms "alkylene," "alkenylene," "phenylene," and the like, refer to alkyl, alkenyl, and phenyl groups, respectively, which are connected by two bonds to the rest of the structure. Such "alkylene," "alkenylene," "phenylene," and the like, can alternatively and equivalently be denoted herein as "-(alkyl)-", "-(alkyenyl)-" and "(phenyl)-", and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl; the term "arylalkyl" represents an aryl group attached through an alkyl bridge.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which can be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic" is intended to mean a stable 5- to 7-membered monocyclic or bicyclic or 7- to 10-membered bicyclic heterocyclic ring that can be saturated, partially unsaturated, or aromatic, and that consists of carbon atoms and from 1 to 4 heteroatoms independently selected from the group consisting of N, O, and S and wherein the nitrogen and sulfur heteroatoms can optionally be oxidized, and the nitrogen can optionally be quaternized, and including any bicyclic group in which any of the above-defined heterocyclic rings is fused to a benzene ring. The heterocyclic ring can be attached to its pendant group at any heteroatom or carbon atom that results in a stable structure. The heterocyclic rings described herein can be substituted on carbon or on a nitrogen atom if the resulting compound is stable. Examples or such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, isoxazolinyl, isoxazolyl, quinolinyl, isoquinolinyl, benzimidazolyl, piperidinyl, 4-piperidinyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5 thiadiazinyl, 2H,6H-1,5,2-dithiazinyl, thianthrenyl, pyranyl, isobenzofuranyl, chromenyl, xanthenyl, phenoxathiinyl, 2H-pyrrolyl,-pyrrolyl, imidazolyl, pyrazolyl, isothiazolyl, isoxazolinyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazole, carbazole, ,β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Also included are fused ring and spiro compounds containing, for example, the above heterocycles.

As used herein, the term "heteroaryl" refers to aromatic heterocyclic groups. Such heteroaryl groups are preferably 5- to 6-membered monocyclic groups or 8- to 10-membered fused bicyclic groups. Examples of such heteroaryl groups include, but are not limited to pyridyl (pyridinyl), pyrimidinyl, furanyl (furyl), thiazolyl, thienyl, pyrrolyl, pyrazolyl, imidazolyl, indolyl, isoxazolyl, oxazolyl, pyrazinyl, pyrimidinyl, pyridazinyl, benzofuranyl, benzothienyl, benzimidazolyl, quinolinyl, or isoquinolinyl.

As used herein, "prodrugs" refer to any covalently bonded carriers that release the active parent drug in vivo when such prodrug is administered to a mammalian subject. Prodrugs of the CAR antagonist compounds specified herein are prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds, and the like.

As used herein, "pharmaceutically acceptable salts" refer to derivatives of the disclosed compounds wherein the parent compound is modified by making acid or base salts of the compound. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the compounds useful in the present invention include the conventional non-toxic salts or the quaternary ammonium salts of the compounds, formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glutaric, glutaconic, tricarballylic, glycolic, stearic, lactic, malic, tartaric, citric, ascorbic, pamoic, maleic, hydroxymaleic, phenylacetic, glutamic, benzoic, naphthoic, salicylic, sulfanilic, 2-acetoxybenzoic, fumaric, toluenesulfonic, methanesulfonic, ethane disulfonic, oxalic, isothionic, and the like. Suitably acceptable salts also include inorganic base salts, such as alkali metal salts, for example, sodium or potassium salts.

The pharmaceutically acceptable salts of the compounds of the present invention that contain a basic or acidic moiety can be prepared by conventional chemical methods. Generally, the salts are prepared by reacting the free base or acid with stoichiometric amounts or with an excess of the desired salt-forming inorganic or organic acid or base in a suitable solvent or various combinations of solvents.

Pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found on p. 1418 in *Remington's Pharmaceutical Sciences,* 17th ed., Mack Publishing Company, Easton, Pa. (1985), the disclosure of which is hereby incorporated by reference.

In one embodiment (designated embodiment IV), the device includes, and can be used to deliver, a compound of Formula I:

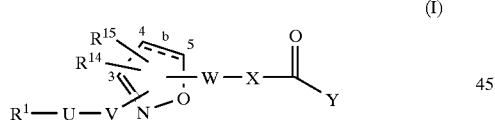

or pharmaceutically acceptable salt forms thereof, wherein:
b is a carbon-carbon single or double bond;
$R^1$ is selected from:
$R^2(R^3)N(CH_2)_qZ-$, $R^2(R^3)N(R^2N=)CN(R^2)(CH_2)_qZ-$, piperazinyl-$(CH_2)_qZ-$, or

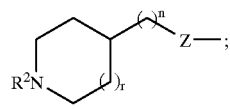

Z is selected from: O, S, S(=O), or S(=O)$_2$;
$R^2$ and $R^3$ are selected independently from:
H, $C_1$–$C_{10}$ alkyl, $C_2$–$C_6$ alkenyl, $C_3$–$C_{11}$ cycloalkyl, $C_4$–$C_{11}$ cycloalkylalkyl, $C_6$–$C_{10}$ aryl, $C_7$–$C_{11}$, arylalkyl, $C_2$–$C_7$ alkylcarbonyl, $C_6$–$C_{10}$ arylcarbonyl, $C_2$–$C_{10}$ alkoxycarbonyl, $C_4$–$C_{11}$ cycloalkoxycarbonyl, $C_7$–$C_{11}$ bicycloalkoxycarbonyl, $C_6$–$C_{10}$ aryloxycarbonyl, aryl($C_1$–$C_{10}$ alkoxy)carbonyl, $C_1$–$C_6$ alkylcarbonyloxy($C_1$–$C_4$ alkoxy)carbonyl, $C_6$–$C_{10}$ arylcarbonyloxy($C_1$–$C_4$ alkoxy)carbonyl, $C_4$–$C_{11}$ cycloalkylcarbonyloxy($C_1$–$C_4$ alkoxy)carbonyl;

U is selected from:
a single bond, -($C_1$–$C_7$ alkyl)-, -($C_2$–$C_7$ alkenyl)-, -($C_2$–$C_7$ alkynyl)-, -(aryl)-, substituted with 0–3 $R^{6a}$, or -(pyridyl)-, substituted with 0–3 $R^{6a}$;

V is selected from:
a single bond;
-($C_1$–$C_7$ alkyl)-, substituted with 0–3 groups selected independently from $R^6$ or $R^7$;
-($C_2$–$C_7$ alkenyl)-, substituted with 0–3 groups selected independently from $R^6$ or $R^7$;
-($C_2$–$C_7$ alkynyl)-, substituted with 0–2 groups selected independently from $R^6$ or $R^7$;
-(aryl)-, substituted with 0–2 groups selected independently from $R^6$ or $R^7$;
-(pyridyl)-, substituted with 0–2 groups selected independently from $R^6$ or $R^7$; or
-(pyridazinyl)-, substituted with 0–2 groups selected independently from $R^6$ or $R^7$;

W is selected from:
a single bond, -($C_1$–$C_7$ alkyl)-, -($C_2$–$C_7$ alkenyl)-, -($C_2$–$C_7$ alkynyl)-, or —(C($R^5$)$_2$)$_n$C(=O)N($R^{5a}$)—;

X is selected from:
a single bond;
-($C_1$–$C_7$ alkyl)-, substituted with 0–3 groups selected independently from $R^4$, $R^8$, and $R^{14}$;
-($C_2$–$C_7$ alkenyl)-, substituted with 0–3 groups selected independently from: $R^4$, $R^8$, and $R^{14}$;
-($C_2$–$C_7$ alkynyl)- substituted with 0–2 groups selected independently from $R^4$, $R^8$, and $R^{14}$; or

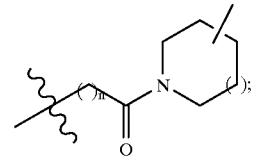

Y is selected from:
hydroxy, $C_1$–$C_{10}$ alkyloxy, $C_3$–$C_{11}$ cycloalkyloxy, $C_6$–$C_{10}$ aryloxy, $C_7$–$C_{11}$ aralkyloxy, $C_3$–$C_{10}$ alkylcarbonyloxyalkyloxy, $C_3$–$C_{10}$ alkoxycarbonyloxyalkyloxy, $C_2$–$C_{10}$ alkoxycarbonylalkyloxy, $C_5$–$C_{10}$ cycloalkylcarbonyloxyalkyloxy, $C_5$–$C_{10}$ cycloalkoxycarbonyloxyalkyloxy, $C_5$–$C_{10}$ cycloalkoxycarbonylalkyloxy, $C_7$–$C_{11}$ aryloxycarbonylalkyloxy, $C_8$–$C_{12}$ aryloxycarbonyloxyalkyloxy, $C_8$–$C_{12}$ arylcarbonyloxyalkyloxy, $C_5$–$C_{10}$ alkoxyalkylcarbonyloxyalkyloxy, $C_5$–$C_{10}$ (5-alkyl-1,3-dioxa-cyclopenten-2-one-yl)-methyloxy, $C_{10}$–$C_{14}$ (5-aryl-1,3-dioxa-cyclopenten-2-one-yl)-methyloxy; or
($R^2$)($R^3$)N—($C_1$–$C_{10}$ alkoxy)-;

$R^4$ and $R^{4b}$ are selected independently from:
H, $C_1$–$C_{10}$ alkyl, hydroxy, $C_1$–$C_{10}$ alkoxy, nitro, $C_1$–$C_{10}$ alkylcarbonyl, or —N($R^{12}$)$R^{13}$;

$R^5$ is selected from:
H, $C_1$–$C_8$ alkyl, $C_2$–$C_6$ alkenyl, $C_3$ cycloalkyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^{4b}$;

$R^{5a}$ is selected from:
hydrogen, hydroxy, $C_1$–$C_8$ alkyl, $C_2$–$C_6$ alkenyl, $C_3$–$C_{11}$ cycloalkyl, $C_4$–$C_{11}$ cycloalkylmethyl, $C_1$–$C_6$ alkoxy, benzyloxy, $C_6$–$C_{10}$ aryl, heteroaryl, heteroarylalkyl, $C_7$–$C_{11}$ arylalkyl, adamantylmethyl or $C_1$–$C_{10}$ alkyl substituted with 0–2 $R^{4b}$;

alternately, $R^5$ and $R^{5a}$ can be taken together to be:
3-azabicyclononyl, 1-piperidinyl, 1-morpholinyl or 1-piperazinyl, each optionally substituted with $C_1$–$C_6$ alkyl, $C_6$–$C_{10}$ aryl, heteroaryl, $C_7$–$C_{11}$ arylalkyl, $C_1$–$C_6$ alkylcarbonyl, $C_3$–$C_7$ cycloalkylcarbonyl, $C_1$–$C_6$ alkoxycarbonyl, $C_7$–$C_{11}$ arylalkoxycarbonyl, $C_1$–$C_6$ alkylsulfonyl or $C_6$–$C_{10}$ arylsulfonyl;

$R^{5b}$ is selected from:
$C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^{4b}$;

$R^6$ is selected from:
H, $C_1$–$C_{10}$ alkyl, hydroxy, $C_1$–$C_{10}$ alkoxy, nitro, $C_1$–$C_{10}$ alkylcarbonyl, —$N(R^{12})R^{13}$, cyano, halo, $CF_3$, CHO, $CO_2R^5$, $C(=O)R^{5a}$, $CONR^5R^{5a}$, $OC(=O)R^{5a}$, $OC(=O)OR^{5b}$, $OR^{5a}$, $OC(=O)NR^5R^{5a}$, $OCH_2CO_2R^5$, $CO_2CH_2CO_2R^5$, $NO_2$, $NR^{5a}C(=O)R^{5a}$, $NR^{5a}C(=O)OR^{5b}$, $NR^{5a}C(=O)NR^5R^{5a}$, $NR^{5a}SO_2NR^5R^{5a}$, $NR^{5a}SO_2R^5$, $S(O)_pR^{5a}$, $SO_2NR^5R^{5a}$, $C_2$–$C_6$ alkenyl, $C_3$–$C_{11}$ cycloalkyl, $C_4$–$C_{11}$ cycloalkylmethyl; $C_6$–$C_{10}$ aryl optionally substituted with 1–3 groups selected from:
halogen, $C_1$–$C_6$ alkoxy, $C_1$–$C_6$ alkyl, $CF_3$, $S(O)_mCH_3$, or —$N(CH_3)_2$;
$C_7$–$C_{11}$ arylalkyl, the aryl being optionally substituted with 1–3 groups selected from:
halogen, $C_1$–$C_6$ alkoxy, $C_1$–$C_6$ alkyl, $CF_3$, $S(O)_mCH_3$, or —$N(CH_3)_2$;
methylenedioxy when $R^6$ is a substituent on aryl; or
a 5–10 membered heterocyclic ring containing 1–3 N, O, or S heteroatoms, wherein the heterocyclic ring can be saturated, partially saturated, or fully unsaturated, the heterocyclic ring being substituted with 0–2 $R^7$; $R^{6a}$ is selected from $C_1$–$C_4$ alkyl, $C_1$–$C_4$ alkoxy, halo, $CF_3$, $NO_2$, or $NR^{12}R^{13}$;

$R^7$ is selected from:
H, $C_1$–$C_{10}$ alkyl, hydroxy, $C_1$–$C_{10}$ alkoxy, nitro, $C_1$–$C_{10}$ alkylcarbonyl, —$N(R^{12})R^{13}$, cyano, halo, $CF_3$, CHO, $CO_2R^5$, $C(=O)R^{5a}$, $CONR^5R^{5a}$, $OC(=O)R^{5a}$, $OC(=O)OR^{5b}$, $OR^{5a}$, $OC(=O)NR^5R^{5a}$, $OCH_2CO_2R^5$, $CO_2CH_2CO_2R^5$, $NO_2$, $NR^{5a}C(=O)R^{5a}$, $NR^{5a}C(=O)OR^{5b}$, $NR^{5a}C(=O)NR^5R^{5a}$, $NR^{5a}SO_2NR^5R^{5a}$, $NR^{5a}SO_2R^5$, $S(O)_pR^{5a}$, $SO_2NR^5R^{5a}$, $C_2$–$C_6$ alkenyl, $C_3$–$C_{11}$ cycloalkyl, $C_4$–$C_{11}$ cycloalkylmethyl, $C_6$–$C_{10}$ aryl, or $C_7$–$C_{11}$ arylalkyl;

$R^8$ is selected from:
H, $R^6$, $C_1$–$C_{10}$ alkyl, substituted with 0–3 $R^6$, $C_2$–$C_{10}$ alkenyl, substituted with 0–3 $R^6$, $C_2$–$C_{10}$ alkynyl, substituted with 0–3 $R_6$, $C_3$–$C_8$ cycloalkyl, substituted with 0–3 $R^6$, $C_5$–$C_6$ cycloalkenyl, substituted with 0–2 $R^6$, aryl, substituted with 0–2 $R^6$; 5–10 membered heterocyclic ring containing 1–3 N, O, or S heteroatoms, wherein the heterocyclic ring can be saturated, partially saturated, or fully unsaturated, the heterocyclic ring being substituted with 0–2 $R^6$;

$R^{12}$ and $R^{13}$ are selected independently from:
H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, aryl, $C_2$–$C_6$ alkenyl, $C_3$–$C_{11}$ cycloalkyl, $C_4$–$C_{11}$ cycloalkylalkyl, $C_7$–$C_{11}$ arylalkyl, $C_2$–$C_7$ alkylcarbonyl, $C_7$–$C_{11}$ arylcarbonyl, $C_2$–$C_{10}$ alkoxycarbonyl, $C_4$–$C_{11}$ cycloalkoxycarbonyl, $C_7$–$C_{11}$ bicycloalkoxycarbonyl, $C_7$–$C_{11}$ aryloxycarbonyl, heteroarylcarbonyl, heteroarylsulfonyl, heteroarylalkylcarbonyl or aryl($C_1$–$C_{10}$ alkoxy)carbonyl;

$R^{14}$ is selected from:
H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or $C_1$–$C_{10}$ alkoxycarbonyl, $CO_2R^5$, or —$C(=O)N(R^5)R^{5a}$;

$R^{15}$ is selected from:
H; $R^6$; $C_1$–$C_{10}$ alkyl, substituted with 0–8 $R^6$; $C_2$–$C_{10}$ alkenyl, substituted with 0–6 $R^6$; $C_1$–$C_{10}$ alkoxy, substituted with 0–6 $R^6$; aryl, substituted with 0–5 $R^6$; 5–6 membered heterocyclic ring containing 1–2 N, O, or S heteroatoms, wherein the heterocyclic ring can be saturated, partially saturated, or fully unsaturated, the heterocyclic ring being substituted with 0–5 $R^6$; $C_1$–$C_{10}$ alkoxycarbonyl substituted with 0–8 $R^6$; $CO_2R^5$; or —$C(=O)N(R^5)R^{5a}$;

provided that when b is a double bond, only one of $R^{14}$ or $R^{15}$ is present;

m is 0–2;

n is 0–4;

q is 2–7;

r is 0–3;

provided that n, q, and r are chosen such that the number of in-chain atoms between $R^1$ and Y is in the range of 8–18.

The integrin inhibitors of this embodiment include compounds of Formula II:

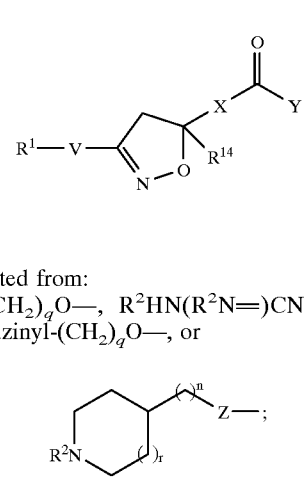

(II)

wherein:
$R^1$ is selected from:
$R^2HN(CH_2)_qO$—, $R^2HN(R^2N=)CNH(CH_2)_qO$—, piperazinyl-$(CH_2)_qO$—, or

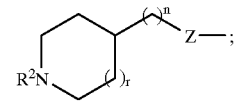

$R^2$ is selected from:
H, aryl($C_1$–$C_{10}$ alkoxy)carbonyl, $C_1$–$C_{10}$ alkoxycarbonyl;

$R^8$ is selected from:
H, $C_1$–$C_{10}$ alkyl, $C_2$–$C_{10}$ alkenyl, $C_3$–$C_8$ cycloalkyl, $C_5$–$C_6$ cycloalkenyl, aryl, 5–6 membered heterocyclic ring containing 1–2 N, O, or S heteroatoms, wherein the heterocyclic ring can be saturated, partially saturated, or fully unsaturated; and $R^6$ and $R^7$ are selected independently from:
H, $C_1$–$C_{10}$ alkyl, hydroxy, $C_1$–$C_{10}$ alkoxy, nitro, $C_1$–$C_{10}$ alkylcarbonyl, —$N(R^{12})R^{13}$, cyano, or halo.

Suitable compounds of this embodiment also include compounds wherein:

X is selected from:
a single bond; -($C_1$-$C_7$ alkyl)-, substituted with 0–2 groups selected independently from $R^4$, $R^8$ or $R^{14}$; -($C_1$-$C_7$ alkenyl)-, substituted with 0–2 groups selected independently from $R^4$, $R^8$ or $R^{14}$; -($C_1$-$C_7$ alkynyl)-, substituted with 0–2 groups selected independently from $R^4$, $R^8$ or $R^{14}$; and $R^8$ is selected from:
H, $C_1$-$C_6$ alkyl, $C_2$-$C_6$ alkenyl, $C_3$-$C_8$ cycloalkyl, $C_5$-$C_6$ cycloalkenyl, aryl, 5–6 membered heterocyclic ring containing 1–2 N, O, or S heteroatoms, wherein the heterocyclic ring can be saturated, partially saturated, or fully unsaturated.

This embodiment further includes compounds wherein:
$R^1$ is:

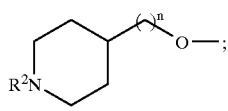

V is phenylene or pyridylene;
n is 1 or 2;
X is -($C_1$-$C_2$)alkyl- substituted with 0–2 $R^4$;
Y is selected from:
hydroxy; $C_1$-$C_{10}$ alkoxy; methylcarbonyloxymethoxy; ethylcarbonyloxymethoxy;
t-butylcarbonyloxymethoxy; cyclohexylcarbonyloxymethoxy;
1-(methylcarbonyloxy)-ethoxy; 1-(ethylcarbonyloxy)-ethoxy;
1-(t-butylcarbonyloxy)-ethoxy; 1-(cyclohexylcarbonyloxy)-ethoxy;
i-propyloxycarbonyloxymethoxy; t-butyloxycarbonyloxymethoxy;
1-(i-propyloxycarbonyloxy)-ethoxy; 1-(cyclohexyloxycarbonyloxy)-ethoxy;
1-(t-butyloxycarbonyloxy)-ethoxy; dimethylaminoethoxy; diethylaminoethoxy;
(5-methyl-1,3-dioxacyclopenten-2-on-4-yl)-methoxy;
(5-(t-butyl)-1,3-dioxacyclopenten-2-on-4 yl)-methoxy;
(1,3-dioxa-5-phenyl-cyclopenten-2-on-4-yl)-methoxy;
1-(2-(2-methoxypropyl)-carbonyloxy)-ethoxy;
$R^4$ is —$NR^{12}R^{13}$;
$R^{12}$ is selected from:
H, $C_1$-$C_4$ alkoxycarbonyl, $C_1$-$C_4$ alkylcarbonyl, $C_1$-$C_4$ alkylsulfonyl, arylalkylsulfonyl, heteroarylsulfonyl, arylsulfonyl, benzyl, benzoyl, phenoxycarbonyl, benzyloxycarbonyl, arylalkylsulfonyl, pyridylcarbonyl, or pyridylmethylcarbonyl; and
$R^{13}$ is H.

Accordingly, this embodiment includes compounds of Formula I including the following exemplary compounds, or pharmaceutically acceptable salt forms thereof:
5(R,S)-3-[[4-(2-piperidin-4-yl)-ethoxyphenyl]isoxazolin-5-yl]acetic acid;
5(R,S)-N-(butanesulfonyl)-L-{3-[4-(2-piperidin-4 yl)-ethoxyphenyl]-isoxazoline-5-yl}-glycine;
5(R,S)-N-(α-toluenesulfonyl)-L-{3-[4-(2-piperidin-4-yl)-ethoxyphenyl]-isoxazolin-5-yl}-glycine;
5(R,S)-N-[(benzyloxy)-carbonyl]-L-{3-[4-(2-piperidin-4-yl)-ethoxyphenyl]-isoxazolin-5-yl}-glycine;
5(R,S)-N-(pentanoyl)-L-{3-[4-(2-piperidin-4-yl)-ethoxyphenyl]isoxazolin-5-yl}-glycine;
5(R,S)-3-{[4-(piperidin-4-yl)-methoxyphenyl]isoxazolin-5-yl}-propanoic acid;
2(R,S)-5(R,S)-N-(butanesulfonyl)-amino-{3-[4-(piperidin-4-yl)-methoxyphenyl]-isoxalin-5-yl}-propanoic acid;
2(R,S)-5(R,S)-N-(α-toluenesulfonyl)-amino-{3-[4-(piperidin-4-yl)-methoxyphenyl]-isoxazolin-5-yl)-propanoic acid;
2(R,S)-5(R,S)-N-[(benzyloxy)-carbonyl]amino-{3-[4-(piperidin-4-yl)-methoxyphenyl]isoxazolin-5-yl}-propanoic acid; and
2(R,S)-5(R,S)-N-(pentanoyl)-amino-{3-[4-(piperidin-4-yl)-methoxyphenyl]isoxazolin-5-yl}-propanoic acid.

In another embodiment (designated embodiment IX), the iontophoretic device of the invention includes a compound having Formula I:

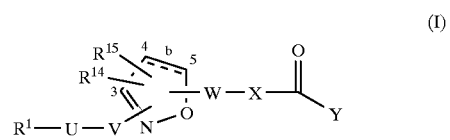

(I)

or a pharmaceutically acceptable salt form thereof, wherein:
b is a carbon-carbon single or double bond;
$R^1$ is selected from:
$R^{2a}(R^3)N$—, $R^2(R^3)N(R^2N$=$)C$—, $R^{2a}(R^3)N(CH_2)_{p'}$Z—, $R^2(R^3)N(R^2N$=$)C(CH_2)_{p''}$Z—, $R^2(R^3)N(R^2N$=$)CN(R^2)$—, $R^2(R^3)NC(O)$—, $R^2(R^5O)N(R^2N$=$)C$—, $R^2(R^3)N(R^5ON$=$)C$—,

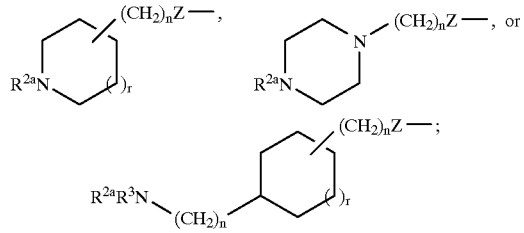

Z is selected from:
a bond, O, S, S(=O), S(=O)$_2$;
$R^2$ and $R^3$ are selected independently from:
H; $C_1$-$C_{10}$ alkyl; $C_3$-$C_6$ alkenyl; $C_3$-$C_{11}$ cycloalkyl; $C_4$-$C_{11}$ cycloalkylalkyl; $C_6$-$C_{10}$ aryl optionally substituted with 0–3 groups selected from hydroxy, halogen, $C_1$-$C_6$ alkoxy, $C_1$-$C_6$ alkyl, $CF_3$, $S(O)_m CH_3$, —$N(CH_3)_2$, $C_1$-$C_4$ haloalkyl, methylenedioxydiyl, ethylenedioxydiyl;
$C_7$-$C_{11}$ arylalkyl optionally substituted with 0–3 groups selected from hydroxy, halogen, $C_1$-$C_6$ alkoxy, $C_1$-$C_6$ alkyl, $CF_3$, $S(O)_m CH_3$, —$N(CH_3)_2$, $C_1$-$C_4$ haloalkyl, methylenedioxydiyl, ethylenedioxydiyl;
$C_2$-$C_7$ alkylcarbonyl;
$C_7$-$C_{11}$ arylcarbonyl optionally substituted with 0–3 groups selected from hydroxy, halogen, $C_1$-$C_6$ alkoxy, $C_1$-$C_6$ alkyl, $CF_3$, $S(O)_m CH_3$, —$N(CH_3)_2$, $C_1$-$C_4$ haloalkyl, methylenedioxydiyl, ethylenedioxydiyl;
($C_1$-$C_{10}$ alkoxy)carbonyl;
$C_4$-$C_{11}$ cycloalkoxycarbonyl;
$C_7$-$C_{11}$ bicycloalkoxycarbonyl;
$C_7$-$C_{11}$ aryloxycarbonyl optionally substituted with 0–3 groups selected from hydroxy, halogen, $C_1$-$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl;

aryl($C_1$–$C_{10}$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl;

($C_1$–$C_6$ alkyl)carbonyloxy($C_1$–$C_4$ alkoxy)carbonyl;

($C_6$–$C_{10}$ aryl)carbonyloxy($C_1$–$C_4$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl;

($C_4$–$C_{11}$ cycloalkylcarbonyl)oxy($C_1$–$C_4$ alkoxy) carbonyl;

heteroaryl optionally substituted with 0–2 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; or heteroaryl($C_1$–$C_5$)alkyl where the heteroaryl group is optionally substituted with 0–2 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl;

provided that only one of $R^2$ and $R^3$ can be hydroxy;

$R^{2a}$ is:
$R^2$ or $R^2(R^3)N(R^2N=)C$—;

U is selected from:
a single bond, -($C_1$–$C_7$ alkyl)-, -($C_2$–$C_7$ alkenyl)-, -($C_2$–$C_7$ alkynyl)-;

V is selected from:
a single bond; -($C_2$–$C_7$ alkyl)-, substituted with 0–3 groups selected independently from $R^6$ or $R^7$; -($C_2$–$C_7$ alkenyl)-, substituted with 0–3 groups selected independently from $R^6$ or $R^7$; -($C_2$–$C_7$ alkynyl)-, substituted with 0–3 groups selected independently from $R^6$ or $R^7$; -(phenyl)-Q-, the phenyl substituted with 0–2 groups selected independently from $R^6$ or $R^7$; -(pyridyl)-Q-, the pyridyl substituted with 0–2 groups selected independently from $R^6$ or $R^7$; or -(pyridazinyl)-Q-, the pyridazinyl substituted with 0–2 groups selected independently from $R^6$ or $R^7$;

Q is selected from:
a single bond, —O—, —$S(O)_m$—, —$N(R^{12})$—, —$(CH_2)_m$—, with —C(=O)—, —$N(R^{5a})C(=O)$—, —$C(=O)N(R^{5a})$—, —$CH_2O$—, —$OCH_2$—, —$CH_2N(R^{12})$—, —$N(R^{12})CH_2$—, —$CH_2C(=O)$—, —$C(=O)CH_2$—, —$CH_2S(O)_m$—, or —$S(O)_mCH_2$—, provided that:
when b is a single bond, and $R^1$—U—V— is a substituent on $C^5$ of the central 5-membered ring of Formula I, then Q is not —O—, —$S(O)_m$—, —$N(R^{12})$—, —$C(=O)N(R^{5a})$—, —$CH_2O$—, —$CH_2N(R^{12})$—, or —$CH_2S(O)_m$—;

W is selected from:
—$(C(R^4)_2)_{n'}C(=O)N(R^{5a})$—, or —$C(=O)$—N$(R^{5a})$—$(C(R^4)_2)_{n'}$—;

X is:
—$(C(R^4)_2)_{n'}$—$C(R^4)(R^8)$—$C(R^4)(R^{4a})$—;

Y is selected from:
hydroxy, $C_1$–$C_{10}$ alkyloxy, $C_3$–$C_{11}$ cycloalkyloxy, $C_6$–$C_{10}$ aryloxy, $C_7$–$C_{11}$ aralkyloxy, $C_3$–$C_{10}$ alkylcarbonyloxyalkyloxy, $C_3$–$C_{10}$
alkoxycarbonyloxyalkyloxy, $C_2$–$C_{10}$
alkoxycarbonylalkyloxy, $C_5$–$C_{10}$
cycloalkylcarbonyloxyalkyloxy, $C_5$–$C_{10}$
cycloalkoxycarbonyloxyalkyloxy, $C_5$–$C_{10}$
cycloalkoxycarbonylalkyloxy, $C_7$–$C_{11}$
aryloxycarbonylalkyloxy, $C_8$–$C_{12}$
aryloxycarbonyloxyalkyloxy, $C_8$–$C_{12}$
arylcarbonyloxyalkyloxy, $C_5$–$C_{10}$
alkoxyalkylcarbonyloxyalkyloxy, $C_5$–$C_{10}$ (5-alkyl-1,3-dioxa-cyclopenten-2-one-yl)-methyloxy, $C_{10}$–$C_{14}$ (5-aryl-1,3-dioxa-cyclopenten-2-one-yl)-methyloxy, $(R^2)(R^3)N$—$(C_1$–$C_{10}$ alkoxy)—;

$R^4$ is selected from:
H, $C_1$–$C_{10}$ alkyl, $C_1$–$C_{10}$ alkylcarbonyl, aryl, arylalkyl, cycloalkyl, or cycloalkylalkyl;

alternately, two $R^4$ groups on adjacent carbon atoms can join to form a carbon-carbon double or triple bond between such adjacent carbon atoms;

$R^{4a}$ is selected from:
hydroxy, $C_1$–$C_{10}$ alkoxy, nitro, —$N(R^5)R^{5a}$, —$N(R^{12})R^{13}$, —$N(R^{16})R^{17}$, aryl substituted with 0–3 $R^6$, or ($C_1$–$C_{10}$ alkyl)carbonyl;

$R^{4b}$ is selected from:
H, $C_1$–$C_6$ alkyl, $C_2$–$C_6$ alkenyl, $C_2$–$C_6$ alkynyl, $C_3$–$C_7$ cycloalkyl, $C_7$–$C_{14}$ bicycloalkyl, hydroxy, $C_1$–$C_6$ alkoxy, $C_1$–$C_6$ alkylthio, $C_1$–$C_6$ alkylsulfinyl, $C_1$–$C_6$ alkylsulfonyl, nitro, ($C_1$–$C_6$ alkyl)carbonyl, $C_6$–$C_{10}$ aryl, —$N(R^{12})R^{13}$, halo, $CF_3$, CN, ($C_1$–$C_6$ alkoxy)carbonyl, carboxy, piperidinyl, morpholinyl, or pyridinyl;

$R^5$ is selected from:
H, $C_1$–$C_8$ alkyl, $C_3$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–6 $R^{4b}$;

$R^{5a}$ is selected from:
hydrogen, hydroxy, $C_1$–$C_8$ alkyl, $C_3$–$C_6$ alkenyl, $C_3$–$C_{11}$ cycloalkyl, $C_4$–$C_{11}$ cycloalkylmethyl, $C_1$–$C_6$ alkoxy, benzyloxy, $C_6$–$C_{10}$ aryl, heteroaryl, heteroarylalkyl, $C_7$–$C_{11}$ arylalkyl, adamantylmethyl, or $C_1$–$C_{10}$ alkyl substituted with 0–2 $R^{4b}$;

alternately, $R^5$ and $R^{5a}$ when both are substituents on the same nitrogen atom (as in —$NR^5R^{5a}$) can be taken together with the nitrogen atom to which they are attached to form 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, or 1-piperazinyl, each being optionally substituted with $C_1$–$C_6$ alkyl, $C_6$–$C_{10}$ aryl, heteroaryl, $C_7$–$C_{11}$ arylalkyl, ($C_1$–$C_6$ alkyl)carbonyl, ($C_3$–$C_7$ cycloalkyl)carbonyl, ($C_1$–$C_6$ alkoxy)carbonyl, ($C_7$–$C_{11}$ arylalkoxy) carbonyl, $C_1$–$C_6$ alkylsulfonyl or $C_6$–$C_{10}$ arylsulfonyl;

$R^{5b}$ is selected from:
$C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^{4b}$;

$R^6$ is selected from:
H, $C_1$–$C_{10}$ alkyl, hydroxy, $C_1$–$C_{10}$ alkoxy, nitro, ($C_1$–$C_{10}$ alkyl)carbonyl, —$N(R^{12})R^{13}$, cyano, halo, $CF_3$, CHO, $CO_2R^5$, $C(=O)R^{5a}$, $CONR^5R^{5a}$, $OC(=O)R^{5a}$, $OC(=O)OR^{5b}$, $OR^{5a}$, $OC(=O)NR^5R^{5a}$, $OCH_2CO_2R^5$, $CO_2CH_2CO_2R^5$, $NO_2$, $NR^{5a}C(=O)R^{5a}$, $NR^{5a}C(=O)OR^{5b}$, $NR^{5a}C(=O)NR^5R^{5a}$, $NR^{5a}SO_2NR^5R^{5a}$, $NR^{5a}SO_2R^5$, $SR^{5a}$, $SOR^{5a}$, $SO_2R^{5a}$, $SO_2NR^5R^{5a}$, $Si(CH_3)_3$, $C_2$–$C_6$ alkenyl, $C_3$–$C_{11}$ cycloalkyl, $C_4$–$C_{11}$ cycloalkylmethyl;

$C_6-C_{10}$ aryl optionally substituted with 1–3 groups selected from halogen, $C_1-C_6$ alkoxy, $C_1-C_6$ alkyl, $CF_3$, $S(O)_mCH_3$, or $-N(CH_3)_2$;

$C_7-C_{11}$ arylalkyl, the aryl being optionally substituted with 1–3 groups selected from halogen, $C_1-C_6$ alkoxy, $C_1-C_6$ alkyl, $CF_3$, $S(O)_mCH_3$, or $-N(CH_3)_2$;

methylenedioxy when $R^6$ is a substituent on aryl; or a 5–10 membered heterocyclic ring containing 1–3 N, O, or S heteroatoms, wherein the heterocyclic ring can be saturated, partially saturated, or fully unsaturated, the heterocyclic ring being substituted with 0–2 $R^7$;

$R^7$ is selected from:
H, $C_1-C_{10}$ alkyl, hydroxy, $C_1-C_{10}$ alkoxy, nitro, ($C_1-C_{10}$ alkyl)carbonyl, $-N(R^{12})R^{13}$, cyano, halo, $CF_3$, CHO, $CO_2R^5$, $C(=O)R^{5a}$, $CONR^5R^{5a}$, $OC(=O)R^{5a}$, $OC(=O)OR^{5b}$, $OR^{5a}$, $OC(=O)NR^5R^{5a}$, $OCH_2CO_2R^5$, $CO_2CH_2CO_2R^5$, $NO_2$, $NR^{5a}C(=O)R^{5a}$, $NR^{5a}C(=O)OR^{5b}$, $NR^{5a}C(=O)NR^5R^{5a}$, $NR^{5a}SO_2NR^5R^{5a}$, $NR^{5a}SO_2R^5$, $S(O)_mR^{5a}$, $SO_2NR^5R^{5a}$, $C_2-C_6$ alkenyl, $C_3-C_{11}$ cycloalkyl, $C_4-C_{11}$ cycloalkylmethyl, $C_6-C_{10}$ aryl, or $C_7-C_{11}$ arylalkyl;

$R^8$ is selected from:
$R^6$; $C_1-C_{10}$ alkyl, substituted with 0–3 $R^6$; $C_2-C_{10}$ alkenyl, substituted with 0–3 $R^6$; $C_2-C_{10}$ alkynyl, substituted with 0–3 $R^6$; $C_3-C_8$ cycloalkyl, substituted with 0–3 $R^6$; $C_5-C_6$ cycloalkenyl, substituted with 0–3 $R^6$; aryl, substituted with 0–3 $R^6$; 5–10 membered heterocyclic ring containing 1–3 N, O, or S heteroatoms, wherein the heterocyclic ring can be saturated, partially saturated, or fully unsaturated, the heterocyclic ring being substituted with 0–2 $R^6$;

$R^{12}$ and $R^{13}$ are selected independently from:
H, $C_1-C_{10}$ alkyl, ($C_1-C_{10}$ alkoxy)carbonyl, ($C_1-C_{10}$ alkyl)carbonyl, $C_1-C_{10}$ alkylsulfonyl, aryl($C_1-C_{10}$ alkyl)sulfonyl, arylsulfonyl, aryl($C_2-C_{10}$ alkenyl)sulfonyl, heteroarylsulfonyl, aryl, $C_2-C_6$ alkenyl, $C_3-C_{11}$ cycloalkyl, $C_4-C_{11}$ cycloalkylalkyl, $C_7-C_{11}$ arylalkyl, $C_7-C_{11}$ arylcarbonyl, $C_4-C_{11}$ cycloalkoxycarbonyl, $C_7-C_{11}$ bicycloalkoxycarbonyl, $C_7-C_{11}$ aryloxycarbonyl, heteroarylcarbonyl, heteroarylsulfonyl, heteroarylalkylcarbonyl, or aryl($C_1-C_{10}$ alkoxy)carbonyl, wherein the aryl groups are optionally substituted with 0–3 substituents selected from the group consisting of: $C_1-C_4$ alkyl, $C_1-C_4$ alkoxy, halo, $CF_3$, and $NO_2$;

$R^{14}$ is selected from:
H, $C_1-C_{10}$ alkyl, $C_2-C_{10}$ alkenyl, $C_2-C_{10}$ alkynyl, $C_1-C_{10}$ alkoxy, aryl, heteroaryl or ($C_1-C_{10}$ alkoxy)carbonyl, $CO_2R^5$, or $-C(=O)N(R^5)R^{5a}$;

$R^{15}$ is selected from:
H; $R^6$; $-CO_2R^5$; $-C(=O)N(R^5)R^{5a}$; $C_1-C_{10}$ alkoxycarbonyl substituted with 0–2 $R^6$;
$C_1-C_{10}$ alkyl, substituted with 0–3 $R^6$; $C_2-C_{10}$ alkenyl, substituted with 0–3 $R^6$;
$C_1-C_{10}$ alkoxy, substituted with 0–3 $R^6$; aryl, substituted with 0–3 $R^6$; or 5–10 membered heterocyclic ring containing 1–3 N, O, or S heteroatoms, wherein the heterocyclic ring can be saturated, partially saturated, or fully unsaturated, the heterocyclic ring being substituted with 0–2 $R^6$;

provided that when b is a double bond, only one of $R^{14}$ or $R^{15}$ is present;

$R^{16}$ is selected from:
$-C(=O)-O-R^{18a}$, $-C(=O)-R^{18b}$, $-C(=O)N(R^{18b})_2$, $-C(=O)NHSO_2R^{18a}$, $-C(=O)NHC(=O)R^{18b}$, $-C(=O)NHC(=O)OR^{18a}$, $-C(=O)NHSO_2NHR^{18b}$, $-C(=S)-NH-R^{18b}$, $-NH-C(=O)-O-R^{18a}$, $-NH-C(=O)-R^{18b}$, $-NH-C(=O)-NH-R^{18b}$, $-SO_2-O-R^{18a}$, $-SO_2-R^{18a}$, $-SO_2-N(R^{18b})_2$, $-SO_2-NHC(=O)OR^{18b}$, $-P(=S)(OR^{18a})_2$, $-P(=O)(OR^{18a})_2$, $-P(=S)(R^{18a})_2$, $-P(=O)(R^{18a})_2$, or

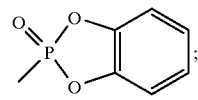

$R^{17}$ is selected from:
H, $C_1-C_{10}$ alkyl, $C_2-C_6$ alkenyl, $C_3-C_{11}$ cycloalkyl, $C_4-C_{15}$ cycloalkylalkyl, aryl, aryl($C_1-C_{10}$ alkyl)-;

$R^{18a}$ is selected from: $C_1-C_8$ alkyl substituted with 0–2 $R^{19}$, $C_2-C_8$ alkenyl substituted with 0–2 $R^{19}$, $C_2-C_8$ alkynyl substituted with 0–2 $R^{19}$, $C_3-C_8$ cycloalkyl substituted with 0–2 $R^{19}$, aryl substituted with 0–4 $R^{19}$, aryl($C_1-C_6$ alkyl)- substituted with 0–4 $R^{19}$;

a 5–10 membered heterocyclic ring system having 1–3 heteroatoms selected independently from O, S, and N, the heterocyclic ring being substituted with 0–4 $R^{19}$;

$C_1-C_6$ alkyl substituted with a 5–10 membered heterocyclic ring system having 1–3 heteroatoms selected independently from O, S, and N, the heterocyclic ring being substituted with 0–4 $R^{19}$;

$R^{18b}$ is selected from: $R^{18a}$ or H;

$R^{19}$ is selected from:
H, halogen, $CF_3$, CN, $NO_2$, $-NR^{12}R^{13}$, $C_1-C_8$ alkyl, $C_2-C_6$ alkenyl, $C_2-C_6$ alkynyl, $C_3-C_{11}$ cycloalkyl, $C_4-C_{11}$ cycloalkylalkyl, aryl, aryl($C_1-C_6$ alkyl)-, $C_1-C_6$ alkoxy, heteroaryl, ($C_1-C_4$ alkyl)sulfonyl, aryl-sulfonyl, or $C_1-C_4$ alkoxycarbonyl;

m is 0–2;

n is 0–4;

n' is 0–4;

p' is 1–7;

p" is 1–7;

r is 0–3;

provided that:
n' is chosen such that the number of in-chain atoms connecting $R^1$ and Y is in the range of 8–18.

In this embodiment, the compound can be a of Formula Ic:

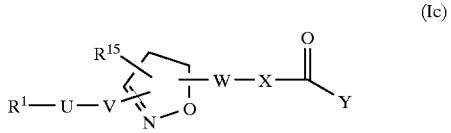

(Ic)

wherein:

$R^1$ is selected from:
$R^{2a}(R^3)N-$, $R^2(R^3)N(R^2N=)C-$, $R^{2a}(R^3)N(CH_2)_{p'}Z-$, $R^2(R^3)N(R^2N=)C(CH_2)_{p''}Z-$, $R^2(R^3)N(R^2N=)CN(R^2)-$, $R^2(R^3)NC(O)-$, $R^2(R^5O)N(R^2N=)C-$, $R^2(R^3)N(R^5ON=)C-$;

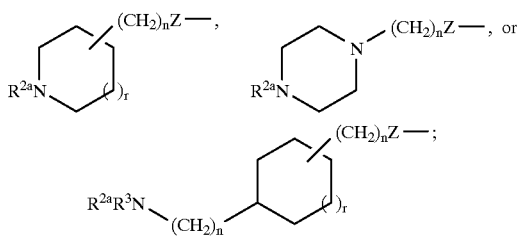

Z is selected from a bond, O, or S;

$R^2$ and $R^3$ are selected independently from:
H; $C_1-C_6$ alkyl; $C_7-C_{11}$ arylalkyl optionally substituted with 0–3 groups selected from hydroxy, halogen, $C_1-C_6$ alkoxy, $C_1-C_6$ alkyl, $CF_3$, $S(O)_mCH_3$, —$N(CH_3)_2$, $C_1-C_4$ haloalkyl, methylenedioxydiyl, ethylenedioxydiyl; ($C_1-C_{10}$ alkoxy)carbonyl;

aryl($C_1-C_{10}$ alkoxy)carbonyl where the aryl group is optionally substituted with 0–3 groups selected from hydroxy, halogen, $C_1-C_6$ alkoxy, $C_1-C_6$ alkyl, $CF_3$, $S(O)_mCH_3$, —$N(CH_3)_2$, $C_1-C_4$ haloalkyl, methylenedioxydiyl, ethylenedioxydiyl; or heteroaryl($C_1-C_5$)alkyl where the heteroaryl group is optionally substituted with 0–2 groups selected from hydroxy, halogen, $C_1-C_6$ alkoxy, $C_1-C_6$ alkyl, $CF_3$, $S(O)_mCH_3$, —$N(CH_3)_2$, $C_1-C_4$ haloalkyl, methylenedioxydiyl, ethylenedioxydiyl;

$R^{2a}$ is $R^2$ or $R^2(R^3)N(R^2N=)C$;

U is a single bond;

V is selected from:
a single bond; -($C_1-C_7$ alkyl)-, substituted with 0–3 groups selected independently from $R^6$ or $R^7$; -($C_2-C_7$ alkenyl)-, substituted with 0–3 groups selected independently from $R^6$ or $R^7$; -($C_2-C_7$ alkynyl)-, substituted with 0–3 groups selected independently from $R^6$ or $R^7$; -(phenyl)-Q-, the phenyl substituted with 0–2 groups selected independently from $R^6$ or $R^7$; -(pyridyl)-Q-, the pyridyl substituted with 0–2 groups selected independently from $R^6$ or $R^7$; or -(pyridazinyl)-Q-, the pyridazinyl substituted with 0–2 groups selected independently from $R^6$ or $R^7$;

Q is selected from:
a single bond, —O—, —$S(O)_m$—, —$N(R^{12})$—, —$(CH_2)_m$—, —C(=O)—, —$N(R^{5a})C(=O)$—, —C(=O)$N(R^{5a})$—, —$CH_2O$—, —$OCH_2$—, —$CH_2N(R^{12})$—, —$N(R^{12})CH_2$—, —$CH_2C(=O)$—, —C(=O)$CH_2$—, —$CH_2S(O)_m$—, —$S(O)_m CH_2$—;

provided that when $R^1$—U—V— is a substituent on $C^5$ of the central 5-membered ring of Formula Ic, then Q is not —O—, $S(O)_m$, —$N(R^{12})$—, —C(=O)$N(R^{5a})$—, —$CH_2O$—, —$CH_2N(R^{12})$— or —$CH_2S(O)_m$—;

W is selected from:
—$(C(R^4)_2)$—C(=O)—$N(R^{5a})$—, or —C(=O)—N$(R^{5a})$—$(C(R^4)_2)$—;

X is:
—$C(R^4)(R^8)$—$CHR^{4a}$—;

$R^4$ is selected from:
H, $C_1-C_{10}$ alkyl, $C_1-C_{10}$ alkylcarbonyl, aryl, arylalkyl, cycloalkyl, or cycloalkylalkyl;

$R^{4a}$ is selected from:
hydroxy, $C_1-C_{10}$ alkoxy, nitro, —$N(R^5)R^{5a}$, —$N(R^{12})R^{13}$, or —$N(R^{16})R^{17}$, aryl substituted with 0–3 $R^6$, or ($C_1-C_{10}$ alkyl)carbonyl;

$R^{4b}$ is selected from:
H, $C_1-C_6$ alkyl, $C_2-C_6$ alkenyl, $C_2-C_6$ alkynyl, hydroxy, $C_1-C_6$ alkoxy, $C_1-C_6$ alkylthio, $C_1-C_6$ alkylsulfinyl, $C_1-C_6$ alkylsulfonyl, nitro, ($C_1-C_6$ alkyl)carbonyl, $C_6-C_{10}$ aryl, —$N(R^{12})R^{13}$, halo, $CF_3$, CN, ($C_1-C_6$ alkoxy)carbonyl, carboxy, piperidinyl, morpholinyl or pyridyl;

$R^5$ is selected from:
H or $C_1-C_{10}$ alkyl substituted with 0–6 $R^{4b}$;

$R^{5a}$ is selected from:
hydrogen, hydroxy, $C_1-C_8$ alkyl, $C_2-C_6$ alkenyl, $C_3-C_{11}$ cycloalkyl, $C_4-C_{11}$ cycloalkylmethyl, $C_1-C_6$ alkoxy, benzyloxy, $C_6-C_{10}$ aryl, heteroaryl, heteroarylalkyl, $C_7-C_{11}$ arylalkyl, or adamantylmethyl, $C_1-C_{10}$ alkyl substituted with 0–2 $R^{4b}$;

alternately, $R^5$ and $R^{5a}$ can be taken together to be:
3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl, each being optionally substituted with $C_1-C_6$ alkyl, $C_6-C_{10}$ aryl, heteroaryl, $C_7-C_{11}$ arylalkyl, ($C_1-C_6$ alkyl)carbonyl, ($C_3-C_7$ cycloalkyl)carbonyl, ($C_1-C_6$ alkoxy)carbonyl, or ($C_7-C_{11}$ arylalkoxy)carbonyl;

$R^{5b}$ is selected from:
$C_1-C_8$ alkyl, $C_2-C_6$ alkenyl, $C_3-C_{11}$ cycloalkyl, $C_4-C_{11}$ cycloalkylmethyl, $C_6-C_{10}$ aryl, $C_7-C_{11}$ arylalkyl, or $C_1-C_{10}$ alkyl substituted with 0–2 $R^{4b}$;

Y is selected from:
hydroxy, $C_1-C_{10}$ alkyloxy, $C_3-C_{11}$ cycloalkyloxy, $C_6-C_{10}$ aryloxy, $C_7-C_{11}$ aralkyloxy, $C_3-C_{10}$ alkylcarbonyloxyalkyloxy, $C_3-C_{10}$ alkoxycarbonyloxyalkyloxy, $C_2-C_{10}$ alkoxycarbonylalkyloxy, $C_5-C_{10}$ cycloalkylcarbonyloxyalkyloxy, $C_5-C_{10}$ cycloalkoxycarbonyloxyalkyloxy, $C_5-C_{10}$ cycloalkoxycarbonylalkyloxy, $C_7-C_{11}$ aryloxycarbonylalkyloxy, $C_8-C_{12}$ aryloxycarbonyloxyalkyloxy, $C_8-C_{12}$ arylcarbonyloxyalkyloxy, $C_5-C_{10}$ alkoxyalkylcarbonyloxyalkyloxy, $C_5-C_{10}$ (5-alkyl-1,3-dioxa-cyclopenten-2-one-yl)-methyloxy, or $C_{10}-C_{14}$ (5-aryl-1,3-dioxa-cyclopenten-2-one-yl)-methyloxy;

$R^6$ and $R^7$ are each selected independently from:
H, $C_1-C_{10}$ alkyl, hydroxy, $C_1-C_{10}$ alkoxy, nitro, ($C_1-C_{10}$ alkyl)carbonyl, —$N(R^{12})R^{13}$, cyano, or halo;

$R^{12}$ and $R^{13}$ are each selected independently from:
H, $C_1-C_{10}$ alkyl, ($C_1-C_{10}$ alkoxy)carbonyl, ($C_1-C_{10}$ alkyl)carbonyl, $C_1-C_{10}$ alkylsulfonyl, aryl($C_1-C_{10}$ alkyl)sulfonyl, arylsulfonyl, heteroarylsulfonyl, heteroarylcarbonyl, heteroarylalkylcarbonyl or aryl, wherein the aryl groups being optionally substituted with 0–3 substituents selected from the group consisting of: $C_1-C_4$ alkyl, $C_1-C_4$ alkoxy, halo, $CF_3$, and $NO_2$;

$R^{15}$ is selected from:
H, $C_1-C_{10}$ alkyl, $C_2-C_{10}$ alkenyl, $C_2-C_{10}$ alkynyl, $C_1-C_{10}$ alkoxy, aryl, heteroaryl or ($C_1-C_{10}$ alkoxy)carbonyl, $CO_2R^5$ or —C(=O)$N(R^5)R^{5a}$;

$R^{16}$ is selected from:
—C(=O)—O—$R^{18a}$, —C(=O)—$R^{18b}$, —C(=O)N$(R^{18b})_2$, —$SO_2$—$R^{18a}$, or —$SO_2$—$N(R^{18b})_2$;

$R^{17}$ is selected from:

H or $C_1$–$C_5$ alkyl;

$R^{18a}$ is selected from:
   $C_1$–$C_8$ alkyl substituted with 0–2 $R^{19}$, $C_2$–$C_8$ alkenyl substituted with 0–2 $R^{19}$, $C_2$–$C_8$ alkynyl substituted with 0–2 $R^{19}$, $C_3$–$C_8$ cycloalkyl substituted with 0–2 $R^{19}$, aryl substituted with 0–4 $R^{19}$, aryl($C_1$–$C_6$ alkyl)- substituted with 0–4 $R^{19}$, a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, pyrrolidinyl, piperidinyl, indolinyl, or morpholinyl, the heterocyclic ring being substituted with 0–4 $R^{19}$;
   $C_1$–$C_6$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, pyrrolidinyl, piperidinyl, indolinyl, or morpholinyl, the heterocyclic ring being substituted with 0–4 $R^{19}$;

$R^{18b}$ is selected from:
   $R^{18a}$ or H;

$R^{19}$ is selected from:
   H, halogen, $CF_3$, CN, $NO_2$, $NR^{12}R^{13}$, $C_1$–$C_8$ alkyl, $C_2$–$C_6$ alkenyl, $C_2$–$C_6$ alkynyl, $C_1$–$C_6$ alkoxy, $C_3$–$C_{11}$ cycloalkyl, $C_4$–$C_{11}$ cycloalkylalkyl, aryl, heteroaryl, aryl($C_1$–$C_6$ alkyl)-, ($C_1$–$C_4$ alkyl) sulfonyl, aryl-sulfonyl, or $C_1$–$C_4$ alkoxycarbonyl;

n is 0–4;

p' is 1–7;

p" is 1–7;

r is 0–3.

Alternatively in the embodiment, the device can include a compound of Formula Ib:

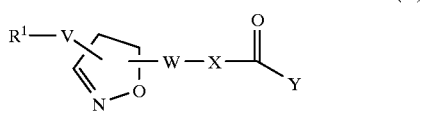

(Ib)

wherein:
$R^1$ is selected from:
   $R^{2a}(R^3)N$—, $R^2NH(R^2N=)C$—, $R^2NH(R^2N=)CNH$—, $R^{2a}R^3N(CH_2)_{p'}Z$—, $R^2NH(R^2N=)C(CH_2)_{p''}Z$—, $R^2(R^3)NC(O)$—, $R^2(R^5O)N(R^2N=)C$—, $R^2(R^3)N(R^5ON=)C$—;

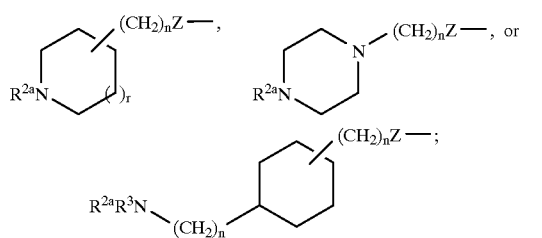

n is 0–1;
p' is 4–6;

p" is 2–4;

Z is selected from:
   a bond or O;

V is selected from:
   a single bond, -(phenyl)-, or -(pyridyl)-;

W is selected from:
   —$C(R^4)_2$—$C(=O)$—$N(R^{5a})$—, or —$C(=O)$—$N(R^{5a})$—$CH_2$—;

X is selected from:
   —$CH_2$—$CH(N(R^{16})R^{17})$—, or —$CH_2$—$CH(NR^5R^{5a})$—;

Y is selected from:
   hydroxy; $C_1$–$C_{10}$ alkoxy; methylcarbonyloxymethoxy; ethylcarbonyloxymethoxy;
   t-butylcarbonyloxymethoxy; cyclohexylcarbonyloxymethoxy;
   1-(methylcarbonyloxy)-ethoxy; 1-(ethylcarbonyloxy)-ethoxy;
   1-(t-butylcarbonyloxy)-ethoxy; 1-(cyclohexylcarbonyloxy)-ethoxy;
   i-propyloxycarbonyloxymethoxy; t-butyloxycarbonyloxymethoxy;
   1-(i-propyloxycarbonyloxy)-ethoxy; t-(cyclohexyloxycarbonyloxy)-ethoxy;
   1-(t-butyloxycarbonyloxy)-ethoxy; dimethylaminoethoxy; diethylaminoethoxy;
   (5-methyl-1,3-dioxacyclopenten-2-on-4-yl)-methoxy;
   (5-(t-butyl)-1,3-dioxacyclopenten-2-on-4 yl)-methoxy;
   (1,3-dioxa-5-phenyl-cyclopenten-2-on-4-yl)-methoxy;
   1-(2-(2-methoxypropyl)carbonyloxy)-ethoxy;

$R^{16}$ is selected from:
   —$C(=O)$—$O$—$R^{18a}$, —$C(=O)$—$R^{18b}$, —$S(=O)_2$—$R^{8a}$, or —$SO_2$—$N(R^{18b})_2$;

$R^{17}$ is selected from: H or $C_1$–$C_5$ alkyl;

$R^{18a}$ is selected from:
   C–$C_8$ alkyl substituted with 0–2 $R^{19}$, $C_2$–$C_8$ alkenyl substituted with 0–2 $R^{19}$, $C_2$–$C_8$ alkynyl substituted with 0–2 $R^{19}$, $C_3$–$C_8$ cycloalkyl substituted with 0–2 $R^{19}$, aryl substituted with 0–4 $R^{19}$, aryl($C_1$–$C_6$ alkyl)- substituted with 0–4 $R^{19}$, a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, pyrrolidinyl, or morpholinyl, the heterocyclic ring being substituted with 0–4 $R^{19}$;
   $C_1$–$C_6$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolinyl, quinolinyl, isoquinolinyl, benzimidazolyl, piperidinyl, tetrahydrofuranyl, pyranyl, 3H-indolyl, pyrrolidinyl, or morpholinyl, the heterocyclic ring being substituted with 0–4 $R^{19}$.

Therefore, the device can include this compound wherein: either:

$R^1$ is $R^2NH(R^2N=)C$— or $R^2HN(R^2N=)CNH$— and V is phenylene or pyridylene, or:

$R^1$ is

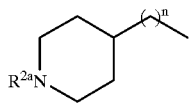

and V is a single bond, and n is 1 or 2;

$R^{18a}$ is selected from:

$C_1$–$C_4$ alkyl substituted with 0–2 $R^{19}$, $C_2$–$C_4$ alkenyl substituted with 0–2 $R^{19}$, $C_2$–$C_4$ alkynyl substituted with 0–2 $R^{19}$, $C_3$–$C_7$ cycloalkyl substituted with 0–2 $R^{19}$, aryl substituted with 0–4 $R^{19}$, aryl($C_1$–$C_4$ alkyl)- substituted with 0–4 $R^{19}$, a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, pyrrolidinyl, or morpholinyl, the heterocyclic ring being substituted with 0–4 $R^{19}$;

$C_1$–$C_4$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolinyl, quinolinyl, isoquinolinyl, benzimidazolyl, piperidinyl, tetrahydrofuranyl, pyranyl, 3H-indolyl, pyrrolidinyl, piperidinyl, or morpholinyl, the heterocyclic ring being substituted with 0–4 $R^{19}$.

Preferably, the device of this embodiment includes a compound, or a pharmaceutically acceptable salt form thereof, selected from:

$N^3$-[2-{3-(4-formamidinophenyl)-isoxazolin-5(R,S)-yl}-acetyl]-$N^2$-(phenylsulfonyl)-2,3(S)-diaminopropanoic acid;

$N^3$-[2-{3-(4-formamidinophenyl)-isoxazolin-5-(R,S)-yl}-acetyl]-$N^2$-(4-methyl-phenyl-sulfonyl)-2,3(S)-diaminopropanoic acid;

$N^3$-[2-{3-(4-formamidinophenyl)-isoxazolin-5(R,S)-yl}-acetyl]-$N^2$-(butanesulfonyl)-2,3(S)-diaminopropanoic acid;

$N^3$-[2-{3-(4-formamidinophenyl)-isoxazolin-5(R,S)-yl}-acetyl]-$N^2$-(propanesulfonyl)-2,3(S)-diaminopropanoic acid;

$N^3$-[2-{3-(4-formamidinophenyl)-isoxazolin-5(R,S)-yl}-acetyl]-$N^2$-(ethanesulfonyl)-2,3(S)-diaminopropanoic acid;

$N^3$-[2-{3-(4-formamidinophenyl)-isoxazolin-5(R,S)-yl}-acetyl]-$N^2$-(methyloxycarbonyl)-2,3(S)-diaminopropanoic acid;

$N^3$-[2-{3-(4-formamidinophenyl)-isoxazolin-5(R,S)-yl}-acetyl]-$N^2$-(ethyloxycarbonyl)-2,3(S) diaminopropanoic acid;

$N^3$-[2-{3-(4-formamidinophenyl)-isoxazolin-5(R,S)-yl}-acetyl]-$N^2$-(1-propyloxycarbonyl)-2,3(S)-diaminopropanoic acid;

$N^3$-[2-{3-(4-formamidinophenyl)-isoxazolin-5(R,S)-yl}-acetyl]-$N^2$-(2-propyloxycarbonyl)-2,3(S)-diaminopropanoic acid;

$N^3$-[2-{3-(4-formamidinophenyl)-isoxazolin-5(R,S)-yl}-acetyl]-$N^2$-(n-butyloxycarbonyl)-2,3(S)-diaminopropanoic acid;

$N^3$-[2-{3-(4-formamidinophenyl)-isoxazolin-5(R)-yl}-acetyl]-$N^2$-(n-butyloxycarbonyl)-2,3(S)-diaminopropanoic acid;

$N^3$-[2-{3-(4-formamidinophenyl)-isoxazolin-5(S)-yl}-acetyl]-$N^2$-(n-butyloxycarbonyl)-2,3(S)-diaminopropanoic acid;

$N^3$-[2-{3-(4-formamidinophenyl)-isoxazolin-5(R)-yl}-acetyl]-$N^2$-(n-butyloxycarbonyl)-2,3(R)-diaminopropanoic acid;

$N^3$-[2-{3-(4-formamidinophenyl)-isoxazolin-5(S)-yl}-acetyl]-$N^2$-(n-butyloxycarbonyl)-2,3(R)-diaminopropanoic acid;

$N^3$-[2-{3-(4-formamidinophenyl)-isoxazolin-5(R,S)-yl}-acetyl]-$N^2$-(2-butyloxycarbonyl)-2,3(S)-diaminopropanoic acid;

$N^3$-[2-{3-(4-formamidinophenyl)-isoxazolin-5(R,S)-yl}-acetyl]-$N^2$-(1-(2-methyl)-propyloxycarbonyl)-2,3(S)-diaminopropanoic acid;

$N^3$-[2-{3-(4-formamidinophenyl)-isoxazolin-5(R,S)-yl}-acetyl]-$N^2$-(2-(2-methyl)-propyloxycarbonyl)-2,3(S)-diaminopropanoic acid;

$N^3$-[2-{3-(4-formamidinophenyl)-isoxazolin-5(R,S)-yl}-acetyl]-$N^2$-(benzyloxycarbonyl)-2,3(S)-diaminopropanoic acid;

$N^3$-[2-{3-(4-formamidinophenyl)-isoxazolin-5(R)-yl}-acetyl]-$N^2$-(benzyloxycarbonyl)-2,3(S)-diaminopropanoic acid;

$N^3$-[2-{3-(4-formamidinophenyl)-isoxazolin-5(S)-yl}-acetyl]-$N^2$-(benzyloxycarbonyl)-2,3(S)-diaminopropanoic acid;

$N^3$-[2-{3-(4-formamidinophenyl)-isoxazolin-5(R,S)-yl}-acetyl]-$N^2$-(4-methylbenzyloxycarbonyl)-2,3(S)-diaminopropanoic acid;

$N^3$-[2-{3-(4-formamidinophenyl)-isoxazolin-5(R,S)-yl}-acetyl]-$N^2$-(4-methoxybenzyloxycarbonyl)-2,3(S)-diaminopropanoic acid;

$N^3$-[2-{3-(4-formamidinophenyl)-isoxazolin-5(R,S)-yl}-acetyl]-$N^2$-(4-chlorobenzyloxycarbonyl)-2,3(S)-diaminopropanoic acid;

$N^3$-[2-{3-(4-formamidinophenyl)-isoxazolin-5(R,S)-yl}-acetyl]-$N^2$-(4-bromobenzyloxycarbonyl)-2,3(S)-diaminopropanoic acid;

$N^3$-[2-{3-(4-formamidinophenyl)-isoxazolin-5(R,S)-yl}-acetyl]-$N^2$-(4-fluorobenzyloxycarbonyl)-2,3(S)-diaminopropanoic acid;

$N^3$-[2-{3-(4-formamidinophenyl)-isoxazolin-5(R,S)-yl}-acetyl]-$N^2$-(4-phenoxybenzyloxycarbonyl)-2,3(S)-diaminopropanoic acid;

$N^3$-[2-{3-(4-formamidinophenyl)-isoxazolin-5(R,S)-yl}-acetyl]-$N^2$-(2-(methyloxyethyl)-oxycarbonyl)-2,3(S)-diaminopropanoic acid;

$N^3$-[2-{3-(4-formamidinophenyl)-isoxazolin-5(R,S)-yl}-acetyl]-$N^2$-(2-pyridinylcarbonyl)-2,3(S)-diaminopropanoic acid;

$N^3$-[2-{3-(4-formamidinophenyl)-isoxazolin-5(R,S)-yl}-acetyl]-$N^2$-(3-pyridinylcarbonyl)-2,3(S)-diaminopropanoic acid;

$N^3$-[2-{3-(4-formamidinophenyl)-isoxazolin-5(R,S)-yl}-acetyl]-$N^2$-(4-pyridinyl-carbonyl)-2,3(S)-diaminopropanoic acid;

$N^3$-[2-{3-(4-formamidinophenyl)-isoxazolin-5(R,S)-yl}-acetyl]-$N^2$-(2-(2-pyridinyl)-acetyl)-2,3(S)-diaminopropanoic acid;

$N^3$-[2-{3-(4-formamidinophenyl)-isoxazolin-5(R,S)-yl}-acetyl]-$N^2$-(2-(3-pyridinyl)-acetyl)-2,3(S)-diaminopropanoic acid;

$N^3$-[2-{3-(4-formamidinophenyl)-isoxazolin-5(R,S)-yl}-acetyl]-$N^2$-(2-(4-pyridinyl)-acetyl)-2,3(S)-diaminopropanoic acid;

$N^3$-[2-{3-(4-formamidinophenyl)-isoxazolin-5(R,S)-yl}-acetyl]-$N^2$-(2-pyridyl-methyloxycarbonyl)-2,3(S)-diaminopropanoic acid;

$N^3$-[2-{3-(4-formamidinophenyl)-isoxazolin-5(R,S)-yl}-acetyl]-$N^2$-(3-pyridyl-methyloxycarbonyl)-2,3(S)-diaminopropanoic acid;

$N^3$-[2-{3-(4-formamidinophenyl)-isoxazolin-5(R,S)-yl}-acetyl]-$N^2$-(4-pyridyl-methyloxycarbonyl)-2,3(S)-diaminopropanoic acid;

$N^3$-[2-{3-(4-formamidinophenyl)-isoxazolin-5(R,S)-yl}-acetyl]-$N^2$-(4-butyloxyphenylsulfonyl)-2,3(S)-diaminopropanoic acid;

$N^3$-[2-{3-(4-formamidinophenyl)-isoxazolin-5(R,S)-yl}-acetyl]-$N^2$-(2-thienylsulfonyl)-2,3(S)-diaminopropanoic acid;

$N^3$-[2-{3-(4-formamidinophenyl)-isoxazolin-5(R,S)-yl}-acetyl]-$N^2$-(3-methylphenylsulfonyl)-2,3(R,S)-diaminopropanoic acid;

$N^3$-[2-{3-(4-formamidinophenyl)-isoxazolin-5(R,S)-yl}-acetyl]-$N^2$-(3-methylphenylsulfonyl)-2,3(S)-diaminopropanoic acid;

$N^3$-[2-{3-(4-formamidinophenyl)-isoxazolin-5(R,S)-yl}-acetyl]-$N^2$-(3-methylphenylsulfonyl)-2,3(R)-diaminopropanoic acid;

$N^3$-[2-{3-(4-formamidinophenyl)-isoxazolin-5(R)-yl}-acetyl]-$N^2$-(3-methylphenylsulfonyl)-2,3(S)-diaminopropanoic acid;

$N^3$-[2-{3-(4-formamidinophenyl)-isoxazolin-5(S)-yl}-acetyl]-$N^2$-(3-methylphenylsulfonyl)-2,3(S)-diaminopropanoic acid;

$N^3$-[2-{3-(4-formamidinophenyl)-isoxazolin-5(S)-yl}-acetyl]-$N^2$-(3-methylphenylsulfonyl)-2,3(R)-diaminopropanoic acid;

$N^3$-[2-{3-(4-formamidinophenyl)-isoxazolin-5(R)-yl}-acetyl]-$N^2$-(3-methylphenylsulfonyl)-2,3(R)-diaminopropanoic acid;

$N^3$-[2-{3-(4-formamidinophenyl)-isoxazolin-5(R,S)-yl}-acetyl]-$N^2$-(4-iodophenylsulfonyl)-2,3(S)-diaminopropanoic acid;

$N^3$-[2-{3-(4-formamidinophenyl)-isoxazolin-5(R,S)-yl}-acetyl]-$N^2$-(3-trifluoromethylphenylsulfonyl)-2,3(S)-diaminopropanoic acid;

$N^3$-[2-{3-(4-formamidinophenyl)-isoxazolin-5(R,S)-yl}-acetyl]-$N^2$-(3-chlorophenylsulfonyl)-2,3(S)-diaminopropanoic acid;

$N^3$-[2-{3-(4-formamidinophenyl)-isoxazolin-5(R,S)-yl}-acetyl]-$N^2$-(3-2-methoxycarbonylphenylsulfonyl)-2,3(S)-diaminopropanoic acid;

$N^3$-[2-{3-(4-formamidinophenyl)-isoxazolin-5(R,S)-yl}-acetyl]-$N^2$-(2,4,6-trimethylphenylsulfonyl)-2,3(S)-diaminopropanoic acid;

$N^3$-[2-{3-(4-formamidinophenyl)-isoxazolin-5(R,S)-yl}-acetyl]-$N^2$-(2-chlorophenylsulfonyl)-2,3(S)-diaminopropanoic acid;

$N^3$-[2-{3-(4-formamidinophenyl)-isoxazolin-5(R,S)-yl}-acetyl]-$N^2$-(4-trifluoromethylphenylsulfonyl)-2,3(S)-diaminopropanoic acid;

$N^3$-[2-{3-(4-formamidinophenyl)-isoxazolin-5(R,S)-yl}-acetyl]-$N^2$-(2-trifluoromethylphenylsulfonyl)-2,3(S)-diaminopropanoic acid;

$N^3$-[2-{3-(4-formamidinophenyl)-isoxazolin-5(R,S)-yl}-acetyl]-$N^2$-(2-fluoropentylsulfonyl)-2,3(S)-diamninopropanoic acid;

$N^3$-[2-{3-(4-formamidinophenyl)-isoxazolin-5(R,S)-yl}-acetyl]-$N^2$-(4-fluorophenylsulfonyl)-2,3(S)-diaminopropanoic acid;

$N^3$-[2-{3-(4-formamidinophenyl)-isoxazolin-5(R,S)-yl}-acetyl]-$N^2$-(4-methoxyphenylsulfonyl)-2,3(S)-diaminopropanoic acid;

$N^3$-[2-{3-(4-formamidinophenyl)-isoxazolin-5(R,S)-yl}-acetyl]-$N^2$-(2,3,5,6-tetramethylphenylsulfonyl)-2,3(S)-diaminopropanoic acid;

$N^3$-[2-{3-(4-formamidinophenyl)-isoxazolin-5(R,S)-yl}-acetyl]-$N^2$-(4-cyanophenylsulfonyl)-2,3(S)-diaminopropanoic acid;

$N^3$-[2-{3-(4-formamidinophenyl)-isoxazolin-5(R,S)-yl}-acetyl]-$N^2$-(4-chlorophenylsulfonyl)-2,3(S)-diaminopropanoic acid;

$N^3$-[2-{3-(4-formamidinophenyl)-isoxazolin-5(R,S)-yl}-acetyl]-$N^2$-(4-propylphenylsulfonyl)-2,3(S)-diaminopropanoic acid;

$N^3$-[2-{3-(4-formamidinophenyl)-isoxazolin-5(R,S)-yl}-acetyl]-$N^2$-(2-phenylethylsulfonyl)-2,3(S)-diaminopropanoic acid;

$N^3$-[2-{3-(4-formamidinophenyl)-isoxazolin-5(R,S)-yl}-acetyl]-$N^2$-(4-isopropylphenylsulfonyl)-2,3(S)-diaminopropanoic acid;

$N^3$-[2-{3-(4-formamidinophenyl)-isoxazolin-5(R,S)-yl}-acetyl]-$N^2$-(3-phenylpropylsulfonyl)-2,3(S)-diaminopropanoic acid;

$N^3$-[2-{3-(4-formamidinophenyl)-isoxazolin-5(R,S)-yl}-acetyl]-$N^2$-(3-pyridylsulfonyl)-2,3(S)-diaminopropanoic acid;

$N^3$-[2-{3-(4-formamidinophenyl)-isoxazolin-5(R,S)-yl}-acetyl]-$N^2$-(phenylaminosulfonyl)-2,3(S)-diaminopropanoic acid;

$N^3$-[2-{3-(4-formamidinophenyl)-isoxazolin-5(R,S)-yl}-acetyl]-$N^2$-(benzylaminosulfonyl)-2,3(S)-diaminopropanoic acid;

$N^3$-[2-{3-(4-formamidinophenyl)-isoxazolin-5(R,S)-yl}-acetyl]-$N^2$-(dimethylaminosulfonyl)-2,3(S)-diaminopropanoic acid;

$N^3$-[2-{3-(2-fluoro-4-formamidinophenyl)-isoxazolin-5(R,S)-yl}-acetyl]-$N^2$-(3-methylphenylsulfonyl)-2,3(S)-diaminopropanoic acid;

$N^3$-[2-{3-(2-formamidino-5-pyridinyl)-isoxazolin-5(R,S)-yl}-acetyl]-$N^2$-(n-butyloxycarbonyl)-2,3(S)-diaminopropanoic acid;

$N^3$-[2-{3-(2-formamidino-5-pyridinyl)-isoxazolin-5(R,S)-yl}-acetyl]-$N^2$-(3-methylphenylsulfonyl)-2,3(S)-diaminopropanoic acid;

$N^3$-[2-{3-(3-formamidino-6-pyridinyl)-isoxazolin-5(R,S)-yl}-acetyl]-$N^2$-(n-butyloxycarbonyl)-2,3(S)-diaminopropanoic acid;

$N^3$-[2-{3-(3-formamidino-6-pyridinyl)-isoxazolin-5(R,S)-yl}-acetyl]-$N^2$-(3-methylphenylsulfonyl)-2,3(S)-diaminopropanoic acid;

$N^3$-[2-{3-(4-formamidinophenyl)-isoxazolin-5(R,S)-yl}-acetyl]-$N^2$-(phenylaminocarbonyl)-2,3(S)-diaminopropanoic acid;

$N^3$-[2-{3-(4-formamidinophenyl)-isoxazolin-5(R,S)-yl}-acetyl]-$N^2$-(4-fluorophenylaminocarbonyl)-2,3(S)-diaminopropanoic acid;

$N^3$-[2-{3-(4-formamidinophenyl)-isoxazolin-5(R,S)-yl}-acetyl]-$N^2$-(1-naphthylaminocarbonyl)-2,3(S)-diaminopropanoic acid;

$N^3$-[2-{3-(4-formamidinophenyl)-isoxazolin-5(R,S)-yl}-acetyl]-$N^2$-(benzylaminocarbonyl)-2,3(S)-diaminopropanoic acid;

$N^3$-[2-{3-(4-formamidinophenyl)-isoxazolin-5(R,S)-yl}-acetyl]-$N^2$-(3-bromo-2-thienylsulfonyl)-2,3(S)-diaminopropanoic acid;

$N^3$-[2-{3-(4-formamidinophenyl)-isoxazolin-5(R,S)-yl}-acetyl]-$N^2$-(3-methyl-2-benzothienylsulfonyl)-2,3(S)-diaminopropanoic acid;

$N^3$-[2-{3-(4-formamidinophenyl)-isoxazolin-5(R,S)-yl}-acetyl]-$N^2$-(isobutyloxycarbonyl)-2,3(S)-diaminopropanoic acid;

$N^3$-[2-{3-(4-formamidinophenyl)-isoxazolin-5(R)-yl}-acetyl]-$N^2$-(isobutyloxycarbonyl)-2,3(S)-diaminopropanoic acid;

N³-[2-{3-(4-formamidinophenyl)-isoxazolin-5(S)-yl}-acetyl]-N²-(isobutyloxycarbonyl)-2,3(S)-diaminopropanoic acid;

N³-[2-{3-(4-formamidinophenyl)-isoxazolin-5(R,S)-yl}-acetyl]-N²-(2-cyclopropylethoxycarbonyl)-2,3(,S)-diaminopropanoic acid;

N³-[2-{3-(4-formamidinophenyl)-isoxazolin-5(R)-yl}-acetyl]-N²-(2-cyclopropylethoxycarbonyl)-2,3(S)-diaminopropanoic acid;

N³-[2-{3-(4-formamidinophenyl)-isoxazolin-5(S)-yl}-acetyl]-N²-(2-cyclopropylethoxycarbonyl)-2,3(S)-diaminopropanoic acid;

N³-[2-{3-(4-guanidinophenyl)-isoxazolin-5(R,S)-yl}-acetyl]-N²-(n-butyloxycarbonyl)-2,3(S)-diaminopropanoic acid;

N³-[2-{3-(4-guanidinophenyl)-isoxazolin-5(R)-yl}-acetyl]-N²-(n-butyloxycarbonyl)-2,3(S)-diaminopropanoic acid;

N³-[2-{3-(4-guanidinophenyl)-isoxazolin-5(R)-yl}-acetyl]-N²-(3-methylphenylsulfonyl)-2,3(S)-diaminopropanoic acid;

N³-[2-{5-(4-formamidinophenyl)-isoxazolin-3(R,S)-yl}-acetyl]-N²-(n-butyloxycarbonyl)-2,3(S)-diaminopropanoic acid;

or a propanoate ester prodrug form of the compound, wherein the hydrogen of the hydroxy group of the diaminopropanoic acid moiety is substituted with a group selected from:

methyl; ethyl; isopropyl; methylcarbonyloxymethyl; ethylcarbonyloxymethyl;

t-butylcarbonyloxymethyl; cyclohexylcarbonyloxymethyl;

1-(methylcarbonyloxy)-ethyl; 1-(ethylcarbonyloxy)-ethyl;

1-(t-butylcarbonyloxy)-ethyl; 1-(cyclohexylcarbonyloxy)-ethyl;

i-propyloxycarbonyloxymethyl; cyclohexylcarbonyloxymethyl;

t-butyloxycarbonyloxymethyl; 1-(i-propyloxycarbonyloxy)-ethyl;

1-(cyclohexyloxycarbonyloxy)-ethyl; 1-(t-butyloxycarbonyloxy)-ethyl;

dimethylaminoethyl; diethylaminoethyl;

(5-methyl-1,3-dioxacyclopenten-2-on-4-yl)-methyl;

(5-(t-butyl)-1,3-dioxacyclopenten-2-on 4-yl)-methyl;

(1,3-dioxa-5-phenyl-cyclopenten-2-on-4-yl)-methyl;

1-(2-(2-methoxypropyl)carbonyloxy)-ethyl.

Alternatively, the device of this embodiment preferably includes a compound, or an enantiomeric or diastereomeric form thereof, or a mixture of enantiomeric or diastereomeric forms thereof, or a pharmaceutically acceptable salt form thereof, selected from:

N³-[2-{3-(4-formamidinophenyl)-isoxazolin-5-yl}-acetyl]-N²-(phenylsulfonyl)-2,3-diaminopropanoic acid;

N³-[2-{3-(4-formamidinophenyl)-isoxazolin-5-yl}-acetyl]-N²-(4-methyl-phenyl-sulfonyl)-2,3-diaminopropanoic acid;

N³-[2-{3-(4-formamidinophenyl)-isoxazolin-5-yl}-acetyl]-N²-(butanesulfonyl)-2,3-diaminopropanoic acid;

N³-[2-{3-(4-formamidinophenyl)-isoxazolin-5-yl}-acetyl]-N²-(propanesulfonyl)-2,3-diaminopropanoic acid;

N³-[2-{3-(4-formamidinophenyl)-isoxazolin-5-yl}-acetyl]-N²-(ethanesulfonyl)-2,3-diaminopropanoic acid;

N³-[2-{3-(4-formamidinophenyl)-isoxazolin-5-yl}-acetyl]-N²-(methyloxycarbonyl)-2,3-diaminopropanoic acid;

N³-[2-{3-(4-formamidinophenyl)-isoxazolin-5-yl}-acetyl]-N²-(ethyloxycarbonyl)-2,3-diaminopropanoic acid;

N³-[2-{3-(4-formamidinophenyl)-isoxazolin-5-yl}-acetyl]-N²-(1-propyloxycarbonyl)-2,3-diaminopropanoic acid;

N³-[2-{3-(4-formamidinophenyl)-isoxazolin-5-yl}-acetyl]-N²-(2-propyloxycarbonyl)-2,3-diaminopropanoic acid;

N³-[2-{3-(4-formamidinophenyl)-isoxazolin-5-yl}-acetyl]-N²-(n-butyloxycarbonyl)-2,3-diaminopropanoic acid;

N³-[2-{3-(4-formamidinophenyl)-isoxazolin-5-yl}-acetyl]-N²-(1-(2-methyl)-propyloxycarbonyl)-2,3-diaminopropanoic acid;

N³-[2-{3-(4-formamidinophenyl)-isoxazolin-5-yl}-acetyl]-N²-(2-(2-methyl)-propyloxycarbonyl)-2,3-diaminopropanoic acid;

N³-[2-{3-(4-formamidinophenyl)-isoxazolin-5-yl}-acetyl]-N²-(benzyloxycarbonyl)-2,3-diaminopropanoic acid;

N³-[2-{3-(4-formamidinophenyl)-isoxazolin-5-yl}-acetyl]-N²-(4-methylbenzyloxycarbonyl)-2,3-diaminopropanoic acid;

N³-[2-{3-(4-formamidinophenyl)-isoxazolin-5-yl}-acetyl]-N²-(4-methoxybenzyloxycarbonyl)-2,3-diaminopropanoic acid;

N³-[2-{3-(4-formamidinophenyl)-isoxazolin-5-yl}-acetyl]-N²-(4-chlorobenzyloxycarbonyl)-2,3-diaminopropanoic acid;

N³-[2-{3-(4-formamidinophenyl)-isoxazolin-5-yl}-acetyl]-N²-(4-bromobenzyloxycarbonyl)-2,3-diaminopropanoic acid;

N³-[2-{3-(4-formamidinophenyl)-isoxazolin-5-yl}-acetyl]-N²-(4-fluorobenzyloxycarbonyl)-2,3-diaminopropanoic acid;

N³-[2-{3-(4-formamidinophenyl)-isoxazolin-5-yl}-acetyl]-N²-(4-phenoxybenzyloxycarbonyl)-2,3-diaminopropanoic acid;

N³-[2-{3-(4-formamidinophenyl)-isoxazolin-5-yl}-acetyl]-N²-(2-(methyloxyethyl)-oxycarbonyl)-2,3-diaminopropanoic acid;

N³-[2-{3-(4-formamidinophenyl)-isoxazolin-5-yl}-acetyl]-N²-(2-pyridinylcarbonyl)-2,3-diaminopropanoic acid;

N³-[2-{3-(4-formamidinophenyl)-isoxazolin-5-yl}-acetyl]-N²-(3-pyridinylcarbonyl)-2,3-diaminopropanoic acid;

N³-[2-{3-(4-formamidinophenyl)-isoxazolin-5-yl}-acetyl]-N²-(4-pyridinyl-carbonyl)-2,3-diaminopropanoic acid;

N³-[2-{3-(4-formamidinophenyl)-isoxazolin-5-yl}-acetyl]-N²-(2-(2-pyridinyl)-acetyl)-2,3-diaminopropanoic acid;

N³-[2-{3-(4-formamidinophenyl)-isoxazolin-5-yl}-acetyl]-N²-(2-(3-pyridinyl)-acetyl)-2,3-diaminopropanoic acid;

N³-[2-{3-(4-formamidinophenyl)-isoxazolin-5-yl}-acetyl]-N²-(2-(4-pyridinyl)-acetyl)-2,3-diaminopropanoic acid;

N³-[2-{3-(4-formamidinophenyl)-isoxazolin-5-yl}-acetyl]-N²-(2-pyridyl-methyloxycarbonyl)-2,3-diaminopropanoic acid;

N³-[2-{3-(4-formamidinophenyl)-isoxazolin-5-yl}-acetyl]-N²-(3-pyridyl-methyloxycarbonyl)-2,3-diaminopropanoic acid;

N³-[2-{3-(4-formamidinophenyl)-isoxazolin-5-yl}-acetyl]-N²-(4-pyridyl-methyloxycarbonyl)-2,3-diaminopropanoic acid;

N³-[2-{3-(4-formamidinophenyl)-isoxazolin-5-yl}-acetyl]-N²-(4-butyloxyphenylsulfonyl)-2,3-diaminopropanoic acid;

N³-[2-{3-(4-formamidinophenyl)-isoxazolin-5-yl}-acetyl]-N²-(2-thienylsulfonyl)-2,3-diaminopropanoic acid;

N³-[2-{3-(4-formamidinophenyl)-isoxazolin-5-yl}-acetyl]-N²-(3-methylphenylsulfonyl)-2,3-diaminopropanoic acid;

N³-[2-{3-(4-formamidinophenyl)-isoxazolin-5-yl}-acetyl]-N²-(4-iodophenylsulfonyl)-2,3-diaminopropanoic acid;

N³-[2-{3-(4-formamidinophenyl)-isoxazolin-5-yl}-acetyl]-N²-(3-trifluoromethylphenylsulfonyl)-2,3-diaminopropanoic acid;

N³-[2-{3-(4-formamidinophenyl)-isoxazolin-5-yl}-acetyl]-N²-(3-chlorophenylsulfonyl)-2,3-diaminopropanoic acid;

N³-[2-{3-(4-formamidinophenyl)-isoxazolin-5-yl}-acetyl]-N²-(2-methoxycarbonylphenylsulfonyl)-2,3-diaminopropanoic acid;

N³-[2-{3-(4-formamidinophenyl)-isoxazolin-5-yl}-acetyl]-N²-(2,4,6-trimethylphenylsulfonyl)-2,3-diaminopropanoic acid;

N³-[2-{3-(4-formamidinophenyl)-isoxazolin-5-yl}-acetyl]-N²-(2-chlorophenylsulfonyl)-2,3-diaminopropanoic acid;

N³-[2-{3-(4-formamidinophenyl)-isoxazolin-5-yl}-acetyl]-N²-(4-trifluoromethylphenylsulfonyl)-2,3-diaminopropanoic acid;

N³-[2-{3-(4-formamidinophenyl)-isoxazolin-5-yl}-acetyl]-N²-(2-trifluoromethylphenylsulfonyl)-2,3-diaminopropanoic acid;

N³-[2-{3-(4-formamidinophenyl)-isoxazolin-5-yl}-acetyl]-N²-(2-fluorophenylsulfonyl)-2,3-diaminopropanoic acid;

N³-[2-{3-(4-formamidinophenyl)-isoxazolin-5-yl}-acetyl]-N²-(4-fluorophenylsulfonyl)-2,3-diaminopropanoic acid;

N³-[2-{3-(4-formamidinophenyl)-isoxazolin-5-yl}-acetyl]-N²-(4-methoxyphenylsulfonyl)-2,3-diaminopropanoic acid;

N³-[2-{3-(4-formamidinophenyl)-isoxazolin-5-yl}-acetyl]-N²-(2,3,5,6-tetramethylphenylsulfonyl)-2,3-diaminopropanoic acid;

N³-[2-{3-(4-formamidinophenyl)-isoxazolin-5-yl}-acetyl]-N²-(4-cyanophenylsulfonyl)-2,3-diaminopropanoic acid;

N³-[2-{3-(4-formamidinophenyl)-isoxazolin-5-yl}-acetyl]-N²-(4-chlorophenylsulfonyl)-2,3-diaminopropanoic acid;

N³-[2-{3-(4-formamidinophenyl)-isoxazolin-5-yl}-acetyl]-N²-(4-propylphenylsulfonyl)-2,3-diaminopropanoic acid;

N³-[2-{3-(4-formamidinophenyl)-isoxazolin-5-yl}-acetyl]-N²-(2-phenylethylsulfonyl)-2,3-diaminopropanoic acid;

N³-[2-{3-(4-formamidinophenyl)-isoxazolin-5-yl}-acetyl]-N²-(4-isopropylphenylsulfonyl)-2,3-diaminopropanoic acid;

N³-[2-{3-(4-formamidinophenyl)-isoxazolin-5-yl}-acetyl]-N²-(3-phenylpropylsulfonyl)-2,3-diaminopropanoic acid;

N³-[2-{3-(4-formamidinophenyl)-isoxazolin-5-yl}-acetyl]-N²-(3-pyridylsulfonyl)-2,3-diaminopropanoic acid;

N³-[2-{3-(4-formamidinophenyl)-isoxazolin-5-yl}-acetyl]-N²-(phenylaminosulfonyl)-2,3-diaminopropanoic acid;

N³-[2-{3-(4-formamidinophenyl)-isoxazolin-5-yl}-acetyl]-N²-(benzylaminosulfonyl)-2,3-diaminopropanoic acid;

N³-[2-{3-(4-formamidinophenyl)-isoxazolin-5-yl}-acetyl]-N²-(dimethylaminosulfonyl)-2,3-diaminopropanoic acid;

N³-[2-{3-(2-fluoro-4-formamidinophenyl)-isoxazolin-5-yl}-acetyl]-N²-(3-methylphenylsulfonyl)-2,3-diaminopropanoic acid;

N³-[2-{3-(2-formamidino-5-pyridinyl)-isoxazolin-5-yl}-acetyl]-N²-(n-butyloxycarbonyl)-2,3-diaminopropanoic acid;

N³-[2-{3-(2-formamidino-5-pyridinyl)-isoxazolin-5-yl}-acetyl]-N²-(3-methylphenylsulfonyl)-2,3-diaminopropanoic acid;

N³-[2-{3-(3-formamidino-6-pyridinyl)-isoxazolin-5-yl}-acetyl]-N²-(n-butyloxycarbonyl)-2,3-diaminopropanoic acid, N³-[2-{3-(3-formamidino-6-pyridinyl)-isoxazolin-5-yl}-acetyl]-N²-(3-methylphenylsulfonyl)-2,3-diaminopropanoic acid, N³-[2-{3-(4-formamidinophenyl)-isoxazolin-5-yl}-acetyl]-N²-(phenylaminocarbonyl)-2,3-diaminopropanoic acid;

N³-[2-{3-(4-formamidinophenyl)-isoxazolin-5-yl}-acetyl]-N²-(4-fluorophenylaminocarbonyl)-2,3-diaminopropanoic acid;

N³-[2-{3-(4-formamidinophenyl)-isoxazolin-5-yl}-acetyl]-N²-(1-naphthylaminocarbonyl)-2,3-diaminopropanoic acid;

N³-[2-{3-(4-formamidinophenyl)-isoxazolin-5-yl}-acetyl]-N²-(benzylaminocarbonyl)-2,3-diaminopropanoic acid;

N³-[2-{3-(4-formamidinophenyl)-isoxazolin-5-yl}-acetyl]-N²-(3-bromo-2-thienylsulfonyl)-2,3-diaminopropanoic acid;

N³-[2-{3-(4-formamidinophenyl)-isoxazolin-5-yl}-acetyl]-N²-(3-methyl-2-benzothienylsulfonyl)-2,3-diaminopropanoic acid, N³-[2-{3-(4-formamidinophenyl)-isoxazolin-5-yl}-acetyl]-N²-(isobutyloxycarbonyl)-2,3-diaminopropanoic acid, N³-[2-{3-(4-formamidinophenyl)-isoxazolin-5-yl}-acetyl]-N²-(isobutyloxycarbonyl)-2,3-diaminopropanoic acid, N³-[2-{3-(4-formamidinophenyl)-isoxazolin-5-yl}-acetyl]-N²-(isobutyloxycarbonyl)-2,3-diaminopropanoic acid, N³-[2-{3-(4-formamidinophenyl)-isoxazolin-5-yl}-acetyl]-N²-(2-cyclopropylethoxycarbonyl)-2,3-diaminopropanoic acid, N³-[2-{3-(4-guanidinophenyl)-isoxazolin-5-yl}-acetyl]-N²-(n-butyloxycarbonyl)-2,3-diaminopropanoic acid;

N³-[2-{3-(4-guanidinophenyl)-isoxazolin-5-yl}-acetyl]-N²-(3-methylphenylsulfonyl)-2,3-diaminopropanoic acid;

N³-[2-{5-(4-formamidinophenyl)-isoxazolin-3-yl}-acetyl]-N²-(n-butyloxycarbonyl)-2,3-diaminopropanoic acid;

N³-[2-{3-(4-formamidinophenyl)-isoxazolin-5-yl}-acetyl]-N²-(2-bromo-phenylsulfonyl)-2,3-diaminopropionic acid;

N³-[2-{3-(4-formamidinophenyl)-isoxazolin-5-yl}-acetyl]-N²-(2-methyl-phenylsulfonyl)-2,3-diaminopropionic acid;

N³-[2-{3-(3-formamidino-6-pyridinyl)-isoxazolin-5-yl}-acetyl]-N²-(3-methylphenylsulfonyl)-2,3-diaminopropionic acid;

N³-[2-{3-(2-formamidino-5-pyridinyl)-isoxazolin-5-yl}-acetyl]-N²-(3-methylphenylsulfonyl)-2,3-diaminopropionic acid;

N³-[2-{3-(2-fluoro-4-formamidinophenyl)-isoxazolin-5-yl}-acetyl]-N²-(3-methylphenylsulfonyl)-2,3-diaminopropionic acid;

N³-[2-{3-(4-formamidinophenyl)-isoxazolin-5-yl-acetyl]-N²-(3-bromo-phenylsulfonyl)-2,3-diaminopropionic acid; and N³-[2-{3-(4-formamidinophenyl)-isoxazolin-5-yl}-acetyl]-N²-(4-bromo-phenylsulfonyl)-2,3-diaminopropionic acid;

or a propanoate ester prodrug form of the compound, wherein the hydrogen of the hydroxy group of the propanoic acid moiety is substituted with a group selected from:

methyl; ethyl; isopropyl; methylcarbonyloxymethyl; ethylcarbonyloxymethyl;

t-butylcarbonyloxymethyl; cyclohexylcarbonyloxymethyl;

1-(methylcarbonyloxy)-ethyl; 1-(ethylcarbonyloxy)-ethyl;

1-(t-butylcarbonyloxy)-ethyl; 1-(cyclohexylcarbonyloxy)-ethyl;

1-propyloxycarbonyloxymethyl; cyclohexylcarbonyloxymethyl;

t-butyloxycarbonyloxymethyl; 1-(i-propyloxycarbonyloxy)-ethyl;

1-(cyclohexyloxycarbonyloxy)-ethyl; 1-(t-butyloxycarbonyloxy)-ethyl;

dimethylaminoethyl; diethylaminoethyl;

(5-methyl-1,3-dioxacyclopenten-2-on-4-yl)-methyl;

(5-(t-butyl)-1,3-dioxacyclopenten-2-on-4-yl)-methyl;
(1,3-dioxa-5-phenyl-cyclopenten-2-on-4-yl)-methyl; and
1-(2-(2-methoxypropyl)carbonyloxy)-ethyl;

the enantiomeric and diastereomeric forms being selected from:
(R,S), (R,S);
(R), (R,S);
(S), (R,S);
(R), (R);
(S), (R);
(R), (S); and
(S), (S).

More preferably, the prodrug ester is selected from the group consisting of: methyl; ethyl; and isopropyl.

Preferred pharmaceutically acceptable salt forms include, for example, acetate, methanesulfonate, hydrochloride, benzenesulfonate, or para-toluenesulfonate.

Highly preferred compounds of this embodiment include:
$N^3$-[2-{3-(4-formamidinophenyl)-isoxazolin-5(R)-yl}-acetyl]-$N^2$-(n-butyloxycarbonyl)-2,3-(S)-diaminopropanoic acid, and pharmaceutically acceptable salt forms and propanoate ester prodrug forms thereof.

Still more preferred is a compound:
methyl-$N^3$-[2-{3-(4-formamidinophenyl)-isoxazolin-5(R)-yl}-acetyl]-$N^2$-(n-butyloxycarbonyl)-2,3-(S)-diaminopropanoate methanesulfonate salt.

The iontophoretic device of this embodiment IX can alternatively include compounds of Formula Ia:

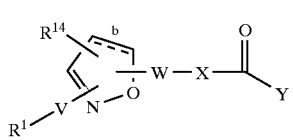

(I)

wherein:
Z is selected from: a bond, O, or S;
$R^2$ is selected from: H, aryl($C_1$–$C_{>10}$ alkoxy)carbonyl, or $C_1$–$C_{10}$ alkoxycarbonyl;
W is —$(CH_2)_nC(=O)N(R^{5a})$—;
X is —$(C(R^4)_2)_n$—$C(R^4)(R^8)$—$CH(R^4)$—, with the proviso that:
  when n is 0 or 1, then at least one of $R^{4a}$ or $R^8$ is other than H or methyl;
$R^5$ is selected from: H or $C_1$–$C_{10}$ alkyl substituted with 0–6 $R^{4b}$;
$R^6$ is selected from:
  H, $C_1$–$C_{10}$ alkyl, hydroxy, $C_1$–$C_{10}$ alkoxy, nitro, $C_1$–$C_{10}$ alkylcarbonyl, —$N(R^{12})R^{13}$, —$NR^5R^{5a}$, $CO_2R^5$, $S(O)_mR^5$, $OR^5$, cyano, halo;
  $C_6$–$C_{10}$ aryl optionally substituted with 1–3 groups selected from halogen, $C_1$–$C_6$ alkoxy, $C_1$–$C_6$ alkyl, $CF_3$, $S(O)_mCH_3$, or —$N(CH_3)_2$;
  $C_7$–$C_{11}$ arylalkyl, the aryl being optionally substituted with 1–3 groups selected from halogen, $C_1$–$C_6$ alkoxy, $C_1$–$C_6$ alkyl, $CF_3$, $S(O)_mCH_3$, or —$N(CH_3)_2$;
  methylenedioxy when $R^6$ is a substituent on aryl; or
  a 5–10 membered heterocyclic ring containing 1–3 N, O, or S heteroatoms, wherein the heterocyclic ring can be saturated, partially saturated, or fully unsaturated, the heterocyclic ring being substituted with 0–2 $R^7$;

$R^7$ is selected from:
  H, $C_1$–$C_{10}$ alkyl, hydroxy, $C_1$–$C_{10}$ alkoxy, nitro, $C_1$–$C_{10}$ alkylcarbonyl, —$N(R^{12})R^{13}$, cyano, or halo;

$R^8$ is selected from:
  —$CONR^5NR^{5a}$; —$CO_2R^5$; $C_1$–$C_{10}$ alkyl, substituted with 0–3 $R^6$; $C_2$–$C_{10}$ alkenyl, substituted with 0–3 $R^6$; $C_2$–$C_{10}$ alkynyl, substituted with 0–3 $R^6$, $C_3$–$C_8$ cycloalkyl, substituted with 0–3 $R^6$; $C_5$–$C_6$ cycloalkenyl, substituted with 0–3 $R^6$; aryl, substituted with 0–2 $R^6$; 5–10 membered heterocyclic ring containing 1–3 N, O, or S heteroatoms, wherein the heterocyclic ring can be saturated, partially saturated, or fully unsaturated, the heterocyclic ring being substituted with 0–2 $R^6$;

$R^{12}$ and $R^{13}$ are selected independently from:
  H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, aryl, heteroarylcarbonyl, heteroarylsulfonyl, or heteroarylalkylcarbonyl, wherein the aryl groups are optionally substituted with 0–3 substituents selected from the group consisting of: $C_1$–$C_4$ alkyl, $C_1$–$C_4$ alkoxy, halo, $CF_3$, and $NO_2$.

Still more preferably, in a compound of Formula Ia:
Z is selected from: a bond or O;
W is —$(CH_2)_nC(=O)N(R^{12})$—; and
X is —$C(R^4)(R^8)$—$C(R^4)_2$—.

The compounds of this embodiment also include compounds of Formula Ia, wherein:
either:
  $R^1$ is selected from:
    $R^2NHC(=NR^2)$— or $R^2NHC(=NR^2)NH$— and V is phenylene or pyridylene,
or:
  $R^1$ is

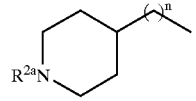

and V is a single bond;
n is 1 or 2;
X is —$CHR^8CH_2$—;
Y is selected from:
  hydroxy; $C_1$–$C_{10}$ alkoxy; methylcarbonyloxymethoxy; ethylcarbonyloxymethoxy;
  t-butylcarbonyloxymethoxy; cyclohexylcarbonyloxymethoxy;
  1-(methylcarbonyloxy)-ethoxy; 1-(ethylcarbonyloxy)-ethoxy;
  1-(t-butylcarbonyloxy)-ethoxy;
  1-(cyclohexylcarbonyloxy)-ethoxy;
  i-propyloxycarbonyloxymethoxy;
  t-butyloxycarbonyloxymethoxy;
  1-(i-propyloxycarbonyloxy)-ethoxy;
  1-(cyclohexyloxycarbonyloxy)-ethoxy;
  1-(t-butyloxycarbonyloxy)-ethoxy; dimethylaminoethoxy; diethylaminoethoxy;
  (5-methyl-1,3-dioxacyclopenten-2-on-4-yl)-methoxy;
  (5-(t-butyl)-1,3-dioxacyclopenten-2-on-4-yl)-methoxy;
  (1,3-dioxa-S-phenyl-cyclopenten-2-on-4-yl)-methoxy;
  1-(2-(2-methoxypropyl)-carbonyloxy)-ethoxy;

$R^6$ is selected from:

H, $C_1$–$C_4$ alkyl, hydroxy, $C_1$–$C_4$ alkoxy, nitro, $C_1C_{10}$ alkylcarbonyl, —N($R^{12}$)$R^{13}$, —N$R^5R^{5a}$, $CO_2R^5$, $S(O)_mR^5$, $OR^5$, cyano, halo;

$C_6$–$C_{10}$ aryl optionally substituted with 1–3 groups selected from halogen, $C_1$–$C_6$ alkoxy, $C_1$–$C_6$ alkyl, $CF_3$, $S(O)_mCH_3$, or —N$(CH_3)_2$;

methylenedioxy when $R^6$ is a substituent on aryl; or a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, benzimidazolyl, piperidinyl, tetrahydrofuranyl, pyranyl, pyridinyl, 3H-indolyl, carbazolyl, pyrrolidinyl, piperidinyl, indolinyl, isoxazolyl, isoxazolinyl or morpholinyl;

$R^8$ is selected from:

—CON$R^5NR^{5a}$; —$CO_2R^5$; $C_1$–$c_{10}$ alkyl, substituted with 0–3 $R^6$; $C_2$–$C_{10}$ alkenyl, substituted with 0–3 $R^6$; $C_2$–$C_{10}$ alkynyl, substituted with 0–3 $R^6$, $C_3$–$C_8$ cycloalkyl, substituted with 0–3 $R^6$; aryl, substituted with 0–2 $R^6$; a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl isoxazolinyl, benzimidazolyl, piperidinyl, tetrahydrofuranyl, pyranyl, pyridinyl, 3H-indolyl, carbazolyl, pyrrolidinyl, piperidinyl, indolinyl, or morpholinyl, the heterocyclic ring being substituted with 0–2 $R^6$;

$R^{12}$ is selected from:

H, $C_1$–$C_6$ alkyl, $C_1$–$C_4$ alkoxycarbonyl, $C_1$–$C_6$ alkylcarbonyl, $C_1$–$C_6$ alkylsulfonyl, aryl($C_1$–$C_4$ alkyl)sulfonyl, arylsulfonyl, aryl, heteroarylsulfonyl, pyridylcarbonyl or pyridylmethylcarbonyl, wherein the aryls are optionally substituted with 0–3 substituents selected from the group consisting of: $C_1$–$C_4$ alkyl, $C_1$–$C_4$ alkoxy, halo, $CF_3$, and $NO_2$; and $R^{13}$ is H.

Suitable integrin inhibitors of this embodiment include, among others, the following compounds of Formula I, and pharmaceutically acceptable salt forms thereof:

3(R,S)-{5(R,S)-N-[3-(4-amidinophenyl)-isoxazolin-5-yl-acetyl]-amino}-3-phenylpropanoic acid;

3(R,S)-{5(R,S)-N-[3-(4-amidinophenyl)-isoxazolin-5-yl-acetyl]-amino}-pentanoic acid;

3(R)-{5(R,S)-N-[3-(4-amidinophenyl)-isoxazolin-5-yl-acetyl]-amino}-heptanoic acid;

3(R,S)-{5(R,S)-N-[3-(4-amidinophenyl)-isoxazolin-5-yl-acetyl]-amino}-4-(phenylthio)butanoic acid;

3(R,S)-{5(R,S)-N-[3-(4-amidinophenyl)-isoxazolin-5-yl-acetyl]-amino}-4-(phenylsulfonamido)butanoic acid;

3(R,S)-{5(R,S)-N-[3-(4-amidinophenyl)-isoxazolin-5-yl-acetyl]-amino}-4-(n-butylsulfonamido)butanoic acid;

3(S)-{5(R,S)-N-[3-(4-amidinophenyl)-isoxazolin-5-yl-acetyl]-amino}-3-(adamantylmethylaminocarbonyl)-propanoic acid;

3(S)-{5(R,S)-N-[3-(4-amidinophenyl)-isoxazolin-5-yl-acetyl]-amino}-3-(1-azabicyclo[3.2.2]nonylcarbonyl)-propanoic acid;

3(S)-{5(R,S)-N-[3-(4-amidinophenyl)-isoxazolin-5-yl-acetyl]-amino}-3-(phenethylaminocarbonyl)-propanoic acid;

3(R)-{5(R,S)-N-[3-(4-amidinophenyl)-isoxazolin-5-yl-acetyl]-amino}-3-(3-pyridylethyl)-propanoic acid;

3(R)-{5(R,S)-N-[3-(4-amidinophenyl)-isoxazolin-5-yl-acetyl]-amino}-3-(2-pyridylethyl)-propanoic acid; and 3(R)-{5(R,S)-N-[3-(4-amidinophenyl)-isoxazolin-5-yl-acetyl]-amino}-3-(phenylpropyl)-propanoic acid.

In another embodiment, (designated embodiment XIX), the device includes, and can be used to deliver, a compound of Formula Id:

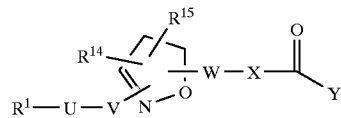

(Id)

or a pharmaceutically acceptable salt form thereof, wherein:

$R^1$ is selected from is selected from:

$R^2(R^3)N$—, $R^2(R^3)N(R^2N$=$)C$—, $R^2(R^3)N(R^2N$=$)CN(R^2)$—, $R^2(R^3)N(CH_2)_qZ$—, $R^2(R^3)N(R^2N$=$)C(CH_2)_qZ$—, $R^2(R^3)N(R^2N$=$)CN(R^2)(CH_2)_qZ$—, piperazinyl-$(CH_2)_qZ$—, $R^2(R^3)NC(O)$—, $R^2(R^5O)N(R^2N$=$)C$—, $R^2(R^3)N(R^5ON$=$)C$—,

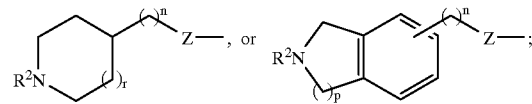

Z is selected from a bond, O, S, S(=O), or S(=O)$_2$;

$R^2$ and $R^3$ are selected independently from:

H; $C_1$–$C_{10}$ alkyl; $C_3$–$C_6$ alkenyl; $C_3$–$C_{11}$ cycloalkyl; $C_4$–$C_{11}$ cycloalkylalkyl; $C_6$–$C_{10}$ aryl optionally substituted with 0–3 groups selected from hydroxy, halogen, $C_1$–$C_6$ alkoxy, $C_1$–$C_6$ alkyl, $CF_3$, $S(O)_mCH_3$, —N$(CH_3)_2$, $C_1$–$C_4$ haloalkyl, methylenedioxydiyl, ethylenedioxydiyl; , $C_7$–$C_{11}$ arylalkyl optionally substituted with 0–3 groups selected from hydroxy, halogen, $C_1$–$C_6$ alkoxy, $C_1$–$C_6$ alkyl, $CF_3$, $S(O)_mCH_3$, —N$(CH_3)_2$, $C_1$–$C_4$ haloalkyl, methylenedioxydiyl, ethylenedioxydiyl; $C_2$–$C_7$ alkylcarbonyl; $C_7$–$C_{11}$ arylcarbonyl optionally substituted with 0–3 groups selected from hydroxy, halogen, $C_1$–$C_6$ alkoxy, $C_1$–$C_6$ alkyl, $CF_3$, $S(O)_mCH_3$, —N$(CH_3)_2$, $C_1$–$C_4$ haloalkyl, methylenedioxydiyl, ethylenedioxydiyl; $C_1$–$C_{10}$ alkoxycarbonyl; $C_4$–$C_{11}$ cycloalkoxycarbonyl; $C_7$–$C_{11}$ bicycloalkoxycarbonyl; $C_7$–$C_{11}$ aryloxycarbonyl optionally substituted with 0–3 groups selected from hydroxy, halogen, $C_1$–$C_6$ alkoxy, $C_1$–$C_6$ alkyl, $CF_3$, $S(O)_mCH_3$, —N$(CH_3)_2$, $C_1$–$C_4$ haloalkyl, methylenedioxydiyl, ethylenedioxydiyl; aryl($C_1$–$C_{10}$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, —N$(CH_3)_2$, $C_1$–$C_4$ haloalkyl, methylenedioxydiyl, ethylenedioxydiyl; $C_1$–$C_6$ alkylcarbonyloxy($C_1$–$C_4$ alkoxy)carbonyl;

$C_6$–$C_{10}$ arylcarbonyloxy($C_1$–$C_4$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, —N$(CH_3)_2$, $C_1$–$C_4$ haloalkyl, methylenedioxydiyl, ethylenedioxydiyl; $C_4$–$C_{11}$ cycloalkylcarbonyloxy($C_1$–$C_4$ alkoxy)carbonyl; heteroaryl optionally substituted with 0–2 groups selected from hydroxy, halogen, $C_1$–$C_6$ alkoxy, $C_1$–$C_6$ alkyl, $CF_3$, $S(O)_mCH_3$, —N$(CH_3)_2$, $C_1$–$C_4$ haloalkyl, methylenedioxydiyl, ethylenedioxydiyl; or heteroaryl($C_1$–$C_5$)alkyl where the heteroaryl group is optionally substituted with 0–2 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl;

provided that only one of $R^2$ and $R^3$ can be hydroxy;

U is selected from:
a single bond, $C_1$–$C_7$ alkylene, $C_2$–$C_7$ alkenylene, $C_2$–$C_7$ alkynylene, arylene substituted with 0–3 $R^{6a}$, or pyridylene substituted with 0–3 $R^{6a}$;

V is selected from:
a single bond; $C_1$–$C_7$ alkylene substituted with 0–6 $R^6$ or $R^7$; $C_2$–$C_7$ alkenylene substituted with 0–4 $R^6$ or $R^7$; $C_2$–$C_7$ alkynylene substituted with 0–4 $R^6$ or $R^7$; phenylene substituted with 0–4 $R^6$ or $R^7$; pyridylene substituted with 0–3 $R^6$ or $R^7$; pyridazinylene substituted with 0–3 $R^6$ or $R^7$;

X is selected from:
a single bond; —$(CH_2)_nC(=O)N(R^{12})$—; $C_1$–$C_7$ alkylene substituted with 0–6 $R^4$, $R^8$ or $R^{15}$; $C_2$–$C_7$ alkenylene substituted with 0–4 $R^4$, $R^8$ or $R^{15}$; $C_2$–$C_7$ alkynylene with 0–4 $R^4$, $R^8$ or $R^{15}$;

Y is selected from:
hydroxy, $C_1$–$C_{10}$ alkyloxy, $C_3$–$C_{11}$ cycloalkyloxy, $C_6$–$C_{10}$ aryloxy, $C_7$–$C_{11}$ aralkyloxy, $C_3$–$C_{10}$ alkylcarbonyloxyalkyloxy, $C_3$–$C_{10}$ alkoxycarbonyloxyalkyloxy, $C_2$–$C_{10}$ alkoxycarbonylalkyloxy, $C_5$–$C_{10}$ cycloalkylcarbonyloxyalkyloxy, $C_5$–$C_{10}$ cycloalkoxycarbonyloxyalkyloxy, $C_5$–$C_{10}$ cycloalkoxycarbonylalkyloxy, $C_7$–$C_{11}$ aryloxycarbonylalkyloxy, $C_8$–$C_{12}$ aryloxycarbonyloxyalkyloxy, $C_8$–$C_{12}$ arylcarbonyloxyalkyloxy, $C_5$–$C_{10}$ alkoxyalkylcarbonyloxyalkyloxy, $C_5$–$C_{10}$ (5-alkyl-1,3-dioxa-cyclopenten-2-one-yl)-methyloxy, $C_{10}$–$C_{14}$ (5-aryl-1,3-dioxa-cyclopenten-2-one-yl)-methyloxy; $(R^2)(R^3)N$—$(C_1$–$C_{10}$ alkoxy)-;

$R^{14}$ and W are attached to the same carbon and taken together to form a spiro-fused, 5–7 membered ring structure of the formula:

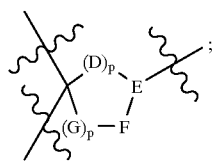

D, E, F, and G are each selected independently from:
$C(R^{6a})_2$; carbonyl; a heteroatom moiety selected from N, $N(R^{12})$, O, provided that no more than 2 of D, E, F and G are N, $N(R^{12})$, O, S, or $C(=O)$; alternatively, the bond between D and E, E and F, or F and G in such spiro-fused ring can be a carbon-nitrogen double bond or a carbon-carbon double bond;

$R^4$ is selected from:
H, $C_1$–$C_{10}$ alkyl, hydroxy, $C_1$–$C_{10}$ alkoxy, nitro, $C_1$–$C_{10}$ alkylcarbonyl, or —$N(R^{12})R^{13}$;

$R^6$ and $R^7$ are each selected independently from:
H, $C_1$–$C_{10}$ alkyl, hydroxy, $C_1$–$C_{10}$ alkoxy, nitro, $C_1$–$C_{10}$ alkylcarbonyl, —$N(R^{12})R^{13}$, cyano, halo, $CF_3$, CHO, $CO_2R^{5a}$, $C(=O)R^{5a}$, $CONHR^{5a}$, $CON(R^{12})_2$, $OC(=O)R^{5a}$, $OC(=O)OR^{5a}$, $OR^{5a}$, $OC(=O)N(R^{12})_2$, $OCH_2CO_2R^{5a}$, $CO_2CH_2CO_2R^{5a}$, $N(R^{12})_2$, $NO_2$, $NR^{12}C(=O)R^{5a}$, $NR^{12}C(=O)OR^{5a}$, $NR^{12}C(=O)N(R^{12})_2$, $NR^{12}SO_2N(R^{12})_2$, $NR^{12}SO_2R^{5a}$, $S(O)_pR^{5a}$, $SO_2N(R^{12})_2$, $C_2$–$C_6$ alkenyl, $C_3$–$C_{11}$ cycloalkyl, $C_4$–$C_{11}$ cycloalkylmethyl; $C_6$–$C_{10}$ aryl optionally substituted with 1–3 groups selected from halogen, $C_1$–$C_6$ alkoxy, $C_1$–$C_6$ alkyl, $CF_3$, $S(O)_mCH_3$, or —$N(CH_3)_2$; $C_7$–$C_{11}$, the aryl being optionally substituted with 1–3 groups selected from halogen, $C_1$–$C_6$ alkoxy, $C_1$–$C_6$ alkyl, $CF_3$, $S(O)_mCH_3$, or —$N(CH_3)_2$; methylenedioxy when $R^6$ is a substituent on aryl;

$R^{6a}$ is selected from $C_1$–$C_4$ alkyl, $C_1$–$C_4$ alkoxy, halo, $CF_3$, $NO_2$, or $NR^{12}R^{13}$;

$R^8$ is selected from:
H; $R^6$; $C_1$–$C_{10}$ alkyl, substituted with 0–8 $R^6$; $C_2$–$C_{10}$ alkenyl, substituted with 0–6 $R^6$;
$C_2$–$C_{10}$ alkynyl, substituted with 0–6 $R^6$; $C_3$–$C_8$ cycloalkyl, substituted with 0–6 $R^6$;
$C_5$–$C_6$ cycloalkenyl, substituted with 0–5 $R^6$; aryl, substituted with 0–5 $R^6$; 5–6 membered heterocyclic ring containing 1–2 N, O, or S heteroatoms, wherein the heterocyclic ring can be saturated, partially saturated, or fully unsaturated, the heterocyclic ring being substituted with 0–5 $R^6$;

$R^{12}$ and $R^{13}$ are selected independently from:
H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, aryl, $C_2$–$C_6$ alkenyl, $C_3$–$C_{11}$ cycloalkyl, $C_4$–$C_{11}$ cycloalkylalkyl, $C_7$–$C_{11}$ arylalkyl, $C_2$–$C_7$ alkylcarbonyl, $C_7$–$C_{11}$ arylcarbonyl, $C_2$–$C_{10}$ alkoxycarbonyl, $C_4$–$C_{11}$ cycloalkoxycarbonyl, $C_7$–$C_{11}$ bicycloalkoxycarbonyl, $C_7$–$C_{11}$ aryloxycarbonyl, heteroarylcarbonyl, heteroarylsulfonyl, heteroarylalkylcarbonyl or aryl($C_1$–$C_{10}$ alkoxy)carbonyl, wherein the aryl groups and heteroaryl groups are optionally substituted with 0–3 substituents selected from: $C_1$–$C_4$ alkyl, $C_1$–$C_4$ alkoxy, halo, $CF_3$, and $NO_2$;

$R^5$ and $R^{5a}$ are selected independently from:
H, $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–8 $R^4$;

$R^{15}$ is selected from:
H; $R^6$; $C_1$–$C_{10}$ alkyl, substituted with 0–8 $R^6$; $C_2$–$C_{10}$ alkenyl, substituted with 0–6 $R^6$;
$C_1$–$C_{10}$ alkoxy, substituted with 0–6 $R^6$; aryl, substituted with 0–5 $R^6$; 5–6 membered heterocyclic ring containing 1–2 N, O, or S heteroatoms, wherein the heterocyclic ring can be saturated, partially saturated, or fully unsaturated, the heterocyclic ring being substituted with 0–5 $R^6$; $C_1$–$C_{10}$ alkoxycarbonyl substituted with 0–8 $R^6$; $CO_2R^5$; or —$C(=O)N(R^{12})R^{13}$;

m is 0–2;
n is 0–4;
p is 1–3;
q is 1–7;
r is 0–3;

provided that n, p, q and r are chosen such that the number of atoms between $R^1$ and Y is in the range of 8–17.

The integrin inhibitor in this embodiment can be a compound of Formula III:

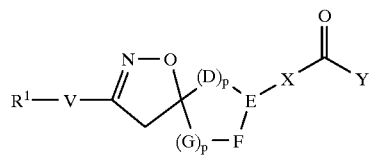

(III)

wherein:

$R^1$ is selected from:
$R^2HN-$, $H_2N(R^2N=)C-$, $H_2N(R^2N=)CNH-$, $R^2HN(CH_2)_qO-$, $H_2N(R^2N=)CNH(CH_2)_qO-$, piperazinyl-$(CH_2)_qO-$, $R^2(R^3)NC(O)-$, $R^2(R^5O)N(R^2N=)C-$, $R^2(R^3)N(R^5ON=)C-$,

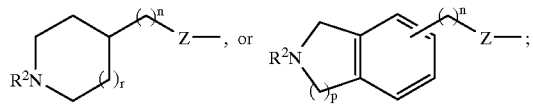

$R^2$ and $R^3$ are selected independently from:
H; $C_1$–$C_6$ alkyl; $C_7$–$C_{11}$ arylalkyl optionally substituted with 0–3 groups selected from hydroxy, halogen, $C_1$–$C_6$ alkoxy, $C_1$–$C_6$ alkyl, $CF_3$, $S(O)_mCH_3$, $-N(CH_3)_2$, $C_1$–$C_4$ haloalkyl, methylenedioxydiyl, ethylenedioxydiyl; aryl($C_1$–$C_{10}$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, $-N(CH_3)_2$, $C_1$–$C_4$ haloalkyl, methylenedioxydiyl, ethylenedioxydiyl; heteroaryl($C_1$–$C_5$)alkyl wherein the heteroaryl group is optionally substituted with 0–2 groups selected from hydroxy, halogen, $C_1$–$C_6$ alkoxy, $C_1$–$C_6$ alkyl, $CF_3$, $S(O)_mCH_3$, $-N(CH_3)_2$, $C_1$–$C_4$ haloalkyl, methylenedioxydiyl, ethylenedioxydiyl; or $C_1$–$C_{10}$ alkoxycarbonyl;

$R^4$ is selected from:
H, $C_1$–$C_{10}$ alkyl, hydroxy, $C_1$–$C_{10}$ alkoxy, nitro, $C_1$–$C_{10}$ alkylcarbonyl, or $-N(R^{12})R^{13}$;

V is selected from:
a single bond; $C_1$–$C_7$ alkylene substituted with 0–6 $R^6$ or $R^7$; $C_2$–$C_7$ alkenylene substituted with 0–4 $R^6$ or $R^7$; $C_2$–$C_7$ alkynylene substituted with 0–4 $R^6$ or $R^7$; phenylene substituted with 0–3 $R^6$ or $R^7$; pyridylene substituted with 0–3 $R^6$ or $R^7$; pyridazinylene substituted with 0–3 $R^6$ or $R^7$;

X is selected from:
$-(CH_2)_nC(=O)N(R^{12})-$, $C_1$–$C_7$ alkylene substituted with 0–1 $R^4$, $C_2$–$C_7$ alkenylene, or $C_2$–$C_7$ alkynylene;

Y is selected from:
hydroxy, $C_1$–$C_{10}$ alkyloxy, $C_3$–$C_{11}$ cycloalkyloxy, $C_6$–$C_{10}$ aryloxy, $C_7$–$C_{11}$ aralkyloxy, $C_3$–$C_{10}$ alkylcarbonyloxyalkyloxy, $C_3$–$C_{10}$
alkoxycarbonyloxyalkyloxy, $C_2$–$C_{10}$
alkoxycarbonylalkyloxy, $C_5$–$C_{10}$
cycloalkylcarbonyloxyalkyloxy, $C_5$–$C_{10}$
cycloalkoxycarbonyloxyalkyloxy, $C_5$–$C_{10}$
cycloalkoxycarbonylalkyloxy, $C_7$–$C_{11}$
aryloxycarbonylalkyloxy, $C_8$–$C_{12}$
aryloxycarbonyloxyalkyloxy, $C_8$–$C_{12}$
arylcarbonyloxyalkyloxy, $C_5$–$C_{10}$
alkoxyalkylcarbonyloxyalkyloxy, $C_5$–$C_{10}$ (5-alkyl-1,3-dioxa-cyclopenten-2-one-yl)-methyloxy, or $C_{10}$–$C_{14}$ (5-aryl-1,3-dioxa-cyclopenten-2-one-yl)-methyloxy;

Z is selected from:
O or $CH_2$;

D, E, F and G are each selected independently from:
$C_2$; carbonyl; a heteroatom moiety selected from N, NH, O, provided that no more than 2 of D, E, F and G are N, NH, O or S; alternatively, the bond between D and E, E and F, or F and G in such spiro-fused ring can be a carbon-nitrogen double bond or a carbon-carbon double bond;

$R^6$ and $R^7$ are each selected independently from:
H, $C_1$–$C_{10}$ alkyl, hydroxy, $C_1$–$C_{10}$ alkoxy, nitro, $C_1$–$C_{10}$ alkylcarbonyl, $-N(R^{12})R^{13}$, cyano, or halo;

$R^{12}$ and $R^{13}$ are each selected independently from:
H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl ($C_1$–$C_{10}$ alkyl) sulfonyl, arylsulfonyl, heteroarylsulfonyl, heteroarylcarbonyl, heteroaryalkylcarbonyl or aryl;

n is 0–4;
p is 1–3;
q is 1–7;
r is 0–3;
provided that n, p, q and r are chosen such that the number of atoms between $R^1$ and Y is in the range of 8–17.

This embodiment also includes compounds wherein:
either:
$R^1$ is $R^2NHC(=NR^2)-$ and V is phenyl or pyridyl
or:
$R^1$ is

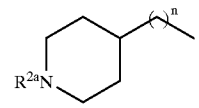

and V is a single bond;
n is 1 or 2;
X is $C_1$–$C_4$ alkylene substituted with 0–1 $R^4$;
Y is selected from:
hydroxy; $C_1$–$C_{10}$ alkoxy; methylcarbonyloxymethoxy; ethylcarbonyloxymethoxy;
t-butylcarbonyloxymethoxy; cyclohexylcarbonyloxymethoxy;
1-(methylcarbonyloxy)-ethoxy; 1-(ethylcarbonyloxy)-ethoxy;
1-(t-butylcarbonyloxy)-ethoxy; 1-(cyclohexylcarbonyloxy)-ethoxy;
i-propyloxycarbonyloxymethoxy; t-butyloxycarbonyloxymethoxy;
1-(i-propyloxycarbonyloxy)-ethoxy; 1-(cyclohexyloxycarbonyloxy)-ethoxy;
1-(t-butyloxycarbonyloxy)-ethoxy; dimethylaminoethoxy; diethylaminoethoxy;
(5-methyl-1,3-dioxacyclopenten-2-on-4-yl)-methoxy;
(5-(t-butyl)-1,3-dioxacyclopenten-2-on-4-yl)-methoxy;
(1,3-dioxa-5-phenyl-cyclopenten-2-on-4-yl)-methoxy;
1-(2-(2-methoxypropyl)carbonyloxy)-ethoxy;

$R^{12}$ and $R^{13}$ are each selected independently from:
H, $C_1$–$C_6$ alkyl, $C_1$–$C_4$ alkoxycarbonyl, $C_1$–$C_4$ alkylcarbonyl, $C_1$–$C_4$ alkylsulfonyl, aryl($C_1$–$C_4$ alkyl)sulfonyl, heteroarylsulfonyl, arylsulfonyl, heteroarylcarbonyl, heteroaryalkylcarbonyl or aryl; and $R^{13}$ is H.

The compounds of this embodiment include the following exemplary compounds, and pharmaceutically acceptable salt forms thereof:

5(R,S)-3-(4-amidinophenyl)-8-(2-carboxyethyl)-1-oxa-2,8-diazaspiro[4.4]non-2-ene-7,9-dione;
5(R,S)-3-(4-amidinophenyl)-8-(3-carboxypropyl)-1-oxa-2,8-diazaspiro[4.4]non-2-ene-7,9-dione;
5(R,S)-3-(4-amidinophenyl)-8-(2-carboxyethyl)-1-oxa-2,8-diazaspiro[4.4]non-2-ene-5-one;
5(R,S)-3-(4-amidinophenyl)-8-(3-carboxypropyl)-1-oxa-2,8-diazaspiro[4.4]non-2-ene-5-one;
5(R,S)-3-(4-amidinophenyl)-8-(2-carboxyethyl)-1-oxa-2-azaspiro[4.4]nona-2,8-diene-5-one;
5(R,S)-3-(4-amidinophenyl)-8-(3-carboxypropyl)-1-oxa-2-azaspiro[4.4]nona-2,8-diene-5-one;
5(R,S)-3-(4-amidinophenyl)-8-(2-carboxyethyl)-1-oxa-2,8-diazaspiro[4.4]dec-2-ene-7,9-dione;
5(R,S)-3-(4-amidinophenyl)-8-(3-carboxypropyl)-1-oxa-2,8-diazaspiro[4.4]dec-2-ene-7,9-dione;
5(R,S)-3-(4-amidinophenyl)-8-(2-carboxyethyl)-1-oxa-2,8-diazaspiro[4.4]dec-2-ene-S-one;
5(R,S)-3-(4-amidinophenyl)-8-(3-carboxypropyl)-1-oxa-2,8-diazaspiro[4.4]dec-2-ene-5-one;
5(R,S)-3-(4-amidinophenyl)-8-(2-carboxyethyl)-1-oxa-2-azaspiro[4.4]deca-2,8-diene-5-one;
5(R,S)-3-(4-amidinophenyl)-8-(3-carboxypropyl)-1-oxa-2-azaspiro[4.4]deca-2,8-diene-5-one;
5(R,S)-3-(4-amidinophenyl)-8-(2-carboxyethyl)-1-oxa-2,8-diazaspiro[4.4]undec-2-ene-7,9-dione;
5(R,S)-3-(4-amidinophenyl)-8-(3-carboxypropyl)-1-oxa-2,8-diazaspiro[4.4]undec-2-ene-7,9-dione;
5(R,S)-3-(4-amidinophenyl)-8-(2-carboxyethyl)-1-oxa-2,8-diazaspiro[4.4]undec-2-ene-5-one;
5(R,S)-3-(4-amidinophenyl)-8-(3-carboxypropyl)-1-oxa-2,8-diazaspiro[4.4]undec-2-ene-5-one;
5(R,S)-3-(4-amidinophenyl)-8-(2-carboxyethyl)-1-oxa-2-azaspiro[4.4]undeca-2,8-diene-5-one;
5(R,S)-3-(4-amidinophenyl)-8-(3-carboxypropyl)-1-oxa-2-azaspiro[4.4]undeca-2,8-diene-5-one;
5(R,S)-3-[2-(piperidin-4-yl)-ethyl]-8-(2-carboxyethyl)-1-oxa-2,8-diazaspiro[4.4]non-2-ene-7,9-dione;
5(R,S)-3-[2-(piperidin-4-yl)-ethyl]-8-(3-carboxypropyl)-1-oxa-2,8-diazaspiro[4.4]non-2-ene-7,9-dione;
5(R,S)-3-[2-(piperidin-4-yl)-ethyl]-8-(2-carboxyethyl)-1-oxa-2,8-diazaspiro[4.4]non-2-ene-5-one;
5(R,S)-3-[2-(piperidin-4-yl)-ethyl]-8-(3-carboxypropyl)-1-oxa-2,8-diazaspiro[4.4]non-2-ene-5-one;
5(R,S)-3-[2-(piperidin-4-yl)-ethyl]-8-(2-carboxyethyl)-1-oxa-2-azaspiro[4.4]nona-2,8-diene-5-one;
5(R,S)-3-[2-(piperidin-4-yl)-ethyl]-8-(3-carboxypropyl)-1-oxa-2-azaspiro[4.4]nona-2,8-diene-5-one;
5(R,S)-3-[2-(piperidin-4-yl)-ethyl]-8-(2-carboxyethyl)-1-oxa-2,8-diazaspiro[4.4]dec-2-ene-7,9-dione;
5(R,S)-3-[2-(piperidin-4-yl)-ethyl]-8-(3-carboxypropyl)-1-oxa-2,8-diazaspiro[4.4]dec-2-ene-5,7-dione;
5(R,S)-3-[2-(piperidin-4-yl)-ethyl]-8-(2-carboxyethyl)-1-oxa-2,8-diazaspiro[4.4]dec-2-ene-5-one;
5(R,S)-3-[2-(piperidin-4-yl)-ethyl]-8-(3-carboxypropyl)-1-oxa-2,8-diazaspiro[4.4]dec-2-ene-5-one;
5(R,S)-3-[2-(piperidin-4-yl)-ethyl]-8-(2-carboxyethyl)-1-oxa-2-azaspiro[4.4]deca-2,8-diene-5-one;
5(R,S)-3-[2-(piperidin-4-yl)-ethyl]-8-(3-carboxypropyl)-1-oxa-2-azaspiro[4.4]deca-2,8-diene-5-one;
5(R,S)-3-[2-(piperidin-4-yl)-ethyl]-8-(2-carboxyethyl)-1-oxa-2,8-diazaspiro[4.4]undec-2-ene-7,9-dione;
5(R,S)-3-[2-(piperidin-4-yl)-ethyl]-8-(3-carboxypropyl)-1-oxa-2,8-diazaspiro[4.4]undec-2-ene-7,9-dione;
5(R,S)-3-[2-(piperidin-4-yl)-ethyl]-8-(2-carboxyethyl)-1-oxa-2,8-diazaspiro[4.4]undec-2-ene-5-one;
5(R,S)-3-[2-(piperidin-4-yl)-ethyl]-8-(3-carboxypropyl)-1-oxa-2,8-diazaspiro[4.4]undec-2-ene-5-one;
5(R,S)-3-[2-(piperidin-4-yl)-ethyl]-8-(2-carboxyethyl)-1-oxa-2-azaspiro[4.4]undeca-2,8-diene-5-one;
5(R,S)-3-[2-(piperidin-4-yl)-ethyl]-8-(3-carboxypropyl)-1-oxa-2-azaspiro[4.4]undeca-2,8-diene-5-one; and
5(R,S)-3-(4-amidinophenyl)-8-[2-(benzyloxycarbonylamino)-2-carboxyethyl]-1-oxa-2,8-diazaspiro[4.5]dec-2-ene.

In an alternative embodiment (designated embodiment XXIII), the device includes, and can be used to deliver, a compound of Formula I:

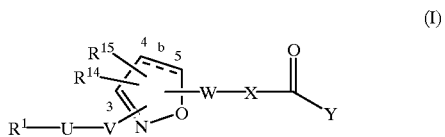

(I)

or a pharmaceutically acceptable salt form thereof, wherein:
b is a carbon-carbon single bond or double bond;
$R^1$ is selected from:
$R^2(R^3)N(CH_2)_qZ$—, $R^2(R^3)N(R^2N\!\!=\!\!)C(CH_2)_qZ$—, $R^2(R^3)N(R^2N\!\!=\!\!)CN(R^2)(CH_2)_qZ$—, piperazinyl-$(CH_2)_qZ$—, or

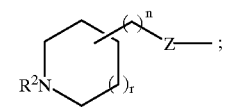

Z is selected from:
O, S, S(=O), S(=O)$_2$;
$R^2$ and $R^3$ are selected independently from:
H, $C_1$–$C_{10}$ alkyl, $C_2$–$C_6$ alkenyl, $C_3$–$C_{11}$ cycloalkyl, $C_4$–$C_{11}$ cycloalkylalkyl, $C_6$–$C_{10}$ aryl, $C_7$–$C_{11}$ arylalkyl, $C_2$–$C_7$ alkylcarbonyl, $C_7$–$C_{11}$ arylcarbonyl, $C_2$–$C_{10}$ alkoxycarbonyl, $C_4$–$C_{11}$ cycloalkoxycarbonyl, $C_7$–$C_{11}$ bicycloalkoxycarbonyl, $C_7$–$C_{11}$ aryloxycarbonyl, or aryl ($C_1$–$C_{10}$ alkoxy)carbonyl, $C_1$–$C_6$ alkylcarbonyloxy($C_1$–$C_4$ alkoxy)carbonyl, $C_6$–$C_{10}$ arylcarbonyloxy($C_1$–$C_4$ alkoxy)carbonyl, $C_4$–$C_{11}$ cycloalkylcarbonyloxy ($C_1$–$C_4$ alkoxy) carbonyl;

U is optionally present and is selected from:
$C_1$–$C_7$ alkylene, $C_2$–$C_7$ alkenylene, $C_2$–$C_7$ alkynylene, arylene, or pyridylene;

V is selected from:
a single bond; $C_1$–$C_7$ alkylene substituted with 0–6 $R^6$ or $R^7$; $C_2$–$C_7$ alkenylene substituted with 0–4 $R^6$ or $R^7$; $C_2$–$C_7$ alkynylene substituted with 0–4 $R^6$ or $R^7$;
phenylene substituted with 0–4 $R^6$ or $R^7$; pyridylene substituted with 0–3 $R^6$ or $R^7$;
pyridazinylene substituted with 0–3 $R^6$ or $R^7$;

W is -(aryl)-$Z^1$, wherein the aryl is substituted with 0–6 $R^6$ or $R^7$;

$Z^1$ is selected from a single bond, —$CH_2$—, O or S;

X is selected from:
a single bond; $C_1$–$C_7$ alkylene substituted with 0–6 $R^4$, $R^8$ or $R^{15}$; $C_2$–$C_7$ alkenylene substituted with 0–4 $R^4$, $R^8$ or $R^{15}$; $C_2$–$C_7$ alkynylene substituted with 0–4 $R^4$, $R^8$ or $R^{15}$;

Y is selected from:

hydroxy, $C_1$–$C_{10}$ alkyloxy, $C_3$–$C_{11}$ cycloalkyloxy, $C_6$–$C_{10}$ aryloxy, $C_7$–$C_{11}$ aralkyloxy, $C_3$–$C_{10}$ alkylcarbonyloxyalkyloxy, $C_3$–$C_{10}$ alkoxycarbonyloxyalkyloxy, $C_2$–$C_{10}$ alkoxycarbonylalky, $C_5$–$C_{10}$ cycloalkylcarbonyloxyalkyloxy, $C_5$–$C_{10}$ cycloalkoxycarbonylalkyloxy, $C_5$–$C_{10}$ cycloalkoxycarbonylalkyloxy, $C_7$–$C_{11}$ aryloxycarbonylalkyloxy, $C_8$–$C_{12}$ aryloxycarbonyloxyalkyloxy, $C_8$–$C_{12}$ arylcarbonyloxyalkyloxy, $C_5$–$C_{10}$ alkoxyalkylcarbonyloxyalkyloxy, $C_5$–$C_{10}$ (5-alkyl-1,3-dioxa-cyclopenten-2-one-yl)-methyloxy, $C_{10}$–$C_{14}$ (5-aryl-1,3-dioxa-cyclopenten-2-one-yl)-methyloxy; $(R^2)(R^3)N$—$(C_1$–$C_{10}$ alkoxy)-;

$R^4$ is selected from:
H, $C_1$–$C_{10}$ alkyl, hydroxy, $C_1$–$C_{10}$ alkoxy, nitro, $C_1$–$C_{10}$ alkylcarbonyl, or —$N(R^{12})R^{13}$;

$R^6$ and $R^7$ are each selected independently from:
H, $C_1$–$C_{10}$ alkyl, hydroxy, $C_1$–$C_{10}$ alkoxy, nitro, $C_1$–$C_{10}$ alkylcarbonyl, —$N(R^{12})R^{13}$, cyano, halo, $CF_3$, CHO, $CO_2R^{5a}$, $C(=O)R^{5a}$, $CONHR^{5a}$, $CON(R^{12})_2$, $OC(=O)R^{5a}$, $OC(=O)OR^{5a}$, $OR^{5a}$, $OC(=O)N(R^{12})_2$, $OCH_2CO_2R^{5a}$, $CO_2CH_2CO_2R^{5a}$, $N(R^{12})_2$, $NO_2$, $NR^{12}C(=O)R^{5a}$, $NR^{12}C(=O)OR^{5a}$, $NR^{12}C(=O)N(R^{12})_2$, $NR^{12}SO_2N(R^{12})_2$, $NR^{12}SO_2R^{5a}$, $S(O)_pR^{5a}$, $SO_2N(R^{12})_2$, $C_2$–$C_6$ alkenyl, $C_3$–$C_{11}$ cycloalkyl, $C_4$–$C_{11}$ cycloalkylmethyl;
$C_6$–$C_{10}$ aryl optionally substituted with halogen, alkoxy, alkyl, $CF_3$, $S(O)_mCH_3$, or —$N(CH_3)_2$; or $C_7$–$C_{11}$ arylalkyl the aryl being optionally substituted with halogen, alkoxy, alkyl, $CF_3$, $S(O)_mCH_3$, or —$N(CH_3)_2$;

$R^8$ is selected from:
H; $R^6$; $C_1$–$C_{10}$ alkyl, substituted with 0–8 $R^6$; $C_2$–$C_{10}$ alkenyl, substituted with 0–6 $R^6$;
$C_2$–$C_{10}$ alkynyl, substituted with 0–6 $R^6$; $C_3$–$C_{10}$ cycloalkyl, substituted with 0–6 $R^6$;
$C_5$–$C_6$ cycloalkenyl, substituted with 0–5 $R^6$; aryl, substituted with 0–5 $R^6$; 5–6 membered heterocyclic ring containing 1–2 N, O, or S heteroatoms, wherein the heterocyclic ring can be saturated, partially saturated, or fully unsaturated, the heterocyclic ring being substituted with 0–5 $R^6$;

$R^{12}$ and $R^{13}$ are selected independently from:
H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, heteroarylsulfonyl, arylsulfonyl, aryl, $C_2$–$C_6$ alkenyl, $C_3$–$C_{11}$ cycloalkyl, $C_4$–$C_{11}$ cycloalkylalkyl, $C_7$–$C_{11}$ arylalkyl, $C_2$–$C_7$ alkylcarbonyl, $C_7$–$C_{11}$ arylcarbonyl, $C_2$–$C_{10}$ alkoxycarbonyl, $C_4$–$C_{11}$ cycloalkoxycarbonyl, $C_7$–$C_{11}$ bicycloalkoxycarbonyl, $C_7$–$C_{11}$ aryloxycarbonyl, heteroarylcarbonyl, heteroarylalkylcarbonyl or aryl($C_1$–$C_{10}$ alkoxy)carbonyl;

$R^{14}$ is selected from:
H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or $C_1$–$C_{10}$ alkoxycarbonyl, $CO_2R^5$ or —$C(=O)N(R^{12})R^{13}$;

$R^5$ and $R^{5a}$ are selected independently from:
H, $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–8 $R^4$;

$R^{15}$ is selected from:
H; $R^6$; $C_1$–$C_{10}$ alkyl, substituted with 0–8 $R^6$; $C_2$–$C_{10}$ alkenyl, substituted with 0–6 $R^6$;

$C_1$–$C_{10}$ alkoxy, substituted with 0–6 $R^6$; aryl, substituted with 0–5 $R^6$; 5–6 membered heterocyclic ring containing 1–2 N, O, or S heteroatoms, wherein the heterocyclic ring can be saturated, partially saturated, or fully unsaturated, the heterocyclic ring being substituted with 0–5 $R^6$; $C_1$–$C_{10}$ alkoxycarbonyl substituted with 0–8 $R^6$;
$CO_2R^5$; or —$(=O)N(R^{12})R^{13}$;

m is 0–2;
n is 0–4;
q is 2–7;
r is 0–3;
provided that n, q, and r are chosen such that the number of atoms between $R^1$ and Y is about 8–17.

The compounds of this embodiment include compounds of Formula IV:

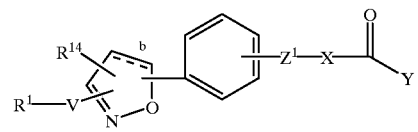

(IV)

wherein:
b is a carbon-carbon single bond or double bond;
$R^1$ is selected from:
$R^2HN(CH_2)_qO$—, $R^2HN(R^2N=C)NH(CH_2)_qO$—, piperazinyl-$CH_2)_qO$—, or

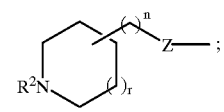

Z is O;
$R^2$ is selected from:
H, aryl($C_1$–$C_{10}$)alkoxycarbonyl, $C_1$–$C_{10}$ alkoxycarbonyl;
V is selected from:
a single bond; $C_1$–$C_7$ alkylene substituted with 0–6 $R^6$ or $R^7$; $C_2$–$C_7$ alkenylene substituted with 0–4 $R^6$ or $R^7$; $C_2$–$C_7$ alkynylene substituted with 0–4 $R^6$ or $R^7$;
phenylene substituted with 0–3 $R^6$ or $R^7$; pyridylene substituted with 0–3 $R^6$ or $R^7$;
pyridazinylene substituted with 0–3 $R^6$ or $R^7$;
$Z^1$ is selected from a single bond, O or S;
X is selected from:
a single bond; $C_1$–$C_7$ alkylene substituted with 0–4 $R^4$, $R^8$ or $R^{15}$; $C_2$–$C_7$ alkenylene substituted with 0–3 $R^4$, $R^8$ or $R^{15}$; $C_2$–$C_7$ alkynylene substituted with 0–3 $R^4$, $R^8$ or $R^{15}$;
Y is selected from:
hydroxy, $C_1$–$C_{10}$ alkyloxy, $C_3$–$C_{11}$ cycloalkyloxy, $C_6$–$C_{10}$ aryloxy, $C_7$–$C_{11}$ aralkyloxy, $C_3$–$C_{10}$ alkylcarbonyloxyalkyloxy, $C_3$–$C_{10}$ alkoxycarbonyloxyalkyloxy, $C_2$–$C_{10}$ alkoxycarbonylalkyloxy, $C_5$–$C_{10}$ cycloalkylcarbonyloxyalkyloxy, $C_5$–$C_{10}$ cycloalkoxycarbonyloxyalkyloxy, $C_5$–$C_{10}$ cycloalkoxycarbonylalkyloxy, $C_7$–$C_{11}$ aryloxycarbonylalkyloxy, $C_8$–$C_{12}$ aryloxycarbonyloxyalkyloxy, $C_8$–$C_{12}$ arylcarbonyloxyalkyloxy, $C_5$–$C_{10}$ alkoxyalkylcarbonyloxyalkyloxy, $C_5$–$C_{10}$ (5-alkyl-1,3-dioxa-cyclopenten-2-one-yl)-methyloxy, or $C_{10}$–$C_{14}$ (5-aryl-1,3-dioxa-cyclopenten-2-one-yl)-methyloxy;

$R^4$ is selected from:
H, $C_1$–$C_{10}$ alkyl, hydroxy, $C_1$–$C_{10}$ alkoxy, nitro, $C_1$–$C_{10}$ alkylcarbonyl, or —$(R^{12})R^{13}$;

$R^6$ and $R^7$ are selected independently from:
H, $C_1$–$C_{10}$ alkyl, hydroxy, $C_1$–$C_{10}$ alkoxy, nitro, $C_1$–$C_{10}$ alkylcarbonyl, —$N(R^{12})R^{13}$, cyano, or halo;

$R^8$ is selected from:
H, $C_1$–$C_{10}$ alkyl, $C_2$–$C_{10}$ alkenyl, $C_3$–$C_8$ cycloalkyl, $C_5$–$C_6$ cycloalkenyl, aryl, 5–6 membered heterocyclic ring containing 1–2 N, O, or S, where the heterocyclic ring can be saturated, partially saturated, or fully unsaturated;

$R^{12}$ and $R^{13}$ are selected independently from:
H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, heteroarylcarbonyl, heteroarylsulfonyl, heteroarylalkylcarbonyl or aryl;

$R^{14}$ is selected from:
H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or $C_1$–$C_{10}$ alkoxycarbonyl, $CO_2R^5$ or —(=ON$(R^{12})R^{13}$;

$R^5$ is selected from:
H or $C_1$–$C_{10}$ alkyl substituted with 0–6 $R^4$;

n is 0–4;
q is 2–7;

provided that n and q are chosen such that the number of atoms between $R^1$ and Y is in the range of 8–17.

Thus, this embodiment includes compounds wherein:
$R^1$ is $R^2HN(CH_2)_qO$— or

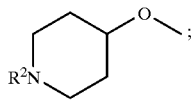

V is $C_1$–$C_3$ alkylene;
$Z^1$ is a single bond or O;
X is $C_1$–$C_3$ alkylene substituted with 0–1 $R^4$;
Y is selected from:
hydroxy; $C_1$–$C_{10}$ alkoxy; methylcarbonyloxymethoxy; ethylcarbonyloxymethoxy;
t-butylcarbonyloxymethoxy; cyclohexylcarbonyloxymethoxy;
1-(methylcarbonyloxy)-ethoxy; 1-(ethylcarbonyloxy)-ethoxy;
1-(t-butylcarbonyloxy)-ethoxy; 1-(cyclohexylcarbonyloxy)-ethoxy;
i-propyloxycarbonyloxymethoxy; t-butyloxycarbonyloxymethoxy;
1-(i-propyloxycarbonyloxy)-ethoxy; 1-(cyclohexyloxycarbonyloxy)-ethoxy;
1-(t-butyloxycarbonyloxy)-ethoxy; dimethylaminoethoxy; diethylaminoethoxy;
(5-methyl-1,3-dioxacyclopenten-2-on-4-yl)-methoxy;
(5-(t-butyl)-1,3-dioxacyclopenten-2-on-4yl)-methoxy;
(1,3-dioxa-5-phenyl-cyclopenten-2-on-4-yl)-methoxy;
1-(2-(2-methoxypropyl)carbonyloxy)-ethoxy;

$R^{12}$ and $R^{13}$ are selected independently from:
H, $C_1$–$C_6$ alkyl, $C_1$–$C_4$ alkoxycarbonyl, $C_1$–$C_4$ alkylcarbonyl, $C_1$–$C_6$ alkylsulfonyl, aryl($C_1$–$C_4$ alkyl)sulfonyl, arylsulfonyl, heteroarylcarbonyl, heteroarylsulfonyl, heteroarylalkylcarbonyl or aryl; and $R^{13}$ is H.

The compounds of this embodiment include the following exemplary compounds, and pharmaceutically acceptable salt forms thereof:
5(R,S)-4-[3-(piperidin-4-yl)oxymethylisoxazolin-5-yl] hydrocinnamic acid;
5(R,S)-4-[3-(2-aminoethoxymethyl)-isoxazolin-5-yl] hydrocinnamic acid;
5(R,S)-4-[3-(3-aminopropyloxymethyl)-isoxazolin-5-yl] hydrocinnamic acid;
5(R,S)-4-[3-(piperidin-4-yl)oxymethylisoxazolin-5-yl] phenoxyacetic acid;
5(R,S)-4-[3-(2-aminoethoxymethyl)-isoxazolin-5-yl] phenoxyacetic acid; and
5(R,S)-4-[3-(3-aminopropyloxymethyl)-isoxazolin-5-yl] phenoxyacetic acid.

In a further embodiment (designated embodiment XXVII), the device includes, and can be used to deliver, a compound of Formula I:

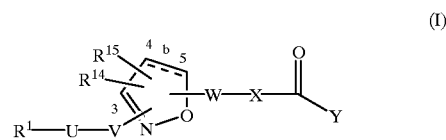

(I)

or a pharmaceutically acceptable salt form thereof, wherein:
b is a carbon-carbon single or double bond;
$R^1$ is selected from:
$R^{2a}(R^3)N$—, $R^2(R^3)N(R^2N=)C$—, $R^{2a}(R^3)N(CH_2)_q Z$—, $R^2(R^3)N(R^2N=)C(CH_2)_qZ$—, $R^2(R^3)NC(O)$—, $R^2(R^5O)N(R^2N=)C$—, $R^2(R^3)N(R^5ON=)C$—;

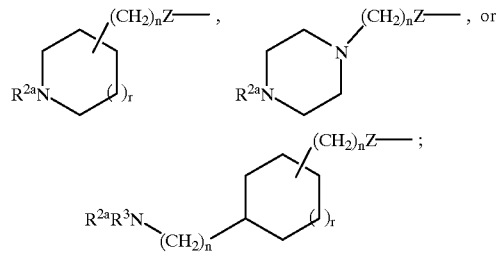

Z is selected from: a bond, O, S, S(=O), and S(=O)$_2$;
$R^2$ and $R^3$ are selected independently from:
H; $C_1$–$C_{10}$ alkyl; $C_3$–$C_6$ alkenyl; $C_3$–$C_{11}$ cycloalkyl; $C_4$–$C_{11}$ cycloalkylalkyl; $C_6$–$C_{10}$ aryl optionally substituted with 0–3 groups selected from hydroxy, halogen, $C_1$–$C_6$ alkoxy, $C_1$–$C_6$ alkyl, $CF_3$, $S(O)_m CH_3$, —$N(CH_3)_2$, $C_1$–$C_4$ haloalkyl, methylenedioxydiyl, ethylenedioxydiyl; $C_7$–$C_{11}$ arylalkyl optionally substituted with 0–3 groups selected from hydroxy, halogen, $C_1$–$C_6$ alkoxy, $C_1$–$C_6$ alkyl, $CF_3$, $S(O)_m CH_3$, —$N(CH_3)_2$, $C_1$–$C_4$ haloalkyl, methylenedioxydiyl, ethylenedioxydiyl; $C_2$–$C_7$ alkylcarbonyl;
$C_7$–$C_{11}$ arylcarbonyl optionally substituted with 0–3 groups selected from hydroxy, halogen, $C_1$–$C_6$ alkoxy, $C_1$–$C_6$ alkyl, $CF_3$, $S(O)_m CH_3$, —$N(CH_3)_2$, $C_1$–$C_4$ haloalkyl, methylenedioxydiyl, ethylenedioxydiyl; $C_1$–$C_{10}$ alkoxycarbonyl;

$C_4-C_{11}$ cycloalkoxycarbonyl; $C_7-C_{11}$ bicycloalkoxycarbonyl; $C_7-C_{11}$ aryloxycarbonyl optionally substituted with 0–3 groups selected from hydroxy, halogen, $C_1-C_6$ alkoxy, $C_1-C_6$ alkyl, $CF_3$, $S(O)_m CH_3$, $-N(CH_3)_2$, $C_1-C_4$ haloalkyl, methylenedioxydiyl, ethylenedioxydiyl; aryl $(C_1-C_{10}$ alkoxy)carbonyl where the aryl group is optionally substituted with 0–3 groups selected from hydroxy, halogen, $C_1-C_6$ alkoxy, $C_1-C_6$ alkyl, $CF_3$, $S(O)_m CH_3$, $-N(CH_3)_2$, $C_1-C_4$ haloalkyl, methylenedioxydiyl, ethylenedioxydiyl; $C_1-C_6$ alkylcarbonyloxy($C_1-C_4$ alkoxy)carbonyl;

$C_6-C_{10}$ arylcarbonyloxy($C_1-C_4$ alkoxy)carbonyl where the aryl group is optionally substituted with 0–3 groups selected from hydroxy, halogen, $C_1-C_6$ alkoxy, $C_1-C_6$ alkyl, $CF_3$, $S(O)_m CH_3$, $-N(CH_3)_2$, $C_1-C_4$ haloalkyl, methylenedioxydiyl, ethylenedioxydiyl; $C_4-C_{11}$ cycloalkylcarbonyloxy($C_1-C_4$ alkoxy)carbonyl; heteroaryl optionally substituted with 0–2 groups selected from hydroxy, halogen, $C_1-C_6$ alkoxy, $C_1-C_6$ alkyl, $CF_3$, $S(O)_m CH_3$, $-N(CH_3)_2$, $C_1-C_4$ haloalkyl, methylenedioxydiyl, ethylenedioxydiyl; or heteroaryl($C_1-C_5$)alkyl where the heteroaryl group is optionally substituted with 0–2 groups selected from hydroxy, halogen, $C_1-C_6$ alkoxy, $C_1-C_6$ alkyl, $CF_3$, $S(O)_m CH_3$, $-N(CH_3)_2$, $C_1-C_4$ haloalkyl, methylenedioxydiyl, ethylenedioxydiyl;

provided that only one of $R^2$ and $R^3$ can be hydroxy;

$R^{2a}$ is $R^2$ or $R^2(R^3)N(RN=)C$;

U is selected from:
a single bond, $-(C_1-C_7$ alkyl)-, $-(C_2-C_7$ alkenyl)-, $-(C_2-C_7$ alkynyl)-, -(aryl)- substituted with 0–3 $R^{6a}$, or -(pyridyl)- substituted with 0–3 $R^{6a}$;

V is selected from:
a single bond;
$-(C_1-C_7$ alkyl)-, substituted with 0–3 groups selected independently from $R^6$ or $R^7$;
$-(C_2-C_7$ alkenyl)-, substituted with 0–3 groups selected independently from $R^6$ or $R^7$;
$-(C_2-C_7$ alkynyl)-, substituted with 0–3 groups selected independently from $R^6$ or $R^7$;
-(phenyl)-, substituted with 0–2 groups selected independently from $R^6$ or $R^7$;
-(pyridyl)-, substituted with 0–2 groups selected independently from $R^6$ or $R^7$; or
-(pyridazinyl)-, substituted with 0–2 groups selected independently from $R^6$ or $R^7$;

W is selected from:

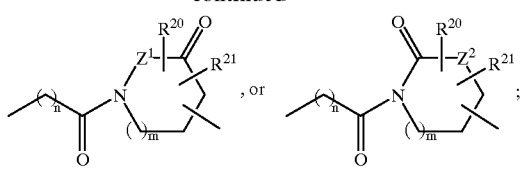

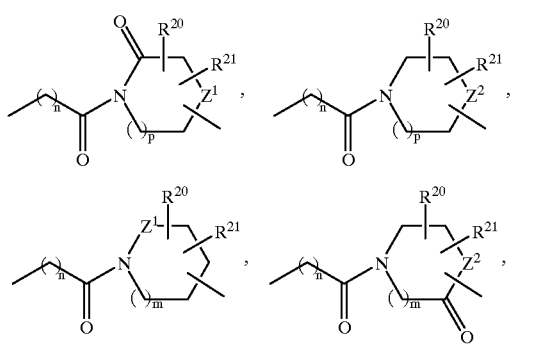

X is selected from:
a single bond, $-(C(R^4)_2)_n-C(R^4)(R^8)-C(R^4)(R^{4a})-$, with the proviso that when n is 0 or 1, then at least one of $R^{4a}$ or $R^8$ is other than H or methyl;

Y selected from:
hydroxy, $C_1-C_{10}$ alkyloxy, $C_3-C_{11}$ cycloalkyloxy, $C_6-C_{10}$ aryloxy, $C_7-C_{11}$ aralkyloxy, $C_3-C_{10}$ alkylcarbonyloxyalkyloxy, $C_3-C_{10}$
alkoxycarbonyloxyalkyloxy, $C_2-C_{10}$
alkoxycarbonylalkyloxy, $C_5-C_{10}$
cycloalkylcarbonyloxyalkyloxy, $C_5-C_{10}$
cycloalkoxycarbonyloxyalkyloxy, $C_5-C_{10}$
cycloalkoxycarbonylalkyloxy, $C_7-C_{11}$
aryloxycarbonylalkyloxy, $C_8-C_{12}$
aryloxycarbonyloxyalkyloxy, $C_8-C_{12}$
arylcarbonyloxyalkyloxy, $C_5-C_{10}$
alkoxyalkylcarbonyloxyalkyloxy, $C_5-C_{10}$ (5-alkyl-1,3-dioxa-cyclopenten-2-one-yl)-methyloxy, $C_{10}-C_{14}$ (5-aryl-1,3-dioxa-cyclopenten-2-one-yl)-methyloxy, $(R^2)(R^3)N-(C_1-C_{10}$ alkoxy)-;

$Z^1$ is $-C-$, $-O-$, or $-NR^{22}-$;

$Z^2$ is $-O-$, or $-NR^{22}-$;

$R^4$ is selected from:
H, $C_1-C_{10}$ alkyl, $C_1-C_{10}$ alkylcarbonyl, aryl, arylalkylene cycloalkyl, or cycloalkylalkylene;

alternately, two $R^4$ groups on adjacent carbon atoms can join to form a bond, thereby to form a carbon-carbon double or triple bond between such adjacent carbon atoms;

$R^{4a}$ is selected from:
H, hydroxy, $C_1-C_{10}$ alkoxy, nitro, $-N(R^5)R^{5a}$, $-N(R^{12})R^{13}$, $-N(R^{16})R^{17}$, $C_1-C_{10}$ alkyl substituted with 0–3 $R^6$, aryl substituted with 0–3 $R^6$, or $C_1-C_{10}$ alkylcarbonyl;

$R^{4b}$ is selected from:
H, $C_1-C_6$ alkyl, $C_2-C_6$ alkenyl, $C_2-C_6$ alkynyl, hydroxy, $C_1-C_6$ alkoxy, $C_1-C_6$ alkylthio, $C_1-C_6$ alkylsulfinyl, $C_1-C_6$ alkylsulfonyl, nitro-, $C_1-C_6$ alkylcarbonyl, $C_6-C_{10}$ aryl, $-N(R^{12})R^{13}$; halo, $CF_3$, CN, $C_1-C_6$ alkoxycarbonyl, carboxy, piperidinyl, or pyridyl;

$R^5$ is selected from:
H, $C_1-C_8$ alkyl, $C_2-C_6$ alkenyl, $C_3-C_{11}$ cycloalkyl, $C_4-C_{11}$ cycloalkylmethyl, $C_6-C_{10}$ aryl, $C_7-C_{11}$ arylalkyl, or $C_1-C_{10}$ alkyl substituted with 0–2 $R^{4b}$;

$R^{5a}$ is selected from:
hydrogen, hydroxy, $C_1-C_8$ alkyl, $C_2-C_6$ alkenyl, $C_3-C_{11}$ cycloalkyl, $C_4-C_{11}$ cycloalkylmethyl, $C_1-C_6$ alkoxy, benzyloxy, $C_6-C_{10}$ aryl, heteroaryl, $C_7-C_{11}$ arylalkyl, or $C_1-C_{10}$ alkyl substituted with 0–2 $R^{4b}$;

alternately, $R^5$ and $R^{5a}$ when both are substituents on the same nitrogen atom (as in $-NR^5R^{5a}$) can be taken together with the nitrogen atom to which they are attached to form:
3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, or 1-piperazinyl, each being optionally substituted with $C_1$–$C_6$ alkyl, $C_6$–$C_{10}$ aryl, heteroaryl, $C_7$–$C_{11}$ arylalkyl, $C_1$–$C_6$ alkylcarbonyl, $C_3$–$C_7$ cycloalkylcarbonyl, $C_1$–$C_6$ alkoxycarbonyl, $C_7$–$C_{11}$ arylalkoxycarbonyl, $C_1$–$C_6$ alkylsulfonyl, or $C_6$–$C_{10}$ arylsulfonyl;

$R^{5b}$ is selected from:
$C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^{4b}$;

$R^6$ is selected from:
H, $C_1$–$C_{10}$ alkyl, hydroxy, $C_1$–$C_{10}$ alkoxy, nitro, $C_1$–$C_{10}$ alkylcarbonyl, —N($R^{12}$)$R^{13}$, cyano, halo, $CF_3$, CHO, $CO_2R^5$, C(=O)$R^{5a}$, $CONR^5R^{5a}$, OC(=O)$R^{5a}$, OC(=O)$OR^{5b}$, $OR^5$, OC(=O)$NR^5R^{5a}$, $OCH_2CO_2R^5$, $CO_2CH_2CO_2R^5$, $NO_2$, $NR^{5a}$C(=O)$R^{5a}$, $NR^{5a}$C(=O)$OR^{5b}$, $NR^{5a}$C(=O)$NR^5R^{5a}$, $NR^{5a}SO_2NR^5R^{5a}$, $NR^{5a}SO_2R^5$, $S(O)_pR^5$, $SO_2NR^5R^{5a}$, $C_2$–$C_6$ alkenyl, $C_3$–$C_{11}$ cycloalkyl, $C_4$–$C_{11}$ cycloalkylmethyl;

$C_6$–$C_{10}$ aryl optionally substituted with 1–3 groups selected from halogen, $C_1$–$C_6$ alkoxy, $C_1$–$C_6$ alkyl, $CF_3$, $S(O)_mCH_3$, or —N($CH_3$)$_2$;

$C_7$–$C_{11}$ arylalkyl, the aryl being optionally substituted with 1–3 groups selected from halogen, $C_1$–$C_6$ alkoxy, $C_1$–$C_6$ alkyl, $CF_3$, $S(O)_mCH_3$, or —N($CH_3$)$_2$; methylenedioxy when $R^6$ is a substituent on aryl; or a 5–6 membered heterocyclic ring containing 1–2 N, O, or S heteroatoms, wherein the heterocyclic ring can be saturated, partially saturated, or fully unsaturated, the heterocyclic ring being substituted with 0–2 $R^7$;

$R^{6a}$ is selected from:
$C_1$–$C_4$ alkyl, $C_1$–$C_4$ alkoxy, halo, $CF_3$, $NO_2$, or $NR^{12}R^{13}$;

$R^7$ is selected from:
H, $C_1$–$C_{10}$ alkyl, hydroxy, $C_1$–$C_{10}$ alkoxy, nitro, $C_1$–$C_{10}$ alkylcarbonyl, —N($R^{12}$)$R^{13}$, cyano, halo, $CF_3$, CHO, $CO_2R^5$, C(=O)$R^{5a}$, $CONR^5R^{5a}$, OC(=O)$R^{5a}$, OC(=O)$OR^{5b}$, $OR^{5a}$, OC(=O)$NR^5R^{5a}$, $OCH_2CO_2R^5$, $CO_2CH_2CO_2R^5$, $NO_2$, $NR^{5a}$C(=O)$R^{5a}$, $NR^{5a}$C(=O)$OR^{5b}$, $NR^{5a}$C(=O)$NR^5R^{5a}$, $NR^{5a}SO_2NR^5R^{5a}$, $NR^{5a}SO_2R^5$, $S(O)_mR^{5a}$, $SO_2NR^5R^{5a}$, $C_2$–$C_6$ alkenyl, $C_3$–$C_{11}$ cycloalkyl, Cg–C11 cycloalkylmethyl, $C_6$–$C_{10}$ aryl, or $C_7$–$C_{11}$ arylalkyl;

$R^8$ is selected from:
$R^6$; $C_2$–$C_{10}$ alkyl, substituted with 0–3 $R^6$; $C_2$–$C_{10}$ alkenyl, substituted with 0–3 $R^6$;
$C_2$–$C_{10}$ alkynyl, substituted with 0–3 $R^6$; $C_3$–$C^8$ cycloalkyl, substituted with 0–3 $R^6$;
$C_5$–$C_6$ cycloalkenyl, substituted with 0–3 $R^6$; aryl, substituted with 0–3 $R^6$; 5–6 membered heterocyclic ring containing 1–2 N, O, or S heteroatoms, wherein the heterocyclic ring can be saturated, partially saturated, or fully unsaturated, the heterocyclic ring being substituted with 0–2 $R^6$;

$R^{12}$ and $R^{13}$ are selected independently from:
H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, heteroarylsulfonyl, arylsulfonyl, aryl, $C_2$–$C_6$ alkenyl, $C_3$–$C_{11}$ cycloalkyl, $C_4$–$C_{11}$ cycloalkylalkyl, $C_7$–$C_{11}$ arylalkyl, $C_7$–$C_{11}$ arylcarbonyl, $C_4$–$C_{11}$ cycloalkoxycarbonyl, $C_7$–$C_{11}$ bicycloalkoxycarbonyl, $C_7$–$C_{11}$ aryloxycarbonyl, or aryl($C_1$–$C_{10}$ alkoxy)carbonyl, wherein the aryls are optionally substituted with 0–3 substituents selected from the group consisting of: $C_1$–$C_4$ alkyl, $C_1$–$C_4$ alkoxy, halo, $CF_3$, and $NO_2$;

$R^{14}$ is selected from:
H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or $C_1$–$C_{10}$ alkoxycarbonyl, $CO_2R^5$, or —C(=O)N($R^5$)$R^{5a}$;

$R^{15}$ is selected from:
H; $R^6$; $C_1$–$C_{10}$ alkyl, substituted with 0–3 $R^6$; $C_2$–$C_{10}$ alkenyl, substituted with 0–3 $R^6$;
$C_1$–$C_{10}$ alkoxy, substituted with 0–3 $R^6$; aryl, substituted with 0–3 $R^6$; 5–6 membered heterocyclic ring containing 1–2 N, O, or S heteroatoms, wherein the heterocyclic ring can be saturated, partially saturated, or fully unsaturated, the heterocyclic ring being substituted with 0–2 $R^6$; $C_1$–$C_{10}$ alkoxycarbonyl substituted with 0–2 $R^6$; —$CO_2R^5$; or —C(=O)N($R^{12}$)$R^{13}$;

provided that when b is a double bond, only one of $R^{14}$ or $R^{15}$ is present;

$R^{16}$ is selected from:
—C(=O)—O—$R^{18a}$, —C(=O)—$R^{18b}$, —C(=O)N($R^{18b}$)$_2$, —C(=O)NHSO$_2$$R^{18a}$, —C(=O)NHC(=O)$R^{18b}$, —C(=O)NHC(=O)$OR^{18a}$, —C(=O)NHSO$_2$NHR$^{18b}$, —C(=S)—NH—$R^{18b}$, —NH—C(=O)—O—$R^{18a}$, —NH—C(=O)—$R^{18b}$, —NH—C(=O)—NH—$R^{18b}$, $SO_2$—O—$R^{18a}$, —$SO_2$—$R^{18a}$, —$SO_2$—N($R^{18b}$)$_2$, —$SO_2$—NHC(=O)$OR^{18b}$, —P(=S)($OR^{18a}$)$_2$, —P(=O)($OR^{18a}$)$_2$, —P(=S)($R^{18a}$)$_2$, —P(=O)($R^{18a}$)$_2$, or

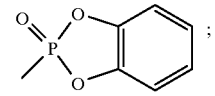

$R^{17}$ is selected from:
H, $C_1$–$C_{10}$ alkyl, $C_2$–$C_6$ alkenyl, $C_3$–$C_{11}$ cycloalkyl, $C_4$–$C_{15}$ cycloalkylalkyl, aryl, aryl($C_1$–$C_{10}$ alkyl);

$R^{18a}$ is selected from:
$C_1$–$C_8$ alkyl substituted with 0–2 $R^{19}$, $C_2$–$C_8$ alkenyl substituted with 0–2 $R^{19}$, $C_2$–$C_8$ alkynyl substituted with 0–2 $R^{19}$, $C_3$–$C_8$ cycloalkyl substituted with 0–2 $R^{19}$, aryl substituted with 0–4 $R^{19}$, aryl($C_1$–$C_6$ alkyl) substituted with 0–4 $R^{19}$, a 5–10 membered heterocyclic ring system having 1–3 heteroatoms selected independently from O, S, and N, the heterocyclic ring being substituted with 0–4 $R^{19}$, $C_1$–$C_6$ alkyl substituted with a 5–10 membered heterocyclic ring system having 1–3 heteroatoms selected independently from O, S, and N, the heterocyclic ring being substituted with 0–4 $R^{19}$;

$R^{18}$b is selected from: $R^{18a}$ or H;

$R^{19}$ is selected from:
H, halogen, $CF_3$, CN, $NO_2$, —$NR^{12}R^{13}$, $C_1$–$C_8$ alkyl, $C_2$–$C_6$ alkenyl, $C_2$–$C_6$ alkynyl, $C_3$–$C_{11}$ cycloalkyl, $C_4$–$C_{11}$ cycloalkylalkyl, aryl, aryl($C_1$–$C_6$ alkyl), $C_1$–$C_6$ alkoxy, or $C_1$–$C_4$ alkoxycarbonyl;

$R^{20}$ and $R^{21}$ are each selected independently from:
H, $C_1$–$C_{10}$ alkyl, $CO_2R^5$, C(=O)$R^{5a}$, $CONR^5R^{5a}$, $NR^5$C(=O)$R^{5a}$, $NR^{12}R^{13}$, $C_2$–$C_6$ alkenyl, $C_3$–$C_{11}$ cycloalkyl, $C_4$–$C_{11}$ cycloalkylmethyl, $C_6$–$C_{10}$ aryl, or $C_7$–$C_{11}$ arylalkyl;

$R^{22}$ is selected from:

$C_1$–$C_{10}$ alkyl, $C_2$–$C_6$ alkenyl, $C_3$–$C_{11}$ cycloalkyl, $C_4$–$C_{15}$ cycloalkylalkyl, aryl, aryl($C_1$–$C_{10}$ alkyl); —C(=O)$R^{5a}$, —$CO_2R^{5b}$, —C(=O)N($R^5$)$R^{5a}$, or a bond to X;

m is 0–2;
n is 0–2;
p is 1–2;
q is 1–7;
r is 0–3;

provided that n, q, and r are chosen such that the number of atoms connecting $R^1$ and Y is in the range of 8–17.

This embodiment includes compounds of Formula Ic:

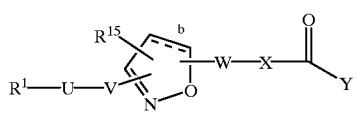

(Ic)

wherein:

Z is selected from: a bond, O, or S;

$R^2$ and $R^3$ are selected independently from:
  H; $C_1$–$C_6$ alkyl; $C_7$–$C_{11}$ arylalkyl optionally substituted with 0–3 groups selected from hydroxy, halogen, $C_1$–$C_6$ alkoxy, $C_1$–$C_6$ alkyl, $CF_3$, S(O)$_m$$CH_3$, —N($CH_3$)$_2$, $C_1$–$C_4$ haloalkyl, methylenedioxydiyl, ethylenedioxydiyl; $C_1$–$C_{10}$ alkoxycarbonyl;
  aryl($C_1$–$C_{10}$ alkoxy)carbonyl where the aryl group is optionally substituted with 0–3 groups selected from hydroxy halogen, $C_1$–$C_6$ alkoxy, $C_1$–$C_6$ alkyl, $CF_3$, S(O)$_m$$CH_3$, —N($C_2$)$_2$, $C_1$–$C_4$ haloalkyl methylenedioxydiyl ethylenedioxydiyl; or
  heteroaryl($C_1$–$C_5$)alkyl wherein the heteroaryl group is optionally substituted with 0–2 groups selected from hydroxy, halogen, $C_1$–$C_6$ alkoxy, $C_1$–$C_6$ alkyl, $CF_3$, S(O)$_m$$CH_3$, —N($CH_3$)$_2$, $C_1$–$C_4$ haloalkyl, methylenedioxydiyl, ethylenedioxydiyl;

U is a single bond;
X is —CHR$^{4a}$—;

$R^5$ is selected from:
  H or $C_1$–$C_{10}$ alkyl substituted with 0–6 $R^{4b}$;

$R^6$ and $R^7$ are each selected independently from:
  H, $C_1$–$C_{10}$ alkyl, hydroxy, $C_1$–$C_{10}$ alkoxy, nitro, $C_1$–$C_{10}$ alkylcarbonyl, —N($R^{12}$)$R^{13}$, cyano, or halo;

$R^{12}$ and $R^{13}$ are each selected independently from:
  H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, heteroarylsulfonyl, or aryl, wherein the aryls are optionally substituted with 0–3 substituents selected from the group consisting of: $C_1$–$C_4$ alkyl, $C_1$–$C_4$ alkoxy, halo, $CF_3$, and $NO_2$;

$R^{15}$ is selected from:
  H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or $C_1$–$C_{10}$ alkoxycarbonyl, $CO_2R^5$ or —C(=O)N($R^5$)$R^{5a}$;

$R^{16}$ is selected from:
  —C(=O)—O—$R^{18a}$, —C(=O)—$R^{18b}$—, and S(=O)$_2$—$R^{18a}$;

$R^{17}$ is selected from: H or $C_1$–$C_4$ alkyl;

$R^{18a}$ is selected from:
  $C_1$–$C_8$ alkyl substituted with 0–2 $R^{19}$, $C_2$–$C_8$ alkenyl substituted with 0–2 $R^{19}$, $C_2$–$C_8$ alkynyl substituted with 0–2 $R^{19}$, $C_3$–$C_8$ cycloalkyl substituted with 0–2 $R^{19}$, aryl substituted with 0–2 $R^{19}$, aryl($C_1$–$C_6$ alkyl) substituted with 0–2 $R^{19}$;

a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyridinyl, 3H-indolyl, carbazolyl, pyrrolidinyl, piperidinyl, indolinyl, or morpholinyl, the heterocyclic ring being substituted with 0–2 $R^{19}$;

$C_1$–$C_6$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, the heterocyclic ring being substituted with 0–2 $R^{19}$.

The compounds of this embodiment also include compounds of Formula Ib:

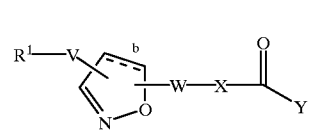

(Ib)

wherein:

$R^1$ is selected from:
  $R^2$($R^3$)N—, $R^2$NH($R^2$N=)C—, $R^2R^3$N(CH$_2$)$_{p''}$Z—, $R^2$NH($R^2$N=)CNH(CH$_2$)$_{p'}$Z—, $R^2$($R^3$)NC(O)—, $R^2$($R^5$O)N($R^2$N=)C—, $R^2$($R^3$)N($R^5$ON=)C—;

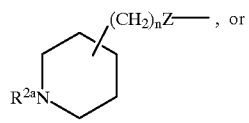 , or 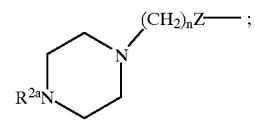 ;

n is 0–1;
p' is 2–4;
p" is 4–6;
Z is selected from: a bond or O;
$R^3$ is H or $C_1$–$C_5$ alkyl;
V is a single bond, or -(phenyl)-;
X is selected from:
  —CH$_2$—, —CHN($R^{16}$)$R^{17}$—, or —CHNR$^5R^{5a}$—;
Y is selected from:
  hydroxy; $C_1$–$C_{10}$ alkoxy; methylcarbonyloxymethoxy; ethylcarbonyloxymethoxy;
  t-butylcarbonyloxymethoxy-; cyclohexylcarbonyloxymethoxy;
  1-(methylcarbonyloxy)-ethoxy; 1-(ethylcarbonyloxy)-ethoxy;
  1-(t-butylcarbonyloxy)-ethoxy; 1-(cyclohexylcarbonyloxy)-ethoxy;
  i-propyloxycarbonyloxymethoxy; t-butyloxycarbonyloxymethoxy;
  1-(i-propyloxycarbonyloxy)-ethoxy; 1-(cyclohexyloxycarbonyloxy)-ethoxy-;
  1-(t-butyloxycarbonyloxy)-ethoxy; dimethylaminoethoxy; diethylaminoethoxy;
  (5-methyl-1,3-dioxacyclopenten-2-on-4-yl)-methoxy;

(5-(t-butyl)-1,3-dioxacyclopenten-2-on-4-yl)-methoxy;

(1,3-dioxa-5-phenyl-cyclopenten-2-on-4-yl)-methoxy;

1-(2-(2-methoxypropyl)carbonyloxy)-ethoxy;

$R^{18a}$ is selected from:

$C_1$–$C_4$ alkyl substituted with 0–2 $R^{19}$, $C_2$–$C_4$ alkenyl substituted with 0–2 $R^{19}$, $C_2$–$C_4$ alkynyl substituted with 0–2 $R^{19}$, $C_3$–$C_4$ cycloalkyl substituted with 0–2 $R^{19}$, aryl substituted with 0–2 $R^{19}$, aryl($C_1$–$C_4$ alkyl) substituted with 0–2 $R^{19}$, a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyridinyl, 3H-indolyl, carbazolyl, pyrrolidinyl, piperidinyl, indolinyl, or morpholinyl, the heterocyclic ring being substituted with 0–2 $R^{19}$;

$C_1$–$C_6$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, carbazoic, pyrrolidinyl, piperidinyl, indolinyl, or morpholinyl, the heterocyclic ring being substituted with 0–2 $R^{19}$.

Accordingly, this embodiment includes compounds having Formula Ib, wherein:

either:

$R^1$ is: $R^2NH(R^2N=)C—$ or $R^2NH(R^2N=)CNH—$, and V is phenyl or pyridyl;

or:

$R^1$ is

[structure]

and V is a single bond;

n is 1–2;

$R^3$ is H or $C_1$–$C_5$ alkyl;

X is selected from:

—$CH_2$—, —$CHN(R^{16})R^{17}$—, or —$CHNR^5R^{5a}$—;

W is selected from:

[structures]

m is 1–3;

Y is selected from:

hydroxy; $C_1$–$C_{10}$ alkoxy; methylcarbonyloxymethoxy; ethylcarbonyloxymethoxy;

t-butylcarbonyloxymethoxy; cyclohexylcarbonyloxymethoxy;

1-(methylcarbonyloxy)-ethoxy; 1-(ethylcarbonyloxy)-ethoxy;

1-(t-butylcarbonyloxy)-ethoxy; 1-(cyclohexylcarbonyloxy)-ethoxy;

i-propyloxycarbonyloxymethoxy; t-butyloxycarbonyloxymethoxy;

1-(i-propyloxycarbonyloxy)-ethoxy; 1-(cyclohexyloxycarbonyloxy)-ethoxy;

1-(t-butyloxycarbonyloxy)-ethoxy; dimethylaminoethoxy; diethylaminoethoxy;

(5-methyl-1,3-dioxacyclopenten-2-on-4-yl)-methoxy;

(5-(t-butyl)-1,3-dioxacyclopenten-2-on-4-yl)-methoxy;

(1,3-dioxa-5-phenyl-cyclopenten-2-on-4-yl)-methoxy;

1-(2-(2-methoxypropyl)carbonyloxy)-ethoxy;

$R^{19}$ is H, halogen, $C_1$–$C_4$ alkyl, $C_3$–$C_7$ cycloalkyl, cyclopropylmethyl, aryl, or benzyl;

$R^{20}$ and $R^{21}$ are both H; and $R^{22}$ is H, $C_1$–$C_4$ alkyl or benzyl.

This embodiment comprises the following exemplary compounds, and pharmaceutically acceptable salt forms thereof:

2(R,S)-2-carboxymethyl-1-{5(R,S)-N-[3-(4-amidinophenyl)-isoxazolin-5-yl-acetyl]piperidine;

2(R,S)-2-carboxymethyl-1-{5(R,S)-N-[3-(4-amidinophenyl)-isoxazolin-5-yl-acetyl]azepine;

2(R,S)-2-carboxymethyl-1-{5(R,S)-N-[3-(4-amidinophenyl)-isoxazolin-5-yl-acetyl]pyrrolidine;

3(R,S)-carboxymethyl-4-{5(R,S)-N-[3-(4-amidinophenyl)-isoxazolin-5-yl-acetyl]piperazine-2-one;

6(R,S)-carboxymethyl-1-{5(R,S)-N-[3-(4-amidinophenyl)-isoxazolin-5-yl-acetyl]piperidine-2-one;

5(R,S)-carboxymethyl-1-{5(R,S)-N-[3-(4-amidinophenyl)-isoxazolin-5-yl-acetyl]pyrrolidine-2-one;

7(R,S)-carboxymethyl-1-{5(R,S)-N-[3-(4-amidinophenyl)-isoxazolin-5-yl-acetyl]azetidine-2-one;

2(R,S)-carboxymethyl-1-{5(R,S)-N-[3-(4-amidinophenyl)-isoxazolin-5-yl-acetyl]pyrazolidine; and 3(R,S)-carboxymethyl-4-{5(R,S)-N-[3-(4-amidinophenyl)-isoxazolin-5-yl-acetyl]morpholine.

In another embodiment (designated embodiment XXXVI), the device includes, and can be used to deliver, a compound of Formula IX:

(IX)

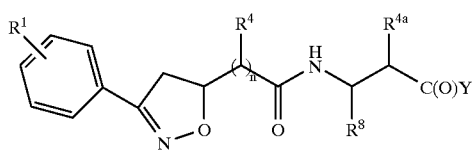

wherein:
Y is selected from:
C$_1$–C$_{10}$ alkyloxy, C$_3$–C$_{11}$ cycloalkyloxy, C$_6$–C$_{10}$ aryloxy, C$_7$–C$_{11}$ aralkyloxy, C$_3$–C$_{10}$ alkylcarbonyloxyalkyloxy, C$_3$–C$_{10}$ alkoxycarbonyloxyalkyloxy, C$_2$–C$_{10}$ alkoxycarbonylalkyloxy, C$_5$–C$_{10}$ cycloalkylcarbonyloxyalkyloxy, C$_5$–C$_{10}$ cycloalkoxycarbonyloxyalkyloxy, C$_5$–C$_{10}$ cycloalkoxycarbonylalkyloxy, C$_7$–C$_{11}$ aryloxycarbonylalkyloxy, C$_8$–C$_{12}$ aryloxycarbonyloxyalkyloxy, C$_8$–C$_{12}$ arylcarbonyloxyalkyloxy, C$_5$–C$_{10}$ alkoxyalkylcarbonyloxyalkyloxy, C$_5$–C$_{10}$ (5-alkyl-1,3-dioxa-cyclopenten-2-one-yl)-methyloxy, C$_{10}$–C$_{14}$ (5-aryl-1,3-dioxa-cyclopenten-2-one-yl)-methyloxy;

R$^1$ is NC—;

R$^4$ is selected from:
H, C$_1$–C$_{10}$ alkyl, C$_1$–C$_{10}$ alkylcarbonyl, aryl, arylalkyl, cycloalkyl, or cycloalkylalkyl;

R$^{4a}$ is selected from:
H, hydroxy, C$_1$–C$_{10}$ alkoxy, nitro, N(R$^5$)R$^{5a}$, —N(R$^{12}$)R$^{13}$, —N(R$^{16}$)R$^{17}$, C$_1$–C$_{10}$ alkyl substituted with 0–3 R$^6$, aryl substituted with 0–3 R$^6$, or pyrrolidinyl, or C$_1$–C$_{10}$ alkylcarbonyl;

R$^{4b}$ is selected from:
H, C$_1$–C$_6$ alkyl, C$_2$–C$_6$ alkenyl, C$_2$–C$_6$ alkynyl, C$_3$–C$_7$ cycloalkyl, C$_7$–C$_{14}$ bicycloalkyl, hydroxy, C$_1$–C$_6$ alkoxy, C$_1$–C$_6$ alkylthio, C$_1$–C$_6$ alkylsulfinyl, C$_1$–C$_6$ alkylsulfonyl, nitro, C$_1$–C$_6$ alkylcarbonyl, C$_6$–C$_{10}$ aryl, —N(R$^{12}$)R$^{13}$; halo, CF$_3$, CN, C$_1$–C$_6$ alkoxycarbonyl, carboxy, piperidinyl, morpholinyl or pyridinyl;

R$^5$ is selected from:
H or C$_1$–C$_{10}$ alkyl substituted with 0–2 R$^{4b}$;

R$^{5a}$ is selected from:
hydrogen, hydroxy, C$_1$–C$_8$ alkyl, C$_3$–C$_6$ alkenyl, C$_3$–C$_{11}$ cycloalkyl, C$_4$–C$_{11}$ cycloalkylmethyl, C$_1$–C$_6$ alkoxy, benzyloxy, C$_6$–C$_{10}$ aryl, heteroaryl, heteroarylalkyl, C$_7$–C$_{11}$ arylalkyl, adamantylmethyl, or C$_1$–C$_{10}$ alkyl substituted with 0–2 R$^{4b}$;

R$^6$ is selected from:
H, C$_1$–C$_4$ alkyl, hydroxy, C$_1$–C$_4$ alkoxy, nitro, C$_1$–C$_{10}$ alkylcarbonyl, —N(R$^{12}$)R$^{13}$, —NR$^5$R$^{5a}$, CO$_2$R$^5$, S(O)$_m$R$^5$, OR$^5$, cyano, halo; C$_6$–C$_{10}$ aryl optionally substituted with 1–3 groups selected from halogen, C$_1$–C$_6$ alkoxy, C$_1$–C$_6$ alkyl, CF$_3$, S(O)$_m$CH$_3$, or —N(CH$_3$)$_2$; methylenedioxy when R$^6$ is a substituent on aryl; or a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, benzimidazolyl, piperidinyl, tetrahydrofuranyl, pyranyl, pyridinyl, 3H-indolyl, carbazolyl, piperidinyl, indolinyl, isoxazolyl, isoxazolinyl or morpholinyl;

R$^8$ is selected from:
—CONR$^5$NR$^{5a}$; —CO$_2$R$^5$; C$_1$–C$_{10}$ alkyl, substituted with 0–3 R$^6$;
C$_2$–C$_{10}$ alkenyl, substituted with 0–3 R$^6$;
C$_2$–C$_{10}$ alkynyl, substituted with 0–3 R$^6$,
C$_3$–C$_8$ cycloalkyl, substituted with 0–3 R$^6$;
aryl, substituted with 0–2 R$^6$;
a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyridinyl, 3H-indolyl, carbazolyl, pyrrolidinyl, piperidinyl, indolinyl, or morpholinyl, the heterocyclic ring being substituted with 0–2 R$^6$;

R$^{12}$ is selected from:
H, C$_1$–C$_6$ alkyl, C$_1$–C$_4$ alkoxycarbonyl, C$_1$–C$_6$ alkylcarbonyl, C$_1$–C$_6$ alkylsulfonyl, aryl(C$_1$–C$_4$ alkyl)sulfonyl, heteroarylsulfonyl, arylsulfonyl, aryl, pyridylcarbonyl, or pyridylmethylcarbonyl, wherein the aryls are optionally substituted with 0–3 substituents selected from the group consisting of: C$_1$–C$_4$ alkyl, C$_1$–C$_4$ alkoxy, halo, CF$_3$, and NO$_2$;

R$^{13}$ is H;

R$^{16}$ is selected from:
—C(=O)—O—R$^{18a}$, —C(=O)—R$^{18b}$, —C(=O)N(R$^{18b}$)$_2$, —SO$_2$—R$^{18a}$, or —SO$_2$—N(R$^{18b}$)$_2$;

R$^{17}$ is selected from:
H or C$_1$–C$_4$ alkyl;

R$^{18a}$ is selected from:
C$_1$–C$_8$ alkyl substituted with 0–2 R$^{19}$, C$_2$–C$_8$ alkenyl substituted with 0–2 R$^{19}$, C$_2$–C$_8$ alkynyl substituted with 0–2 R$^{19}$, C$_3$–C$_8$ cycloalkyl substituted with 0–2 R$^{19}$, aryl substituted with 0–4 R$^{19}$, aryl(C$_1$–C$_6$ alkyl)- substituted with 0–4 R$^{19}$, a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, carbazolyl, pyrrolidinyl, piperidinyl, indolinyl, or morpholinyl, the heterocyclic ring, being substituted with 0–4 R$^{19}$;
C$_1$–C$_6$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, 2S-indolenyl, quinolinyl, isoquinolinyl, benzimidazolyl, piperidinyl, tetrahydrofuranyl, pyranyl, pyridinyl, 3H-indolyl, indolyl, carbazole, pyrrolidinyl, piperidinyl, indolinyl, or morpholinyl, the heterocyclic ring being substituted with 0–4 R$^{19}$;

R$^{18b}$ is selected from: R$^{18a}$ or H;

R$^{19}$ is selected from:
H, halogen, CF$_3$, CN, NO$_2$, NR$^{12}$R$^{13}$, C$_1$–C$_8$ alkyl, C$_2$–C$_6$ alkenyl, C$_2$–C$_6$ alkynyl, C$_3$–C$_{11}$ cycloalkyl, C$_4$–C$_{11}$ cycloalkylalkyl, aryl, aryl(C$_1$–C$_6$ alkyl), C$_1$–C$_6$ alkoxy, or C$_1$–C$_4$ alkoxycarbonyl;

m is 0–2;

n is 0–4;

q is 1–7; and r is 0–3.

In still another embodiment (designated embodiment XXXVIII), the device includes, and can be used to deliver, a compound of Formulae Ie or If:

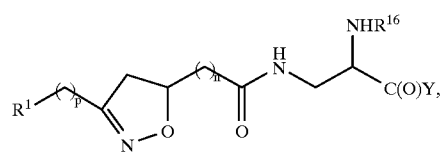

(Ie)

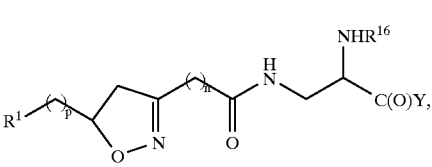

(If)

or enantiomeric or diastereomeric forms thereof, or mixtures of enantiomeric or diastereomeric forms thereof, or a pharmaceutically acceptable salt from thereof, wherein:

$R^1$ is: $R^2(R^3)N(RN=)C-$, $R^2(R^3)N(R^2N=)CN(R^2)-$, or $R^2(R^3)N-$;

$R^2$ and $R^3$ are selected independently from:

H, $C_1$–$C_{10}$ alkyl; $C_3$–$C_6$ alkenyl; $C_3$–$C_{11}$ cycloalkyl; $C_4$–$C_{11}$ cycloalkylalkyl; $C_6$–$C_{10}$ aryl optionally substituted with 0–3 groups selected from hydroxy, halogen, $C_1$–$C_6$ alkoxy, $C_1$–$C_6$ alkyl, $CF_3$, $S(O)_m CH_3$, $-N(CH_3)_2$, $C_1$–$C_4$ haloalkyl, methylenedioxydiyl, ethylenedioxydiyl; $C_7$–$C_{11}$ arylalkyl optionally substituted with 0–3 groups selected from hydroxy, halogen, $C_1$–$C_6$ alkoxy, $C_1$–$C_6$ alkyl, $CF_3$, $S(O)_m CH_3$, $-N(CH_3)_2$, $C_1$–$C_4$ haloalkyl, methylenedioxydiyl, ethylenedioxydiyl; $C_2$–$C_7$ alkylcarbonyl;

$C_7$–$C_{11}$ arylcarbonyl optionally substituted with 0–3 groups selected from hydroxy, halogen, $C_1$–$C_6$ alkoxy, $C_1$–$C_6$ alkyl, $CF_3$, $S(O)_m CH_3$, $-N(CH_3)_2$, $C_1$–$C_4$ haloalkyl, methylenedioxydiyl, ethylenedioxydiyl; $C_1$–$C_{10}$ alkoxycarbonyl;

$C_4$–$C_{11}$ cycloalkoxycarbonyl; $C_7$–$C_{11}$ bicycloalkoxycarbonyl; $C_7$–$C_{11}$ aryloxycarbonyl optionally substituted with 0–3 groups selected from hydroxy, halogen, $C_1$–$C_6$ alkoxy, $C_1$–$C_6$ alkyl, $CF_3$, $S(O)_m CH_3$, $-N(CH_3)_2$, $C_1$–$C_4$ haloalkyl, methylenedioxydiyl, ethylenedioxydiyl; aryl ($C_1$–$C_{10}$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_m CH_3$, $-N(CH_3)_2$, $C_1$–$C_4$ haloalkyl, methylenedioxydiyl, ethylenedioxydiyl; $C_1$–$C_6$ alkylcarbonyloxy($C_1$–$C_4$ alkoxy)carbonyl;

$C_6$–$C_{10}$ arylcarbonyloxy($C_1$–$C_4$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_m CH_3$, $-N(CH_3)_2$, $C_1$–$C_4$ haloalkyl, methylenedioxydiyl, ethylenedioxydiyl; $C_4$–$C_{11}$ cycloalkylcarbonyloxy($C_1$–$C_4$ alkoxy)carbonyl; heteroaryl optionally substituted with 0–2 groups selected from hydroxy, halogen, $C_1$–$C_6$ alkoxy, $C_1$–$C_6$ alkyl, $CF_3$, $S(O)_m CH_3$, $-N(CH_3)_2$, $C_1$–$C_4$ haloalkyl, methylenedioxydiyl; or heteroaryl($C_1$–$C_5$)alkyl where the heteroaryl group is optionally substituted with 0–2 groups selected from hydroxy, halogen, $C_1$–$C_6$ alkoxy, $C_1$–$C_6$ alkyl, $CF_3$, $S(O)_m CH_3$, $-N(CH_3)_2$, $C_1$–$C_4$ haloalkyl, methylenedioxydiyl, ethylenedioxydiyl;

provided that only one of $R^2$ and $R^3$ is hydroxy;

$R^{12}$ and $R^{13}$ are selected independently from:

H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, aryl($C_2$–$C_{10}$ alkenyl)sulfonyl, heteroarylsulfonyl, aryl, $C_2$–$C_6$ alkenyl, $C_3$–$C_{11}$ cycloalkyl, $C_4$–$C_{11}$ cycloalkylalkyl, $C_7$–$C_{11}$ arylalkyl, $C_7$–$C_{11}$ arylcarbonyl, $C_4$–$C_{11}$ cycloalkoxycarbonyl, $C_7$–$C_{11}$ bicycloalkoxycarbonyl, $C_7$–$C_{11}$ aryloxycarbonyl, heteroarylcarbonyl, heteroarylalkylcarbonyl, or aryl ($C_1$–$C_{10}$ alkoxy)carbonyl, wherein the aryls are optionally substituted with 0–3 substituents selected from the group consisting of: $C_1$–$C_4$ alkyl, $C_1$–$C_4$ alkoxy, halo, $CF_3$, and $NO_2$;

$R^{16}$ is selected from:

$-C(=O)-O-R^{18a}$, $-C(=O)-R^{18b}$, $-C(=O)N(R^{18b})_2$, $-C(=O)NHSO_2-R^{18a}$, $-C(=O)NHC(=O)R^{18b}$, $-C(=O)NHC(=O)R^{18a}$, $-C(=O)NHSO_2NHR^{18b}$, $-C(=S)-NH-R^{18b}$, $-NH-C(=O)-O-R^{18a}$, $-NH-C(=O)-R^{18b}$, $-NH-C(=O)-NH-R^{18b}$, $-SO_2-O-R^{18a}$, $-SO_2-R^{18a}$, $-SO_2-N(R^{18b})_2$, $-SO_2-NHC(=O)R^{18b}$, $-P(=S)(OR^{18a})_2$, $-P(=O)(OR^{18a})_2$, $-P(=S)(R^{18a})_2$, $-P(=O)(R^{18a})_2$, or

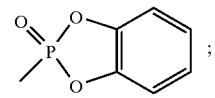

;

$R^{18a}$ is selected from:

$C_1$–$C_8$ alkyl substituted with 0–2 $R^{19}$, $C_2$–$C_8$ alkenyl substituted with 0–2 $R^{19}$, $C_2$–$C_8$ alkynyl substituted with 0–2 $R^{19}$, $C_3$–$C_8$ cycloalkyl substituted with 0–2 $R^{19}$, aryl substituted with 0–4 $R^{19}$, aryl($C_1$–$C_6$ alkyl) substituted with 0–4 $R^{19}$, a 5–10 membered heterocyclic ring system having 1–3 heteroatoms selected independently from O, S, and N, the heterocyclic ring being substituted with 0–4 $R^{19}$, $C_1$–$C_6$ alkyl substituted with a 5–10 membered heterocyclic ring system having 1–3 heteroatoms selected independently from O, S, and N, the heterocyclic ring being substituted with 0–4 $R^{19}$;

$R^{18b}$ is selected from:

$R^{18a}$ or H;

$R^{19}$ is selected from:

H, halogen, $CF_3$, CN, $NO_2$, $NR^{12}R^{13}$, $C_1$–$C_8$ alkyl, $C_2$–$C_6$ alkenyl, $C_2$–$C_6$ alkynyl, $C_3$–$C_{11}$ cycloalkyl, $C_4$–$C_{11}$ cycloalkylalkyl, aryl, aryl($C_1$–$C_6$ alkyl), $C_1$–$C_6$ alkoxy, or $C_1$–$C_4$ alkoxycarbonyl;

Y is selected from:

hydroxy, $C_1$–$C_{10}$ alkyloxy, $C_3$–$C_{11}$ cycloalkyloxy, $C_6$–$C_{10}$ aryloxy, $C_7$–$C_{11}$ aralkyloxy, $C_3$–$C_{10}$ alkylcarbonyloxyalkyloxy, $C_3$–$C_{10}$ alkoxycarbonyloxyalkyloxy, $C_2$–$C_{10}$ alkoxycarbonylalkyloxy, $C_5$–$C_{10}$ cycloalkylcarbonyloxyalkyloxy, $C_5$–$C_{10}$ cycloalkoxycarbonyloxyalkyloxy, $C_5$–$C_{10}$ cycloalkoxycarbonylalkyloxy, $C_7$–$C_{11}$ aryloxycarbonylalkyloxy, $C_8$–$C_{12}$ aryloxycarbonyloxyalkyloxy, $C_8$–$C_{12}$ arylcarbonyloxyalkyloxy, $C_5$–$C_{10}$ alkoxyalkylcarbonyloxyalkyloxy, $C_5$–$C_{10}$ (5-alkyl-1,3-dioxa-cyclopenten-2-one-yl)-methyloxy, $C_{10}$–$C_{14}$ (5-aryl-1,3-dioxa-cyclopenten-2-one-yl)-methyloxy, $(R^2)(R^3)N-(C_1$–$C_{10}$ alkoxy)-;

m is 0–2;

n is 0–2; and p is 1–5.

In another embodiment (designated embodiment XXXIX), the device includes, and can be used to deliver, a compound of the formula:

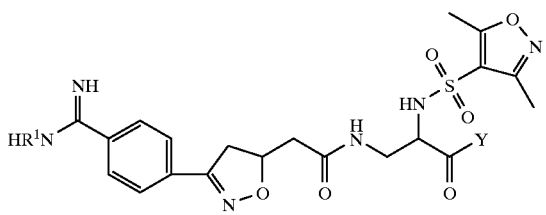

and enantiomeric and diastereomeric forms thereof, and mixtures of enantiomeric and diastereomeric forms thereof, and zwitterion and pharmaceutically acceptable salt forms thereof, wherein:

$R^1$ is:

hydrogen, $(C_1-C_6)$alkoxycarbonyl, $(C_3-C_7)$ cycloalkoxycarbonyl or aryloxycarbonyl;

Y is selected from:

hydroxy, $C_1-C_{10}$ alkyloxy, $C_3-C_{11}$ cycloalkyloxy, aryl $C_1-C_6$ alkyloxy, $C_1-C_6$ alkylcarbonyloxy $C_1-C_4$ alkyloxy, $C_1-C_6$ alkyloxycarbonyloxy $C_1-C_4$ alkyloxy, $C_3-C_7$ cycloalkylcarbonyloxy $C_1-C_4$ alkyloxy, $C_3-C_7$ cycloalkyloxycarbonyloxy $C_1-C_4$ alkyloxy, $C_8-C_{14}$ arylcarbonyloxy $C_1-C_4$ alkyloxy, $C_1-C_6$ alkyloxy $C_1-C_6$ alkylcarbonyloxy $C_1-C_4$ alkyloxy, [5-$(C_1-C_6)$alkyl-1,3-dioxa-cyclopenten-2-one-4-yl]-methyloxy, (5-aryl-1,3-dioxa-cyclopenten-2-one-4-yl)-methyloxy, $(C_1-C_4$ alkyl$)_2$ N—$(C_1-C_{10})$alkyloxy, or morpholinoethoxy; and aryl is: phenyl or naphthyl optionally substituted by 1–3 substituents selected independently from methyl, trifluoromethyl, methoxy, amino, dimethylamino, F, Cl, Br, and I.

This embodiment includes compounds wherein:

$R^1$ is: H, methoxycarbonyl, ethoxycarbonyl, or benzyloxycarbonyl.

Other compounds of this embodiment include compounds wherein:

$R^1$ is H; and

Y is selected from the group consisting of:

hydroxy, methoxy, ethoxy, isopropoxy, n-propoxy, n-butoxy, t-butoxy, i-butoxy, s-butoxy, methylcarbonyloxymethoxy, ethylcarbonyloxymethoxy, t-butylcarbonyloxymethoxy, cyclohexylcarbonyloxymethoxy, 1-(methylcarbonyloxy)-ethoxy, 1-(ethylcarbonyloxy)-ethoxy, 1-(t-butylcarbonyloxy)-ethoxy, 1-(cyclohexylcarbonyloxy)-ethoxy, i-propyloxycarbonyloxymethoxy, cyclohexyloxycarbonyloxymethoxy, t-butyloxycarbonyloxymethoxy, 1-(i-propyloxycarbonyloxy)-ethoxy, 1-(cyclohexyloxycarbonyloxy)-ethoxy, 1-(t-butyloxycarbonyloxy)-ethoxy, dimethylaminoethoxy, diethylaminoethoxy, (5-methyl-1,3-dioxacyclopenten-2-on-4-yl)-methoxy, (5-(t-butyl)-1,3-dioxacyclopenten-2-on-4-yl)-methoxy, (1,3-dioxa-5-phenyl-cyclopenten-2-on-4-yl)-methoxy, and 1-(2-(2-methoxypropyl)-carbonyloxy)-ethoxy.

Thus, the compounds useful according to this embodiment comprise the following exemplary compounds:

$N^2$-(3,5-dimethylisoxazole-4-sulfonyl)-$N^3$-[3-(4,5-amidinophenyl)-isoxazolin-5(R)-yl-acetyl]-(S)-2,3-diaminopropionic acid;

$N^2$-(3,5-dimethylisoxazole-4-sulfonyl)-$N^3$-[3-(4-amidinophenyl)-isoxazolin-5(S)-yl-acetyl]-(s)-2,3-diaminopropionic acid;

$N^2$-(3,5-dimethylisoxazole-4-sulfonyl)-$N^3$-[3-(4-amidinophenyl)-isoxazolin-5(R)-yl-acetyl]-(R)-2,3-diaminopropionic acid;

$N^2$-(3,5-dimethylisoxazole-4-sulfonyl)-$N^3$-[3-(4-amidinophenyl)-isoxazolin-5(S)-yl-acetyl]-(R)-2,3-diaminopropionic acid, and zwitterion and pharmaceutically acceptable salts forms thereof, methyl and ethyl esters thereof, and pharmaceutically acceptable salt forms thereof, Other exemplary compounds of this embodiment include:

$N^2$-(3,5-dimethylisoxazole-4-sulfonyl)-$N^3$-[3-(4-amidinophenyl)-isoxazolin-5(R)-yl-acetyl]-(S)-2,3 diaminopropionic acid;

$N^2$-(3,5-dimethylisoxazole-4-sulfonyl)-$N^3$-[3-(4-amidinophenyl)-isoxazolin-5(R)-yl-acetyl]-(S)-2,3-diaminopropionic acid, trifluoroacetic acid salt;

$N^2$-(3,5-dimethylisoxazole-4-sulfonyl-$N^3$-[3-(4-amidinophenyl)-isoxazolin-5(R)-yl-acetyl]-(S)-2,3-diaminopropionic acid, methanesulfonate salt; and $N^2$-(3,5-dimethylisoxazole-4-sulfonyl)-$N^3$-[3-(4-amidinophenyl)-isoxazolin-5(R)-yl-acetyl]-(S)-2,3-diaminopropionic acid, hydrochloride salt.

In an alternative embodiment, the iontophoretic device of the invention includes an integrin antagonist, such as a peptide or peptidomimetic compound having a structure that binds to the RGD-binding domain of an integrin, provided that the integrin antagonist is not a compound of Formula L:

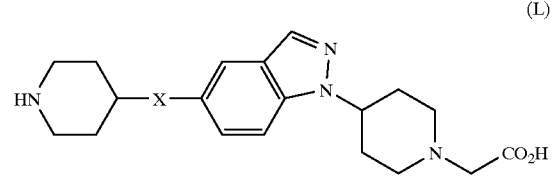

(L)

or a salt solvate or ester thereof, or a salt or solvate of such ester, in which X represents either $CH_2$—$CH_2$ or $CH$=$CH$. An alternative method of the invention, therefore, is to iontophoretically deliver an integrin antagonist, provided that the integrin antagonist is not a compound not a compound of Formula L:

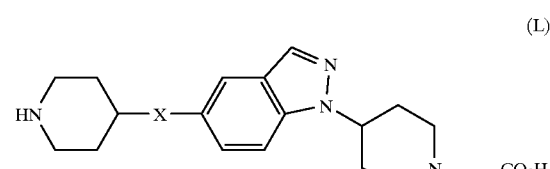

(L)

or a salt solvate or ester thereof, or a salt or solvate of such ester, in which X represents either $CH_2$—$CH_2$ or $CH$=$CH$.

In another alternative embodiment, the invention is an iontophoretic device that includes an integrin antagonist, provided that the integrin antagonist is not a compound of embodiments IV, IX, XIX, XXIII, XXVII, XXXVI, XXXVIII, or XXXIX. An alternative method of the invention, therefore, is to iontophoretically deliver an integrin antagonist, provided that the integrin antagonist is not a compound of embodiments IV, IX, XIX, XXIII, XXVII, XXXVI, XXXVIII, or XXXIX.

A preferred device includes compound having the structure:

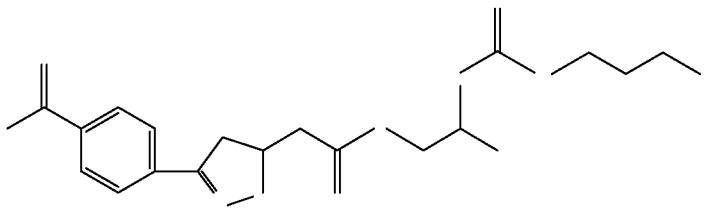

or a pharmaceutically acceptable salt thereof. The mesylate salt is especially preferred.

Thus, the invention includes a method of administering an integrin inhibitor compound as described above, the method comprising iontophoretically administering to a mammal a therapeutically effective amount of the integrin inhibitor using an iontophoresis device.

The invention further includes a method for the treatment of thrombosis, comprising administering to a mammal a therapeutically effective amount of an integrin inhibitor, as described above, using an iontophoresis device.

In particular, the invention includes a method of inhibiting the aggregation of blood platelets, comprising administering to a mammal a therapeutically effective amount of a IIb/IIIa inhibitor using an iontophoresis device.

The invention further includes a method of treating a thromboembolic disorder selected from thrombus or embolus formation, harmful platelet aggregation, reocclusion following thrombolysis, reperfusion injury, restenosis, atherosclerosis, stroke, myocardial infarction, and unstable angina, the method comprising administering to a mammal a therapeutically effective amount of an integrin inhibitor, as described,, using an iontophoresis device.

The entire disclosures of all of the documents cited herein are hereby incorporated herein by reference.

Utility

The CAR antagonist compounds delivered by iontophoresis in accordance with the present invention possess activity as antagonists of CARs such as, for example, IIb/IIIa, $\alpha_v\beta_3$, $\alpha_v\beta_5$ and $\alpha_5\beta_1$, and as such have utility in the treatment of a variety of disease conditions as discussed herein. The CAR antagonist activity of the compounds iontophoretically delivered in the present invention can be demonstrated using assays that measure the binding of a specific CAR to a native ligand, for example, using the ELISA assay described below for the binding of vitronectin to the $\alpha_v\beta_3$ receptor, or for example, an ELISA assay for the binding of fibrinogen to the IIb/IIIa receptor.

Compounds useful in the present invention include those that possess selectivity for the $\alpha_v\beta_3$ receptor relative to the IIb/IIIa receptor as demonstrated by their lack of activity in standard assays of platelet aggregation, such as the platelet aggregation assay described below.

One of the major roles of CARs in vivo is to mediate cellular interactions with adjacent cells. Cell-based adhesion assays can be used to mimic these interactions in vitro. A cell based assay is more representative of the in vivo situation than an ELISA since the receptor is maintained in membranes in the native state. The compounds of the present invention have activity in cell-based assays of adhesion, for example as demonstrated in using the cell adhesion assays described below.

The $\alpha_v\beta_3$ integrin antagonist compounds used in this invention have the ability to suppress/inhibit angiogenesis in vivo, for example, as demonstrated using animal models of ocular neovascularization.

The IIb/IIIa inhibitor compounds used in this invention possess antiplatelet efficacy, as evidenced by their activity in standard platelet aggregation assays or platelet fibrinogen binding assays, as described below.

The utility of the compounds of the present invention can be assessed by testing using any of the methods accepted in the art, including, for example, by one or more of the following assays as described in detail below:

a) Purified $\alpha_v\beta_3$ (Human Placenta)-Vitronectin ELISA;
b) $\alpha_v\beta_3$-Vitronectin Binding Assay;
c) Cell Adhesion Receptor Cell-Based Adhesion Assay;
d) Platelet Aggregation Assay;
e) Purified GPIIb/IIIa-Fibrinogen Binding Assay;
f) Platelet-Fibrinogen Binding Assay;
g) Thrombolytic Assay;
h) Human Aortic Smooth Muscle Cell Migration Assay;
i) In vivo Angiogenesis Model;
j) Pig Restenosis Model;
k) Mouse Retinopathy Model.

As used in the descriptions of the utility assays and elsewhere herein: "μg" denotes microgram, "mg" denotes milligram, "g" denotes gram, "kg" denotes kilogram, "μL" denotes microliter, "mL" denotes milliliter, "L" denotes liter, "nM" denotes nanomolar, "μM" denotes micromolar, "mM" denotes millimolar, "M" denotes molar, "nm" denotes nanometer, "A" denotes ampere, "mA" denotes milliampere, "μA" denotes microampere, "min" denotes minute, and "h" denotes hour. "Sigma" stands for the Sigma-Aldrich Corp. of St. Louis, Mo.

A compound of the present invention is considered to be active if it has an $lC_{50}$ or $K_i$ value of less than about 10 μM for the inhibition of $\alpha_v\beta_3$-Vitronectin Binding Assay, with compounds preferably having $K_i$ values of less than about 0.1 μM. Tested compounds of the present invention are active in the $\alpha_v\beta_3$-Vitronectin Binding Assay.

Purified $\alpha_v\beta_3$ (human placenta)-Vitronectin ELISA

The $\alpha_v\beta_3$ receptor was isolated from human placental extracts prepared using ocrylglucoside. The extracts were passed over an affinity column composed of anti-$\alpha_v\beta_3$ monoclonal antibody (LM609) to Affigel. The column was subsequently washed extensively at pH 7 and pH 4.5 followed by elution at pH 3. The resulting sample was concentrated by wheat germ agglutinin chromatography to provide gave two bands on SDS gel which were confirmed as $\alpha_v\beta_3$ by western blotting.

Affinity purified protein was diluted at different levels and plated to 96 well plates. ELISA was performed using fixed concentration of biotinylated vitronectin (approximately 80 nM/well). This receptor preparation contains the $\alpha_v\beta_3$ with no detectable levels of $\alpha_v\beta_5$ according to the gel ($\alpha_v\beta_3$) and according to effects of blocking antibodies for the $\alpha_v\beta_3$ or $\alpha_v\beta_5$ in the ELISA.

A submaximal concentration of biotinylated vitronectin was selected based on concentration-response curve with fixed receptor concentration and variable concentrations of biotinylated vitronectin.

$\alpha_v\beta_3$-Vitronectin Binding Assay

The purified receptor is diluted with coating buffer (20 mM Tris HCl, 150 mM NaCl, 2.0 mM CaCl$_2$, 1.0 mM MgCl$_2$.6H$_2$O, 1.0 mM MnCl$_2$.4H$_2$O) and coated (100 μL/well) on Costar (3590) high capacity binding plates overnight 5 at 4° C. The coating solution is discarded and the plates washed once with blocking/binding buffer (B/B buffer, 50 mM Tris HCl, 100 mM NaCl, 2.0 mM CaCl$_2$, 1.0 mM MgCl$_2$.6H$_2$O, 1.0 mM MnCl$_2$.4H$_2$O). is then blocked (200 μL/well) with 3.5% BSA in B/B buffer for 2 hours at room temperature. After washing once with 1.0% BSA in B/B buffer, biotinylated vitronectin (100 μL) and either inhibitor (11 μL) or B/B buffer w/1.0% ssA (11 μL) is added to each well. The plates are incubated 2 hours at room temperature. The plates are washed twice with B/B buffer and incubated 1 hour at room temperature with anti-biotin alkaline phosphatase (100 μL/well) in B/B buffer containing 1.0% BSA. The plates are washed twice with B/B buffer and alkaline phosphatase substrate (100 μL) is added. Color is developed at room temperature.

Color development is stopped by addition of 2N NaOH (25 μL/well) and absorbance is read at 405 nm. The IC$_{50}$ is the concentration of test substance needed to block 50% of the vitronectin binding to the receptor.

CAR Cell-Based Adhesion Assays

In the adhesion assays, a 96 well plate was coated with the ligand (i.e., fibrinogen) and incubated overnight at 4° C. The following day, the cells were harvested, washed and loaded with a fluorescent dye. Compounds and cells were added together and then were immediately added to the coated plate. After incubation, loose cells are removed from the plate, and the plate (with adherent cells) is counted on a fluorometer. The ability of test compounds to inhibit cell adhesion by 50% is given by the IC$_{50}$ value and represents a measure of potency of inhibition of CAR mediated binding. Compounds were tested for their ability to block cell adhesion using assays specific for $\alpha_v\beta_3$, $\alpha_v\beta_5$ and $\alpha_5\beta_1$ CAR interactions.

Platelet Aggregation Assay

Venous blood was obtained from anesthetized mongrel dogs or from healthy human donors who were drug- and aspirin-free for at least two weeks prior to blood collection. Blood was collected into citrated Vacutainer tubes. The blood was centrifuged for 15 min at 150×g (850 RPM in a Sorvall RT6000 Tabletop Centrifuge with H-1000 B rotor) at room temperature, and platelet-rich plasma (PRP) was removed. The remaining blood was centrifuged for 15 min at 1500×g (26,780 RPM) at room temperature, and platelet-poor plasma (PPP) was removed. Samples were assayed on a PAP-4 Platelet Aggregation Profiler, using PPP as the blank (100% transmittance). 200 μL of PRP (5×10$^8$ platelets/mL) was added to each micro test tube, and transmittance was set to 0%. 20 μL of ADP (10 μM) was added to each tube, and the aggregation profiles were plotted (% transmittance versus time). Test agent (20 μL) was added at different concentrations prior to the addition of the platelet agonist. Results are expressed as % inhibition of 25 agonist-induced platelet aggregation.

Purified GPIIb/IIIa-Fibrinogen Binding ELISA

The following reagents are used in the GPIIb/IIIa-fibrinogen binding, ELISA:

purified GPIIb/IIIa (148.8 μ/mL);

biotinylated fibrinogen (~1 mg/mL or 3000 nM);

anti-biotin alkaline phosphatase conjugate (Sigma No. A7418);

flat-bottom, high binding, 96-well plates (Costar Cat. No. 3590);

phosphatase substrate (Sigma No. 104) (40 mg capsules);

bovine serum albumin (BSA) (Sigma No. A3294);

Alkaline Phosphatase buffer:
0.1 M glycine-HCl, 1 mM MgCl$_2$.6H$_2$O, 1 mM ZnCl$_2$, pH 10.4;

Binding buffer:
20 mM Tris-HCl, 150 mM NaCl, 1 mM CaCl$_2$.2H$_2$O, 0.02% NaN$_3$, pH 7.0;

Buffer A:
50 mM Tris-HCl, 100 mM NaCl, 2 mM CaCl$_2$.2H$_2$O, 0.02% NaN$_3$, pH 7.4;

Buffer A+3.5% BSA (Blocking buffer);

Buffer A+0.1% BSA (Dilution buffer); and

2N NaOH.

The following method steps are used in the GPIIb/IIIa-fibrinogen binding ELISA:

Coat plates with GPIIb/IIIa in Binding buffer (125 ng/100 μL/well) overnight at 4° C. (Leave first column uncoated for non-specific binding). Cover and freeze plates at –70° C. until used. Thaw plate 1 hour at room temperature or overnight at 4° C. Discard coating solution and wash once with 200 μL Binding buffer per well. Block plate 2 hours at room temperature on shaker with 200 μL Buffer A+3.5% BSA (Blocking buffer) per well. Discard Blocking buffer and wash once with 200 μL Buffer A+0.1% BSA (Dilution buffer) per well. Pipet 11 μL of test compound (10× the concentration to be tested in Dilution buffer) into duplicate wells. Pipet 11 μL Dilution buffer into non-specific and total binding wells. Add 100 μL biotinylated fibrinogen (1/133 in Dilution buffer, final concentration=20 nM) to each well. Incubate plates for 3 hours at room temperature on a plate shaker. Discard assay solution and wash twice with 300 μL Binding buffer per well. Add 100 μL Anti-biotin alkaline phosphatase conjugate (1/1500 in Dilution buffer) to each well. Incubate plates for 1 hour at room temperature on plate shaker. Discard conjugate and wash twice with 300 μL Binding buffer per well. Add 100 μL phosphatase substrate (1.5 mg/mL in alkaline phosphatase buffer) to each well. Incubate plate at room temperature on shaker until color develops. Stop color development by adding 25 μL 2N NaOH per well. Read plate at 405 nm. Blank against non-specific binding (NSB) well. Percent Inhibition is calculated as 100–(Test Compound Abs/Total Abs)×100.

Platelet-Fibrinogen Binding Assay

Binding of $^{125}$I-fibrinogen to platelets was performed as described by Bennett et al., *Proc Natl Acad Sci USA* 80:2417–2422 (1983), with some modifications as described below. Human PRP (h-PRP) was applied to a Sepharose column for the purification of platelet fractions. Aliquots of platelets (5×10$^8$ cells) along with 1 mM calcium chloride were added to removable 96 well plates prior to the activation of the human gel purified platelets (h-GPP). Activation of the human gel purified platelets was achieved using ADP, collagen, arachidonate, epinephrine, and/or thrombin in the presence of the ligand, $^{125}$I-fibrinogen. The $^{125}$I-fibrinogen bound to the activated platelets was separated from the free form by centrifugation and then counted on a gamma counter. For an $IC_{50}$ evaluation, the test compounds were added at various concentrations prior to the activation of the platelets.

Thrombolytic Assay

The CAR antagonist compounds used in the present invention can also possess thrombolytic efficacy, that is, they are capable of lysing (breaking up) already formed platelet-rich fibrin blood clots, and thus are useful in treating a thrombus formation, as evidenced by their activity in the tests described below. Venous blood was obtained from the arm of a healthy human donor who was drug-free and aspirin free for at least two weeks prior to blood collection, and placed into 10 mL citrated vacutainer tubes. The blood was centrifuged for 15 min at 1500×g at room temperature, and platelet rich plasma (PRP) was removed.

To the PRP was then added $1\times10^{-3}$ M of the agonist ADP, epinephrine, collagen, arachidonate, serotonin or thrombin, or a mixture thereof, and the PRP incubated for 30 min. The PRP was centrifuged for 12 min at 2500×g at room temperature. The supernatant was then poured off, and the platelets remaining in the test tube were resuspended in platelet poor plasma (PPP), which served as a plasminogen source. The suspension was then assayed on a Coulter Counter (Coulter Electronics, Inc., Hialeah, Fla.), to determine the platelet count at the zero time point. After obtaining the zero time point, test compounds were added at various concentrations. Test samples were taken at various time points and the platelets were counted using the Coulter Counter. To determine the percent of lysis, the platelet count at a time point subsequent to the addition of the test compound was subtracted from the platelet count at the zero time point, and the resulting number divided by the platelet count at the zero time point. Multiplying this result by 100 yielded the percentage of clot lysis achieved by the test compound. For the $IC_{50}$ evaluation, the test compounds were added at various concentrations, and the percentage of lysis caused by the test compounds was calculated.

Human Aortic Smooth Muscle Cell Migration Assay

A method for assessing $\alpha_v\beta_3$-mediated smooth muscle cell migration and agents that inhibit $\alpha_v\beta_3$-mediated smooth muscle cell migration is described in Liaw et al., *J Clin Invest* 95:713–724 (1995).

In Vivo Angiogenesis Model

A quantitative method for assessing angiogenesis and antiangiogenic agents is described in Passaniti et al., *Lab Invest* 67:519–528 (1992).

Pig Restenosis Model

A method for assessing restenosis and agents that inhibit restenosis is described in Schwartz et al., *J Am College of Cardiology* 19:267–274 (1992).

Mouse Retinopathy Model

A method for assessing retinopathy and agents that inhibit retinopathy is described in Smith et al., *Invest Ophthal & Visual Science* 35:101–111 (1994).

Dosage and Formulation

CAR antagonist compounds are iontophoretically delivered in accordance with this invention by transdermal iontophoretic delivery to provide contact of the active agent with the agents's site of action, the desired CAR, in the body of a mammal.

They can be administered by any conventional iontophoresis means available for use in conjunction with pharmaceuticals, either as individual therapeutic agents or in a combination of therapeutic agents.

The dosage of the CAR antagonist compounds administered will, of course, vary depending upon known factors, such as the pharmacodynamic characteristics of the particular agent; the age, health and weight of the recipient; the nature of the target CAR; the nature and extent of the symptoms; the kind of concurrent treatment; the frequency of treatment; and the effect desired. A daily dosage of active ingredient can be expected to be in the range of from about 0.001 to about 10 milligrams per kilogram (mg/kg) of body weight.

Suitable pharmaceutical carriers are described in *Remington's Pharmaceutical Sciences,* Mack Publishing Company, a standard reference text in this field, the disclosure of which incorporated herein by reference.

The following examples are provided to assist in a further understanding of the invention. The results of the following experiments demonstrate successful iontophoretic delivery of cell adhesion antagonist molecules. The particular materials and conditions employed are intended to be further illustrative of the invention and are not limiting upon the reasonable scope thereof.

EXAMPLE 1

In vitro Excised Skin Delivery Experiments

Patch Designs: The 2 compartment patch design includes an absorbent drug reservoir with 2 cm$^2$ skin-contacting area and volume of 0.30 mL. The drug reservoir is separated from the electrode compartment with a 100 MWCO ultrafiltration membrane. The electrode compartment included a silver anode and cation exchange media in a hydrogel. A monolithic patch design was also used, consisting of a sandwich composed of a silver anode in the middle of 2 layers of absorbent material. The patches are assembled and loaded with the dosing solution just before applying to the skin.

Experimental Protocol: The iontophoretic delivery of a GPIIb/IIIa antagonist was carried out in a flow-through in vitro system. The compound used was methyl-N$^3$-[2-{3-(4-formamidinophenyl)-isoxazolin-5(R)-yl}-acetyl]-N$^2$-(n-butyloxycarbonyl)-2,3-(S)-diaminopropanoate, having the following generalized structure:

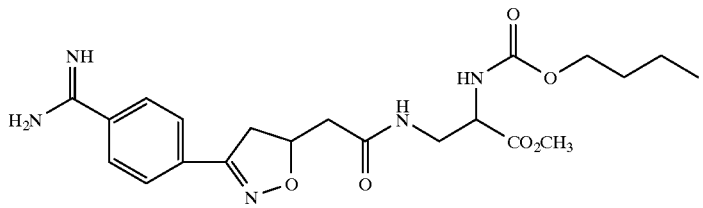

This compound was delivered as the mesylate salt, having a molecular weight of 447, with pKa=1.11, and solubility=80 mg/mL at pH 4. The patch was loaded a 10 mg/mL solution of the IIb/IIIa antagonist in 154 mM saline.

A silver chloride mesh return cathode was located upstream of the polycarbonate flow-through cells. Freshly dermatomed (1 mm) porcine skin was mounted in the cells on a porous support. The patches were dosed with aqueous solutions of the drug and then placed on top of the excised skin. The patches were secured by a spring-loaded mechanism that maintained even pressure over the patch. The cells were "perfused" by means of a peristaltic pump which pulls receiver solution through them. Effluents from the cells were collected with a fraction collector. Flow rates were typically 0.25 mL/min. The receiver solution was an isotonic pH 7.4 buffered saline solution containing 10 mM HEPES, 100 mM NaCl, PEG 400, and a surfactant, Pluronic P-103. Iontophoresis current (50 $\mu$A) was provided by WPI power cells, and the applied currents and cell voltages were recorded with a Fluke databucket.

Results: The effluent receiver solution was measured in a series of six runs, to determine whether the ester was hydrolyzed during the period of the iontophoresis. Results were obtained by means of liquid scintillation counting (radioactivity), and HPLC-UV. The HPLC results are estimates based on calibration for the ester form only. The data are summarized in Table I, below.

TABLE I

| Sample | Liquid Scintillation Assay Total ($\mu$g/mL) | HPLC Assay Ester ($\mu$g/mL) | % Ester | Total ($\mu$g/mL) |
|---|---|---|---|---|
| 1 | 4.76 | 1.41 | 44.8 | 3.15 |
| 2 | 4.15 | 0.62 | 30.5 | 2.03 |
| 3 | 4.05 | 0.62 | 45.3 | 1.37 |
| 4 | 4.87 | 0.65 | 20.9 | 3.11 |
| 5 | 5.56 | 1.03 | 27.6 | 3.73 |
| 6 | 5.19 | 0.81 | 24.8 | 3.27 |

The results summarized in Table I indicate that the positively charged ester (GPIIb/IIIa antagonist) is metabolized, to some extent, in the skin or receptor fluid to the uncharged zwitterion. (Assay of extracts of the patch following completion of iontophoresis showed no detectable acid hydrolysis product.) Even so, the presence of the hydrolyzed form on the distal side of the skin indicates that the compound is traversing the skin during the iontophoresis.

Figure 2:
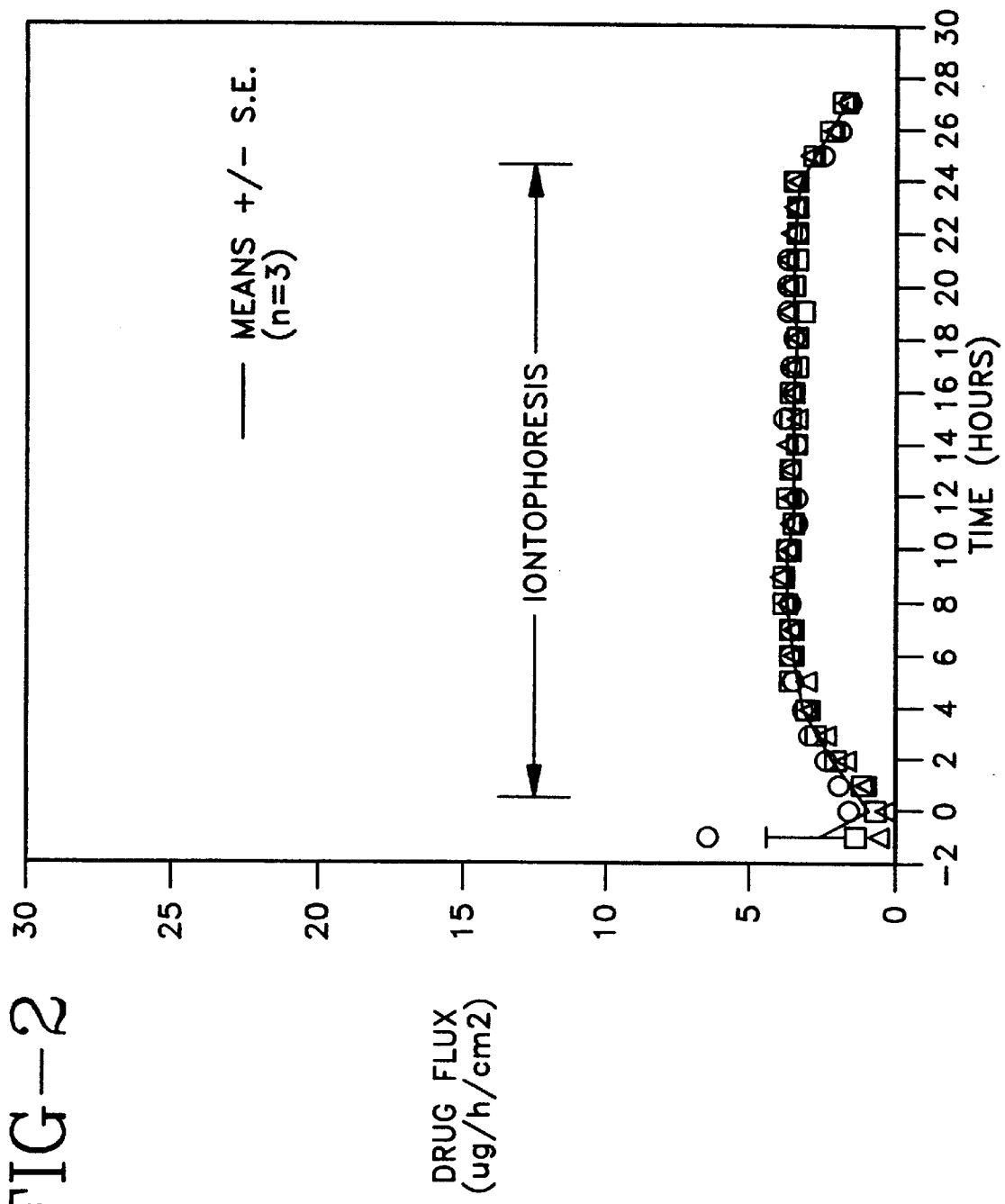
FIG. 2 depicts in vitro delivery with 10 mg/mL of a GPIIb/IIIa antagonist and 154 mM NaCl at 50 $\mu$A with 2 cm$^2$.

FIG. 2 demonstrates very clearly that iontophoresis transport the positively charged ester in a predictable, reproducible and constant manner to constant flux levels over a period of 24 hours. The variability in delivery from skin to skin is also unexpectedly low.

Figure 3:
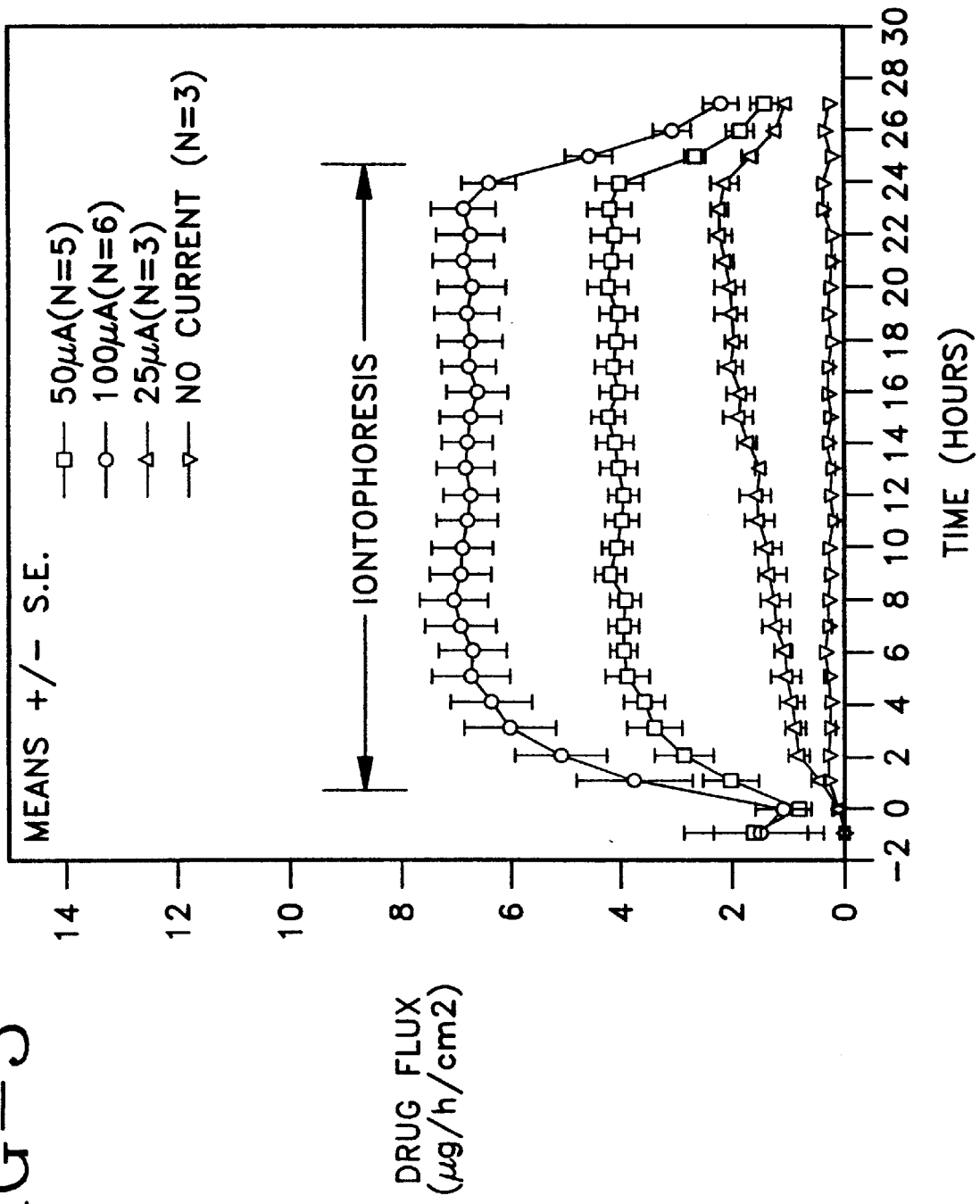
FIG. 3 depicts iontophoretic delivery across excised pig skin of a 10 mg/mL positively charged ester drug (GPIIb/IIa antagonist) and 9 mg/mL NaCl to therapeutic flux levels (1–10 $\mu$g/h).

FIG. 3 shows that the in vitro delivery is proportional to increase in current and that the flux is again very constant over the 24 hour period and between skin specimens as well. In these experiments the flux reaches "steady state" rapidly and it is also evident that flux levels drop rapidly on termination of the current. This latter feature is likely to be valuable in situations where the administration of the drug must be stopped rapidly to avoid a risk of harm or injury to the patient, such a situation may be one in which the patient has an adverse reaction to the drug.

EXAMPLE 2

In vivo Swine Experiments

Patch Design: Same as in Example 1.

Experimental Protocol: In each experiment, the patches were loaded with a 20 mg/mL solution of the same IIb/IIIa antagonist used in Example 1 in 154 mM saline, immediately before application to the skin of the animals. Unanesthetized Yorkshire swine with weights of about 20 to 35 kg were used. The skin sites receiving the patches were wiped clean with moist gauze pads. Patches were overwrapped with an adhesive, elastic wrap to hold the patches in place. Separate constant current (100 $\mu$A) power supplies were provided for each iontophoresis patch system. Current and voltage readings were made and recorded by on-board dataloggers (Fluke databuckets).

Blood samples were withdrawn from the vena cava through an IV catheter into VACUTAINER™ blood collection tubes containing EDTA. After gentle mixing, the tubes were centrifuged to separate the plasma, which was transferred to clean polypropylene tubes and frozen on dry ice. Frozen samples were stored at −80° C. until assayed.

Figure 4:
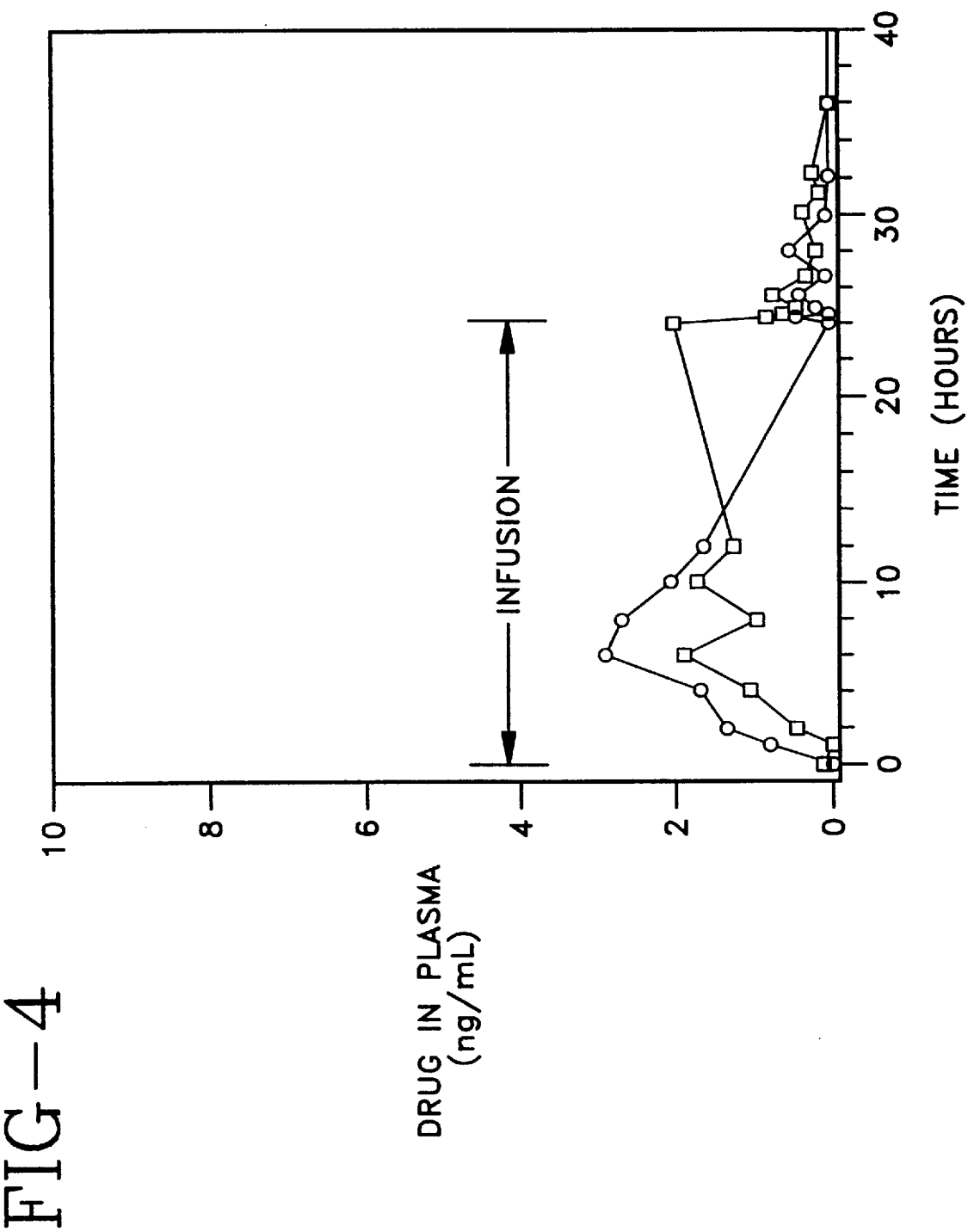
FIG. 4 depicts plasma concentrations of the acid drug form during IV infusion of the acid drug form at a rate equivalent to 10 $\mu$g/h active component of the GPIIb/IIIa antagonist in unanesthetized swine.
Figure 5:
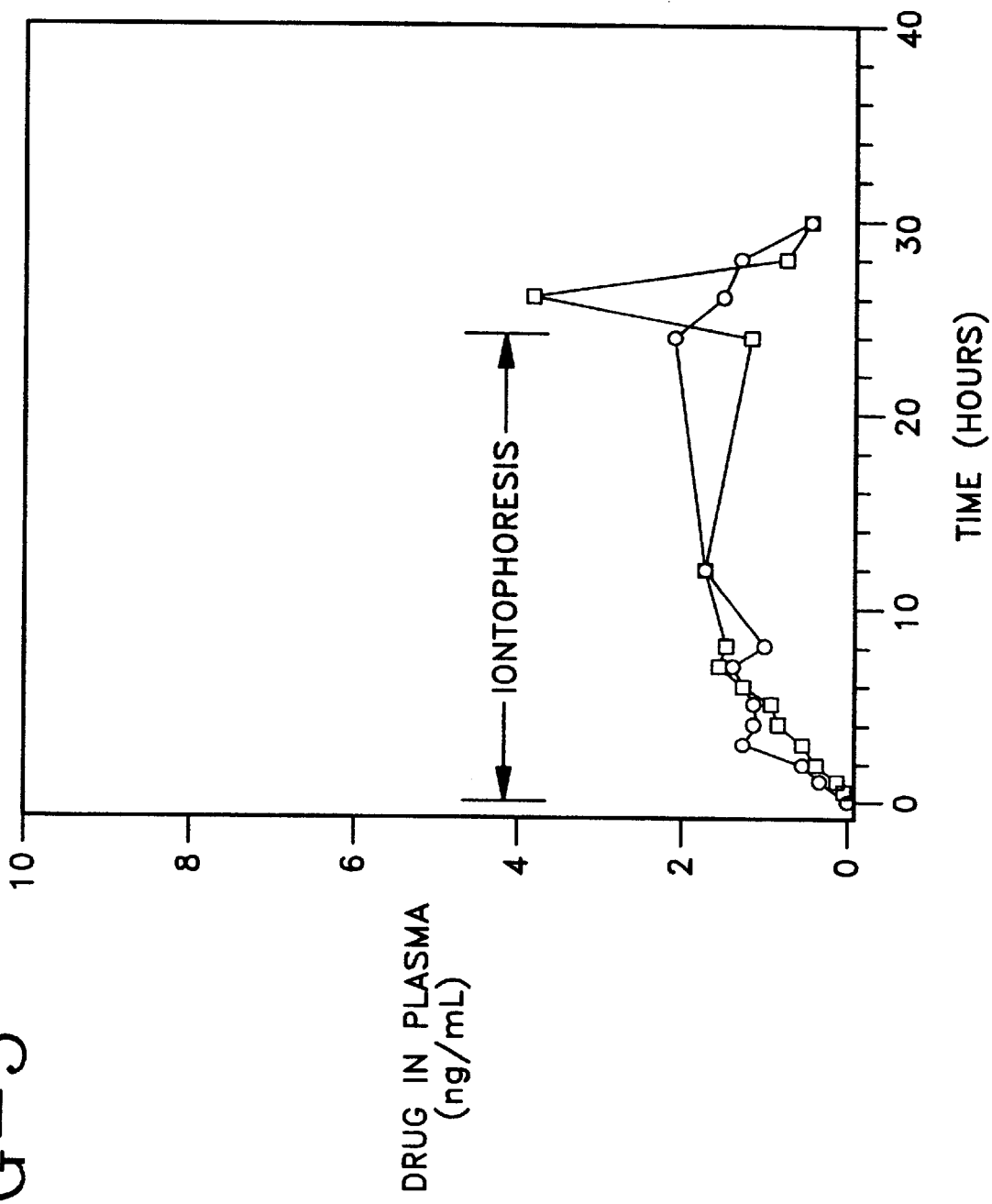
FIG. 5 depicts plasma concentration of the GPIIb/IIIa antagonist acid drug form following iontophoretic delivery in an unanesthetized swine using a 2 cm$^2$ patch with 20 mg/mL of GPIIb/IIIa antagonist and 154 mM NaCl at 200 $\mu$A.

Results: FIGS. 4 and 5 provide a comparative illustration of the in vivo delivery of the GPIIb/IIIa antagonist (mentioned in Example 1) to pigs using constant IV infusion (FIG. 4) and constant iontophoresis (FIG. 5). IV infusion employed the acid form of the drug at an infusion rate of 10 $\mu$g/h. The results show that blood levels obtained from both delivery techniques are similar, and that the variability in plasma levels seen with the iontophoresis is extremely low.

EXAMPLE 3

In Vitro Iontophoretic Delivery of GPIIb/IIIa Antagonist: Effect of Membrane Separator Rationale: Because of the choices of saline concentration, and the fact that any electrolyte ion in the drug reservoir which is a cation will compete for current with the drug, the patch design can fall into one of three profiles:

a) bolus or peaked profile: this is obtained by using a low or near zero saline concentration. With few or no other cations to compete with drug cations in the reservoir, the flux will start high and the fall as electrolyte cations accumulate with time in the drug reservoir. (see, FIG. 6, with 10 mM saline);

b) a nearly a flat profile: if the reservoirs contain about 75 mM saline at the start, then the saline concentration will neither increase nor decrease, and a steady flux will be obtained;

c) a profile which increases with time: similarly, if a high saline concentration is started with, then the saline concentration will fall with time, and due to competition for the current, the drug flux will increase with time.

Patches: A dual compartment 2 cm$^2$ patch design, loaded with 100 mg/mL of the GPIIb/IIIa antagonist of Example 1, with a size exclusion or anion exchange membrane separator.

Experimental Protocol: See Example 1, with current applied at 400 $\mu$A.

Figure 6:
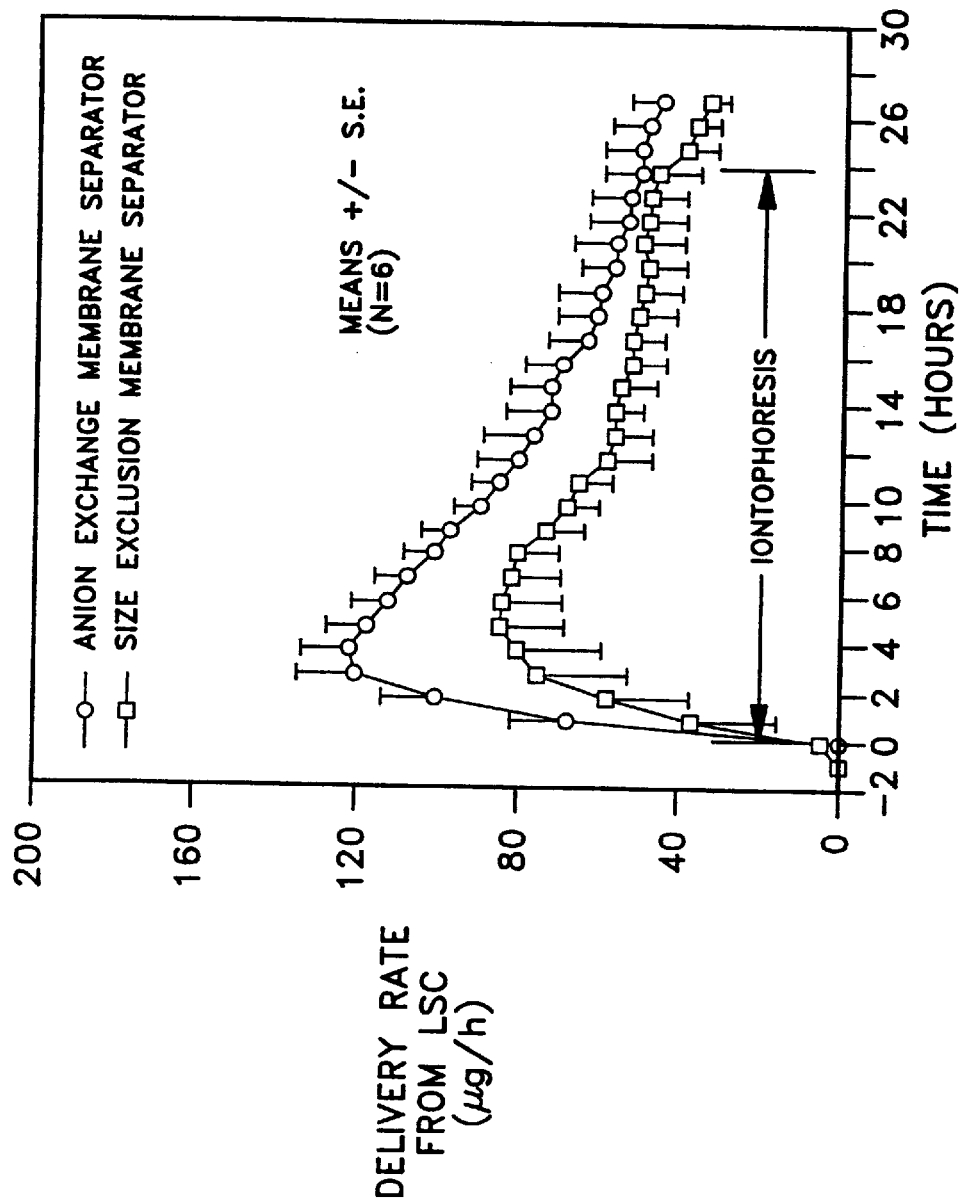
FIG. 6 compares the delivery rate profiles for the dual compartment patches at a current of 400 $\mu$A.

Results: FIG. 6 compares the delivery rate profiles for the dual compartment patches at 400 $\mu$A. While the anion exchange membrane patch provided somewhat greater delivery, the two profiles are similar. These results fit the bolus or peaked profile, the flux starts high, and falls as electrolyte cations accumulate with time.

EXAMPLE 4
In Vitro Iontophoretic Delivery of GPIIb/IIIa Antagonist: Effect of Chloride Salt.

Patches: A dual compartment 2 cm$^2$ patch design, loaded with 50 mg/mL chloride salt of the IIb/IIIa antagonist.

Experimental Protocol: See Example 1, current applied at 100 $\mu$A and 200 $\mu$A.

Figure 7:
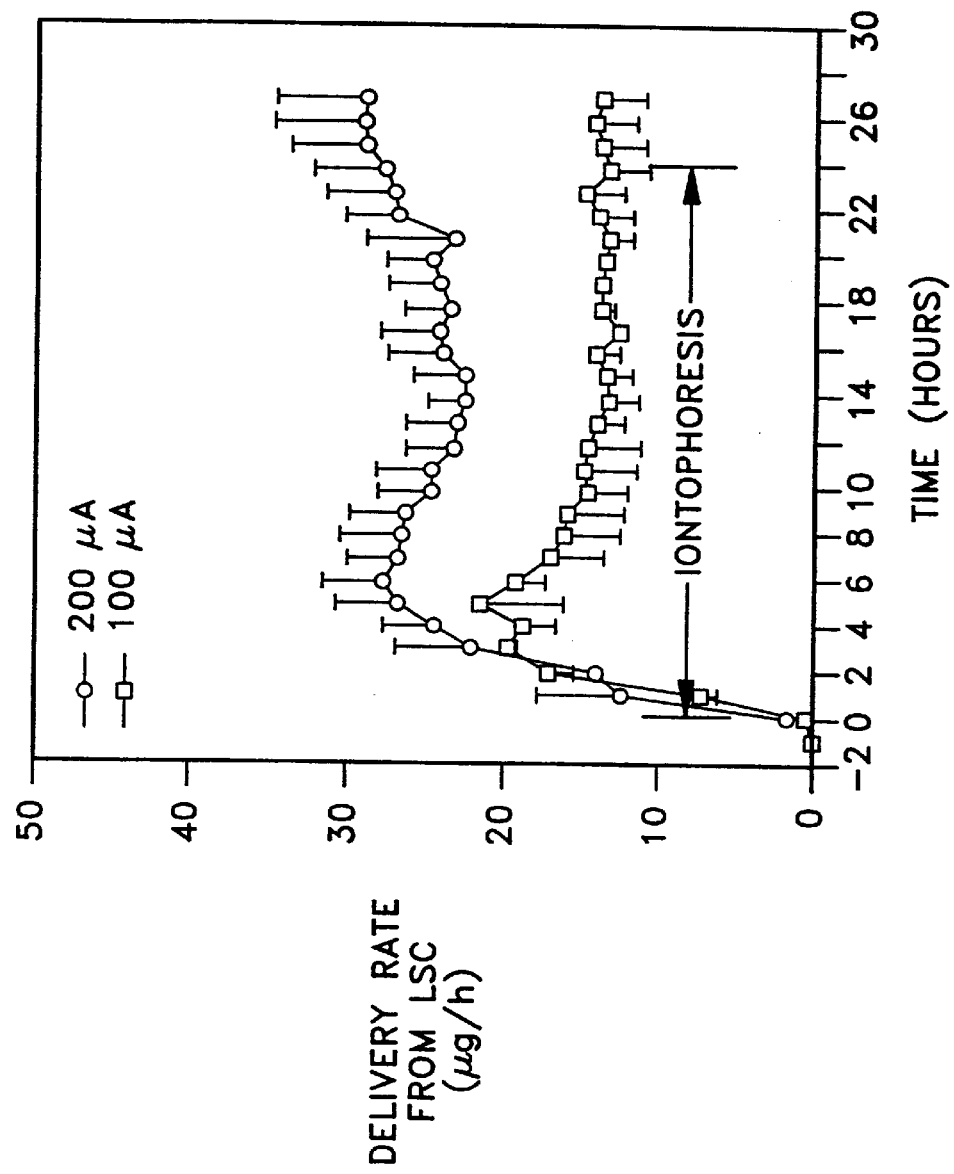
FIG. 7 depicts the delivery profile of dual compartment patches loaded with 50 mg/mL chloride salt and run at a current of 100 $\mu$A and 200 $\mu$A.

Results: The delivery rate profiles for these runs are shown in FIG. 7. The results for the runs at 100 $\mu$A are similar, showing nearly flat delivery at 10–20 $\mu$g/h. The run at higher current (200 $\mu$A) also gave nearly constant delivery in the 20–35 $\mu$g/h range. These results fit the nearly flat profile and a steady flux is obtained.

EXAMPLE 5
In Vitro Iontophoretic Delivery of GPIIb/IIIa Antagonist: Effect of Current, Drug Concentration, and Salinity Patches: A dual compartment 2 cm$^2$ patch design, loaded with either: (1) a 1 mM NaCl, 150 mg/mL formulation of the IIb/IIIa antagonist of Example 1, or (2) a 75 mM NaCl, 100 mg/mL formulation of the drug.

Experimental Protocol: See Example 1, current applied at 100 $\mu$A for the 1 mM NaCl sample, and at 400 $\mu$A for the 75 mM NaCl sample.

Figure 8:
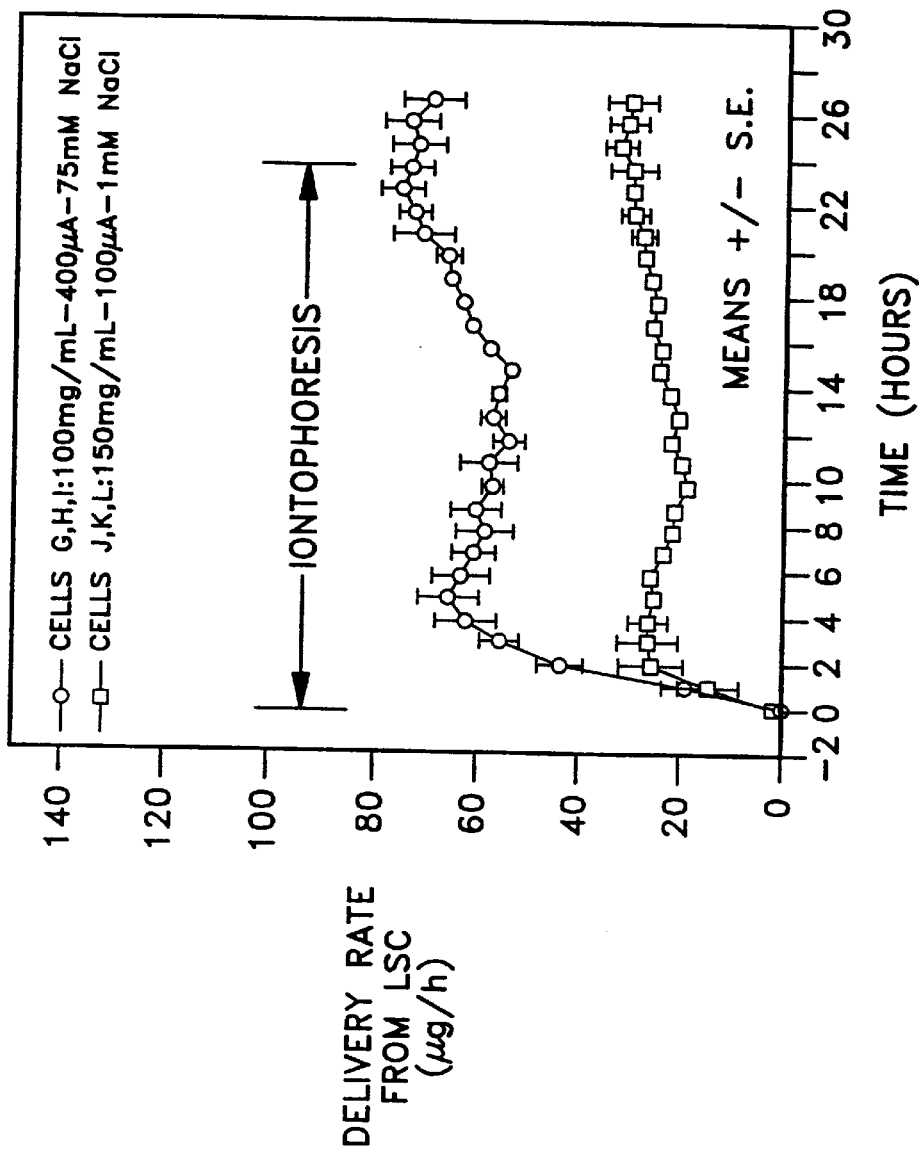
FIG. 8 depicts the delivery rate profile of dual compartment patches loaded with 1 mM NaCl, 150 mg/mL formulation and run at a current of 100 $\mu$A and loaded with 75 mM NaCl, 100 mg/mL formulation and run at a current of 400 $\mu$A.

Results: The delivery rate profiles for these conditions are compared in FIG. 8. Both show an improvement over the earlier profiles, providing much more uniform delivery rates for the 24 hour duration of iontophoresis. These results also fit the nearly flat profile.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth below.

What is claimed is:

1. An iontophoresis device for non-invasively administering a therapeutic dose of an $\alpha_v\beta_3$ integrin antagonist to a mammal at a delivery rate of 0.5 $\mu$g/h or greater, comprising:

(a) a current distributing member;

(b) an agent reservoir containing an ionized or ionizable substance, in electrical communication with the current distributing member and adapted to be placed in ionic communication with an epithelial surface, wherein the ionized or ionizable substance is an $\alpha_v\beta_3$ integrin antagonist; and (c) an electrolyte reservoir containing an electrolyte, in electrical communication with an indifferent electrode and adapted to be placed in ionic communication with an epithelial surface;

(d) an electrical power source in current delivering connection with the current distribution member and the electrolyte reservoir.

2. An iontophoresis device according to claim 1, wherein the agent reservoir further comprises competing ions having a like charge to the ionized form of the $\alpha_v\beta_3$ integrin antagonist.

3. An iontophoresis device for non-invasively administering a therapeutic dose of an $\alpha_v\beta_3$ integrin inhibitor compound to a mammal, comprising (1) a cathode and an anode each disposed so as to be in electrical connection with a source of electrical energy and in contact with skin of a subject; and (2) a drug reservoir electrically connected to the cathode or the anode containing an $\alpha_v\beta_3$ integrin inhibitor compound.

4. An iontophoresis device according to claim 3, wherein the drug reservoir further comprises competing ions having a like charge to the $\alpha_v\beta_3$ integrin inhibitor compound.

5. A method of administering an $\alpha_v\beta_3$ integrin inhibitor compound to a mammal, comprising iontophoretically administering to the mammal a therapeutically effective amount of the $\alpha_v\beta_3$ integrin antagonist using an iontophoresis device according to claim 1.

6. A method according to claim 5, wherein the agent reservoir of the iontophoresis device further comprises competing ions having a like charge to the $\alpha_v\beta_3$ integrin antagonist.

7. A method of non-invasively administering a therapeutic dose of a $\alpha_v\beta_3$ integrin antagonist to a mammal, comprising the step of iontophoretically driving the $\alpha_v\beta_3$ integrin antagonist through a predetermined area of skin of the mammal at a delivery rate of 0.5 $\mu$g/h or greater.

8. A method according to claim 7, wherein the iontophoretically driving step comprises driving the $\alpha_v\beta_3$ integrin antagonist with competing ions thereto.

9. A method according to claim 7, wherein the $\alpha_v\beta_3$ integrin antagonist is administered continuously at a current of from about 10 $\mu$A to about 3 mA over a period of time up to about 24 hours.

10. A method according to claim 7, wherein the $\alpha_v\beta_3$ integrin antagonist is administered discontinuously at a current of from about 10 $\mu$A to about 3 mA over a period of time up to about 24 hours.

11. An iontophoretic device for non-invasively administering a therapeutic dose of an $\alpha_v\beta_3$ integrin antagonist to a mammal at a delivery rate of 0.5 $\mu$g/h or greater, comprising:

(a) a current distributing member;

(b) an agent reservoir containing an ionized or ionizable substance, in electrical communication with the current distributing member and adapted to be placed in ionic communication with an epithelial surface, wherein the ionized or ionizable substance comprises an $\alpha_v\beta_3$ integrin antagonist and competing ions thereto having a like charge to the ionized form of the $\alpha_v\beta_3$ integrin antagonist; and (c) an electrolyte reservoir containing an electrolyte, in electrical communication with an indifferent electrode and adapted to be placed in ionic communication with an epithelial surface;

(d) an electrical power source in current delivering connection with the current distribution member and the electrolyte reservoir.

12. An iontophoretic device for non-invasively administering a therapeutic dose of a cell adhesion inhibitor compound and competing compound ion thereto to a mammal, comprising:

(a) a current distributing member;

(b) an agent reservoir containing an ionized or ionizable substance, in electrical communication with the current distributing member and adapted to be placed in ionic communication with an epithelial surface, wherein the ionized or ionizable substance is a cell adhesion inhibitor compound; and (c) an electrolyte reservoir containing an electrolyte, in electrical communication with an indifferent electrode and adapted to be placed in ionic communication with an epithelial surface;

(d) an electrical power source in current delivering connection with the current distribution member and the electrolyte reservoir, wherein the cell adhesion inhibitor compound has Formula I:

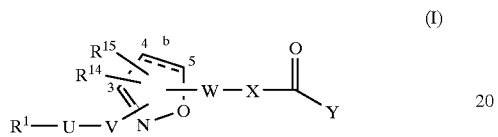

(I)

or a pharmaceutically acceptable salt form thereof, wherein:
b is a carbon-carbon single or double bond;
$R^1$ is selected from:
  $R^{2a}(R^3)N-$, $R^2(R^3)N(R^2N=)C-$, $R^{2a}(R^3)N(CH_2)_{p'}Z-$, $R^2(R^3)N(R^2N=)C(CH_2)_{p''}Z-$, $R^2(R^3)N(R^2N=)CN(R^2)-$, $R^2(R^3)NC(O)-$, $R^2(R^5O)N(R^2N=)C-$, $R^2(R^3)N(R^5ON=)C-$,

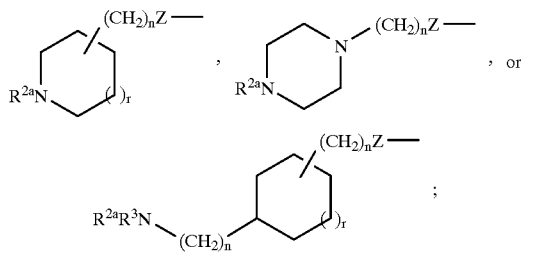

Z is selected from:
  a bond, O, S, $S(=O)$, $S(=O)_2$;
$R^2$ and $R^3$ are selected independently from:
  H; $C_1-C_{10}$ alkyl; $C_3-C_6$ alkenyl, $C_3-C_{11}$ cycloalkyl; $C_4-C_{11}$ cycloalkylalkyl; $C_6-C_{10}$ aryl optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl;
  $C_7-C_{11}$ arylalkyl optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl;
  $C_2-C_7$ alkylcarbonyl;
  $C_7-C_{11}$ arylcarbonyl optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl;
  $(C_1-C_{10}$ alkoxy)carbonyl;
  $C_4-C_{11}$ cycloalkoxycarbonyl;
  $C_7-C_{11}$ bicycloalkoxycarbonyl;
  $C_7-C_{11}$ aryloxycarbonyl optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; aryl($C_1-C_{10}$ alkoxy)carbonyl where the aryl group is optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl;
  $(C_1-C_6$ alkyl)carbonyloxy($C_1-C_4$ alkoxy)carbonyl;
  $(C_6-C_{10}$ aryl)carbonyloxy($C_1-C_4$ alkoxy)carbonyl where the aryl group is optionally substituted with 0–3 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl;
  $(C_4-C_{11}$ cycloalkylcarbonyl)oxy($C_1-C_4$ alkoxy)carbonyl;
  heteroaryl optionally substituted with 0–2 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl; or
  heteroaryl($C_1-C_5$)alkyl where the heteroaryl group is optionally substituted with 0–2 groups selected from hydroxy, halogen, $C_1-C_6$ alkoxy, $C_1-C_6$ alkyl, $CF_3$, $S(O)_mCH_3$, $-N(CH_3)_2$, $C_1-C_4$ haloalkyl, methylenedioxydiyl, ethylenedioxydiyl;
  provided that only one of $R^2$ and $R^3$ can be hydroxy;

$R^{2a}$ is:
  $R^2$ or $R^2(R^3)N(R^2N=)C-$;

U is selected from:
  a single bond, $-(C_1-C_7$ alkyl)-, $-(C_2-C_7$ alkenyl)-, $-(C_2-C_7$ alkynyl)-;

V is selected from:
  a single bond, $-(C_2-C_7$ alkyl)-, substituted with 0–3 groups selected independently from $R^6$ or $R^7$; $-(C_2-C_7$ alkenyl)-, substituted with 0–3 groups selected independently from $R^6$ or $R^7$; $-(C_2-C_7$ alkynyl)-, substituted with 0–3 groups selected independently from $R^6$ or $R^7$; -(phenyl)-Q—, the phenyl substituted with 0–2 groups selected independently from $R^6$ or $R^7$; -(pyridyl)-Q—, the pyridyl substituted with 0–2 groups selected independently from $R^6$ or $R^7$; or -(pyridazinyl)-Q—, the pyridazinyl substituted with 0–2 groups selected independently from $R^6$ or $R^7$;

Q is selected from:
  a single bond, $-O-$, $-S(O)_m-$, $-N(R^{12})-$, $-(CH_2)_m-$, $-C(=O)-$, $-N(R^{5a})C(=O)-$, $-C(=O)N(R^{5a})$, $-CH_2O-$, $-OCH_2-$, $-CH_2N(R^{12})-$, $-N(R^{12})CH_2-$, $-CH_2C(=O)-$, $-C(=O)CH_2-$, $-CH_2S(O)_m-$, or $-S(O)_mCH_2-$, provided that:
  when b is a single bond, and $R^1-U-V-$ is a substituent on $C^5$ of the central 5-membered ring of Formula I, then Q is not $-O-$, $-S(O)_m-$, $-N(R^{12})-$, $-C(=O)N(R^{5a})-$, $-CH_2O-$, $-CH_2N(R^{12})-$, or $-CH_2S(O)_m-$;

W is selected from:
  $-(C(R^4)_2)_nC(=O)N(R^{5a})-$, or $-C(=O)-N(R^{5a})-(C(R^4)_2)_{n'}-$;

X is:
  $-(C(R^4)_2)_n-C(R^4)(R^8)-C(R^4)(R^{4a})-$;

Y is selected from:
  hydroxy, $C_1-C_{10}$ alkyloxy, $C_3-C_{11}$ cycloalkyloxy, $C_6-C_{10}$ aryloxy, $C_7-C_{11}$ aralkyloxy, $C_3-C_{10}$ alkylcarbonyloxyalkyloxy, $C_3$–$C_{10}$
alkoxycarbonyloxyalkyloxy, $C_2$–$C_{10}$
alkoxycarbonylalkyloxy, $C_5$–$C_{10}$
cycloalkylcarbonyloxyalkyloxy, $C_5$–$C_{10}$
cycloalkoxycarbonyloxyalkyloxy, $C_5$–$C_{10}$
cycloalkoxycarbonylalkyloxy, $C_7$–$C_{11}$
aryloxycarbonylalkyloxy, $C_8$–$C_{12}$
aryloxycarbonyloxyalkyloxy, $C_8$–$C_{12}$
arylcarbonyloxyalkyloxy, $C_5$–$C_{10}$
alkoxyalkylcarbonyloxyalkyloxy, $C_5$–$C_{10}$ (5-alkyl-1,3-dioxa-cyclopenten-2-one-yl)-methyloxy, $C_{10}$–$C_{14}$ (5-aryl-1,3-dioxa-cyclopenten-2-one-yl)-methyloxy, $(R^2)(R^3)N$—$(C_1$–$C_{10}$ alkoxy)—;

$R^4$ is selected from:
H, $C_1$–$C_{10}$ alkyl, $C_1$–$C_{10}$ alkylcarbonyl, aryl, arylalkyl, cycloalkyl, or cycloalkylalkyl;

alternately, two $R^4$ groups on adjacent carbon atoms can join to form a carbon-carbon double or triple bond between such adjacent carbon atoms;

$R^{4a}$ is selected from:
hydroxy, $C_1$–$C_{10}$ alkoxy, nitro, —$N(R^5)R^{5a}$, —$N(R^{12})R^{13}$, —$N(R^{16})R^{17}$, aryl substituted with 0–3 $R^6$, or $(C_1$–$C_{10}$ alkyl)carbonyl;

$R^{4b}$ is selected from:
H, $C_1$–$C_6$ alkyl, $C_2$–$C_6$ alkenyl, $C_2$–$C_6$ alkynyl, $C_3$–$C_7$ cycloalkyl, $C_7$–$C_{14}$ bicycloalkyl, hydroxy, $C_1$–$C_6$ alkoxy, $C_1$–$C_6$ alkylthio, $C_1$–$C_6$ alkylsulfinyl, $C_1$–$C_6$ alkylsulfonyl, nitro, $(C_1$–$C_6$ alkyl)carbonyl, $C_6$–$C_{10}$ aryl, —$N(R^{12})R^{13}$, halo, $CF_3$, CN, $(C_1$–$C_6$ alkoxy)carbonyl, carboxy, piperidinyl, morpholinyl, or pyridinyl;

$R^5$ is selected from:
H, $C_1$–$C_8$ alkyl, $C_3$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–6 $R^{4b}$;

$R^{5a}$ is selected from:
hydrogen, hydroxy, $C_1$–$C_8$ alkyl, $C_3$–$C_6$ alkenyl, $C_3$–$C_{11}$ cycloalkyl, $C_4$–$C_{11}$ cycloalkylmethyl, $C_1$–$C_6$ alkoxy, benzyloxy, $C_6$–$C_{10}$ aryl, heteroaryl, heteroarylalkyl, $C_7$–$C_{11}$ arylalkyl, adamantylmethyl, or $C_1$–$C_{10}$ alkyl substituted with 0–2 $R^{4b}$;

alternately, $R^5$ and $R^{5a}$ when both are substituents on the same nitrogen atom (as in —$NR^5R^{5a}$)
can be taken together with the nitrogen atom to which they are attached to form 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, or 1-piperazinyl, each being optionally substituted with $C_1$–$C_6$ alkyl, $C_6$–$C_{10}$ aryl, heteroaryl, $C_7$–$C_{11}$ arylalkyl, $(C_{1-C6}$ alkyl)carbonyl, $(C_3$–$C_7$ cycloalkyl)carbonyl, $(C_1$–$C_6$ alkoxy)carbonyl, $(C_7$–$C_{11}$ arylalkoxy)carbonyl, $C_1$–$C_6$ alkylsulfonyl or $C_6$–$C_{10}$ arylsulfonyl;

$R^{5b}$ is selected from:
$C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^{4b}$;

$R^6$ is selected from:
H, $C_1$–$C_{10}$ alkyl, hydroxy, $C_1$–$C_{10}$ alkoxy, nitro, $(C_1$–$C_{10}$ alkyl)carbonyl, —$N(R^{12})R^{13}$, cyano, halo, $CF_3$, CHO, $CO_2R^5$, $C(=O)R^{5a}$, $CONR^5R^{5a}$, $OC(=O)R^{5a}$, $OC(=O)OR^{5b}$, $OR^{5a}$, $OC(=O)NR^5R^{5a}$, $OCH_2CO_2R^5$, $CO_2CH_2CO_2R^5$, $NO_2$, $NR^{5a}C(=O)R^{5a}$, $NR^{5a}C(=O)OR^{5b}$, $NR^{5a}C(=O)NR^5R^{5a}$, $NR^{5a}SO_2NR^5R^{5a}$, $NR^{5a}SO_2R^5$, $SR^{5a}$, $SOR^{5a}$, $SO_2R^{5a}$, $SO_2NR^5R^{5a}$, $Si(CH_3)_3$, $C_2$–$C_6$ alkenyl, $C_3$–$C_{11}$ cycloalkyl, $C_4$–$C_{11}$ cycloalkylmethyl;

$C_6$–$C_{10}$ aryl optionally substituted with 1–3 groups selected from halogen, $C_1$–$C_6$ alkoxy, $C_1$–$C_6$ alkyl, $CF_3$, $S(O)_mCH_3$, or —$N(CH_3)_2$;

$C_7$–$C_{11}$ arylalkyl, the aryl being optionally substituted with 1–3 groups selected from halogen, $C_1$–$C_6$ alkoxy, $C_1$–$C_6$ alkyl, $CF_3$, $S(O)_mCH_3$, or —$N(CH_3)_2$;

methylenedioxy when $R^6$ is a substituent on aryl; or
a 5–10 membered heterocyclic ring containing 1–3 N, O, or S heteroatoms, wherein the heterocyclic ring can be saturated, partially saturated, or fully unsaturated, the heterocyclic ring being substituted with 0–2 $R^7$;

$R^7$ is selected from:
H, $C_1$–$C_{10}$ alkyl, hydroxy, $C_1$–$C_{10}$ alkoxy, nitro, $(C_1$–$C_{10}$ alkyl)carbonyl, —$N(R^{12})R^{13}$, cyano, halo, $CF_3$, CHO, $CO_2R^5$, $C(=O)R^{5a}$, $CONR^5R^{5a}$, $OC(=O)R^{5a}$, $OC(=O)OR^{5b}$, $OR^{5a}$, $OC(=O)NR^5R^{5a}$, $OCH_2CO_2R^5$, $CO_2CH_2CO_2R^5$, $NO_2$, $NR^{5a}C(=O)R^{5a}$, $NR^{5a}C(=O)OR^{5b}$, $NR^{5a}C(=O)NR^5R^{5a}$, $NR^{5a}SO_2NR^5R^{5a}$, $NR^{5a}SO_2R^5$, $S(O)_mR^{5a}$, $SO_2NR^5R^{5a}$, $C_2$–$C_6$ alkenyl, $C_3$–$C_{11}$ cycloalkyl, $C_4$–$C_{11}$ cycloalkylmethyl, $C_6$–$C_{10}$ aryl, or $C_7$–$C_{11}$ arylalkyl;

$R^8$ is selected from:
$R^6$; $C_1$–$C_{10}$ alkyl, substituted with 0–3 $R^6$; $C_2$–$C_{10}$ alkenyl, substituted with 0–3 $R^6$;
$C_2$–$C_{10}$ alkynyl, substituted with 0–3 $R^6$; $C_3$–$C_8$ cycloalkyl, substituted with 0–3 $R^6$;
$C_5$–$C_6$ cycloalkenyl, substituted with 0–3 $R^6$; aryl, substituted with 0–3 $R^6$; 5–10 membered heterocyclic ring containing 1–3 N, O, or S heteroatoms, wherein the heterocyclic ring can be saturated, partially saturated, or fully unsaturated, the heterocyclic ring being substituted with 0–2 $R^6$;

$R^{12}$ and $R^{13}$ are selected independently from:
H, $C_1$–$C_{10}$ alkyl, $(C_1$–$C_{10}$ alkoxy)carbonyl, $(C_1$–$C_{10}$ alkyl)carbonyl, $C_1$–$C_{10}$ alkylsulfonyl, aryl$(C_1$–$C_{10}$ alkyl)sulfonyl, arylsulfonyl, aryl$(C_2$–$C_{10}$ alkenyl)sulfonyl, heteroarylsulfonyl, aryl, $C_2$–$C_6$ alkenyl, $C_3$–$C_{11}$ cycloalkyl, $C_4$–$C_{11}$ cycloalkylalkyl, $C_7$–$C_{11}$ arylalkyl, $C_7$–$C_{11}$ arylcarbonyl, $C_4$–$C_{11}$ cycloalkoxycarbonyl, $C_7$–$C_{11}$ bicycloalkoxycarbonyl, $C_7$–$C_{11}$ aryloxycarbonyl, heteroarylcarbonyl, heteroarylsulfonyl, heteroarylalkylcarbonyl, or aryl$(C_1$–$C_{10}$ alkoxy)carbonyl, wherein the aryl groups are optionally substituted with 0–3 substituents selected from the group consisting of $C_1$–$C_4$ alkyl, $C_1$–$C_4$ alkoxy, halo, $CF_3$, and $NO_2$;

$R^{14}$ is selected from:
H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or $(C_1$–$C_{10}$ alkoxy)carbonyl, $CO_2R^5$, or —$C(=O)N(R^5)R^{5a}$;

$R^{15}$ is selected from:
H; $R^6$; —$CO_2R^5$; —$C(=O)N(R^5)R^{5a}$; $C_1$–$C_{10}$ alkoxycarbonyl substituted with 0–2 $R^6$;
$C_1$–$C_{10}$ alkyl, substituted with 0–3 $R^6$; $C_2$–$C_{10}$ alkenyl, substituted with 0–3 $R^6$;
$C_1$–$C_{10}$ alkoxy, substituted with 0–3 $R^6$; aryl, substituted with 0–3 $R^6$; or 5–10 membered heterocyclic ring containing 1–3 N, O, or S heteroatoms, wherein the heterocyclic ring can be saturated, partially saturated, or fully unsaturated, the heterocyclic ring being substituted with 0–2 $R^6$;

provided that when b is a double bond, only one of $R^{14}$ or $R^{15}$ is present;

$R^{16}$ is selected from:

—C(=O)—O—$R^{18a}$, —C(=O)—$R^{18b}$, —C(=O)N($R^{18b}$)$_2$, —C(=O)NHSO$_2$$R^{18a}$, —C(=O)NHC(=O)$R^{18b}$, —C(=O)NHC(=O)O$R^{18a}$, —C(=O)NHSO$_2$NHR$^{18b}$, —C(=S)—NH—$R^{18b}$, —NH—C(=O)—O—$R^{18a}$, —NH—C(=O)$R^{18b}$, —NH—C(=O)—NH—$R^{18b}$, —SO$_2$—O—$R^{18a}$, —SO$_2$—$R^{18a}$, —SO$_2$—N($R^{18b}$)$_2$, —SO$_2$—NHC(=O)OR$^{18b}$, —P(=S)(OR$^{18a}$)$_2$, —P(=O)(OR$^{18a}$)$_2$, —P(=S)($R^{18a}$)$_2$, —P(=O)($R^{18a}$)$_2$, or

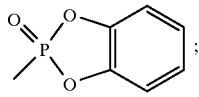

;

$R^{17}$ is selected from:

H, $C_1$–$C_{10}$ alkyl, $C_2$–$C_6$ alkenyl, $C_3$–$C_{11}$ cycloalkyl, $C_4$–$C_{15}$ cycloalkylalkyl, aryl, aryl($C_1$–$C_{10}$ alkyl)-;

$R^{18a}$ is selected from:

$C_1$–$C_8$ alkyl substituted with 0–2 $R^{19}$, $C_2$–$C_8$ alkenyl substituted with 0–2 $R^{19}$, $C_2$–$C_8$ alkynyl substituted with 0–2 $R^{19}$, $C_3$–$C_8$ cycloalkyl substituted with 0–2 $R^{19}$, aryl substituted with 0–4 $R^{19}$, aryl($C_1$–$C_6$ alkyl)- substituted with 0–4 $R^{19}$;

a 5–10 membered heterocyclic ring system having 1–3 heteroatoms selected independently from O, S, and N, the heterocyclic ring being substituted with 0–4 $R^{19}$;

$C_1$–$C_6$ alkyl substituted with a 5–10 membered heterocyclic ring system having 1–3 heteroatoms selected independently from O, S, and N, the heterocyclic ring being substituted with 0–4 $R^{19}$;

$R^{18b}$ is selected from: $R^{18a}$ or H;

$R^{19}$ is selected from:

H, halogen, $CF_3$, CN, $NO_2$, —$NR^{12}R^{13}$, $C_1$–$C_8$ alkyl, $C_2$–$C_6$ alkenyl, $C_2$–$C_6$ alkynyl, $C_3$–$C_{11}$ cycloalkyl, $C_4$–$C_{11}$ cycloalkylalkyl, aryl, aryl($C_1$–$C_6$ alkyl)-, $C_1$–$C_6$ alkoxy, heteroaryl, ($C_1$–$C_4$ alkyl)sulfonyl, aryl-sulfonyl, or $C_1$–$C_4$ alkoxycarbonyl;

m is 0–2;

n is 0–4;

n' is 0–4;

p" is 1–7;

p" is 1–7;

r is 0–3;

provided that:

n' is chosen such that the number of in-chain atoms connecting $R^1$ and Y is in the range of 8–18.

13. An iontophoresis device according to claim 12, wherein said compound is a cell adhesion inhibitor compound of Formula Ic:

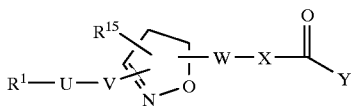

(Ic)

wherein:

$R^1$ is selected from:

$R^{2a}(R^3)N$—, $R^2(R^3)N(R^2N$=$)C$—, $R^{2a}(R^3)N(CH^2)_{p'}$Z—, $R^2(R^3)N(R^2N$=$)C(CH_2)_{p''}$Z—, $R^2(R^3)N(R^2N$=$)CN(R^2)$—, $R^2(R^3)NC(O)$—, $R^2(R^5O)N(R^2N$=$)C$—, $R^2(R^3)N(R^5ON$=$)C$—;

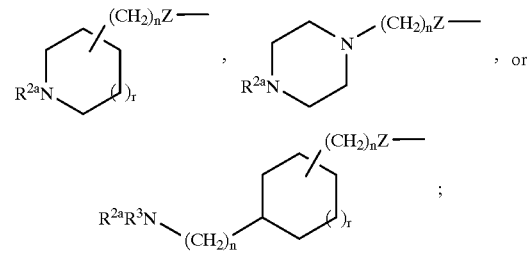

;

Z is selected from a bond, O, or S;

$R^2$ and $R^3$ are selected independently from:

H; $C_1$–$C_6$ alkyl; $C_7$–$C_{11}$ arylalkyl optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; ($C_1$–$C_{10}$ alkoxy)carbonyl;

aryl($C_1$–$C_{10}$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; or heteroaryl($C_1$–$C_5$)alkyl where the heteroaryl group is optionally substituted with 0–2 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl;

$R^{2a}$ is $R^2$ or $R^2(R^3)N(R^2N$=$)C$;

U is a single bond;

V is selected from:

a single bond; -($C_1$–$C_7$ alkyl)-, substituted with 0–3 groups selected independently from $R^6$ or $R^7$; -($C_2$–$C_7$ alkenyl)-, substituted with 0–3 groups selected independently from $R^6$ or $R^7$; -($C_2$–$C_7$ alkynyl)-, substituted with 0–3 groups selected independently from $R^6$ or $R^7$; -(phenyl)-Q—, the phenyl substituted with 0–2 groups selected independently from $R^6$ or $R^7$; -(pyridyl)-Q—, the pyridyl substituted with 0–2 groups selected independently from $R^6$ or $R^7$; or -(pyridazinyl)-Q—, the pyridazinyl substituted with 0–2 groups selected independently from $R^6$ or $R^7$;

Q is selected from:

a single bond, —O—, —$S(O)_m$—, —$N(R^{12})$—, —$(CH_2)_m$—, —C(=O)—, —$N(R^{5a})C(=O)$—, —C(=O)$N(R^{5a})$—, —$CH_2O_m$—, —$OCH_2$—, —$CH_2N(R^{12})$—, —$N(R^{12})CH_2$—, —$CH_2C(=O)$—, —C(=O)$CH_2$—, —$CH_2S(O)_m$—, —$S(O)_m CH_2$—;

provided that when $R^1$—U—V— is a substituent on $C^5$ of the central 5-membered ring of Formula Ic, then Q is not —O—, S(O)$_m$, —N(R$^{12}$)—, —C(=O)N(R$^{5a}$)—, —CH$_2$O$_m$—, —CH$_2$N(R$^{12}$)— or —CH$_2$S(O)$_m$—;

W is selected from:
—(C(R$^4$)$_2$)—C(=O)—N(R$^{5a}$)—, or —C(=O)—N(R$^{5a}$)—(C(R$^4$)$_2$)—;

X is:
—C(R$^4$)(R$^8$)—CHR$^{4a}$—;

R$^4$ is selected from:
H, C$_1$–C$_{10}$ alkyl, C$_1$–C$_{10}$ alkylcarbonyl, aryl, arylalkyl, cycloalkyl, or cycloalkylalkyl;

R$^{4a}$ is selected from:
hydroxy, C$_1$–C$_{10}$ alkoxy, nitro, —N(R$^5$)R$^{5a}$, —N(R$^{12}$)R$^{13}$, or —N(R$^{16}$)R$^{17}$, aryl substituted with 0–3 R$^6$, or (C$_1$–C$_{10}$ alkyl)carbonyl;

R$^{4b}$ is selected from:
H, C$_1$C$_6$ alkyl, C$_2$–C$_6$ alkenyl, C$_2$–C$_6$ alkynyl, hydroxy, C$_1$–C$_6$ alkoxy, C$_1$–C$_6$ alkylthio, C$_1$–C$_6$ alkylsulfinyl, C$_1$–C$_6$ alkylsulfonyl, nitro, (C$_1$–C$_6$ alkyl)carbonyl, C$_6$–C$_{10}$ aryl, —N(R$^{12}$)R$^{13}$, halo, CF$_3$, CN, (C$_1$–C$_6$ alkoxy)carbonyl, carboxy, piperidinyl, morpholinyl or pyridyl;

R$^5$ is selected from:
H or C$_1$–C$_{10}$ alkyl substituted with 0–6 R$^{4b}$;

R$^{5a}$ is selected from:
hydrogen, hydroxy, C$_1$–C$_8$ alkyl, C$_2$–C$_6$ alkenyl, C$_3$–C$_{11}$ cycloalkyl, C$_4$–C$_{11}$ cycloalkylmethyl, C$_1$–C$_6$ alkoxy, benzyloxy, C$_6$–C$_{10}$ aryl, heteroaryl, heteroarylalkyl, C$_7$–C$_{11}$ arylalkyl, or adamantylmethyl, C$_1$–C$_{10}$ alkyl substituted with 0–2 R$^{4b}$;

alternately, R$^5$ and R$^{5a}$ can be taken together to be:
3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl, each being optionally substituted with C$_1$–C$_6$ alkyl, C$_6$–C$_{10}$ aryl, heteroaryl, C$_7$–C$_{11}$ arylalkyl, (C$_1$–C$_6$ alkyl)carbonyl, (C$_3$–C$_7$ cycloalkyl)carbonyl, (C$_1$–C$_6$ alkoxy) carbonyl, or (C$_7$–C$_{11}$ arylalkoxy)carbonyl;

R$^{5b}$ is selected from:
C$_1$–C$_8$ alkyl, C$_2$–C$_6$ alkenyl, C$_3$–C$_{11}$ cycloalkyl, C$_4$–C$_{11}$ cycloalkylmethyl, C$_6$–C$_{10}$ aryl, C$_7$–C$_{11}$ arylalkyl, or C$_1$–C$_{10}$ alkyl substituted with 0–2 R$^{4b}$;

Y is selected from:
hydroxy, C$_1$–C$_{10}$ alkyloxy, C$_3$–C$_{11}$ cycloalkyloxy, C$_6$–C$_{10}$ aryloxy, C$_7$–C$_{11}$ aralkyloxy, C$_3$–C$_{10}$ alkylcarbonyloxyalkyloxy, C$_3$–C$_{10}$ alkoxycarbonyloxyalkyloxy, C$_2$–C$_{10}$ alkoxycarbonylalkyloxy, C$_5$–C$_{10}$ cycloalkylcarbonyloxyalkyloxy, C$_5$–C$_{10}$ cycloalkoxycarbonyloxyalkyloxy, C$_5$–C$_{10}$ cycloalkoxycarbonylalkyloxy, C$_7$–C$_{11}$ aryloxycarbonylalkyloxy, C$_8$–C$_{12}$ aryloxycarbonyloxyalkyloxy, C$_8$–C$_{12}$ arylcarbonyloxyalkyloxy, C$_5$–C$_{10}$ alkoxyalkylcarbonyloxyalkyloxy, C$_5$–C$_{10}$ (5-alkyl-1,3-dioxa-cyclopenten-2-one-yl)-methyloxy, or C$_{10}$–C$_{14}$ (5-aryl-1,3-dioxa-cyclopenten-2-one-yl)-methyloxy;

R$^6$ and R$^7$ are each selected independently from:
H, C$_1$–C$_{10}$ alkyl, hydroxy, C$_1$–C$_{10}$ alkoxy, nitro, (C$_1$–C$_{10}$ alkyl)carbonyl, —N(R$^{12}$)R$^{13}$, cyano, or halo;

R$^{12}$ and R$^{13}$ are each selected independently from:
H, C$_1$–C$_{10}$ alkyl, (C$_1$–C$_{10}$ alkoxy)carbonyl, C$_1$–C$_{10}$ alkyl)carbonyl, C$_1$–C$_{10}$ alkylsulfonyl, aryl(C$_1$–C$_{10}$ alkyl)sulfonyl, arylsulfonyl, heteroarylsulfonyl, heteroarylcarbonyl, heteroarylalkylcarbonyl or aryl, wherein the aryl groups being optionally substituted with 0–3 substituents selected from the group consisting of: C$_1$–C$_4$ alkyl, C$_1$–C$_4$ alkoxy, halo, CF$_3$, and NO$_2$;

R$^{15}$ is selected from:
H, C$_1$–C$_{10}$ alkyl, C$_2$–C$_{10}$ alkenyl, C$_2$–C$_{10}$ alkynyl, C$_1$–C$_{10}$ alkoxy, aryl, heteroaryl or (C$_1$–C$_{10}$ alkoxy) carbonyl, CO$_2$R$^5$ or —C(=O)N(R$^5$)R$^{5a}$;

R$^{16}$ is selected from:
—C(=O)—O—R$^{18a}$, —C(=O)—R$^{18b}$, —C(=O)N(R$^{18b}$)$_2$, —SO$_2$—R$^{18a}$, or —SO$_2$—N(R$^{18b}$)$_2$;

R$^{17}$ is selected from:
H or C$_1$–C$_5$ alkyl;

R$^{18a}$ is selected from:
C$_1$–C$_8$ alkyl substituted with 0–2 R$^{19}$, C$_2$–C$_8$ alkenyl substituted with 0–2 R$^{19}$, C$_2$–C$_8$ alkynyl substituted with 0–2 R$^{19}$, C$_3$–C$_8$ cycloalkyl substituted with 0–2 R$^{19}$, aryl substituted with 0–4 R$^{19}$, aryl(C$_1$–C$_6$ alkyl)- substituted with 0–4 R$^{19}$, a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, pyrrolidinyl, piperidinyl, indolinyl, or morpholinyl, the heterocyclic ring being substituted with 0–4 R$^{19}$;

C$_1$–C$_6$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, pyrrolidinyl, piperidinyl, indolinyl, or morpholinyl, the heterocyclic ring being substituted with 0–4 R$^{19}$;

R$^{18b}$ is selected from:
R$^{18a}$ or H;

R$^{19}$ is selected from:
H, halogen, CF$_3$, CN, NO$_2$, NR$^{12}$R$^{13}$, C$_1$–C$_8$ alkyl, C$_2$–C$_6$ alkenyl, C$_2$–C$_6$ alkynyl, C$_1$–C$_6$ alkoxy, C$_3$–C$_{11}$ cycloalkyl, C$_4$–C$_{11}$ cycloalkylalkyl, aryl, heteroaryl, aryl(C$_1$–C$_6$ alkyl)-, (C$_1$–C$_4$ alkyl) sulfonyl, aryl-sulfonyl, or C$_1$–C$_4$ alkoxycarbonyl;

n is 0–4;

p' is 1–7;

p'' is 1–7;

r is 0–3.

14. An iontophoresis device according to claim 12, comprising a compound of Formula Ib:

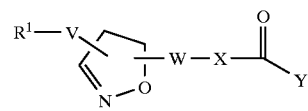

(Ib)

wherein:
R$^1$ is selected from:
R$^{2a}$(R$^3$)N—, R$^2$NH(R$^2$N=)C—, R$^2$NH(R$^2$N=)CNH—, R$^{2a}$R$^3$N(CH$_2$)$_{p'}$Z—, R$^2$NH(R$^2$N=)C(CH$_2$)$_{p''}$Z—, R$^2$(R$^3$)NC(O)—, R$^2$(R$^5$O)N(R$^2$N=)C—, R$^2$(R$^3$)N(R$^5$ON=)C—;

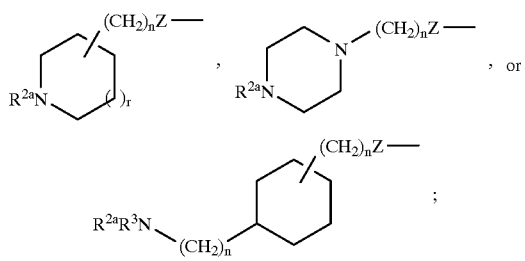

n is 0–1;
p' is 4–6;
p" is 2–4;
Z is selected from:
  a bond or O
V is selected from:
  a single bond, -(phenyl)-, or -(pyridyl)-;
W is selected from:
  —(C(R$^4$)$_2$)—C(=O)—N(R$^{5a}$)—, or —C(=O)—N(R$^{5a}$)—CH$_2$—;
X is selected from:
  —CH$_2$—CH(N(R$^{16}$)R$_{17}$)—, or —CH$_2$—CH(NR$^5$R$^{5a}$)—;
Y is selected from:
  hydroxy; C$_1$–C$_{10}$ alkoxy; methylcarbonyloxymethoxy; ethylcarbonyloxymethoxy;
  t-butylcarbonyloxymethoxy; cyclohexylcarbonyloxymethoxy;
  1-(methylcarbonyloxy)-ethoxy; 1-(ethylcarbonyloxy)-ethoxy;
  1-(t-butylcarbonyloxy)-ethoxy; 1-(cyclohexylcarbonyloxy)-ethoxy;
  i-propyloxycarbonyloxymethoxy; t-butyloxycarbonyloxymethoxy;
  1-(i-propyloxycarbonyloxy)-ethoxy; 1-(cyclohexyloxycarbonyloxy)-ethoxy;
  1-(t-butyloxycarbonyloxy)-ethoxy; dimethylaminoethoxy; diethylaminoethoxy;
  (5-methyl-1,3-dioxacyclopenten-2-on-4-yl)-methoxy;
  (5-(t-butyl)-1,3-dioxacyclopenten-2-on-4yl)-methoxy;
  (1,3-dioxa-5-phenyl-cyclopenten-2-on-4-yl)-methoxy;
  1-(2-(2-methoxypropyl)carbonyloxy)-ethoxy;
R$^{16}$ is selected from:
  —C(=O)—O—R$^{18a}$, —C(=O)—R$^{18b}$, —S(=O)$_2$—R$^{18a}$, or —SO$_2$—N(R$^{18b}$)$_2$;
R$^{17}$ is selected from: H or C$_1$–C$_5$ alkyl;
R$^{18a}$ is selected from:
  C$_1$–C$_8$ alkyl substituted with 0–2 R$^{19}$, C$_2$–C$_8$ alkenyl substituted with 0–2 R$^{19}$, C$_2$–C$_8$ alkynyl substituted with 0–2 R$^{19}$, C$_3$–C$_8$ cycloalkyl substituted with 0–2 R$^{19}$, aryl substituted with 0–4 R$^{19}$, aryl(C$_1$–C$_6$ alkyl)- substituted with 0–4 R$^{19}$, a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, pyrrolidinyl, or morpholinyl, the heterocyclic ring being substituted with 0–4 R$^{19}$;
  C$_1$–C$_6$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolinyl, quinolinyl, isoquinolinyl, benzimidazolyl, piperidinyl, tetrahydrofuranyl, pyranyl, 3H-indolyl, pyrrolidinyl, or morpholinyl, the heterocyclic ring being substituted with 0–4 R$^{19}$.

15. An iontophoresis device according to claim 14, comprising a compound wherein:
either:
  R$^1$ is R$^2$NH(R$^2$N=)C— or R$^2$HN(R$^2$N=)CNH— and V is phenylene or pyridylene,
or:
  R$^1$ is

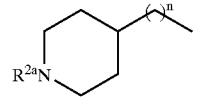

and V is a single bond, and n is 1 or 2;
R$^{18a}$ is selected from:
  C$_1$–C$_4$ alkyl substituted with 0–2 R$^{19}$, C$_2$–C$_4$ alkenyl substituted with 0–2 R$^{19}$ C$_2$–C$_4$ alkynyl substituted with 0–2 R$^{19}$, C$_3$–C$_7$ cycloalkyl substituted with 0–2 R$^{19}$, aryl substituted with 0–4 R$^{19}$, aryl(C$_1$–C$_4$ alkyl)- substituted with 0–4 R$^{19}$, a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, pyrrolidinyl, or morpholinyl, the heterocyclic ring being substituted with 0–4 R$^{19}$;
  C$_1$–C$_4$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolinyl, quinolinyl, isoquinolinyl, benzimidazolyl, piperidinyl, tetrahydrofuranyl, pyranyl, 3H-indolyl, pyrrolidinyl, piperidinyl, or morpholinyl, the heterocyclic ring being substituted with 0–4 R$^{19}$.

16. An iontophoresis device according to claim 12, comprising a compound, or a pharmaceutically acceptable salt form thereof, selected from:
N$^3$-[2-{3-(4-formamidinophenyl)-isoxazolin-5(R,S)-yl}-acetyl]-N$^2$-(phenylsulfonyl)-2,3(S)-diaminopropanoic acid;
N$^3$-[2-{3-(4-formamidinophenyl)-isoxazolin-5-(R,S)-yl}-acetyl]-N$^2$-(4-methyl-phenyl-sulfonyl)-2,3(S)-diaminopropanoic acid;
N$^3$-[2-{3-(4-formamidinophenyl)-isoxazolin-5(R,S)-yl}-acetyl]-N$^2$-(butanesulfonyl)-2,3(S)-diaminopropanoic acid;
N$^3$-[2-{3-(4-formamidinophenyl)-isoxazolin-5(R,S)-yl}-acetyl]-N$^2$-(propanesulfonyl)-2,3(S)-diaminopropanoic acid;
N$^3$-[2-{3-(4-formamidinophenyl)-isoxazolin-5(R,S)-yl}-acetyl]-N$^2$-(ethanesulfonyl)-2,3(S)-diaminopropanoic acid;
N$^3$-[2-{3-(4-formamidinophenyl)-isoxazolin-5(R,S)-yl}-acetyl]-N$^2$-(methyloxycarbonyl)-2,3(S)-diaminopropanoic acid;
N$^3$-[2-{3-(4-formamidinophenyl)-isoxazolin-5(R,S)-yl}-acetyl]-N$^2$-(ethyloxycarbonyl)-2,3(S) diaminopropanoic acid;

$N^3$-[2-{3-(4-formamidinophenyl)-isoxazolin-5(R,S)-yl}-acetyl]-$N^2$-(1-propyloxycarbonyl)-2,3(S)-diaminopropanoic acid;

$N^3$-[2-{3-(4-formamidinophenyl)-isoxazolin-5(R,S)-yl}-acetyl]-$N^2$-(2-propyloxycarbonyl)-2,3(S)-diaminopropanoic acid;

$N^3$-[2-{3-(4-formamidinophenyl)-isoxazolin-5(R,S)-yl}-acetyl]-$N^2$-(n-butyloxycarbonyl)-2,3(S)-diaminopropanoic acid;

$N^3$-[2-{3-(4-formamidinophenyl)-isoxazolin-5(R)-yl}-acetyl]-$N^2$-(n-butyloxycarbonyl)-2,3(S)-diaminopropanoic acid;

$N^3$-[2-{3-(4-formamidinophenyl)-isoxazolin-5(S)-yl}-acetyl]-$N^2$-(n-butyloxycarbonyl)-2,3(S)-diaminopropanoic acid;

$N^3$-[2-{3-(4-formamidinophenyl)-isoxazolin-5(R)-yl}-acetyl]-$N^2$-(n-butyloxycarbonyl)-2,3(R)-diaminopropanoic acid;

$N^3$-[2-{3-(4-formamidinophenyl)-isoxazolin-5(S)-yl}-acetyl]-$N^2$-(n-butyloxycarbonyl)-2,3(R)-diaminopropanoic acid;

$N^3$-[2-{3-(4-formamidinophenyl)-isoxazolin-5(R,S)-yl}-acetyl]-$N^2$-(2-butyloxycarbonyl)-2,3(S)-diaminopropanoic acid;

$N^3$-[2-{3-(4-formamidinophenyl)-isoxazolin-5(R,S)-yl}-acetyl]-$N^2$-(1-(2-methyl)-propyloxycarbonyl)-2,3(S)-diaminopropanoic acid;

$N^3$-[2-{3-(4-formamidinophenyl)-isoxazolin-5(R,S)-yl}-acetyl]-$N^2$-(2-(2-methyl)-propyloxycarbonyl)-2,3(S)-diaminopropanoic acid;

$N^3$-[2-{3-(4-formamidinophenyl)-isoxazolin-5(R,S)-yl}-acetyl]-$N^2$-(benzyloxycarbonyl)-2,3(S)-diaminopropanoic acid;

$N^3$-[2-{3-(4-formamidinophenyl)-isoxazolin-5(R)-yl}-acetyl]-$N^2$-(benzyloxycarbonyl)-2,3(S)-diaminopropanoic acid;

$N^3$-[2-{3-(4-formamidinophenyl)-isoxazolin-5(S)-yl}-acetyl]-$N^2$-(benzyloxycarbonyl)-2,3(S)-diaminopropanoic acid;

$N^3$-[2-{3-(4-formamidinophenyl)-isoxazolin-5(R,S)-yl}-acetyl]-$N^2$-(4-methylbenzyloxycarbonyl)-2,3(S)-diaminopropanoic acid;

$N^3$-[2-{3-(4-formamidinophenyl)-isoxazolin-5(R,S)-yl}-acetyl]-$N^2$-(4-methoxybenzyloxycarbonyl)-2,3(S)-diaminopropanoic acid;

$N^3$-[2-{3-(4-formamidinophenyl)-isoxazolin-5(R,S)-yl}-acetyl]-$N^2$-(4-chlorobenzyloxycarbonyl)-2,3(S)-diaminopropanoic acid;

$N^3$-[2-{3-(4-formamidinophenyl)-isoxazolin-5(R,S)-yl}-acetyl]-$N^2$-(4-bromobenzyloxycarbonyl)-2,3(S)-diaminopropanoic acid;

$N^3$-[2-{3-(4-formamidinophenyl)-isoxazolin-5(R,S)-yl}-acetyl]-$N^2$-(4-fluorobenzyloxycarbonyl)-2,3(S)-diaminopropanoic acid;

$N^3$-[2-{3-(4-formamidinophenyl)-isoxazolin-5(R,S)-yl}-acetyl]-$N^2$-(4-phenoxybenzyloxycarbonyl)-2,3(S)-diaminopropanoic acid;

$N^3$-[2-{3-(4-formamidinophenyl)-isoxazolin-5(R,S)-yl}-acetyl]-$N^2$-(2-(methyloxyethyl)-oxycarbonyl)-2,3(S)-diaminopropanoic acid;

$N^3$-[2-{3-(4-formamidinophenyl)-isoxazolin-5(R,S)-yl}-acetyl]-$N^2$-(2-pyridinylcarbonyl)-2,3(S)-diaminopropanoic acid;

$N^3$-[2-{3-(4-formamidinophenyl)-isoxazolin-5(R,S)-yl}-acetyl]-$N^2$-(3-pyridinylcarbonyl)-2,3(S)-diaminopropanoic acid;

$N^3$-[2-{3-(4-formamidinophenyl)-isoxazolin-5(R,S)-yl}-acetyl]-$N^2$-(4-pyridinyl-carbonyl)-2,3(S)-diaminopropanoic acid;

$N^3$-[2-{3-(4-formamidinophenyl)-isoxazolin-5(R,S)-yl}-acetyl]-$N^2$-(2-(2-pyridinyl)-acetyl)-2,3(S)-diaminopropanoic acid;

$N^3$-[2-{3-(4-formamidinophenyl)-isoxazolin-5(R,S)-yl}-acetyl]-$N^2$-(2-(3-pyridinyl)-acetyl)-2,3(S)-diaminopropanoic acid;

$N^3$-[2-{3-(4-formamidinophenyl)-isoxazolin-5(R,S)-yl}-acetyl]-$N^2$-(2-(4-pyridinyl)-acetyl)-2,3(S)-diaminopropanoic acid;

$N^3$-[2-{3-(4-formamidinophenyl)-isoxazolin-5(R,S)-yl}-acetyl]-$N^2$-(2-pyridyl-methyloxycarbonyl)-2,3(S)-diaminopropanoic acid;

$N^3$-[2-{3-(4-formamidinophenyl)-isoxazolin-5(R,S)-yl}-acetyl]-$N^2$-(3-pyridyl-methyloxycarbonyl)-2,3(S)-diaminopropanoic acid;

$N^3$-[2-{3-(4-formamidinophenyl)-isoxazolin-5(R,S)-yl}-acetyl]-$N^2$-(4-pyridyl-methyloxycarbonyl)-2,3(S)-diaminopropanoic acid;

$N^3$-[2-{3-(4-formamidinophenyl)-isoxazolin-5(R,S)-yl}-acetyl]-$N^2$-(4-butyloxyphenylsulfonyl)-2,3(S)-diaminopropanoic acid;

$N^3$-[2-{3-(4-formamidinophenyl)-isoxazolin-5(R,S)-yl}-acetyl]-$N^2$-(2-thienylsulfonyl)-2,3(S)-diaminopropanoic acid;

$N^3$-[2-{3-(4-formamidinophenyl)-isoxazolin-5(R,S)-yl}-acetyl]-$N^2$-(3-methylphenylsulfonyl)-2,3(R,S)-diaminopropanoic acid, $N^3$-[2-{3-(4-formamidinophenyl)-isoxazolin-5(R,S)-yl}-acetyl]-$N^2$-(3-methylphenylsulfonyl)-2,3(S)-diaminopropanoic acid;

$N^3$-[2-{3-(4-formamidinophenyl)-isoxazolin-5(R,S)-yl}-acetyl]-$N^2$-(3-methylphenylsulfonyl)-2,3(R)-diaminopropanoic acid;

$N^3$-[2-{3-(4-formamidinophenyl)-isoxazolin-5(R)-yl}-acetyl]-$N^2$-(3-methylphenylsulfonyl)-2,3(S)-diaminopropanoic acid;

$N^3$-[2-{3-(4-formamidinophenyl)-isoxazolin-5(S)-yl}-acetyl]-$N^2$-(3-methylphenylsulfonyl)-2,3(S)-diaminopropanoic acid;

$N^3$-[2-{3-(4-formamidinophenyl)-isoxazolin-5(S)-yl}-acetyl]-$N^2$-(3-methylphenylsulfonyl)-2,3(R)-diaminopropanoic acid;

$N^3$-[2-{3-(4-formamidinophenyl)-isoxazolin-5(R)-yl}-acetyl]-$N^2$-(3-methylphenylsulfonyl)-2,3(R)-diaminopropanoic acid;

$N^3$-[2-{3-(4-formamidinophenyl)-isoxazolin-5(R,S)-yl}-acetyl]-$N^2$-(4-iodophenylsulfonyl)-2,3(S)-diaminopropanoic acid;

$N^3$-[2-{3-(4-formamidinophenyl)-isoxazolin-5(R,S)-yl}-acetyl]-$N^2$-(3-trifluoromethylphenylsulfonyl)-2,3(S)-diaminopropanoic acid;

$N^3$-[2-{3-(4-formamidinophenyl)-isoxazolin-5(R,S)-yl}-acetyl]-$N^2$-(3-chlorophenylsulfonyl)-2,3(S)-diaminopropanoic acid;

$N^3$-[2-{3-(4-formamidinophenyl)-isoxazolin-5(R,S)-yl}-acetyl]-$N^2$-(3-2-methoxycarbonylphenylsulfonyl)-2,3(S)-diaminopropanoic acid;

$N^3$-[2-{3-(4-formamidinophenyl)-isoxazolin-5(R,S)-yl}-acetyl]-$N^2$-(2,4,6-trimethylphenylsulfonyl)-2,3(S)-diaminopropanoic acid;

$N^3$-[2-{3-(4-formamidinophenyl)-isoxazolin-5(R,S)-yl}-acetyl]-$N^2$-(2-chlorophenylsulfonyl)-2,3(S)-diaminopropanoic acid;

$N^3$-[2-{3-(4-formamidinophenyl)-isoxazolin-5(R,S)-yl}-acetyl]-$N^2$-(4-trifluoromethylphenylsulfonyl)-2,3(S)-diaminopropanoic acid;

$N^3$-[2-{3-(4-formamidinophenyl)-isoxazolin-5(R,S)-yl}-acetyl]-$N^2$-(2-trifluoromethylphenylsulfonyl)-2,3(S)-diaminopropanoic acid;

N³-[2-{3-(4-formamidinophenyl)-isoxazolin-5(R,S)-yl}-acetyl]-N²-(2-fluorophenylsulfonyl)-2,3(S)-diaminopropanoic acid;

N³-[2-{3-(4-formamidinophenyl)-isoxazolin-5(R,S)-yl}-acetyl]-N²-(4-fluorophenylsulfonyl)-2,3(S)-diaminopropanoic acid;

N³-[2-{3-(4-formamidinophenyl)-isoxazolin-5(R,S)-yl}-acetyl]-N²-(4-methoxyphenylsulfonyl)-2,3(S)-diaminopropanoic acid;

N³-[2-{3-(4-formamidinophenyl)-isoxazolin-5(R,S)-yl}-acetyl]-N²-(2,3,5,6-tetramethylphenylsulfonyl)-2,3(S)-diaminopropanoic acid;

N³-[2-{3-(4-formamidinophenyl)-isoxazolin-5(R,S)-yl}-acetyl]-N²-(4-cyanophenylsulfonyl)-2,3(S)-diaminopropanoic acid;

N³-[2-{3-(4-formamidinophenyl)-isoxazolin-5(R,S)-yl}-acetyl]-N²-(4-chlorophenylsulfonyl)-2,3(S)-diaminopropanoic acid;

N³-[2-{3-(4-formamidinophenyl)-isoxazolin-5(R,S)-yl}-acetyl]-N²-(4-propylphenylsulfonyl)-2,3(S)-diaminopropanoic acid;

N³-[2-{3-(4-formamidinophenyl)-isoxazolin-5(R,S)-yl}-acetyl]-N²-(2-phenylethylsulfonyl)-2,3(S)-diaminopropanoic acid;

N³-[2-{3-(4-formamidinophenyl)-isoxazolin-5(R,S)-yl}-acetyl]-N²-(4-isopropylphenylsulfonyl)-2,3(S)-diaminopropanoic acid;

N³-[2-{3-(4-formamidinophenyl)-isoxazolin-5(R,S)-yl}-acetyl]-N²-(3-phenylpropylsulfonyl)-2,3(S)-diaminopropanoic acid;

N³-[2-{3-(4-formamidinophenyl)-isoxazolin-5(R,S)-yl}-acetyl]-N²-(3-pyridylsulfonyl)-2,3(S)-diaminopropanoic acid;

N³-[2-(3-(4-formamidinophenyl)-isoxazolin-5(R,S)-yl)-acetyl]-N²-(phenylaminosulfonyl)-2,3(S)-diaminopropanoic acid;

N³-[2-{3-(4-formamidinophenyl)-isoxazolin-5(R,S)-yl}-acetyl]-N²-(benzylaminosulfonyl)-2,3(S)-diaminopropanoic acid;

N³-[2-{3-(4-formamidinophenyl)-isoxazolin-5(R,S)-yl}-acetyl]-N²-(dimethylaminosulfonyl)-2,3(S)-diaminopropanoic acid;

N³-[2-{3-(2-fluoro-4-formamidinophenyl)-isoxazolin-5(R,S)-yl}-acetyl]-N²-(3-methylphenylsulfonyl)-2,3(S)-diaminopropanoic acid;

N³-[2-{3-(2-formamidino-5-pyridinyl)-isoxazolin-5(R,S)-yl}-acetyl]-N²-(n-butyloxycarbonyl)-2,3(S)-diaminopropanoic acid;

N³-[2-{3-(2-formamidino-5-pyridinyl)-isoxazolin-5(R,S)-yl}-acetyl]-N²-(3-methylphenylsulfonyl)-2,3(S)-diaminopropanoic acid;

N³-[2-{3-(3-formamidino-6-pyridinyl)-isoxazolin-5(R,S)-yl}-acetyl]-N²-(n-butyloxycarbonyl)-2,3(S)-diaminopropanoic acid;

N³-[2-{3-(3-formamidino-6-pyridinyl)-isoxazolin-5(R,S)-yl}-acetyl]-N²-(3-methylphenylsulfonyl)-2,3(S)-diaminopropanoic acid;

N³-[2-{3-(4-formamidinophenyl)-isoxazolin-5(R,S)-yl}-acetyl]-N²-(phenylaminocarbonyl)-2,3(S)-diaminopropanoic acid;

N³-[2-{3-(4-formamidinophenyl)-isoxazolin-5(R,S)-yl}-acetyl]-N²-(4-fluorophenylaminocarbonyl)-2,3(S)-diaminopropanoic acid;

N³-[2-(3-(4-formamidinophenyl)-isoxazolin-5(R,S)-yl)-acetyl]-N²-(1-naphthylaminocarbonyl)-2,3(S)-diaminopropanoic acid;

N³-[2-{3-(4-formamidinophenyl)-isoxazolin-5(R,S)-yl}-acetyl]-N²-(benzylaminocarbonyl)-2,3(S)-diaminopropanoic acid;

N³-[2-{3-(4-formamidinophenyl)-isoxazolin-5(R,S)-yl}-acetyl]-N²-(3-bromo-2-thienylsulfonyl)-2,3(S)-diaminopropanoic acid;

N³-[2-{3-(4-formamidinophenyl)-isoxazolin-5(R,S)-yl}-acetyl]-N²-(3-methyl-2-benzothienylsulfonyl)-2,3(S)-diaminopropanoic acid;

N³-[2-{3-(4-formamidinophenyl)-isoxazolin-5(R,S)-yl}-acetyl]-N²-(isobutyloxycarbonyl)-2,3(S)-diaminopropanoic acid;

N³-[2-{3-(4-formamidinophenyl)-isoxazolin-5(R)-yl}-acetyl]-N²-(isobutyloxycarbonyl)-2,3(S)-diaminopropanoic acid;

N³-[2-{3-(4-formamidinophenyl)-isoxazolin-5(S)-yl}-acetyl]-N²-(isobutyloxycarbonyl)-2,3(S)-diaminopropanoic acid;

N³-[2-{3-(4-formamidinophenyl)-isoxazolin-5(R,S)-yl}-acetyl]-N²-(2-cyclopropylethoxycarbonyl)-2,3(S)-diaminopropanoic acid;

N³-[2-{3-(4-formamidinophenyl)-isoxazolin-5(R)-yl}-acetyl]-N²-(2-cyclopropylethoxycarbonyl)-2,3(S)-diaminopropanoic acid;

N³-[2-{3-(4-formamidinophenyl)-isoxazolin-5(S)-yl}-acetyl]-N²-(2-cyclopropylethoxycarbonyl)-2,3(S)-diaminopropanoic acid;

N³-[2-{3-(4-guanidinophenyl)-isoxazolin-5(R,S)-yl}-acetyl]-N²-(n-butyloxycarbonyl)-2,3(S)-diaminopropanoic acid;

N³-[2-{3-(4-guanidinophenyl)-isoxazolin-5(R)-yl}-acetyl]-N²-(n-butyloxycarbonyl)-2,3(S)-diaminopropanoic acid;

N³-[2-{3-(4-guanidinophenyl)-isoxazolin-5(R)-yl}-acetyl]-N²-(3-methylphenylsulfonyl)-2,3(S)-diaminopropanoic acid;

N³-[2-{5-(4-formamidinophenyl)-isoxazolin-3(R,S)-yl}-acetyl]-N²-(n-butyloxycarbonyl)-2,3(S)-diaminopropanoic acid;

or a propanoate ester prodrug form of the compound, wherein the hydrogen of the hydroxy group of the diaminopropanoic acid moiety is substituted with a group selected from:

methyl; ethyl; isopropyl; methylcarbonyloxymethyl; ethylcarbonyloxymethyl; t-butylcarbonyloxymethyl; cyclohexylcarbonyloxymethyl; 1-(methylcarbonyloxy)-ethyl; 1-(ethylcarbonyloxy)-ethyl; 1-(1-butylcarbonyloxy)-ethyl; 1-(cyclohexylcarbonyloxy)-ethyl; i-propyloxycarbonyloxymethyl; cyclohexylcarbonyloxymethyl; t-butyloxycarbonyloxymethyl; 1-(i-propyloxycarbonyloxy)-ethyl; 1-(cyclohexyloxycarbonyloxy)-ethyl; 1-(t-butyloxycarbonyloxy)-ethyl; dimethylaminoethyl; diethylaminoethyl; (5-methyl-1,3-dioxacyclopenten-2-on-4-yl)-methyl; (5-(t-butyl)-1,3-dioxacyclopenten-2-on 4-yl)-methyl; (1,3-dioxa-5-phenyl-cyclopenten-2-on-4-yl)-methyl; 1-(2-(2-methoxypropyl)carbonyloxy)-ethyl.

17. An iontophoresis device according to claim 12, comprising a compound, or enantiomeric or diastereomeric forms thereof, or mixtures of enantiomeric or diastereomeric forms thereof, or a pharmaceutically acceptable salt form thereof, selected from:

N³-[2-{3-(4-formamidinophenyl)-isoxazolin-5-yl}-acetyl]-N²-(phenylsulfonyl)-2,3-diaminopropanoic acid;

N³-[2-{3-(4-formamidinophenyl)-isoxazolin-5-yl}-acetyl]-N²-(4-methyl-phenyl-sulfonyl)-2,3-diaminopropanoic acid;

N³-[2-{3-(4-formamidinophenyl)-isoxazolin-5-yl}-acetyl]-N²-(butanesulfonyl)-2,3-diaminopropanoic acid;

$N^3$-[2-{3-(4-formamidinophenyl)-isoxazolin-5-yl}-acetyl]-$N^2$-(propanesulfonyl)-2,3-diaminopropanoic acid;
$N^3$-[2-{3-(4-formamidinophenyl)-isoxazolin-5-yl}-acetyl]-$N^2$-(ethanesulfonyl)-2,3-diaminopropanoic acid;
$N^3$-[2-{3-(4-formamidinophenyl)-isoxazolin-5-yl}-acetyl]-$N^2$-(methyloxycarbonyl)-2,3-diaminopropanoic acid;
$N^3$-[2-{3-(4-formamidinophenyl)-isoxazolin-5-yl}-acetyl]-$N^2$-(ethyloxycarbonyl)-2,3-diaminopropanoic acid;
$N^3$-[2-{3-(4-formamidinophenyl)-isoxazolin-5-yl}-acetyl]-$N^2$-(1-propyloxycarbonyl)-2,3-diaminopropanoic acid;
$N^3$-[2-{3-(4-formamidinophenyl)-isoxazolin-5-yl}-acetyl]-$N^2$-(2-propyloxycarbonyl)-2,3-diaminopropanoic acid;
$N^3$-[2-{3-(4-formamidinophenyl)-isoxazolin-5-yl}-acetyl]-$N^2$-(n-butyloxycarbonyl)-2,3-diaminopropanoic acid;
$N^3$-[2-{3-(4-formamidinophenyl)-isoxazolin-5-yl}-acetyl]-$N^2$-(1-(2-methyl)-propyloxycarbonyl)-2,3-diaminopropanoic acid;
$N^3$-[2-{3-(4-formamidinophenyl)-isoxazolin-5-yl}-acetyl]-$N^2$-(2-(2-methyl)-propyloxycarbonyl)-2,3-diaminopropanoic acid;
$N^3$-[2-{3-(4-formamidinophenyl)-isoxazolin-5-yl}-acetyl]-$N^2$-(benzyloxycarbonyl)-2,3-diaminopropanoic acid;
$N^3$-[2-{3-(4-formamidinophenyl)-isoxazolin-5-yl}-acetyl]-$N^2$-(4-methylbenzyloxycarbonyl)-2,3-diaminopropanoic acid;
$N^3$-[2-{3-(4-formamidinophenyl)-isoxazolin-5-yl}-acetyl]-$N^2$-(4-methoxybenzyloxycarbonyl)-2,3-diaminopropanoic acid;
$N^3$-[2-{3-(4-formamidinophenyl)-isoxazolin-5-yl}-acetyl]-$N^2$-(4-chlorobenzyloxycarbonyl)-2,3-diaminopropanoic acid;
$N^3$-[2-{3-(4-formamidinophenyl)-isoxazolin-5-yl}-acetyl]-$N^2$-(4-bromobenzyloxycarbonyl)-2,3-diaminopropanoic acid;
$N^3$-[2-{3-(4-formamidinophenyl)-isoxazolin-5-yl}-acetyl]-$N^2$-(4-fluorobenzyloxycarbonyl)-2,3-diaminopropanoic acid;
$N^3$-[2-{3-(4-formamidinophenyl)-isoxazolin-5-yl}-acetyl]-$N^2$-(4-phenoxybenzyloxycarbonyl)-2,3-diaminopropanoic acid;
$N^3$-[2-{3-(4-formamidinophenyl)-isoxazolin-5-yl}-acetyl]-$N^2$-(2-(methyloxyethyl)-oxycarbonyl)-2,3-diaminopropanoic acid;
$N^3$-[2-{3-(4-formamidinophenyl)-isoxazolin-5-yl}-acetyl]-$N^2$-(2-pyridinylcarbonyl)-2,3-diaminopropanoic acid;
$N^3$-[2-{3-(4-formamidinophenyl)-isoxazolin-5-yl}-acetyl]-$N^2$-(3-pyridinylcarbonyl)-2,3-diaminopropanoic acid;
$N^3$-[2-{3-(4-formamidinophenyl)-isoxazolin-5-yl}-acetyl]-$N^2$-(4-pyridinyl-carbonyl)-2,3-diaminopropanoic acid;
$N^3$-[2-{3-(4-formamidinophenyl)-isoxazolin-5-yl}-acetyl]-$N^2$-(2-(2-pyridinyl)-acetyl)-2,3-diaminopropanoic acid;
$N^3$-[2-{3-(4-formamidinophenyl)-isoxazolin-5-yl}-acetyl]-$N^2$-(2-(3-pyridinyl)-acetyl)-2,3-diaminopropanoic acid;
$N^3$-[2-{3-(4-formamidinophenyl)-isoxazolin-5-yl}-acetyl]-$N^2$-(2-(4-pyridinyl)-acetyl)-2,3-diaminopropanoic acid;
$N^3$-[2-{3-(4-formamidinophenyl)-isoxazolin-5-yl}-acetyl]-$N^2$-(2-pyridyl-methyloxycarbonyl)-2,3-diaminopropanoic acid:
$N^3$-[2-{3-(4-formamidinophenyl)-isoxazolin-5-yl}-acetyl]-$N^2$-(3-pyridyl-methyloxycarbonyl)-2,3-diaminopropanoic acid;
$N^3$-[2-{3-(4-formamidinophenyl)-isoxazolin-5-yl}-acetyl]-$N^2$-(4-pyridyl-methyloxycarbonyl)-2,3-diaminopropanoic acid;
$N^3$-[2-{3-(4-formamidinophenyl)-isoxazolin-5-yl}-acetyl]-$N^2$-(4-butyloxyphenylsulfonyl)-2,3-diaminopropanoic acid;
$N^3$-[2-{3-(4-formamidinophenyl)-isoxazolin-5-yl}-acetyl]-$N^2$-(2-thienylsulfonyl)-2,3-diaminopropanoic acid;
$N^3$-[2-{3-(4-formamidinophenyl)-isoxazolin-5-yl}-acetyl]-$N^2$-(3-methylphenylsulfonyl)-2,3-diaminopropanoic acid;
$N^3$-[2-{3-(4-formamidinophenyl)-isoxazolin-5-yl}-acetyl]-$N^2$-(4-iodophenylsulfonyl)-2,3-diaminopropanoic acid;
$N^3$-[2-{3-(4-formamidinophenyl)-isoxazolin-5-yl}-acetyl]-$N^2$-(3-trifluoromethylphenylsulfonyl)-2,3-diaminopropanoic acid;
$N^3$-[2-{3-(4-formamidinophenyl)-isoxazolin-5-yl}-acetyl]-$N^2$-(3-chlorophenylsulfonyl)-2,3-diaminopropanoic acid;
$N^3$-[2-{3-(4-formamidinophenyl)-isoxazolin-5-yl}-acetyl]-$N^2$-(2-methoxycarbonylphenylsulfonyl)-2,3-diaminopropanoic acid;
$N^3$-[2-{3-(4-formamidinophenyl)-isoxazolin-5-yl}-acetyl]-$N^2$-(2,4,6-trimethylphenylsulfonyl)-2,3-diaminopropanoic acid;
$N^3$-[2-{3-(4-formamidinophenyl)-isoxazolin-5-yl}-acetyl]-$N^2$-(2-chlorophenylsulfonyl)-2,3-diaminopropanoic acid;
$N^3$-[2-{3-(4-formamidinophenyl)-isoxazolin-5-yl}-acetyl]-$N^2$-(4-trifluoromethylphenylsulfonyl)-2,3-diaminopropanoic acid;
$N^3$-[2-{3-(4-formamidinophenyl)-isoxazolin-5-yl}-acetyl]-$N^2$-(2-trifluoromethylphenylsulfonyl)-2,3-diaminopropanoic acid;
$N^3$-[2-{3-(4-formamidinophenyl)-isoxazolin-5-yl}-acetyl]-$N^2$-(2-fluorophenylsulfonyl)-2,3-diaminopropanoic acid;
$N^3$-[2-{3-(4-formamidinophenyl)-isoxazolin-5-yl}-acetyl]-$N^2$-(4-fluorophenylsulfonyl)-2,3-diaminopropanoic acid;
$N^3$-[2-{3-(4-formamidinophenyl)-isoxazolin-5-yl}-acetyl]-$N^2$-(4-methoxyphenylsulfonyl)-2,3-diaminopropanoic acid;
$N^3$-[2-{3-(4-formamidinophenyl)-isoxazolin-5-yl}-acetyl]-$N^2$-(2,3,5,6-tetramethylphenylsulfonyl)-2,3-diaminopropanoic acid;
$N^3$-[2-{3-(4-formamidinophenyl)-isoxazolin-5-yl}-acetyl]-$N^2$-(4-cyanophenylsulfonyl)-2,3-diaminopropanoic acid;
$N^3$-[2-{3-(4-formamidinophenyl)-isoxazolin-5-yl}-acetyl]-$N^2$-(4-chlorophenylsulfonyl)-2,3-diaminopropanoic acid;
$N^3$-[2-{3-(4-formamidinophenyl)-isoxazolin-5-yl}-acetyl]-$N^2$-(4-propylphenylsulfonyl)-2,3-diaminopropanoic acid;
$N^3$-[2-{3-(4-formamidinophenyl)-isoxazolin-5-yl}-acetyl]-$N^2$-(2-phenylethylsulfonyl)-2,3-diaminopropanoic acid;
$N^3$-[2-{3-(4-formamidinophenyl)-isoxazolin-5-yl}-acetyl]-$N^2$-(4-isopropylphenylsulfonyl)-2,3-diaminopropanoic acid;
$N^3$-[2-{3-(4-formamidinophenyl)-isoxazolin-5-yl}-acetyl]-$N^2$-(3-phenylpropylsulfonyl)-2,3-diaminopropanoic acid;
$N^3$-[2-{3-(4-formamidinophenyl)-isoxazolin-5-yl}-acetyl]-$N^2$-(3-pyridylsulfonyl)-2,3-diaminopropanoic acid;
$N^3$-[2-{3-(4-formamidinophenyl)-isoxazolin-5-yl}-acetyl]-$N^2$-(phenylaminosulfonyl)-2,3-diaminopropanoic acid;
$N^3$-[2-{3-(4-formamidinophenyl)-isoxazolin-5-yl}-acetyl]-$N^2$-(benzylaminosulfonyl)-2,3-diaminopropanoic acid;
$N^3$-[2-{3-(4-formamidinophenyl)-isoxazolin-5-yl}-acetyl]-$N^2$-(dimethylaminosulfonyl)-2,3-diaminopropanoic acid;
$N^3$-[2-{3-(2-fluoro-4-formamidinophenyl)-isoxazolin-5-yl}-acetyl]-$N^2$-(3-methylphenylsulfonyl)-2,3-diaminopropanoic acid;
$N^3$-[2-{3-(2-formamidino-5-pyridinyl)-isoxazolin-5-yl}-acetyl]-$N^2$-(n-butyloxycarbonyl)-2,3-diaminopropanoic acid;
$N^3$-[2-{3-(2-formamidino-5-pyridinyl)-isoxazolin-5-yl}-acetyl]-$N^2$-(3-methylphenylsulfonyl)-2,3-diaminopropanoic acid;
$N^3$-[2-{3-(3-formamidino-6-pyridinyl)-isoxazolin-5-yl}-acetyl]-$N^2$-(n-butyloxycarbonyl)-2,3-diaminopropanoic acid, $N^3$-[2-{3-(3-formamidino-6-pyridinyl)-isoxazolin-5-yl}-acetyl]-$N^2$-(3-methylphenylsulfonyl)-2,3-diaminopropanoic acid, $N^3$-[2-{3-(4-formamidinophenyl)-isoxazolin-5-yl}-acetyl]-$N^2$-(phenylaminocarbonyl)-2,3-diaminopropanoic acid;

$N^3$-[2-{3-(4-formamidinophenyl)-isoxazolin-5-yl}-acetyl]-$N^2$-(4-fluorophenylaminocarbonyl)-2,3-diaminopropanoic acid;

$N^3$-[2-{3-(4-formamidinophenyl)-isoxazolin-5-yl}-acetyl]-$N^2$-(1-naphthylaminocarbonyl)-2,3-diaminopropanoic acid;

$N^3$-[2-{3-(4-formamidinophenyl)-isoxazolin-5-yl}-acetyl]-$N^2$-(benzylaminocarbonyl)-2,3-diaminopropanoic acid;

$N^3$-[2-{3-(4-formamidinophenyl)-isoxazolin-5-yl}-acetyl]-$N^2$-(3-bromo-2-thienylsulfonyl)-2,3-diaminopropanoic acid;

$N^3$-[2-{3-(4-formamidinophenyl)-isoxazolin-5-yl}-acetyl]-$N^2$-(3-methyl-2-benzothienylsulfonyl)-2,3-diaminopropanoic acid, $N^3$-[2-{3-(4-formamidinophenyl)-isoxazolin-5-yl}-acetyl]-$N^2$-(isobutyloxycarbonyl)-2,3-diaminopropanoic acid, $N^3$-[2-{3-(4-formamidinophenyl)-isoxazolin-5-yl}-acetyl]-$N^2$-(isobutyloxycarbonyl)-2,3-diaminopropanoic acid, $N^3$-[2-{3-(4-formamidinophenyl)-isoxazolin-5-yl}-acetyl]-$N^2$-(isobutyloxycarbonyl)-2,3-diaminopropanoic acid, $N^3$-[2-{3-(4-formamidinophenyl)-isoxazolin-5-yl}-acetyl]-$N^2$-($^2$-cyclopropylethoxycarbonyl)-2,3-diaminopropanoic acid, $N^3$-[2-{3-(4-guanidinophenyl)-isoxazolin-5-yl}-acetyl]-$N^2$-(n-butyloxycarbonyl)-2,3-diaminopropanoic acid;

$N^3$-[2-{3-(4-guanidinophenyl)-isoxazolin-5-yl}-acetyl]-$N^2$-(3-methylphenylsulfonyl)-2,3-diaminopropanoic acid;

$N^3$-[2-{5-(4-formamidinophenyl)-isoxazolin-3-yl}-acetyl]-$N^2$-(n-butyloxycarbonyl)-2,3-diaminopropanoic acid;

$N^3$-[2-{3-(4-formamidinophenyl)-isoxazolin-5-yl}-acetyl]-$N^2$-(2-bromo-phenylsulfonyl)-2,3-diaminopropionic acid;

$N^3$-[2-{3-(4-formamidinophenyl)-isoxazolin-5-yl}-acetyl]-$N^2$-(2-methyl-phenylsulfonyl)-2,3-diaminopropionic acid;

$N^3$-[2-{3-(3-formamidino-6-pyridinyl)-isoxazolin-5-yl}-acetyl]-$N^2$-(3-methylphenylsulfonyl)-2,3-diaminopropionic acid;

$N^3$-[2-{3-(2-formamidino-5-pyridinyl)-isoxazolin-5-yl}-acetyl]-$N^2$-(3-methylphenylsulfonyl)-2,3-diaminopropionic acid;

$N^3$-[2-{3-(2-fluoro-4-formamidinophenyl)-isoxazolin-5-yl}-acetyl]-$N^2$-(3-methylphenylsulfonyl)-2,3-diaminopropionic acid;

$N^3$-[2-{3-(4-formamidinophenyl)-isoxazolin-5-yl-acetyl]-$N^2$-(3-bromo-phenylsulfonyl)-2,3-diaminopropionic acid; and $N^3$-[2-{3-(4-formamidinophenyl)-isoxazolin-5-yl}-acetyl]-$N^2$-(4-bromo-phenylsulfonyl)-2,3-diaminopropionic acid;

or a propanoate ester prodrug form of the compound, wherein the hydrogen of the hydroxy group of the propanoic acid moiety is substituted with a group selected from:

methyl; ethyl; isopropyl; methylcarbonyloxymethyl; ethylcarbonyloxymethyl;

t-butylcarbonyloxymethyl; cyclohexylcarbonyloxymethyl;

1-(methylcarbonyloxy)-ethyl; 1-(ethylcarbonyloxy)-ethyl;

1-(t-butylcarbonyloxy)-ethyl; 1-(cyclohexylcarbonyloxy)-ethyl;

1-propyloxycarbonyloxymethyl; cyclohexylcarbonyloxymethyl;

t-butyloxycarbonyloxymethyl; 1-(i-propyloxycarbonyloxy)-ethyl;

1-(cyclohexyloxycarbonyloxy)-ethyl; 1-(t-butyloxycarbonyloxy)-ethyl;

dimethylaminoethyl; diethylaminoethyl;

(5-methyl-1,3-dioxacyclopenten-2-on-4-yl)-methyl;

(5-(t-butyl)-1,3-dioxacyclopenten-2-on-4-yl)-methyl;

(1,3-dioxa-5-phenyl-cyclopenten-2-on-4-yl)-methyl; and 1-(2-methoxypropyl)carbonyloxy)-ethyl;

the enantiomeric and diastereomeric forms being selected from:

(R,S), (R,S);
(R), (R,S);
(S), (R,S);
(R), (R);
(S), (R);
(R), (S); and
(S), (S).

18. An iontophoresis device according to claim 17, wherein the hydrogen of the hydroxy group of the diaminopropanoic acid moiety is substituted with a group selected from:

methyl; ethyl; and isopropyl.

19. An iontophoresis device according to claim 17, wherein the pharmaceutically acceptable salt form is selected from:

acetate, methanesulfonate, hydrochloride, benzenesulfonate, and para-toluenesulfonate.

20. An iontophoresis device according to claim 17, comprising a compound:

$N^3$-[2-{3-(4-formamidinophenyl)-isoxazolin-5(R)-yl}-acetyl]-$N^2$-(n-butyloxycarbonyl)-2,3-(S)-diaminopropanoic acids or a pharmaceutically acceptable salt form or propanoate ester prodrug from thereof.

21. An iontophoresis device according to claim 17, comprising a compound:

methyl-$N^3$-[2-{3-(4-formamidinophenyl)-isoxazolin-5(R)-yl}-acetyl]-$N^2$-(n-butyloxycarbonyl)-2,3-(S)-diaminopropanoate methanesulfonate salt.

22. A method for the treatment of thromboembolic disorders, the method comprising iontophoretically administering to a mammal a therapeutically effective amount of an integrin inhibitor using an iontophoresis device according to claim 12.

23. A method of administering an integrin inhibitor compound, the method comprising iontophoretically administering to a mammal a therapeutically effective amount of the integrin inhibitor using an iontophoresis device according to claim 12.

24. A method for the treatment of thrombosis, the method comprising administering to a mammal a therapeutically effective amount of an integrin inhibitor using an iontophoresis device according to claim 12.

25. A method of inhibiting the aggregation of blood platelets, the method comprising administering to a mammal a therapeutically effective amount of a IIb/IIIa inhibitor using an iontophoresis device according to claim 12.

26. A method of treating a thromboembolic disorder selected from thrombus or embolus formation, harmful platelet aggregation, reocclusion following thrombolysis, reperfusion injury, restenosis, atherosclerosis, stroke, myocardial infarction, and unstable angina, the method comprising administering to a mammal a therapeutically effective amount of an integrin inhibitor using an iontophoresis device according to claim 12.

* * * * *

UNITED STATES PATENT AND TRADEMARK OFFICE
CERTIFICATE OF CORRECTION

PATENT NO. : 5,961,483
APPLICATION NO. : 08/878493
DATED : October 5, 1999
INVENTOR(S) : Sage et al.

It is certified that error appears in the above-identified patent and that said Letters Patent is hereby corrected as shown below:

In Column 8, line 42, delete "cycloalkyl, $C_7$-$C_4$"; and insert -- cycloalkyl, $C_7$-$C_{14}$--.

In Column 12, line 66, delete "Carbonyl, -N($R^{13}$)$R^{13}$"; and insert -- Carbonyl, -N($R^{12}$) $R^{13}$--.

In Column 16, line 22, delete "butytoxycarbonyl"; and insert -- butyloxycarbonyl--, In Column 16, line 60, delete "N²"; and insert --$N^2$--.

In Column 20, line 51, delete "isoxazolin-5-yl)}"; and insert -- isoxazolin-5-yl}--.

In Column 22, lines-34-35, delete "-acetyl]-N 2-(n-butyloxycarbonyl)"; and Insert -- -acetyl]-$N^2$-(n-butyloxycarbonyl)--.

In Column 24, line 45, delete "(GP IIb/IIba antagonist)"; and insert --(GP IIb/IIIa antagonist)--.

In Column 90, line 61, delete "Purified $\alpha_v\beta_3$ (human placenta) - Vitronectin ELISA"; and insert one space between the line before.

In Column 92, line 35, delete "-70°C. until used."; and insert -- -70°C until used.--.

In Column 95, line 13, delete "pKa=1.11"; and insert --pKa=11.1--.

In Column 96, line 41, delete "at -80°C. until assayed."; and insert -- at -80°C until assayed.--.

In Column 103, line 56, delete "p"is 1-7"; and insert --p' Is 1-7;--.

In Column 107, line 25, delete "-$CH_2$-CH(N($R^{16}$) $R_{17}$)-,"; and insert --$CH_2$-CH(N($R^{16}$) $R^{17}$)--.

UNITED STATES PATENT AND TRADEMARK OFFICE
CERTIFICATE OF CORRECTION

PATENT NO. : 5,961,483
APPLICATION NO. : 08/878493
DATED : October 5, 1999
INVENTOR(S) : Sage et al.

It is certified that error appears in the above-identified patent and that said Letters Patent is hereby corrected as shown below:

In Column 108, line 23, delete "substituted with 0-2 $R^{19}$ $C_2$-$C_4$"; and insert --substituted with 0-2 $R^{19}$, $C_2$-$C_4$--.

Signed and Sealed this

First Day of August, 2006

JON W. DUDAS
*Director of the United States Patent and Trademark Office*